(12) United States Patent
Oinuma et al.

(10) Patent No.: US 7,776,890 B2
(45) Date of Patent: Aug. 17, 2010

(54) 1H-INDAZOLE COMPOUNDS

(75) Inventors: Hitoshi Oinuma, Ibaraki (JP); Norihito Ohi, Ibaraki (JP); Nobuaki Sato, Ibaraki (JP); Motohiro Soejima, Ibaraki (JP); Hidenori Seshimo, Saitama (JP); Taro Terauchi, Ibaraki (JP); Takashi Doko, Ibaraki (JP); Naohiro Kohmura, Ibaraki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 12/426,818

(22) Filed: Apr. 20, 2009

(65) Prior Publication Data

US 2009/0203691 A1    Aug. 13, 2009

Related U.S. Application Data

(62) Division of application No. 11/202,234, filed on Aug. 12, 2005, now Pat. No. 7,541,376.

(51) Int. Cl.
*A61K 31/44* (2006.01)
*C07D 23/56* (2006.01)

(52) U.S. Cl. .................... 514/338; 548/361.1
(58) Field of Classification Search .......... 514/338; 548/361.1
See application file for complete search history.

(56) References Cited

U.S. PATENT DOCUMENTS

| | | | |
|---|---|---|---|
| 5,760,028 A | 6/1998 | Jadhav et al. | |
| 6,982,274 B2 * | 1/2006 | Oinuma et al. | 514/338 |
| 7,211,594 B2 | 5/2007 | Bhagwat et al. | |
| 2002/0103229 A1 | 8/2002 | Bhagwat et al. | |

FOREIGN PATENT DOCUMENTS

| | | |
|---|---|---|
| DE | 1266763 B2 | 4/1968 |
| EP | 023633 A1 | 2/1981 |
| EP | 328200 A | 8/1989 |
| EP | 475352 A | 3/1992 |
| EP | 1 110 957 A1 | 6/2001 |
| JP | 51-125281 A1 | 11/1976 |
| JP | 52-122366 A | 10/1977 |
| JP | 1-180878 A | 7/1989 |
| JP | 3-167175 A1 | 7/1991 |
| JP | 6-206872 A | 7/1994 |
| JP | P2000-501105 A | 2/2000 |
| JP | 2000-198734 A | 7/2000 |
| WO | WO-89/10924 A | 11/1989 |
| WO | WO-97/03069 A1 | 1/1997 |
| WO | WO-97/23480 A1 | 7/1997 |
| WO | WO-99/23077 A1 | 5/1999 |
| WO | WO-00/00487 A1 | 1/2000 |
| WO | WO-00/00490 A2 | 1/2000 |
| WO | WO-00/00491 A1 | 1/2000 |
| WO | WO-00/06173 A1 | 2/2000 |
| WO | WO-00/21959 A1 | 4/2000 |
| WO | WO-00/35906 A2 | 6/2000 |
| WO | WO-00/35909 A1 | 6/2000 |
| WO | WO-00/35921 A1 | 6/2000 |
| WO | WO-00/64872 A1 | 11/2000 |
| WO | WO-00/75118 A1 | 12/2000 |
| WO | WO-01/12609 A1 | 2/2001 |
| WO | WO-01/12621 A1 | 2/2001 |
| WO | WO-01/19833 A1 | 3/2001 |
| WO | WO-01/23378 A1 | 4/2001 |
| WO | WO-01/23379 A1 | 4/2001 |
| WO | WO-01/23382 A1 | 4/2001 |
| WO | WO-01/53268 A2 | 7/2001 |
| WO | WO-01/57024 A1 | 8/2001 |
| WO | WO-01/64674 A1 | 9/2001 |
| WO | WO-02/10137 A2 | 2/2002 |

OTHER PUBLICATIONS

Patel, M., et al. Substituents. Bioorg. Med. Chem. Lett., 1999, 9, pp. 3217-3220.
Jones, Jr., W.D., et al. J. Heterocyclic Chem., 1983, 20, pp. 1359-1361.
Kawakubo, Hiroshi, et al. Journal of the Pharmaceutical Society of Japan, 1987, 107(1), pp. 28-36.
Kawakubo, Hiroshi, et al. Indazoles. Chem. Pharm. Bull., 1987, 35(6), pp. 2292-2299.
Cava, M.P., et al. J. Org. Chem., 1973, 38(13), pp. 2394-2397.
Boehm, H.J., et al. J. Med. Chem., 2000, 43, pp. 2664-2674.
Fujimura, Yasuo et al., Journal of the Pharmaceutical Society of Japan, 1986, 106(11), pp. 1002-1007.
Fujimura, Yasuo, et al. Journal of the Pharmaceutical Society of Japan, 1986, 106(11, pp. 995-1001.
Mohit, A.A., et al. NEURON, 1995, 14, pp. 67-78.
Zhu, X. et al. J. NEUROCHEM., 2001, 76, pp. 435-441.

(Continued)

*Primary Examiner*—Rei-tsang Shiao
(74) *Attorney, Agent, or Firm*—Birch, Stewart, Kolasch & Birch, LLP

(57) ABSTRACT

The present invention provides a novel 1H-indazole compound having an excellent JNK inhibitory action. More specifically, it provides a compound represented by the following formula, a salt thereof or a hydrate of them.

(I)

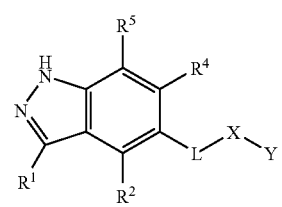

Wherein $R^1$ is a $C_6$-$C_{14}$ aromatic cyclic hydrocarbon group etc.; $R^2$, $R^4$ and $R^5$ each independently represent a hydrogen atom, a halogen atom, a cyano group etc.; L is a single bond, or a $C_1$-$C_6$ alkylene group etc.; X is a single bond, or a group represented by —CO—NH— or —NH—CO—, etc.; and Y is a $C_3$-$C_8$ cycloalkyl group, a $C_6$-$C_{14}$ aromatic cyclic hydrocarbon group or a 5- to 14-membered aromatic heterocyclic group etc.

16 Claims, No Drawings

OTHER PUBLICATIONS

Wrzeciono, U. et al. PHARMAZIE, 1993, 48 (8), pp. 582-584.
Wrzeciono, U., et al. PHARMAZIE, 1992, 47(1) pp. 22-24.
Wrzeciono, U. et al. PHARMAZIE, 1985, 40(2), pp. 105-108.
Bergman, J. et al. TETRAHEDRON, 1999, 55, pp. 10447-10466.
Mochizuki Hideki et al.; Jounal of the Neurological Sciences, vol. 137, 1996, pp. 120-123.
Smale Georgeann et al.; Experimental NEUROLOGY, vol. 133, pp. 225-230, 1995.
Gupta Shashi et al.; The EMBO Journal, vol. 15, No. 11, pp. 2760-2770, 1996.
Sabapathy Kanaga et al.; J. Exp. Med., vol. 193, No. 3, Feb. 5, 2001, pp. 317-328.
Kuan Chia-Yi et al. Neuron, vol. 22, pp. 667-676, Apr. 1999.
Yang Derek D. et al.; Nature, vol. 389, Oct. 23, 1997, pp. 865-870.
Xia Zhengui et al.; Science, vol. 270, Nov. 24, 1995, pp. 1326-1331.
Kyriakis John M.; Nature, vol. 369, May 12, 1994, pp. 156-160.
Takaharu et al.; 1972, CAS: 77: 88502.
Korean Office Action issued Sep. 2, 2008 for Application No. 10-2003-7013494 and partial English translation thereof.

* cited by examiner

1H-INDAZOLE COMPOUNDS

CROSS-REFERENCE

This application is a Divisional of application Ser. No. 11/202,234 filed on Aug. 12, 2005 now U.S. Pat. No. 7,541,376, and for which priority is claimed under 35 U.S.C. §120. Priority under 35 USC §120 is claimed through application Ser. No. 11/202,234 to application Ser. No. 10/469,399, filed on Aug. 28, 2003, now U.S. Pat. No. 6,982,274 B2. Application Ser. No. 10/469,399 is the national phase of PCT International Application No. PCT/JP02/03735 filed on Apr. 15, 2002 under 35 U.S.C. §371. The entire contents of each of the above-identified applications are hereby incorporated by reference. This application also claims priority of Application No. 2001-116521 filed in Japan on Apr. 16, 2001 under 35 U.S.C. §119.

TECHNICAL FIELD

The present invention relates to a novel indazole compound having an excellent inhibitory action on protein phosphatase (protein kinase), especially on JNK protein kinase.

PRIOR ART

A cascade by action of mitogen-activated protein kinase (hereinafter referred to as "MAPK") is universally presents from yeasts to humans and plays a very important role as one of intracellular signaling pathways. Among such MAPK-related kinases in mammalian cells, three types of kinases, namely, extracellular signal-regulation kinase (ERK), p38, and c-Jun amino-terminal kinase (JNK; or also referred to as stress-activated protein kinases (SAPK)) are particularly well known. SAPKs have been found in rats and are JNK homologues, and it is known that isoform groups thereof each have an amino acid sequence 90% or more equivalent to that of a corresponding isoform group of JNKs (Nature, 369, 156, 1994). A multitude of activators relating to MAPK have been identified recently, and it has been clarified that pathways for activating ERK, p38, and JNKs play functionally different roles, respectively. Especially, the JNK system is considered to play a role as one of medically and pharmaceutically worthy intracellular signaling pathways for the following reasons. The JNK system is possibly an important signaling pathway that is activated by, for example, stress factors to cells, such as tumor necrosis factor α (TNF-α), interleukin-1 (IL-1), and other cytokines, as well as heat shock, ultraviolet rays (UV), and X-rays, and induces not only cell proliferation and/or differentiation but also apoptosis (cell death) (Science, 270, 1326, 1995). JNKs were first found as a kinase for phosphatasing orylating Ser 63 and Ser 73 at the N-terminus of c-Jun (Nature, 353, 670, 1991), but in recent, it has been clarified that JNKs phosphorylate many transcription factors such as ATF-2 and Elk-1 and regulate their activities (EMBO J., 15, 2760, 1996). JNKs include three types, JNK 1, JNK 2 and JNK 3. JNK 1 and JNK 2 are expressed in most of tissues, but JNK 3 is particularly highly expressed in the brain (Neuron, 14, 67, 1995; Neuron, 22, 667, 1999). Analyses of knocked out mice lacking JNK 1 or JNK 2 have revealed that these JNKs play important roles in differentiation and/or activation of T cells (J. Exp. Med., 193, 317, 2001). In contrast, it has been reported that knocked out mice lacking JNK 3 have tolerance to spasticity initiated by kainic acid, an excitable amino acid receptor agonist, and that the knocked out mice lacking JNK 3 do not show apoptosis, which apoptosis is found in hippocampus nerve cells of normal mice after such spasticity (nature 389, 865, 1997). Death of nerve cells due to apoptosis is speculated to play an important role in nerve degeneration processes in neurodegenerative diseases such as Alzheimer's disease and Parkinson's disease (Experimental Neurology 133, 225, 1995; J. Neurol. Sci. 137, 120, 1996), and results indicating the possibility that JNKs are involved in the nerve cell death have been accumulated (Neuron, 14, 67, 1995; J. Neurochem., 76, 435, 2001).

For example, the following reports have been made on low-molecular substances having JNK inhibitory action.

(1) Compounds represented by the formula having antiinflammatory action, and compounds represented by the formula ($I^{1a}$) as specific embodiments thereof (WO 00/00491).

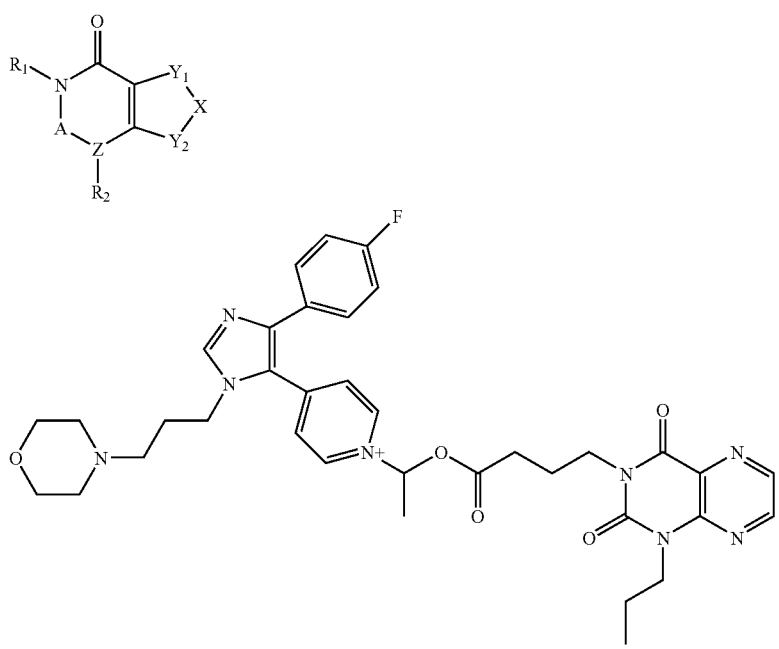

(2) 4-Aryloxyindole compounds represented by the formula (I²), and compounds represented by the formula (I²ᵃ) as specific embodiments thereof (WO 00/35909).

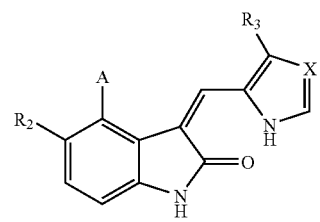
(I²)

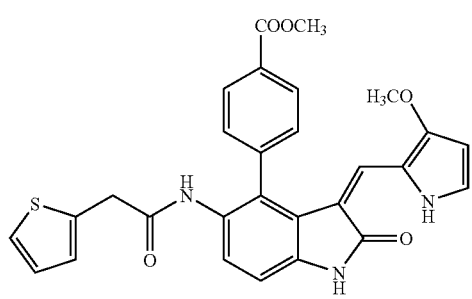
(I²ᵃ)

(3) 4,5-Pyrazinoxyindole compounds represented by the formula (I³), and compounds represented by the formula (I³ᵃ) as specific embodiments thereof (WO 00/35921).

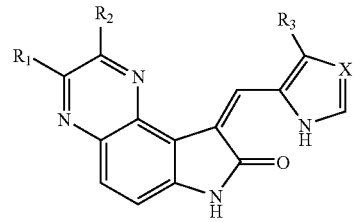
(I³)

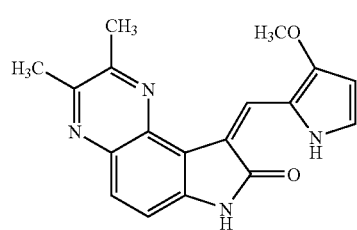
(I³ᵃ)

(4) Compounds represented by the formula (I⁴), and compounds represented by the formula (4a) as specific embodiments thereof (WO 00/64872).

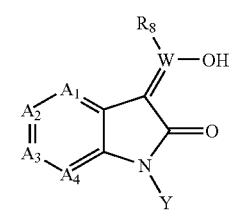
(I⁴)

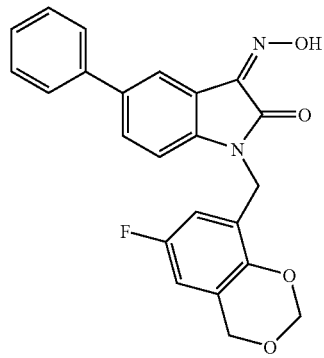
(I⁴ᵃ)

(5) Oxyindole derivatives represented by the formula (I⁵), and compounds represented by the formula (I⁵ᵃ) as specific embodiments thereof (WO 00/35906).

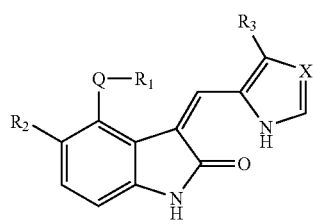
(I⁵)

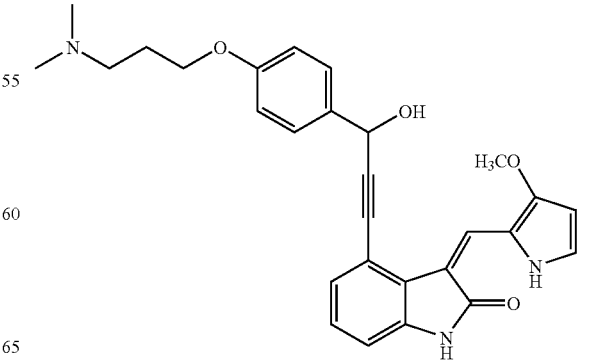
(I⁵ᵃ)

(6) Compounds represented by the formula (I⁶) having JNK inhibitory action, and compounds represented by the formula (I⁶ᵃ) as specific embodiments thereof (WO 00/75118).

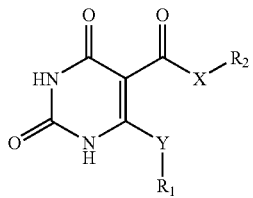
(I⁶)

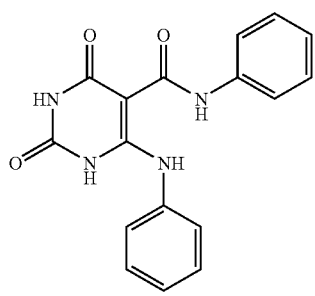
(I⁶ᵃ)

(7) Compounds represented by the formula (I⁷) having JNK inhibitory action, and compounds represented by the formula (I⁷ᵃ) as specific embodiments thereof (WO 01/12609).

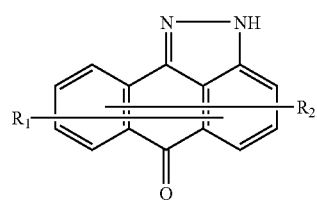
(I⁷)

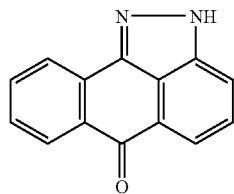
(I⁷ᵃ)

(8) Compounds represented by the formula (I⁸) having JNK inhibitory action, and compounds represented by the formula (I⁸ᵃ) as specific embodiments thereof (WO 01/12621).

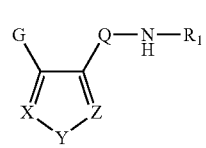
(I⁸)

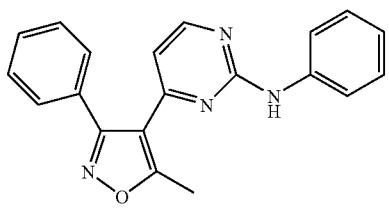
(I⁸ᵃ)

(9) Sulfonamide derivatives represented by the formula (I⁹), and compounds represented by any of the formulae (I⁹ᵃ), (I⁹ᵇ) and (I⁹ᶜ) as specific embodiments thereof (WO 01/23378, WO 01/23379, and WO 01/23382).

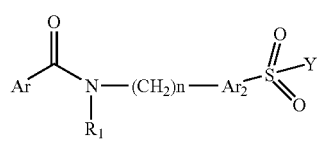
(I⁹)

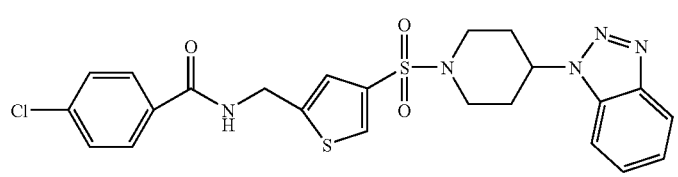
(I⁹ᵃ)

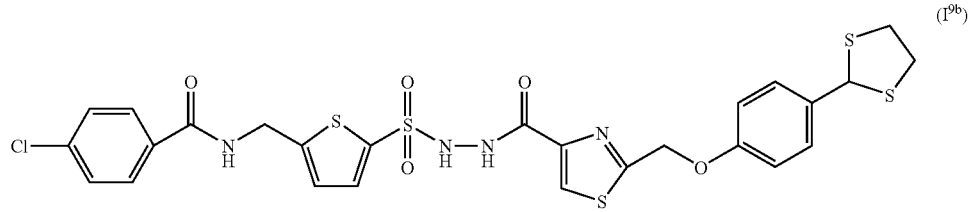
(I⁹ᵇ)

-continued

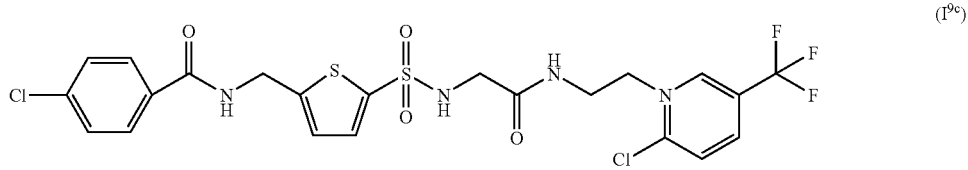

(10) Compounds represented by the formula (I¹⁰) having JNK inhibitory action, and compounds represented by the formula (I¹⁰ᵃ) as specific embodiments thereof (EP 01/110957).

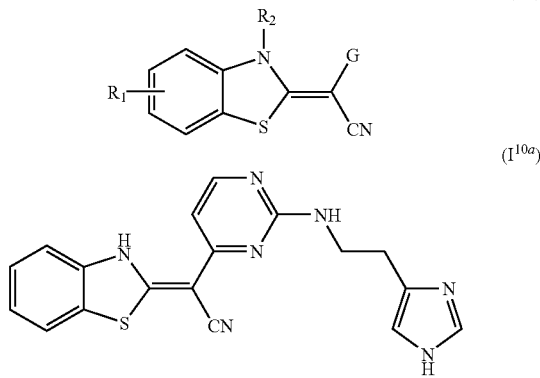

In contrast, reports have been made on compounds each having an indazole skeleton in, for example, JP-A 2000-501105, JP-A 2000-198734 and WO 99/23077. However, relations of all these compounds with protein kinases are neither disclosed nor indicated.

As is described above, the JNK system receives attention as one of important mechanisms relating to activation of various cells, regulation of immunocytes, or apoptosis of neurons induced by various stress signals. Accordingly, compounds exhibiting inhibitory action on the JNK pathway, particularly on JNK protein kinases are expected to be useful as therapeutic agents for various immunologic diseases, inflammatory diseases, and/or neurodegenerative diseases. However, compounds having excellent JNK protein kinase inhibitory action and satisfying requirements in, for example, pharmacological activities, dosage, and safety as pharmaceutical drugs have not yet been found.

DISCLOSURE OF THE INVENTION

After intensive investigations under these circumstances, the present inventors have found novel indazole compounds having JNK inhibitory action. That is, the present invention relates to:

<1> a compound represented by the following formula:

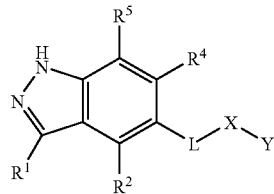

(wherein $R^1$ is a $C_6$-$C_{14}$ aromatic cyclic hydrocarbon group which may be substituted or a 5- to 14-membered aromatic heterocyclic group which may be substituted;

$R^2$, $R^4$ and $R^5$ each independently represent a hydrogen atom, a halogen atom, a hydroxyl group, a cyano group, a nitro group, a carboxyl group, a $C_1$-$C_8$ alkyl group which may be substituted, a $C_1$-$C_6$ alkoxy group which may be substituted, a $C_2$-$C_7$ acyl group which may be substituted, —CO—$NR^{2a}R^{2b}$, —$NR^{2b}$CO—$R^{2a}$ or —$NR^{2a}R^{2b}$ (wherein $R^{2a}$ and $R^{2b}$ each independently represent a hydrogen atom or a $C_1$-$C_6$ alkyl group which may be substituted);

L is a single bond, a $C_1$-$C_6$ alkylene group which may be substituted, a $C_2$-$C_8$ alkenylene group which may be substituted or a $C_2$-$C_6$ alkynylene group which may be substituted;

X is a single bond, or a group represented by —$NR^6$—, —O—, —CO—, —S—, —SO—, —$SO_2$—, —CO—$NR^8$—$V^2$—, —C(O)O—, —$NR^8$—CO—$V^2$—, —$NR^8$—C(O)O—, —$NR^8$—S—, —$NR^8$—SO—, —$NR^8$—$SO_2$—$V^2$—, —$NR^8$—CO—$NR^{10}$—, —$NR^9$—CS—$NR^{10}$—, —S(O)$_m$—$NR^{11}$—$V^2$—, —C(=$NR^{12}$)—$NR^{13}$—, —OC(O)—, —OC(O)—N—$R^{14}$— or —$CH_2$—$NR^8$—$COR^6$ (wherein $R^6$, $R^8$, $R^9R^{10}R^{11}$, $R^{12}$, $R^{13}$ and $R^{14}$ each independently represent a hydrogen atom, a halogen atom, a hydroxyl group, a $C_1$-$C_6$ alkyl group which may be substituted, a $C_2$-$C_6$ alkenyl group which may be substituted, a $C_2$-$C_6$ alkynyl group which may be substituted, a $C_1$-$C_6$ alkoxy group which may be substituted, a $C_2$-$C_6$ alkenyloxy group which may be substituted, a $C_1$-$C_6$ alkylthio group which may be substituted, a $C_2$-$C_6$ alkenylthio group which may be substituted, a $C_3$-$C_8$ cycloalkyl group which may be substituted, a $C_3$-$C_8$ cycloalkenyl group which may be substituted, a 5- to 14-membered non-aromatic heterocyclic group which may be substituted, a $C_6$-$C_{14}$ aromatic cyclic hydrocarbon group which may be substituted or a 5- to 14-membered aromatic heterocyclic group which may be substituted; $V^2$ is a single bond or a $C_1$-$C_6$ alkylene group which may be substituted; and m is 0, 1 or 2); and Y is a hydrogen atom, a halogen atom, a nitro group, a hydroxyl group, a cyano group, a carboxyl group, a $C_1$-$C_6$ alkyl group which may be substituted, a $C_2$-$C_6$ alkenyl group which may be substituted, a $C_2$-$C_6$ alkynyl group which may be substituted, a $C_1$-$C_6$ alkoxy group which may be substituted, a $C_3$-$C_8$ cycloalkyl group which may be substituted, a $C_3$-$C_8$ cycloalkenyl group which may be substituted, a 5- to 14-membered non-aromatic heterocyclic group which may be substituted, a $C_6$-$C_{14}$ aromatic cyclic hydrocarbon group which may be substituted, a 5- to 14-membered aromatic heterocyclic group which may be substituted, an amino group or —W—$R^{15}$ (wherein W is —CO— or —$SO_2$—; and $R^{15}$ is a $C_1$-$C_6$ alkyl group which may be substituted, a $C_6$-$C_{14}$ aromatic cyclic hydrocarbon group which may be substituted, a 5- to 14-membered aromatic heterocyclic group which may be substituted or an amino group)), a salt thereof or a hydrate of them;

<2> the compound according to the above <1>, a salt thereof or a hydrate of them, wherein $R^2$, $R^4$ and $R^5$ each independently represent a hydrogen atom, a halogen atom or a $C_1$-$C_6$ alkoxy group which may be substituted;

<3> the compound according to the above <1> or <2>, a salt thereof or a hydrate of them, wherein $R^5$ is a hydrogen atom;

<4> the compound according to any one of the above <1> to <3>, a salt thereof or a hydrate of them, wherein $R^4$ is a hydrogen atom;

<5> the compound according to any one of the above <1> to <4>, a salt thereof or a hydrate of them, wherein $R^2$ is a hydrogen atom;

<6> the compound according to any one of the above <1> to <5>, a salt thereof or a hydrate of them, wherein at least one of $R^2$, $R^4$ and $R^5$ is not a hydrogen atom;

<7> the compound according to any one of the above <1> to <6>, a salt thereof or a hydrate of them, wherein L is a single bond or a methylene group;

<8> the compound according to any one of the above <1> to <6>, a salt thereof or a hydrate of them, wherein L is a single bond;

<9> the compound according to any one of the above <1> to <8>, a salt thereof or a hydrate of them, wherein $R^1$ is a $C_6$-$C_{14}$ aromatic cyclic hydrocarbon group or a 5- to 14-membered aromatic heterocyclic group; and $R^1$ is a group which may be substituted by one to three groups selected from the following Substituent Group "a":

<Substituent Group "a"> the group consisting of (1) (a) $C_1$-$C_6$ alkyl groups, (b) $C_1$-$C_6$ alkoxy groups, (c) $C_1$-$C_7$ acyl groups, (d) an amido group, (e) an amino group and (f) $C_3$-$C_8$ cycloalkyl groups, each of which may be substituted by one to three groups selected from the following Substituent Group "b", (2) halogen atoms, (3) a hydroxyl group, (4) a nitro group, (5) a cyano group, and (6) a carboxyl group;

<Substituent Group "b"> the group consisting of $C_1$-$C_6$ alkyl groups, halogen atoms, a hydroxyl group, a nitro group, a cyano group and a carboxyl group;

<10> the compound according to any one of the above <1> to <8>, a salt thereof or a hydrate of them, wherein $R^1$ is a phenyl group, a naphthyl group or a 5- to 10-aromatic heterocyclic group; and $R^1$ is a group which may be substituted by one to three groups selected from the Substituent Group "a" as described in the above <9>;

<11> the compound according to any one of the above <1> to <8>, a salt thereof or a hydrate of them, wherein $R^1$ is a phenyl group, 2-naphthyl group, pyridyl group, 2-thienyl group, 2-furyl group, 2-benzofuryl group, 2-quinolyl group or 2-benzothienyl group; and $R^1$ is a group which may be substituted by one to three groups selected from the Substituent Group "a" described in the above <9>;

<12> the compound according to any one of the above <1> to <8>, a salt thereof or a hydrate of them, wherein $R^1$ is a 2-naphthyl group, 2-benzofuryl group or 2-benzothienyl group; and $R^1$ is a group which may be substituted by one to three groups selected from the Substituent Group "a" as described in the above <9>;

<13> the compound according to any one of the above <9> to <12>, a salt thereof or a hydrate of them, wherein the Substituent Group "a" is the group consisting of (1) $C_1$-$C_6$ alkyl groups which may be substituted by one to three groups selected from the group consisting of a halogen atom, a hydroxyl group and a cyano group, (2) $C_1$-$C_6$ alkoxy groups which may be substituted by one to three groups selected from the group consisting of a halogen atom, a hydroxyl group and a cyano group, (3) halogen atoms, (4) a hydroxyl group, and (5) a cyano group;

<14> the compound according to any one of the above <9> to <12>, a salt thereof or a hydrate of them, wherein the Substituent Group "a" is halogen atoms;

<15> the compound according to any one of the above <1> to <14>, a salt thereof or a hydrate of them, wherein X is a group represented by —CO—$NR^8$—$V^2$—, —$NR^8$—CO—$V^2$— or —$NR^8$—$SO_2$—$V^2$— (wherein $R^8$ and $V^2$ have the same meanings as $R^8$ and $V^2$ in the above <1>);

<16> the compound according to the above <15>, a salt thereof or a hydrate of them, wherein $R^8$ is a hydrogen atom;

<17> the compound according to any one of the above <1> to <14>, a salt thereof or a hydrate of them, wherein X is a group represented by —CO—NH—$(CH_2)_t$— (wherein t is 0 or 1);

<18> the compound according to any one of the above <1> to <14>, a salt thereof or a hydrate of them, wherein X is a group represented by —NH—CO—$(CH_2)_t$— (wherein t is 0 or 1);

<19> the compound according to any one of the above <1> to <18>, a salt thereof or a hydrate of them, wherein Y is a $C_1$-$C_6$ alkyl group, a $C_6$-$C_{14}$ aromatic cyclic hydrocarbon group, a $C_1$-$C_6$ alkoxy group, a $C_3$-$C_8$ cycloalkyl group, a 5- to 14-membered non-aromatic heterocyclic group and a 5- to 14-membered aromatic heterocyclic group, and Y is a group which may be substituted by one to three groups selected from the following Substituent Group "a2":

<Substituent Group "a2"> the group consisting of (1) (a) $C_1$-$C_6$ alkyl groups, (b) $C_2$-$C_6$ alkenyl groups, (c) $C_2$-$C_6$ alkynyl groups, (d) $C_1$-$C_6$ alkoxy groups, (e) $C_2$-$C_7$ acyl groups, (f) an amide group, (g) an amino group, (h) a $C_3$-$C_8$ cycloalkyl group, (i) $C_3$-$C_8$ cycloalkenyl groups, (j) $C_6$-$C_{14}$ aromatic cyclic hydrocarbon groups, (k) 5- to 14-membered aromatic heterocyclic groups, (l) $C_6$-$C_{14}$ aryloxy groups, and (m) 5- to 14-membered non-aromatic heterocyclic groups, each of which may be substituted by one to three groups selected from the following <Substituent Group "b2">, (2) halogen atoms, (3) a hydroxyl group, (4) a nitro group, (5) a cyano group, and (6) a carboxyl group;

<Substituent Group "b2"> the group consisting of $C_1$-$C_6$ alkyl groups, halogen atoms, a hydroxyl group, a nitro group, a cyano group, and a carboxyl group;

<20> the compound according to any one of the above <1> to <18>, a salt thereof or a hydrate of them, wherein Y is a $C_3$-$C_8$ cycloalkyl group, a phenyl group, a 5- or 6-membered non-aromatic heterocyclic group or a 5- or 6-membered aromatic heterocyclic group, and Y is a group which may be substituted by one to three groups selected from the Substituent Group "a2" as described in the above <19>;

<21> the compound according to any one of the above <1> to <18>, a salt thereof or a hydrate of them, wherein Y is a furyl group, a thienyl group, a pyrrolyl group, a phenyl group, a pyridyl group, a $C_3$-$C_8$ cycloalkyl group, a tetrahydrofuran-yl group, a tetrahydrothiophenyl group, a pyrrolidinyl group, a tetrahydrofuran-2-one-yl group, a pyrrolidin-2-one-yl group or a group represented by the formula:

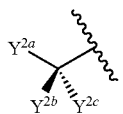

(wherein $Y^{2a}$ is a group represented by —$CONH_2$ or —$CH_2OH$; and $Y^{2b}$ and $Y^{2c}$ each independently represent a hydrogen atom, a phenyl group which may be substituted or a $C_1$-$C_6$ alkyl group which may be substituted), and wherein Y is a group which may be substituted by one to three groups selected from the Substituent Group "a2" as described in the above <19>;

<22> the compound according to any one of the above <1> to <18>, a salt thereof or a hydrate of them, wherein Y is a furyl group or a thienyl group; and Y is a group which may be substituted by one to three groups selected from the Substituent Group "a2" as described in the above <19>;

<23> the compound according to any one of the above <19> to <22>, a salt thereof or a hydrate of them, wherein the Substituent Group "a2" is the group consisting of (1) (a) $C_1$-$C_6$ alkyl groups, (b) $C_1$-$C_6$ alkoxy groups, (c) $C_1$-$C_7$ acyl groups, (d) an amide group, (e) an amino group, and (f) $C_3$-$C_8$ cycloalkyl groups, each of which may be substituted by one to three groups selected from the following <Substituent Group "b2">, (2) halogen atoms, (3) a hydroxyl group, (4) a nitro group, (5) a cyano group, and (6) a carboxyl group, and the Substituent Group "b2" is the group consisting of $C_1$-$C_6$ alkyl groups, halogen atoms, a hydroxyl group, a nitro group, a cyano group, and a carboxyl group;

<24> the compound according to any one of the above <19> to <22>, a salt thereof or a hydrate of them, wherein the Substituent Group "a2" is the group consisting of (1) $C_1$-$C_6$ alkoxy groups, (2) halogen atoms, and (3) a cyano group;

<25> a c-Jun amino-terminal kinase (JNK) inhibitor, comprising the compound according to the above <1>, a salt thereof or a hydrate of them.

<26> c-Jun amino-terminal kinaseamino-terminal kinase 1 (JNK 1), c-Jun amino-terminal kinaseamino-terminal kinase 2 (JNK 2) and/or c-Jun amino-terminal kinaseamino-terminal kinase 3 (JNK 3) inhibitors, comprising the compound according to the above <1>, a salt thereof or a hydrate of them;

<27> an agent for treating or preventing an immunological diseases or inflammatory diseases, comprising the compound according to the above <1>, a salt thereof or a hydrate of them;

<28> the agent for treating or preventing according to the above <27>, wherein the immunological diseases or inflammatory diseases is sepsis, chronic rheumatoid arthritis, osteoarthritis, gout, psoriasis, psoriatic arthritis, bronchitis, chronic obstructive lung disease, cystic fibrosis, insulin-dependent type I diabetes, autoimmune thyroiditis, Crohn's disease, ulcerative colitis, atopic dermatitis, asthma, allergic rhinitis, hepatitis, systemic lupus erythematosus, acute and chronic graft rejection after organ transplantation, graft versus host diseases, eczema, urticaria, myasthenia gravis, acquired immunodeficiency syndrome, idiopathic thrombocytopenic purpura or glomerular nephritis;

<29> an agent for treating or preventing neurodegenerative diseases, comprising the compound according to the above <1>, a salt thereof or a hydrate of them;

<30> the agent for treating or preventing according to the above <29>, wherein the neurodegenerative diseases is acute neurodegenerative disease;

<31> the agent for treating or preventing according to the above <30>, wherein the acute neurodegenerative diseases is acute stage of cerebrovascular disorder, head injury, spinal code injury, or neuropathy due to hypoxia or hypoglycemia;

<32> the agent for treating or preventing according to the above <29>, wherein the neurodegenerative diseases is chronic neurodegenerative disease;

<33> an agent for treating or preventing Alzheimer's disease, Parkinson's disease, Huntington's chorea, amyotrophic lateral sclerosis, multiple sclerosis or spinocerebellar degeneration, which comprises the compound according to the above <1>, a salt thereof or a hydrate of them;

<34> the agent for treating or preventing according to the above <29>, wherein the neurodegenerative disease is epilepsy, hepatic encephalopathy, peripheral neuropathy, Parkinsonian syndrome, L-DOPA-induced dyskinesia in treatment of Parkinson's disease, spastic paralysis, pain or neuralgia;

<35> the agent for treating or preventing according to the above <29>, wherein the neurodegenerative disease is infectious encephalomyelitis, cerebrovascular dementia, dementia or neurosis caused by meningitis;

<36> the agent for treating or preventing according to the above <35>, wherein the infectious encephalomyelitis is HIV encephalomyelitis;

<37> use of the compound according to the above <1>, a salt thereof or a hydrate of them, for therapy or prophylaxis of an immunological diseases, inflammatory diseases and/or neurodegenerative diseases;

<38> use of the compound according to the above <1>, a salt thereof or a hydrate of them, for producing an agent for treating an immunological diseases, inflammatory diseases and/or neurodegenerative diseases;

<39> use of the compound according to the above <1>, a salt thereof or a hydrate of them, for producing a c-Jun amino-terminal kinase 3 (JNK 3) inhibitor;

<40> a method for treating or preventing a disease against which inhibition of c-Jun amino-terminal kinaseamino-terminal kinase 3 (JNK 3) is effective, an immunological disease, an inflammatory disease and/or a neurodegenerative disease, which comprises administering a pharmacologically effective amount of the compound according to the above <1>, a salt thereof or a hydrate of them to a patient, etc.

The present invention provides a pharmaceutical composition comprising the compound according to claim 1, a salt thereof or a hydrate of them, and a pharmacologically acceptable carrier. The present invention also provides use of the compound according to claim 1, a salt thereof or a hydrate of them, for producing an agent for treating or preventing a disease against which inhibition of a c-Jun amino-terminal kinaseamino-terminal kinase (JNK) is effective, an immunological disease, an inflammatory disease or a neurodegenerative disease. The present invention further provides a method for treating or preventing a disease against which inhibition of a c-Jun amino-terminal kinase (JNK) is effective, an immunological disease, an inflammatory disease or a neurodegenerative disease, which comprises administering a pharmacologically effective amount of the compound according to claim 1, a salt thereof or a hydrate of them to a patient.

The meanings of symbols, terms etc. as used in the present description will be described, and the present invention will be illustrated in detail below.

The term "and/or" as used in the present description means and includes both the cases of "and" and "or".

The term "JNK" as used in the present description means an enzyme that phosphorylates the N-terminus region of a c-Jun protein and includes, for example, JNK 1, JNK 2, and JNK 3. Such JNKs include three types, JNK 1, JNK 2 and JNK 3. JNK 1 and JNK 2 are expressed in most of tissues, but JNK 3 is particularly highly expressed in the brain (Neuron, 14, 67, 1995; Neuron, 22, 667, 1999).

The term "neurodegenerative disease(s)" as used in the present description means all of diseases generally classified as neurodegenerative diseases in the field of medicine and includes, but is not specifically limited to, "acute neurodegenerative diseases", "chronic neurodegenerative diseases", epilepsy, hepatic encephalopathy, peripheral neuropathy, Parkinsonian syndrome, L-DOPA-induced dyskinesia in treatment of Parkinson's disease, spastic paralysis, pain, neuralgia, infectious encephalomyelitis, cerebrovascular dementia, and dementia or neurological symptom due to meningitidis. The "acute neurodegenerative diseases" include, for example, acute stage of cerebrovascular disorder (e.g., subarachnoid hemorrhage and cerebral infarction), head injury, spinal code injury, neuropathy due to hypoxia, and neuropathy due to hypoglycemia. The "chronic neurodegenerative diseases" include, for example, Alzheimer's disease, Parkinson's disease, Huntington's chorea, amyotrophic lateral sclerosis, multiple sclerosis, and spinocerebellar degeneration.

The term "immunologic disease(s)" or "inflammatory disease(s)" as used in the present description means all of diseases classified as immunologic diseases in the field of medicine, and examples thereof include, but are not limited to, sepsis, chronic rheumatoid arthritis, osteoarthritis, gout, psoriasis, psoriatic arthritis, bronchitis, chronic obstructive lung disease, cystic fibrosis, insulin-dependent type I diabetes, autoimmune thyroiditis, Crohn's disease, ulcerative colitis, atopic dermatitis, asthma, allergic rhinitis, hepatitis, systemic lupus erythematosus, acute and chronic graft rejection after organ transplantation, graft versus host diseases, eczema, urticaria, myasthenia gravis, acquired immunodeficiency syndrome, idiopathic thrombocytopenic purpura, and glomerular nephritis.

In the specification of the present invention, there is the case where the structural formula of a compound represents a definite isomer. However, the present invention includes isomers such as geometrical isomers, optical isomers based on asymmetric carbon, stereoisomers and tautomers and is not limited by the description of the formula illustrated for the sake of convenience. Accordingly, although it is possible that an asymmetric carbon atom is present in a molecule and accordingly that optically active substance and racemic substance may be present, the present invention is not limited thereto but covers any of them. Further, crystal polymorphism may be present but, again, there is no limitation but any of single crystal form or a mixture will do. The compound (I) or its salt related to the present invention may be an anhydride or a hydrate, and either of them are included in the scope of claim for patent in the present invention. The metabolite which is generated by decomposing the compound (I) related to the present invention in vivo, and the prodrug of the compound (I) or its salt related to the present invention produce are also included in the scope of claim for patent in the present invention.

The salts or hydrates of the compounds of the present invention are preferably those pharmacologically acceptable.

The term "halogen atom(s)" as used in the present description includes, for example, a fluorine atom, chlorine atom, bromine atom, and iodine atom, preferably a fluorine atom and chlorine atom, and more preferably a fluorine atom.

The term "$C_1$-$C_6$ alkyl group(s)" as used in the present description means a linear or branched alkyl group containing 1 to 6 carbon atoms and includes, for example, methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, 1-ethyl-2-methylpropyl group, 1,1,2-trimethylpropyl group, 1-propylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, and 3-methylpentyl group. More preferred examples are methyl group, ethyl group, n-propyl group, iso-propyl group, n-butyl group, iso-butyl group, sec-butyl group, tert-butyl group, and n-pentyl group.

The term "$C_2$-$C_6$ alkenyl group(s)" as used in the present description means a linear or branched alkenyl group containing 2 to 6 carbon atoms and includes, for example, vinyl group, allyl group, 1-propenyl group, 2-propenyl group, iso-propenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexadienyl group, and 1,6-hexadienyl group.

The term "$C_2$-$C_6$ alkynyl group(s)" as used in the present description means a linear or branched alkynyl group containing 2 to 6 carbon atoms and includes, for example, ethynyl group, 1-propynyl group, 2-propynyl group, 1-butynyl group, 2-butynyl group, 3-butynyl group, 3-methyl-1-propynyl group, 1-ethynyl-2propynyl group, 2-methyl-3-propynyl group, 1-pentynyl group, 1-hexynyl group, 1,3-hexadiynyl group, and 1,6-hexadiynyl group.

The term "$C_1$-$C_6$ alkylene group(s)" as used in the present description means a divalent group derived from the above-defined "$C_1$-$C_6$ alkyl group" by removal of one hydrogen atom at an arbitrary position and includes, for example, methylene group, ethylene group, methylethylene group, propylene group, ethylethylene group, 1,1-dimethylethylene group, 1,2-dimethylethylene group, trimethylene group, 1-methyltrimethylene group, 1-ethyltrimethylene group, 2-methyltrimethylene group, 1,1-dimethyltrimethylene group, tetramethylene group, pentamethylene group, and hexamethylene group, of which methylene group and 1,2-ethylene group are preferred.

The term "$C_2$-$C_6$ alkenylene group(s)" as used in the present description means a divalent group derived from the above-defined "$C_2$-$C_6$ alkenyl group" by removal of one hydrogen atom and includes, for example, vinylene groups, propenylene groups, butenylene groups, pentenylene groups, and hexenylene groups. Preferred examples are vinylene groups, propenylene groups, butenylene groups, and pentenylene groups, of which vinylene groups, propenylene groups, and butenylene groups are more preferred. Among them, 1,2-vinylene group and 1,3-propenylene group are further more preferred.

The term "$C_2$-$C_6$ alkynylene group(s)" as used in the present description means a divalent group derived from the above-defined "$C_2$-$C_6$ alkynyl group" by removal of further one hydrogen atom and includes, for example, ethynylene group, propynylene groups, butynylene groups, pentynylene groups, and hexynylene groups. Preferred examples are ethynylene group, propynylene groups, butynylene groups, and pentynylene groups, of which ethynylene group, propynylene groups, and butynylene groups are more preferred. Among them, ethynylene group and propynylene groups are furthermore preferred, of which ethynylene group is most preferred.

The term "$C_3$-$C_8$ cycloalkyl group(s)" as used in the present description means three to eight aliphatic cyclic hydrocarbon groups and includes, for example, cyclopropyl group, cyclobutyl group, cyclopentyl group, cyclohexyl group, cycloheptyl group, and cyclooctyl group, of which cyclopropyl group and cyclobutyl group are preferred.

The term "$C_3$-$C_8$ cycloalkenyl group(s)" as used in the present description means a $C_3$-$C_8$ cycloalkenyl group comprising 3 to 8 carbon atoms and includes, for example, cyclopenten-3-yl, cyclohexen-1-yl, and cyclohexen-3-yl.

The term "$C_1$-$C_6$ alkoxy group(s)" as used in the present description means an oxy group combined with the above-defined "$C_1$-$C_6$ alkyl group" and includes, for example, methoxy group, ethoxy group, n-propoxy group, iso-propoxy group, sec-propoxy group, n-butoxy group, iso-butoxy group, sec-butoxy group, tert-butoxy group, n-pentyloxy group, iso-pentyloxy group, sec-pentyloxy group, n-hexoxy group, iso-hexoxy group, 1,1-dimethylpropyloxy group, 1,2-dimethylpropoxy group, 2,2-dimethylpropyloxy group, 2-ethylpropoxy group, 1-methyl-2-ethylpropoxy group, 1-ethyl-2-methylpropoxy group, 1,1,2-trimethylpropoxy group, 1,1,2-trimethylpropoxy group, 1,1-dimethylbutoxy group, 1,2-dimethylbutoxy group, 2,2-dimethylbutoxy group, 2,3-dimethylbutyloxy group, 1,3-dimethylbutyloxy group, 2-ethylbutoxy group, 1,3-dimethylbutoxy group, 2-methylpentoxy group, 3-methylpentoxy group, and hexyloxy group. Among them, methoxy group, ethoxy group, n-propoxy group, iso-propoxy group, and sec-propoxy group are preferred, of which methoxy group and ethoxy group are more preferred.

The term "$C_2$-$C_6$ alkenyloxy group(s)" as used in the present description means an oxy group combined with the above-defined "$C_2$-$C_6$ alkenyl group".

The term "$C_2$-$C_6$ alkenylthio group(s)" as used in the present description means a thio group combined with the above-defined "$C_2$-$C_6$ alkenyl group".

The term "$C_1$-$C_6$ alkoxycarbonyl group(s)" as used in the present description means a carbonyl group combined with the above-defined "$C_1$-$C_6$ alkoxy group" and includes, for example, methoxycarbonyl group, ethoxycarbonyl group, n-propoxycarbonyl group, i-propoxycarbonyl group, n-butoxycarbonyl group, i-butoxycarbonyl group, sec-butoxycarbonyl group, and t-butoxycarbonyl group.

The term "$C_2$-$C_7$ acyl group(s)" as used in the present description means a carbonyl group combined with the above-defined "$C_1$-$C_6$ alkyl group" and includes, for example, acetyl group, propionyl group, butyryl group, isobutyryl group, valeryl group, isovaleryl group, and pivaloyl group.

The term "$C_1$-$C_6$ alkylcarbamoyl group(s)" as used in the present description includes, for example, methylcarbamoyl group, ethylcarbamoyl group, n-propylcarbamoyl group, iso-propylcarbamoyl group, n-butylcarbamoyl group, iso-butylcarbamoyl group, sec-butylcarbamoyl group, tert-butylcarbamoyl group, n-pentylcarbamoyl group, 1,1-dimethylpropylcarbamoyl group, 1,2-dimethylpropylcarbamoyl group, 2,2-dimethylpropylcarbamoyl group, 1-ethylpropylcarbamoyl group, 2-ethylpropylcarbamoyl group, n-hexylcarbamoyl group, 1-methyl-2-ethylpropylcarbamoyl group, 1-ethyl-2-methylpropylcarbamoyl group, 1,1,2-trimethylpropylcarbamoyl group, 1-propylpropylcarbamoyl group, 1-methylbutylcarbamoyl group, 2-methylbutylcarbamoyl group, 1,1-dimethylbutylcarbamoyl group, 1,2-dimethylbutylcarbamoyl group, 2,2-dimethylbutylcarbamoyl group, 1,3-dimethylbutylcarbamoyl group, 2,3-dimethylbutylcarbamoyl group, 2-ethylbutylcarbamoyl group, 2-methylpentylcarbamoyl group, and 3-methylpentylcarbamoyl group.

The term "$C_1$-$C_6$ alkylcarbonyloxy group(s)" as used in the present description means an oxy group combined with the above-defined "$C_2$-$C_7$ acyl group" and includes, for example, methylcarbonyloxy group, ethylcarbonyloxy group, n-propylcarbonyloxy group, iso-propylcarbonyloxy group, n-butylcarbonyloxy group, iso-butylcarbonyloxy group, sec-butylcarbonyloxy group, tert-butylcarbonyloxy group, n-pentylcarbonyloxy group, 1,1-dimethylpropylcarbonyloxy group, 1,2-dimethylpropylcarbonyloxy group, 2,2-dimethylpropylcarbonyloxy group, 1-ethylpropylcarbonyloxy group, 2-ethylpropylcarbonyloxy group, n-hexylcarbonyloxy group, 1-methyl-2-ethylpropylcarbonyloxy group, 1-ethyl-2-methylpropylcarbonyloxy group, 1,1,2-trimethylpropylcarbonyloxy group, 1-propylpropylcarbonyloxy group, 1-methylbutylcarbonyloxy group, 2-methylbutylcarbonyloxy group, 1,1-dimethylbutylcarbonyloxy group, 1,2-dimethylbutylcarbonyloxy group, 2,2-dimethylbutylcarbonyloxy group, 1,3-dimethylbutylcarbonyloxy group, 2,3-dimethylbutylcarbonyloxy group, 2-ethylbutylcarbonyloxy group, 2-methylpentylcarbonyloxy group, and 3-methylpentylcarbonyloxy group.

The term "$C_1$-$C_6$ alkylsulfonyl group(s)" as used in the present description means a sulfonyl group combined with the above-defined "$C_1$-$C_6$ alkyl group" and includes, for example, methylsulfonyl group, ethylsulfonyl group, n-propylsulfonyl group, iso-propylsulfonyl group, n-butylsulfonyl group, iso-butylsulfonyl group, sec-butylsulfonyl group, tert-butylsulfonyl group, n-pentylsulfonyl group, 1,1-dimethylpropylsulfonyl group, 1,2-dimethylpropylsulfonyl group, 2,2-dimethylpropylsulfonyl group, 1-ethylpropylsulfonyl group, 2-ethylpropylsulfonyl group, n-hexylsulfonyl group, 1-methyl-2-ethylpropylsulfonyl group, 1-ethyl-2-methylpropylsulfonyl group, 1,1,2-trimethylpropylsulfonyl group, 1-propylpropylsulfonyl group, 1-methylbutylsulfonyl group, 2-methylbutylsulfonyl group, 1,1-dimethylbutylsulfonyl group, 1,2-dimethylbutylsulfonyl group, 2,2-dimethylbutylsulfonyl group, 1,3-dimethylbutylsulfonyl group, 2,3-dimethylbutylsulfonyl group, 2-ethylbutylsulfonyl group, 2-methylpentylsulfonyl group, and 3-methylpentylsulfonyl group.

The term "$C_1$-$C_6$ alkylsulfenyl group(s)" as used in the present description means a sulfenyl group combined with the above-defined "$C_1$-$C_6$ alkyl group" and includes, for example, methylsulfenyl group, ethylsulfenyl group, n-propylsulfenyl group, iso-propylsulfenyl group, n-butylsulfenyl group, iso-butylsulfenyl group, sec-butylsulfenyl group, tert-butylsulfenyl group, n-pentylsulfenyl group, 1,1-dimethylpropylsulfenyl group, 1,2-dimethylpropylsulfenyl group, 2,2-dimethylpropylsulfenyl group, 1-ethylpropylsulfenyl group, 2-ethylpropylsulfenyl group, n-hexylsulfenyl group, 1-methyl-2-ethylpropylsulfenyl group, 1-ethyl-2-methylpropylsulfenyl group, 1,1,2-trimethylpropylsulfenyl group, 1-propylpropylsulfenyl group, 1-methylbutylsulfenyl group, 2-methylbutylsulfenyl group, 1,1-dimethylbutylsulfenyl group, 1,2-dimethylbutylsulfenyl group, 2,2-dimethylbutylsulfenyl group, 1,3-dimethylbutylsulfenyl group, 2,3-dimethylbutylsulfenyl group, 2-ethylbutylsulfenyl group, 2-methylpentylsulfenyl group, and 3-methylpentylsulfenyl group.

The term "$C_1$-$C_6$ alkylthio group(s)" as used in the present description means a thio group combined with the above-defined "$C_1$-$C_6$ alkyl group" and includes, for example, methylthio group, ethylthio group, n-propylthio group, iso-propylthio group, n-butylthio group, iso-butylthio group, sec-butylthio group, tert-butylthio group, n-pentylthio group, 1,1-dimethylpropylthio group, 1,2-dimethylpropylthio group, 2,2-dimethylpropylthio group, 1-ethylpropylthio group, 2-ethylpropylthio group, n-hexylthio group, 1-methyl-2-ethylpropylthio group, 1-ethyl-2-methylpropylthio group, 1,1,2-trimethylpropylthio group, 1-propylpropylthio group, 1-methylbutylthio group, 2-methylbutylthio group, 1,1-dimethylbutylthio group, 1,2-dimethylbutylthio group, 2,2-dimethylbutylthio group, 1,3-dimethylbutylthio group, 2,3-dimethylbutylthio group, 2-ethylbutylthio group, 2-methylpentylthio group, and 3-methylpentylthio group.

The term "$C_6$-$C_{14}$ aromatic cyclic hydrocarbon group(s)" as used in the present description means an aromatic cyclic hydrocarbon group comprising 6 to 14 carbon atoms and includes monocyclic groups as well as bicyclic groups, tricyclic groups, and other condensed rings. Examples of these groups include phenyl group, indenyl groups, 1-naphthyl group, 2-naphthyl group, azulenyl groups, heptalenyl groups, biphenyl groups, indacenyl groups, acenaphthyl groups, fluorenyl groups, phenalenyl groups, phenanthrenyl groups, anthracenyl groups, cyclopentacyclooctenyl groups, and benzocyclooctenyl groups. In the "$C_6$-$C_{14}$ aromatic cyclic hydrocarbon group", phenyl group, 1-naphthyl group and 2-naphthyl group are preferred, and phenyl group, indenyl group and 2-naphthyl group are more preferred.

The term "$C_6$-$C_{14}$ aryloxy group(s)" as used in the present description means an oxy group combined with the above-defined "$C_6$-$C_{14}$ aromatic cyclic hydrocarbon group".

The term "5- to 14-membered aromatic heterocyclic group(s)" as used in the present description means a monocyclic, bicyclic, or tricyclic 5- to 14-membered heterocyclic group containing one or more hetero atoms selected from the group consisting of nitrogen atoms, sulfur atoms and oxygen atoms. Examples of the group include 1) nitrogen-containing aromatic heterocyclic groups such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolidyl group, phthalazyl group, naphthyridinyl group, quinoxalyl group, quinazolinyl group, cinnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenazinyl group, imidazopyridinyl group, imidazopyrimidinyl group, pyrazolopyridinyl group or pyrazolopyridinyl group; 2) sulfur-containing aromatic heterocyclic groups such as thienyl group or benzothienyl group; 3) oxygen-containing aromatic heterocyclic groups such as furyl group, pyranyl group, benzofuryl group or isobenzofuryl group; and 4) aromatic heterocyclic groups each containing two or more different hetero atoms, such as thiazolyl group, isothiazolyl group, benzothiazolyl group, benzthiadiazolyl group, phenothiazinyl group, isoxazoly group, furazanyl group, phenoxazinyl group, oxazolyl group, isoxazolyl group, benzoxazolyl group, oxadiazolyl group, pyrazoloxazolyl group, imidazothiazolyl group, thienofuranyl group, furopyrrolyl group or pyridooxazinyl group.

The term "5- to 14-membered non-aromatic heterocyclic group(s)" as used in the present description means a non-aromatic heterocyclic group 1) which comprises 5 to 14 atoms, 2) which contains one or more hetero atoms as the atoms constituting the ring, 3) which may contain one to three carbonyl groups, and 4) which is a monocyclic, bicyclic or tricyclic ring.

Examples of the group include pyrrolidyl group, pyrrolyl group, piperidyl group, piperazyl group, imidazolyl group, pyrazolidyl group, imidazolidyl group, morpholyl group, tetrahydrofuryl group, tetrahydropyranyl group, aziridinyl group, oxiranyl group, and oxathiolanyl group. The non-aromatic heterocyclic group includes groups derived from a pyridone ring and non-aromatic condensed rings such as groups derived from phthalimide ring, or succinimide ring. Preferred examples of these groups are pyrrolidyl group, pyrrolyl group, piperidyl group, piperazyl group, imidazolyl group, pyrazolidyl group, imidazolidyl group, morpholyl group, tetrahydrofuryl group, tetrahydropyranyl group, aziridinyl group, oxiranyl group, and oxathiolanyl group.

The term "5- to 10-membered aromatic heterocyclic group(s)" as used in the present description means a monocyclic or bicyclic aromatic heterocyclic group, whose ring comprises 5 to 10 atoms including one or more hetero atoms.

Examples of the group include 1) nitrogen-containing aromatic heterocyclic groups such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolidyl group, phthalazyl group, naphthyridinyl group, quinoxalyl group, quinazolinyl group, cinnolinyl group, pteridinyl group, imidazotriazinyl group, pyrazinopyridazinyl group, imidazopyridinyl group, imidazopyrimidinyl group, pyrazolopyridinyl group or pyrazolopyridinyl group; 2) sulfur-containing aromatic heterocyclic groups such as thienyl group or benzothienyl group; 3) oxygen-containing aromatic heterocyclic groups such as furyl group, pyranyl group, benzofuryl group or isobenzofuryl group; and 4) aromatic heterocyclic groups each containing two or more different hetero atoms, such as thiazolyl group, isothiazolyl group, benzothiazolyl group, benzthiadiazolyl, isoxazoly group, furazanyl group, oxazolyl group, isoxazolyl group, benzoxazolyl group, oxadiazolyl group, pyrazoloxazolyl group, imidazothiazolyl group, thienofuranyl group, furopyrrolyl group or pyridooxazinyl group.

Preferred examples of the group are pyrrolyl group, furyl group, thienyl group, pyridyl group, benzothienyl group, benzyl group, indolyl group, benzoyl group, and indazolyl group, of which furyl group, thienyl group, benzothienyl group and benzofuryl group are more preferred.

The term "5- or 6-membered aromatic heterocyclic group(s)" as used in the present description means a monocyclic aromatic heterocyclic group, whose ring comprises 5 or 6 atoms including one or more hetero atoms. Examples of the group include pyrrolyl group, imidazolyl group, pyrazolyl group, 1,2,3-triazolyl group, pyridyl group, pyridazyl group, pyrimidinyl group, pyrazinyl group, furyl group, thienyl group, thiazolyl group, oxazolyl group, and isoxazolyl group, of which pyrrolyl group, pyridyl group, furyl group and thienyl group are preferred. Among them, furyl group and thienyl group are more preferred.

The term "5- or 6-membered non-aromatic heterocyclic group(s)" as used in the present description means a 5- or 6-membered heterocyclic group containing one or more hetero atoms selected from the group consisting of nitrogen atoms, sulfur atoms and oxygen atoms. Examples of the group include piperidyl group, piperazyl group, morpholyl group, thiomorpholyl group, tetrahydro-2-pyron-yl group, tetrahydropyran-yl groups, tetrahydrothiopyran-yl groups, piperidin-2-one-yl groups, tetrahydrofuran-yl group, tetrahydrothiophen-yl group, pyrrolidinyl group, tetrahydrofuran-2-one-yl groups, and pyrrolidin-2-one-yl groups. Preferred examples of the "5- or 6-membered nonaromatic heterocyclic group" are piperidyl group, piperazyl group, morpholyl group, thiomorpholyl group, tetrahydro-2-pyron-yl groups, tetrahydropyran-yl groups, tetrahydrothiopyran-yl groups, and piperidin-2-one-yl groups.

The term "5-membered non-aromatic heterocyclic group(s)" as used in the present description means a 5-membered heterocyclic group containing one or more hetero atoms selected from the group consisting of nitrogen atoms, sulfur atoms, and oxygen atoms and concretely means, for example, tetrahydrofuran-yl group, tetrahydrothiophen-yl group, pyrrolidinyl group, tetrahydrofuran-2-one-yl groups, or pyrrolidin-2-one-yl groups.

The term "amino group(s)" as used in the present description means a group represented by the formula —$NH_2$.

The term "amide group(s)" as used in the present description means a group represented by the formula —CO—$NH_2$.

The term "furyl group" as used in the present description means 2-furyl group or 3-furyl group, of which 2-furyl group is preferred.

The term "thienyl group" as used in the present description means 2-thienyl group or 3-thienyl group, of which 2-thienyl group is preferred.

The term "pyrrolyl group" as used in the present description means 1-pyrrolyl group, 2-pyrrolyl group, or 3-pyrrolyl group, of which 2-pyrrolyl group is preferred.

The term "tetrahydrofuran-yl group" as used in the present description means tetrahydrofuran-2-yl group or tetrahydrofuran-3-yl group, of which tetrahydrofuran-2-yl group is preferred.

The term "tetrahydrothiophen-yl group" as used in the present description means tetrahydrothiophen-2-yl group or tetrahydrothiophen-3-yl group, of which tetrahydrothiophen-2-yl group is preferred.

The term "pyrrolidinyl group" as used in the present description means 1-pyrrolidinyl group, 2-pyrrolidinyl group, or 3-pyrrolidinyl group, of which 2-pyrrolidinyl group is preferred.

The term "tetrahydrofuran-2-one-yl group" as used in the present description means tetrahydrofuran-2-one-3-yl group, tetrahydrofuran-2-one-4-yl group, or tetrahydrofuran-2-one-5-yl group, of which tetrahydrofuran-2-one-5-yl group is preferred.

The term "pyrrolidin-2-one-yl group" as used in the present description means pyrrolidin-2-one-1-yl group, pyrrolidin-2-one-3-yl group, pyrrolidin-2-one-4-yl group, or pyrrolidin-2-one-5-yl group, of which pyrrolidin-2-one-5-yl group is preferred.

The term "quinolyl group" as used in the present description means a monovalent group derived from a quinoline ring by removal of any one hydrogen atom and includes, for example, 2-quinolyl group, 3-quinolyl group, 4-quinolyl group, 5-quinolyl group, 6-quinolyl group, 7-quinolyl group, and 8-quinolyl group, of which 2-quinolyl group is preferred.

Preferred examples of the group represented by the formula:

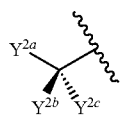

(wherein $Y^{2a}$, $Y^{2b}$ and $Y^{2c}$ have the same meanings as defined above) are groups represented by the following formulae:

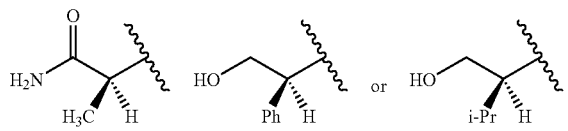

The term "may be substituted" as used in the present description has the same meaning as in "may have one or plural substituents in an arbitrary combination at positions(s) that can be substituted".

Typical examples of the substituent in the term "may be substituted" as used in the present description include:

(1) halogen atoms (e.g., fluorine atom, chlorine atom, bromine atom, and iodine atom);

(2) hydroxyl group;

(3) cyano group;

(4) nitro group;

(5) carboxyl group;

(6) amino group;

(7) $C_1$-$C_6$ alkyl groups (e.g., methyl group, ethyl group, n-propyl group, iso-propyl group, n-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, and n-hexyl group);

(8) $C_2$-$C_6$ alkenyl groups (e.g., vinyl group, allyl group, 1-propenyl group, 2-propenyl group, isopropenyl group, 2-methyl-1-propenyl group, and 3-methyl-1-propenyl group);

(9) $C_2$-$C_6$ alkynyl groups (e.g., ethynyl group, 1-propynyl group, 2-propynyl group, 1-butynyl group, 2-butynyl group, 3-butynyl group, 3-methyl-1-propynyl group, 1-ethynyl-2propynyl group, and 2-methyl-3-propynyl group);

(10) $C_3$-$C_8$ cycloalkyl groups (e.g., cyclopropyl group, cyclobutyl group, cyclopentyl group, cyclohexyl group, cycloheptyl group, and cyclooctyl group);

(11) $C_3$-$C_8$ cycloalkenyl groups (e.g., cyclopropen-1-yl, cyclopropen-3-yl, cyclobuten-1-yl, cyclobuten-3-yl, 1,3-cyclobutadien-1-yl, cyclopenten-1-yl, cyclopenten-3-yl, cyclopenten-4-yl, 1,3-cyclopentadien-1-yl, 1,3-cyclopentadien-2-yl, 1,3-cyclopentadien-5-yl, cyclohexen-1-yl, cyclohexen-3-yl, cyclohexen-4-yl, 1,3-cyclohexadien-1-yl, 1,3-cyclohexadien-2-yl, 1,3-cyclohexadien-5-yl, 1,4-cyclohexadien-3-yl, and 1,4-cyclohexadien-1-yl);

(12) $C_1$-$C_6$ alkoxy groups (e.g., methoxy group, ethoxy group, n-propoxy group, iso-propoxy group, sec-propoxy group, n-butoxy group, iso-butoxy group, sec-butoxy group, tert-butoxy group, n-pentyloxy group, iso-pentyloxy group, sec-pentyloxy group, n-hexoxy group, iso-hexoxy group, 1,1-dimethylpropyloxy group, 1,2-dimethylpropoxy group, and 2,2-dimethylpropyloxy group);

(13) $C_1$-$C_6$ alkenyloxy groups (e.g., vinyloxy group, allyloxy group, 1-propenyloxy group, 2-propenyloxy group, isopropenyloxy group, 2-methyl-1-propenyloxy group, 3-methyl-1-propenyloxy group, 2-methyl-2-propenyloxy group, 3-methyl-2-propenyloxy group, 1-butenyloxy group, 2-butenyloxy group, 3-butenyloxy group, 1-pentenyloxy group, 1-hexenyloxy group, 1,3-hexadienyloxy group, and 1,6-hexadienyloxy group);

(14) $C_1$-$C_6$ alkylthio groups (e.g., methylthio group, ethylthio group, n-propylthio group, iso-propylthio group, n-butylthio group, iso-butylthio group, sec-butylthio group, tert-butylthio group, n-pentylthio group, 1,1-dimethylpropylthio group, 1,2-dimethylpropylthio group, 2,2-dimethylpropylthio group, 1-ethylpropylthio group, 2-ethylpropylthio group, n-hexylthio group, and 1-methyl-2-ethylpropylthio group);

(15) $C_1$-$C_6$ alkenylthio groups (e.g., vinylthio group, allylthio group, 1-propenylthio group, 2-propenylthio group, isopropenylthio group, 2-methyl-1-propenylthio group, 3-methyl-1-propenylthio group, 2-methyl-2-propenylthio group, 3-methyl-2-propenylthio group, 1-butenylthio group, 2-butenylthio group, 3-butenylthio group, 1-pentenylthio group, 1-hexenylthio group, 1,3-hexadienylthio group, and 1,6-hexadienylthio group);

(16) $C_1$-$C_{14}$ aryloxy groups (e.g., phenyloxy group);

(17) $C_2$-$C_7$ acyl groups (e.g., acetyl group, propionyl group, and butyloyl group);

(18) $C_6$-$C_{14}$ aromatic cyclic hydrocarbon groups (e.g., phenyl group, 1-naphthyl group, and 2-naphthyl group);

(19) 5- to 14-membered non-aromatic cyclic hydrocarbon groups (e.g., 1) pyrrolidyl group, pyrrolyl group, piperidyl group, piperazyl group, imidazolyl group, pyrazolidyl group, imidazolidyl group, morpholyl group, tetrahydrofuryl group, tetrahydropyranyl group, aziridinyl group, oxiranyl group, and oxathiolanyl group;

2) groups derived from a pyridone ring; and 3) groups derived from condensed rings such as phthalimide ring and succinimide ring);

(20) 5- to 14-membered aromatic heterocyclic groups (e.g., pyrrolyl group, pyridyl group, pyridazinyl group, pyrimidinyl group, pyrazinyl group, imidazolyl group, benzimidazolyl group, indolyl group, indazolyl group, quinolyl group, isoquinolyl group, thienyl group, benzothienyl group, furyl group, pyranyl group, benzofuryl group, thiazolyl group, and benzothiazolyl group);

(21) amide group;

(22) sulfonyl groups each having a $C_1$-$C_6$ aliphatic hydrocarbon group as a substituent;

(23) sulfonamide group;

(24) $C_1$-$C_6$ alkyl-carbamoyl groups;

(25) $C_1$-$C_6$ alkoxy-carbonyl groups;

(26) $C_1$-$C_6$ alkyl-carbonyloxy groups;

(27) $C_1$-$C_6$ alkylsulfonyl groups;

(28) $C_1$-$C_6$ alkylsulfinyl groups;

(29) formyl group;

(30) groups represented by the following formula:

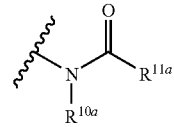

wherein $R^{11a}$ and $R^{11a}$ each independently represent a hydrogen atom or a $C_1$-$C_6$ alkyl group;

(31) groups represented by the following formula:

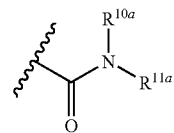

wherein $R^{10a}$ and $R^{11a}$ each independently represent a hydrogen atom or a $C_1$-$C_6$ alkyl group; and

(32) groups represented by the following formula:

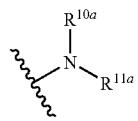

wherein $R^{10a}$ and $R^{11a}$ each independently represent a hydrogen atom or a $C_1$-$C_6$ alkyl group. The term "may be substituted" as used in the present description means that may have one to four substituents selected from the group consisting of these substituents.

Further, in the aforementioned substituents (6) to (23) as the substituent in "may be substituted", the amino group, $C_1$-$C_6$ alkyl groups, $C_2$-$C_6$ alkenyl groups, $C_2$-$C_6$ alkynyl groups, $C_3$-$C_8$ cycloalkyl groups, $C_3$-$C_8$ cycloalkenyl groups, $C_1$-$C_6$ alkoxy groups, $C_1$-$C_6$ alkenyloxy groups, $C_1$-$C_6$ alkylthio groups, $C_1$-$C_6$ alkenylthio groups, $C_1$-$C_{14}$ aryloxy groups, $C_2$-$C_7$ acyl groups, $C_6$-$C_{14}$ aromatic cyclic hydrocarbon groups, 5- to 14-membered non-aromatic cyclic hydrocarbon groups or 5- to 14-membered aromatic heterocyclic groups, amide group, sulfonyl groups each having a $C_1$-$C_6$ aliphatic hydrocarbon group as a substituent, or sulfonamide group may be further substituted by one to four groups selected from the group consisting of:

(a) halogen atoms, (b) hydroxyl group, (c) cyano group, (d) nitro group, (e) carboxyl group, (f) amino group, (g) $C_1$-$C_6$ alkyl groups, (h) $C_2$-$C_6$ alkenyl groups, (i) $C_2$-$C_6$ alkynyl groups, (j) $C_3$-$C_8$ cycloalkyl groups, (k) $C_3$-$C_8$ cycloalkenyl groups, (l) $C_1$-$C_6$ alkoxy groups, (m) $C_1$-$C_6$ alkenyloxy groups, (n) $C_1$-$C_6$ alkylthio groups, (o) $C_1$-$C_6$ alkenylthio groups, (p) $C_1$-$C_{14}$ aryloxy groups, (q) $C_2$-$C_7$ acyl groups, (r) $C_6$-$C_{14}$ aromatic cyclic hydrocarbon groups, (s) 5- to 14-membered non-aromatic cyclic hydrocarbon groups, (t) 5- to 14-membered aromatic heterocyclic groups, (u) amido group, (v) sulfonyl groups each having a $C_1$-$C_6$ aliphatic hydrocarbon group as a substituent, and (w) sulfonamido group described in (1) to (23).

Preferred examples of the substituent in the term "may be substituted" as used in the present description include:

(a-1) halogen atoms, (a-2) hydroxyl group, (a-3) nitrile group, (a-4) $C_1$-$C_6$ alkyl groups, $C_2$-$C_6$ alkenyl groups, $C_2$-$C_6$ alkynyl groups, $C_3$-$C_8$ cycloalkyl groups and $C_1$-$C_6$ alkoxy groups, each of which may be substituted by one to three halogen atoms or hydroxyl groups, (a-5) $C_6$-$C_{10}$ aromatic cyclic hydrocarbon groups, (a-6) 5- to 14-membered aromatic heterocyclic groups, (a-7) 5- to 14-membered heterocyclic groups, (a-8) carboxyl group, (a-9) trifluoromethyl group, (a-10) $C_1$-$C_6$ alkylcarbamoyl groups, (a-11) $C_1$-$C_6$ alkoxycarbonyl groups, (a-12) $C_2$-$C_7$ acyl groups, (a-13) $C_1$-$C_6$ alkylcarbonyloxy groups, (a-14) $C_1$-$C_6$ alkylsulfonyl groups, (a-15) $C_1$-$C_6$ alkylsulfinyl groups, (a-16) $C_1$-$C_6$ alkylthio groups, (a-17) nitro group, (a-18) formyl group, (a-19) groups represented by the formula:

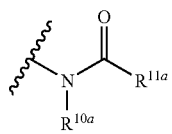

wherein $R^{10a}$ and $R^{11a}$ each independently represent a hydrogen atom or a $C_1$-$C_6$ alkyl group, and (a-20) groups represented by the formula:

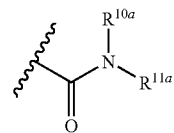

wherein $R^{10a}$ and $R^{11a}$ each independently represent a hydrogen atom or a $C_1$-$C_6$ alkyl group, and (a-21) groups represented by the formula:

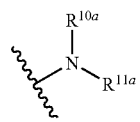

wherein $R^{10a}$ and $R^{11a}$ each independently represent a hydrogen atom or a $C_1$-$C_6$ alkyl group.

More preferred examples of the substituent in the term "may be substituted" as used in the present description include:

(a-1) halogen atoms, (a-2) hydroxyl group, (a-3) nitrile group, (a-4) $C_1$-$C_6$ alkyl groups, $C_3$-$C_8$ cycloalkyl groups or $C_1$-$C_6$ alkoxy groups, each of which may be substituted by one to three halogen atoms or hydroxyl groups, (a-17) nitro group, (a-19) groups represented by the formula:

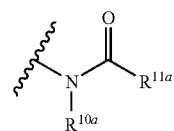

wherein $R^{10a}$ and $R^{11a}$ each independently represent a hydrogen atom or a $C_1$-$C_6$ alkyl group, and (a-20) groups represented by the formula:

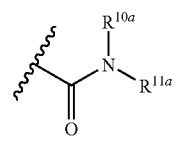

wherein $R^{10a}$ and $R^{11a}$ each independently represent a hydrogen atom or a $C_1$-$C_6$ alkyl group.

Still more preferred examples of the substituent in the term "may be substituted" as used in the present description include halogen atoms, nitrile group, $C_1$-$C_6$ alkyl groups, $C_3$-$C_8$ cycloalkyl groups, $C_1$-$C_6$ alkoxy groups, and trifluoromethyl group.

Further more preferred examples of the substituent in the term "may be substituted" as used in the present description include fluorine atom, cyclopropyl group, trifluoromethyl group, and methoxy group.

General Synthesis Method

Typical production processes of the 1H-indazole compounds represented by the formula (I) according to the present invention will be illustrated below. In reaction schemes of the following Production Processes 1 to 40, R is a $C_1$-$C_8$ alkyl group; $R^1$, $R^2$, $R^4$, and $R^5$ have the same meanings as defined above; $R^3$ is a group represented by the formula -L-X—Y (wherein L, X and Y have the same meanings as the above-defined L, X and Y); $T^1$ is a hydrogen atom, a bromine atom or an iodine atom; $T^2$ is a halogen atom; $T^3$ is a sulfonate or a halogen atom; $T^4$ is a hetero atom (oxygen atom, nitrogen atom or sulfur atom); "Pro" represents a protecting group; Q is a $C_1$-$C_8$ alkyl group; $Q^1$, $Q^2$ and $Q^3$ each independently represent a $C_1$-$C_8$ alkyl group, or $Q^1$ and $Q^2$ may be combined to form a ring; $Q^4$ and $Q^5$ each independently represent a group represented by the formula —Y (wherein Y has the same meaning as defined above); $R^{1a}$ is a group represented by the formula $R^1$ (wherein $R^1$ has the same meaning as defined above); $R^{19}$ has the same meaning as the above-defined group represented by $R^2$, $R^4$ or $R^5$; and p is an integer of 0, 1, 2, or 3.

Production Process 1

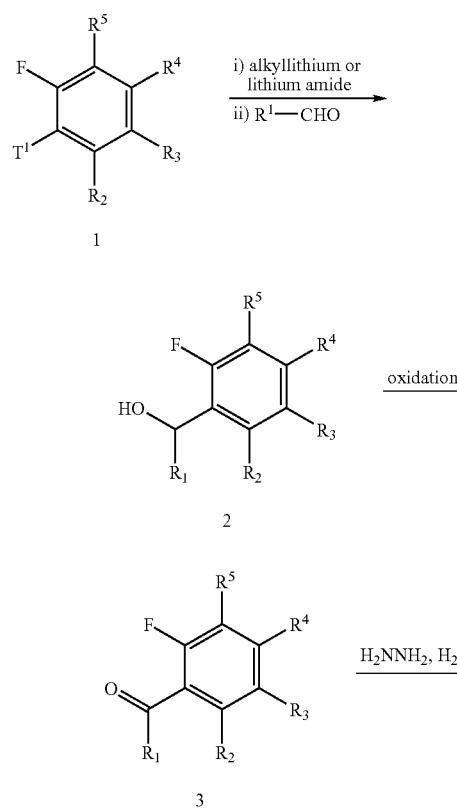

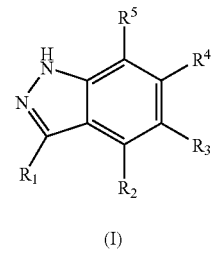

(I)

The compound (I) can be produced by treating the fluorobenzene 1 with, for example, an alkyllithium or lithium amide to thereby yield a metal aryl, allowing the metal aryl to react with an acrylaldehyde to thereby yield the alcohol 2, oxidizing the alcohol 2 into the ketone 3, and then closing the indazole ring with hydrazine. The alkyllithium for converting the fluorobenzene 1 to the metal aryl includes, for example, n-butyllithium, sec-butyllithium, tert-butyllithium, and phenyllithium. Where necessary, an additive such as N,N,N',N'-tetramethylethylenediamine and hexamethylphosphoramide can be added. The lithium amide includes, for example, lithium diisopropylamide, and lithium 2,2,6,6-tetramethylpiperidide. Solvents for use herein are not specifically limited, as long as they are inert to the reaction, and preferred examples thereof are ether solvents such as diethyl ether, tetrahydrofuran, dioxane or dimethoxyethane, as well as benzene and toluene. A reaction temperature is from −78° C. to room temperature. Oxidizing agents for oxidizing the alcohol compound 2 include, for example, manganese dioxide, sulfur trioxide-pyridine complex, N-methylmorpholine-N-oxide, and chromic acid oxidizing agents. The oxidation can also be performed by Swern oxidation or Moffat oxidation. Solvents for use herein can be any solvents that are not involved in the reaction and include, for example, halogenated hydrocarbons such as dichloromethane or chloroform, as well as ethyl acetate, acetonitrile, dimethyl sulfoxide, and dimethylformamide. A reaction temperature is generally from −78° C. to the reflux temperature of the solvent. The reaction for cyclization of the compound 3 with hydrazine monohydrate can be performed in the absence of, or in the presence of, a solvent. Solvents for use herein are not specifically limited, as long as they are inert to the reaction, and include, for example, ether solvents such as diethyl ether, tetrahydrofuran, dioxane or dimethoxyethane, alcohol solvents such as methanol, ethanol or propanol, as well as pyridine, dimethyl sulfoxide, benzene, and toluene. The amount of the hydrazine monohydrate is from 2 to 20 equivalents to the raw material. A reaction temperature is generally from 0° C. to the reflux temperature of the solvent.

Production Process 2

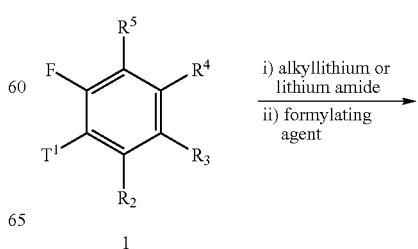

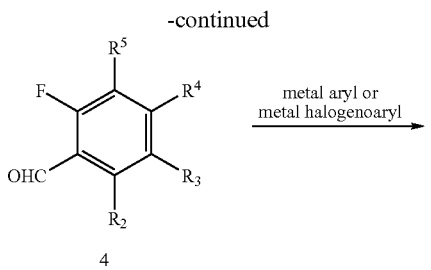

4

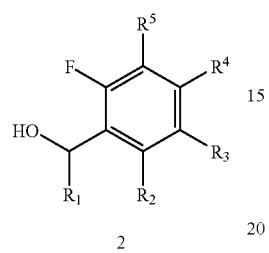

2

The compound 2 can also be produced by Production Process 2. Initially, the fluorobenzene 1 is converted into to a metal aryl by the procedure of Production Process 1, and the metal aryl is allowed to react with a formylation agent to yield the compound 4. The formylation agent includes, for example, dimethylformamide, N-formylpiperidine, and methylphenylformamide. Reaction solvents for use herein are not specifically limited, as long as they are inert to the reaction, and include, for example, ether solvents such as diethyl ether, tetrahydrofuran, dioxane or dimethoxyethane, as well as benzene and toluene. A reaction temperature is from −78° C. to room temperature. The compound 2 can be produced by allowing the compound 4 to react with a metal aryl or metal halogenoaryl. The metal aryl or metal halogenoaryl can be easily prepared, for example, by treating a halogenoaryl using an alkyllithium, magnesium or zinc into an arylithium or metal halogenoaryl. The alkyllithium includes, for example, n-butyllithium, sec-butyllithium, tert-butyllithium, and phenyllithium. Where necessary, an additive such as N,N,N',N'-tetramethylethylenediamine and hexamethylphosphoramide can be added. Reaction solvents for use herein are not specifically limited, as long as they are inert to the reaction, and include, for example, ether solvents such as diethyl ether, tetrahydrofuran, dioxane or dimethoxyethane, as well as benzene and toluene. A reaction temperature is from −78° C. to room temperature.

Production Process 3

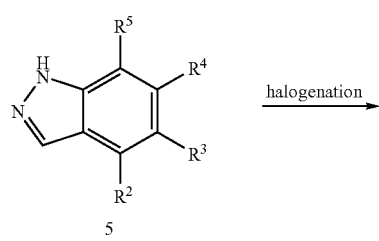

5

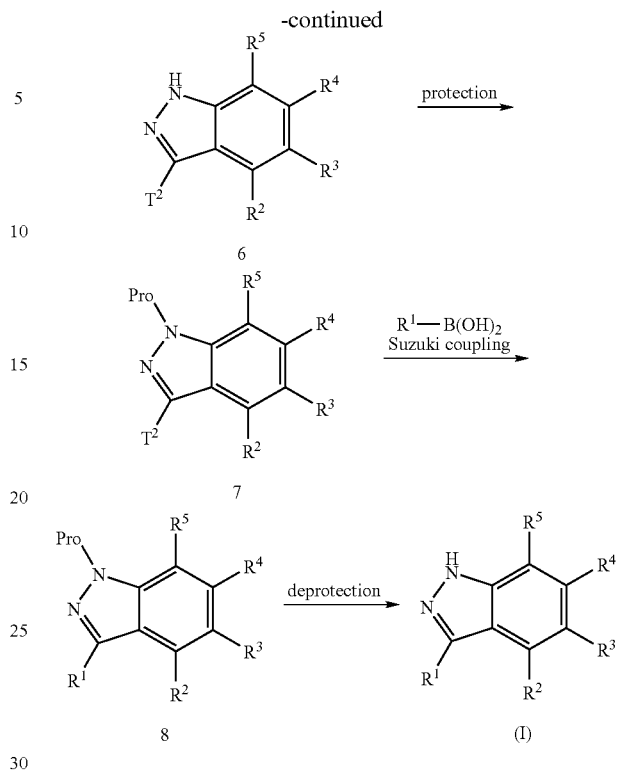

The compound (I) can also be produced by halogenating the 3-position of the indazole compound 5 to yield the compound 6, protecting the 1-position of the compound 6 to yield the compound 7, subjecting the compound 7 to Suzuki coupling with an arylboronic acid to yield the compound 8, and deprotecting the 1-position of the compound 8. Reagents for halogenating the 3-position include, for example, N-bromosuccinimide, N-iodosuccinimide, N-chlorosuccinimide, and bromine. Where necessary, a radical reaction initiator such as 2,2'-azobisisobutyronitrile and benzoyl peroxide can be added. The amount of the halogenation reagent is from 1.05 to 1.2 equivalents to the raw material. Solvents for use herein are not specifically limited, as long as they are inert to the reaction, and include, for example, halogenated hydrocarbons such as dichloromethane, chloroform or carbon tetrachloride, as well as ethyl acetate, acetonitrile, dimethyl sulfoxide, and dimethylformamide. A reaction temperature is generally from room temperature to the reflux temperature of the solvent.

Protecting groups for the 1-position include, for example, tert-butyloxycarbonyl group, p-toluenesulfonyl group, triphenylmethyl group, and methoxymethyl group. The tert-butyloxycarbonyl group or p-toluenesulfonyl group can be introduced by allowing the compound 6 to react with di-tert-butyl dicarbonate or p-toluenesulfonyl chloride in the presence of a base. Such bases are not specifically limited but preferred examples are triethylamine and 4-N,N-dimethylaminopyridine. Solvents for use herein are not specifically limited, as long as they are inert to the reaction and include, for example, ether solvents such as diethyl ether, tetrahydrofuran, dioxane or dimethoxyethane, halogenated hydrocarbons such as dichloromethane or chloroform, as well as ethyl acetate, acetonitrile, dimethyl sulfoxide, and dimethylformamide. A reaction temperature is generally from 0° C. to the reflux temperature of the solvent.

The triphenylmethyl group or methoxymethyl group can be introduced by allowing the compound 6 to react with chlorotriphenylmethane or chloromethyl methyl ether in the presence of a base. Such bases are not specifically limited, but preferred examples are sodium hydride, potassium tert-butoxide, lithium diisopropylamide, potassium carbonate, and sodium hydroxide. Solvents for use herein are not specifically limited, as long as they are inert to the reaction and include, for example, ether solvents such as diethyl ether, tetrahydrofuran, dioxane or dimethoxyethane, as well as ethyl acetate, acetonitrile, dimethyl sulfoxide, and dimethylformamide. A reaction temperature is generally from −20° C. to the reflux temperature of the solvent.

Among arylboronic acids for use in Suzuki coupling, those commercially available will be purchased, and those not commercially available can be easily prepared according to a conventional procedure. Such an arylboronic acid can be prepared, for example, by treating a halogenoaryl with an alkyllithium, magnesium or zinc to convert the same into an arylithium or a metal halogenoaryl, allowing the arylithium or metal halogenoaryl to react with trialkyl-borate into a boric ester, and hydrolyzing the boric ester. The alkyllithium includes, for example, n-butyllithium, sec-butyllithium, tert-butyllithium, and phenyllithium. Where necessary, an additive such as N,N,N',N'-tetramethylethylenediamine, and hexamethylphosphoramide can be added. The boric ester formed as a result of the reaction between the arylithium and the trialkyl-boric acid can be hydrolyzed by adding water or by using an acid such as hydrochloric acid or sulfuric acid. Reaction solvents for use herein are not specifically limited, as long as they are inert to the reaction, of which ether solvents such as diethyl ether, tetrahydrofuran, dioxane or dimethoxyethane are preferred. A reaction temperature is from −78° C. to room temperature. The amount of the arylboronic acid for use in Suzuki coupling is from 1 to 3 equivalents to the raw material. Catalysts for use herein include, for example, palladium(II) acetate, dichlorobis(triphenylphosphine)palladium(II), and tetrakis(triphenylphosphine)palladium(0). The amount of the catalyst is about 5% by mole relative to the raw material. Where necessary, a phosphine ligand in an amount of two times by mole that of the catalyst can be added. Such phosphine ligands include, for example, tri-tert-butylphosphine, 2-(di-tert-butylphosphino)biphenyl, 2-(dicyclohexylphosphino)biphenyl, and triphenylphosphine. Examples of bases for use herein are sodium hydrogencarbonate, sodium carbonate, potassium carbonate, cesium carbonate, and potassium fluoride. Solvents for use herein are not specifically limited, as long as they do not adversely affect the reaction, and include, for example, dimethylformamide, N-methylpyrrolidone, tetrahydrofuran, dioxane, diethylene glycol dimethyl ether, and toluene. A reaction temperature is generally from room temperature to the reflux temperature of the solvent.

The tert-butyloxycarbonyl group and triphenylmethyl group can be easily deprotected (removed) by using an acid. Such acids include, for example, hydrochloric acid, sulfuric acid, and trifluoroacetic acid. Where necessary, a radical scavenger such as thiophenol or tri-iso-propylsilane can be added. Solvents for use herein are not specifically limited, as long as they are inert to the reaction, and include, for example, halogenated hydrocarbons such as dichloromethane or chloroform, alcohol solvents such as methanol or ethanol, and anisole. A reaction temperature is from −20° C. to the reflux temperature of the solvent. The tert-butyloxycarbonyl group and p-toluenesulfonyl group can also be easily deprotected by using a base. Such bases include, but are not specifically limited to, aqueous sodium hydroxide and aqueous potassium hydroxide. Solvents for use herein are not specifically limited, as long as they are inert to the reaction, and include, for example, alcohol solvents such as methanol or ethanol, ether solvents such as diethyl ether, tetrahydrofuran, dioxane or dimethoxyethane. A reaction temperature is room temperature to the reflux temperature of the solvent. The methoxymethyl group can be deprotected by treating the compound with an acid and treating the residual aminal with aqueous ammonia.

Production Process 4

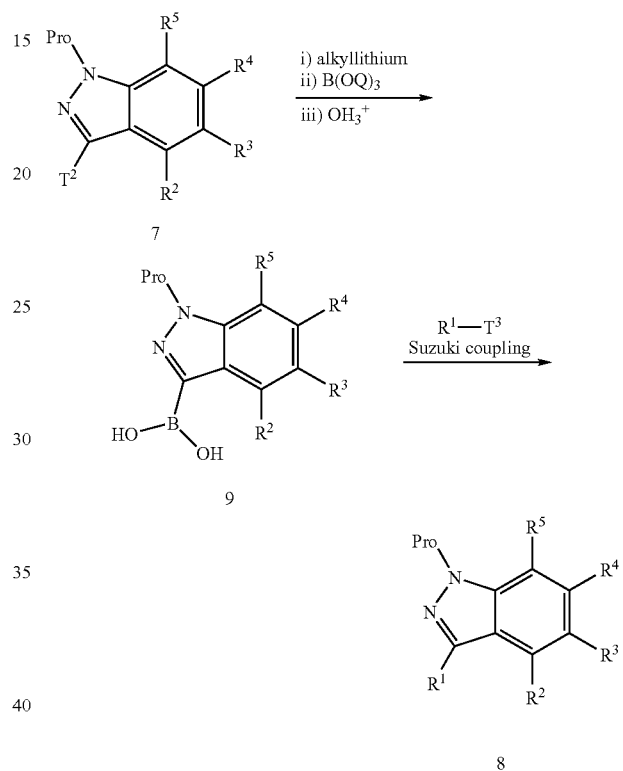

The compound 8 can also be obtained by converting the compound 7 into the boronic acid 9 and subjecting the boronic acid 9 to Suzuki coupling with an aryl halide or aryl sulfonate. The boronic acid 9 can be obtained by converting the compound 7 into an arylithium, allowing the arylithium to react with trialkyl-borate to yield a boric ester, and hydrolyzing the boric ester. The alkyllithium for converting the compound 7 into an arylithium includes, for example, n-butyllithium, sec-butyllithium, tert-butyllithium, and phenyllithium. Where necessary, an additive such as N,N,N', N'-tetramethylethylenediamine and hexamethylphosphoramide can be added. The boric ester formed as a result of the reaction between the arylithium and the trialkyl borate can be hydrolyzed by adding water or by using an acid such as hydrochloric acid or sulfuric acid. Reaction solvents for use herein are not specifically limited, as long as they are inert to the reaction, of which ether solvents such as diethyl ether, tetrahydrofuran, dioxane or dimethoxyethane are preferred. A reaction temperature is from −78° C. to room temperature. The compound 8 can be produced by subjecting the boronic acid 9 and an aryl halide or aryl sulfonate to Suzuki coupling under the conditions of Production Process 3.

Production Process 5

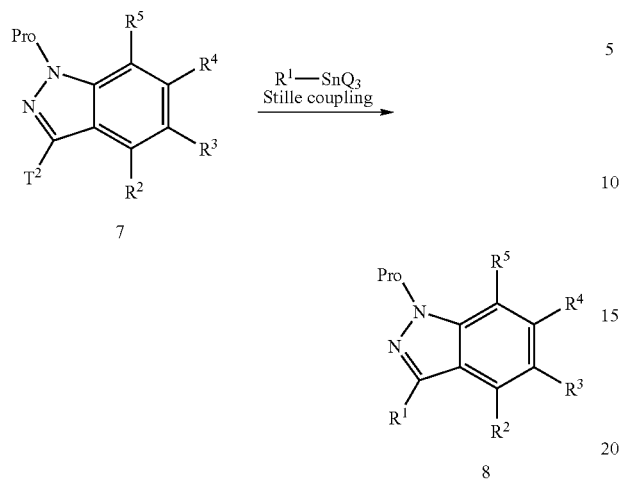

The compound 8 can also be produced by Stille coupling as shown in Production Process 5. Among aryltrialkyltins for use in Stille coupling, those commercially available will be purchased and those not commercially available can be easily prepared. Such an aryltrialkyltin can be prepared, for example, by treating a halogenoaryl with an alkyllithium, magnesium, or zinc to thereby yield an arylithium or metal halogenoaryl, and allowing the arylithium or metal halogenoaryl to react with a chlorotrialkyltin or hexaalkylditin. Reaction solvents for use herein are not specifically limited, as long as they are inert to the reaction, of which ether solvents such as diethyl ether, tetrahydrofuran, dioxane or dimethoxyethane are preferred. A reaction temperature is from −78° C. to room temperature. The amount of the aryltrialkyltin for use in Stille coupling is from 1 to 3 equivalents to the raw material. Catalysts for use herein include, for example, palladium(II) acetate, dichlorobis(triphenylphosphine)palladium(II), and tetrakis(triphenylphosphine)palladium(0). The amount of the catalyst is about 5% by mole relative to the raw material. Where necessary, a phosphine ligand in an amount of two times by mole that of the catalyst can be added. Such phosphine ligands include, for example, tri-tert-butylphosphine, 2-(di-tert-butylphosphino)biphenyl, 2-(dicyclohexylphosphino)biphenyl, and triphenylphosphine. Solvents for use herein are not specifically limited, as long as they do not adversely affect the reaction, and include, for example, dimethylformamide, N-methylpyrrolidone, tetrahydrofuran, dioxane, diethylene glycol dimethyl ether, toluene, and xylenes. A reaction temperature is generally from room temperature to the reflux temperature of the solvent.

Production Process 6

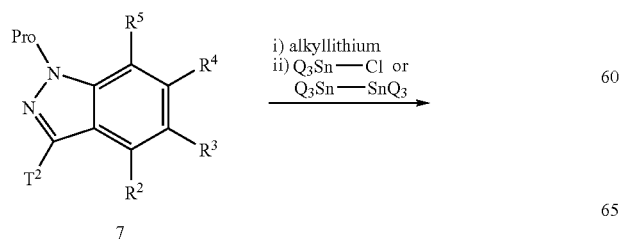

The compound 8 can also be obtained by converting the compound 7 into the tin compound 10, and subjecting the tin compound 10 to Stille coupling with an aryl halide or aryl sulfonate. The tin compound 10 can be obtained by converting the compound 7 into an arylithium under the same conditions as in Production Process 4, and allowing the arylithium to react with a chlorotrialkyltin or hexaalkylditin. Reaction solvents for use herein are not specifically limited, as long as they are inert to the reaction, of which ether solvents diethyl ether, tetrahydrofuran, dioxane or dimethoxyethane are preferred. A reaction temperature is from −78° C. to room temperature. The compound 8 can be produced by subjecting the tin compound 10 and an aryl halide or aryl sulfonate to Stille coupling under conditions of Production Process 5.

Production Process 7

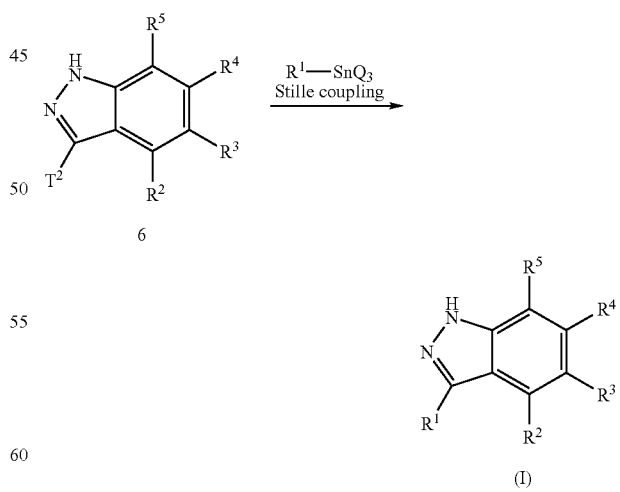

The compound (I) can also be produced by subjecting the compound 6 in which the 1-position is not protected to Stille coupling under conditions of Production Process 5, as shown in Production Process 7.

Production Process 8

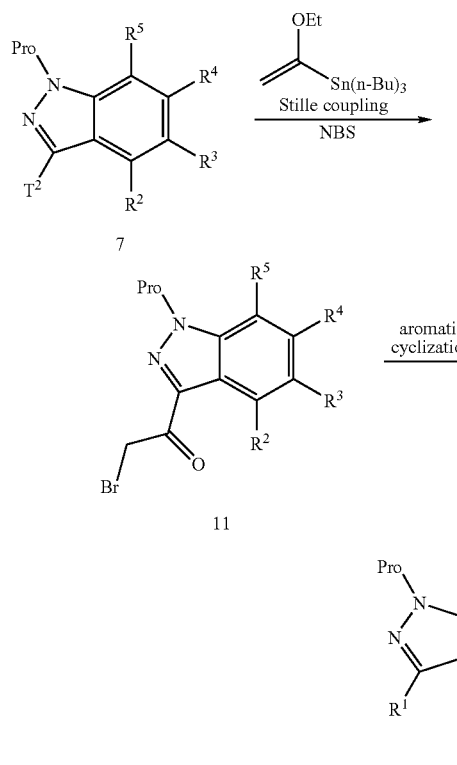

Production Process 9

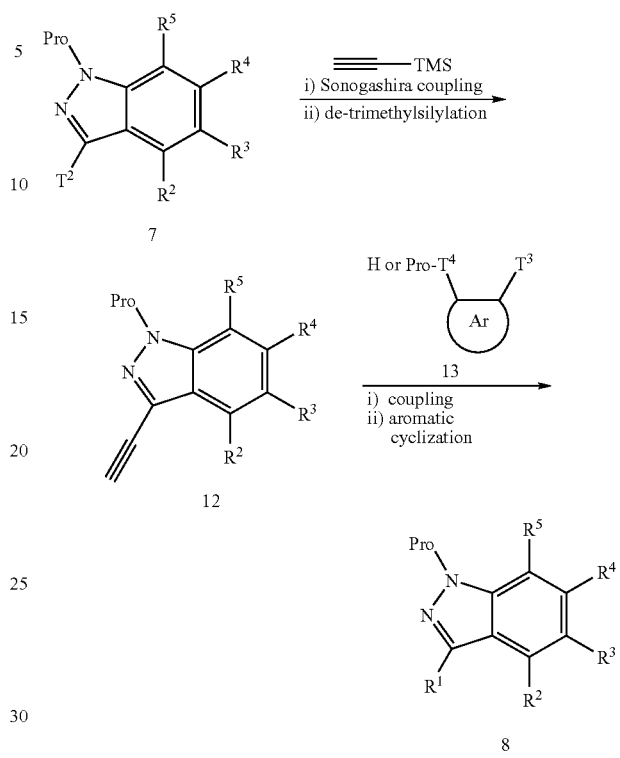

The compound 8 can also be produced by subjecting to Stille coupling with tributyl(1-ethoxyvinyl)tin, treating the resulting compound with N-bromosuccinimide to yield the bromoacetyl 11, and converting the bromoacetyl 11 to an aromatic ring, as shown in Production Process 8. The tributyl (1-ethoxyvinyl)tin for use in Stille coupling is commercially available. The amount of the tributyl(1-ethoxyvinyl)tin is from 1 to 3 equivalents to the raw material. Catalysts for use herein are not specifically limited, of which tetrakis(triphenylphosphine)palladium(0) is preferred. The amount of the catalyst is about 5% by mole relative to the raw material. Solvents for use herein are not specifically limited, as long as they do not adversely affect the reaction, and preferred examples thereof are tetrahydrofuran, dioxane, diethylene glycol dimethyl ether, toluene, and xylenes. A reaction temperature is generally from room temperature to the reflux temperature of the solvent. The bromination can be performed by exchanging the solvent with tetrahydrofuran or dioxane, and adding about 1 equivalent of N-bromosuccinimide. The compound 11 can be converted into an aromatic ring by allowing the compound to react with, for example, 2-aminopyridine or thiourea in the presence of a base. Such bases include, but are not specifically limited to, sodium hydrogencarbonate, sodium carbonate, potassium carbonate, and sodium hydride. Solvents for use herein are not specifically limited, as long as they are inert to the reaction, and include, for example, alcohol solvents methanol or ethanol, ether solvents such as diethyl ether, tetrahydrofuran, dioxane or dimethoxyethane, as well as ethyl acetate, acetonitrile, dimethyl sulfoxide, and dimethylformamide. A reaction temperature is generally 0° C. to the reflux temperature of the solvent.

As shown in Production Process 9, the compound 8 can also be produced by subjecting the compound 7 to Sonogashira coupling with trimethylsilylacetylene, detrimethylsililating the resulting compound to yield the compound 12, subjecting the compound 12 to coupling with the halogenated aromatic cyclic compound 13 having a hydroxyl group, amino group or thiol group at the ortho-position, each of which may be protected by a protecting group, and aromatically cyclizing the resulting compound under the same conditions after deprotecting the protecting group, if any. The trimethylsilylacetylene for use in Sonogashira coupling is commercially available. The amount of the trimethylsilylacetylene is from 1 to 3 equivalents to the raw material. Catalysts for use herein include, but are not specifically limited to, palladium(II) acetate, dichlorobis(triphenylphosphine)palladium(II), and tetrakis(triphenylphosphine)palladium(0). The amount of the catalyst is about 10% by mole relative to the raw material. Where necessary, an additive such as copper(I) iodide or triphenylphosphine can be added in an amount 1 to 2 times that of the catalyst. Bases for use herein include, but are not specifically limited to, triethylamine, diisopropylamine, and piperidine. Solvents for use herein are not specifically limited, as long as they do not adversely affect the reaction, of which dimethylformamide, tetrahydrofuran, dioxane, diethylene glycol dimethyl ether, toluene, and xylenes are preferred. A reaction temperature is generally from room temperature to the reflux temperature of the solvent.

The detrimethylsilanization can be easily performed by using a fluorine anion or an acid. Such fluorine anions for use herein include, for example, tetrabutylammonium fluoride, hydrogen fluoride, potassium fluoride, and cesium fluoride. Solvents for use herein are not specifically limited, as long as they are inert to the reaction, and include, for example, halogenated hydrocarbons such as dichloromethane or chloroform, alcohol solvents such as methanol or ethanol, water, diethyl ether, tetrahydrofuran, dioxane; and toluene. A reaction temperature is from −20° C. to the reflux temperature of the solvent. Acids for use herein include, for example, hydrochloric acid, sulfuric acid, and trifluoroacetic acid. Solvents for use herein are not specifically limited, as long as they are inert to the reaction, and include, for example, halogenated hydrocarbons such as dichloromethane or chloroform, alcohol solvents such as methanol or ethanol, diethyl ether, and tetrahydrofuran. A reaction temperature is from −20° C. to the reflux temperature of the solvent.

Among the compounds 13, those commercially available will be purchased, and those not commercially available can be produced, for example, by protecting a hetero atom of an aromatic cyclic compound having a hydroxyl group, amino group or thiol group, treating the protected compound with an alkyllithium or lithium amide to yield a metal aryl, and halogenating the metal aryl.

Protecting groups for $T^4$ include, for example, tert-butyloxycarbonyl group, pivaloyl group, and methoxymethyl group. These protecting groups can be introduced by allowing an aromatic cyclic compound having a hydroxyl group, amino group or thiol group to react with di-tert-butyl dicarbonate, pivaloyl chloride or chloromethoxymethyl in the presence of a base. Such bases for use herein include, but are not specifically limited to, triethylamine, 4-N,N-dimethylaminopyridine, sodium hydride, potassium tert-butoxide, lithium diisopropylamide, potassium carbonate, and sodium hydroxide. Solvents for use herein are not specifically limited, as long as they are inert to the reaction, and include, for example, ether solvents such as diethyl ether, tetrahydrofuran, dioxane or dimethoxyethane, halogenated hydrocarbons such as dichloromethane or chloroform, as well as ethyl acetate, acetonitrile, dimethyl sulfoxide, and dimethylformamide. A reaction temperature is generally from 0° C. to the reflux temperature of the solvent.

The alkyllithium for converting the aromatic cyclic compound having the protected $T^4$ into the metal aryl includes, for example, n-butyllithium, sec-butyllithium, tert-butyllithium, and phenyllithium. Where necessary, an additive such as N,N,N',N'-tetramethylethylenediamine or hexamethylphosphoramide can be added. The lithium amide includes, for example, lithium diisopropylamide, and lithium 2,2,6,6-tetramethylpiperidide. Preferred examples of the halogenating agent are iodine, N-iodosuccinimide, bromine, and N-bromosuccinimide. Solvents for use herein are not specifically limited, as long as they are inert in the reaction, and include, for example, ether solvents such as diethyl ether, tetrahydrofuran, dioxane or dimethoxyethane, as well as benzene and toluene. A reaction temperature is from −78° C. to room temperature.

The amount of the compound 13 for use in the coupling reaction between the compounds 12 and 13 is from 1 to 2 equivalents to the raw material 12. Catalysts for use herein include, but are not specifically limited to, palladium(II) acetate, dichlorobis(triphenylphosphine)palladium(II), and tetrakis(triphenylphosphine)palladium(0). The amount of the catalyst is about 10% by mole relative to the raw material. Where necessary, an additive such as copper(I) iodide or triphenylphosphine can be added in an amount 1 to 2 times that of the catalyst. Bases for use herein include, but are not specifically limited to, triethylamine, diisopropylamine, and piperidine. Solvents for use herein are not specifically limited, as long as they do not adversely affect the reaction, of which dimethylformamide, tetrahydrofuran, dioxane, diethylene glycol dimethyl ether, toluene, and xylenes are preferred. A reaction temperature is generally from room temperature to the reflux temperature of the solvent. When the hetero atom of the compound 13 is not protected, the compound can undergo aromatic cyclization under these conditions.

When the hetero atom of the compound 13 is protected, the compound is deprotected after coupling and can undergo aromatic cyclization under the same conditions as in coupling. The protecting group of $T^4$ can be easily deprotected by using an acid or a base. Such acids include, for example, hydrochloric acid, sulfuric acid, and trifluoroacetic acid. Solvents for use herein are not specifically limited, as long as they are inert to the reaction, and include, for example, halogenated hydrocarbons dichloromethane or chloroform, alcohol solvents such as methanol or ethanol. A reaction temperature is from −20° C. to the reflux temperature of the solvent. The base is not specifically limited and includes, for example, aqueous sodium hydroxide and aqueous potassium hydroxide. Solvents for use herein are not specifically limited, as long as they are inert to the reaction, and include, for example, alcohol solvents methanol or ethanol, ether solvents such as diethyl ether, tetrahydrofuran, dioxane or dimethoxyethane. A reaction temperature is from room temperature to the reflux temperature of the solvent.

Production Process 10

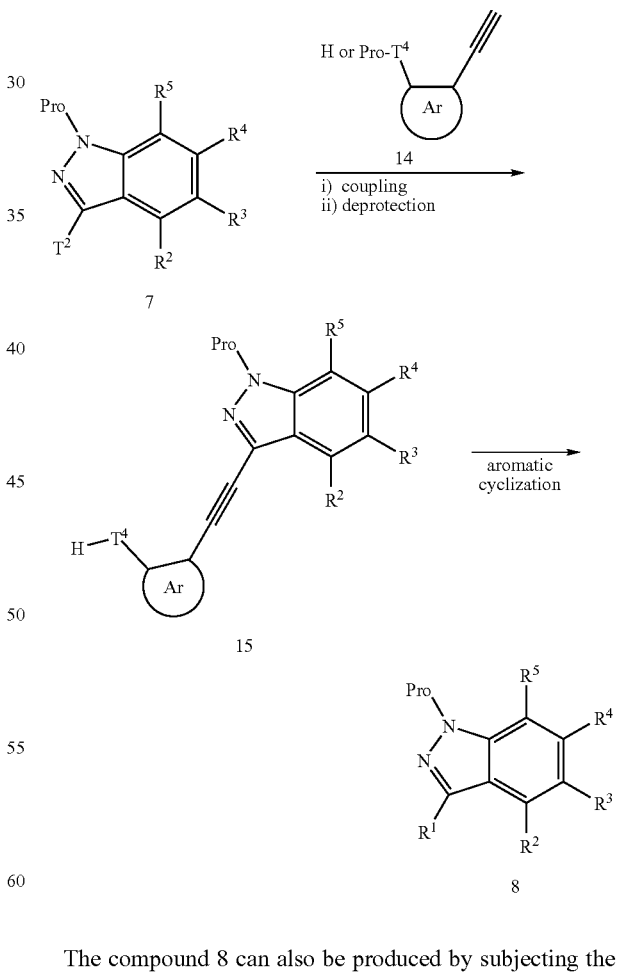

The compound 8 can also be produced by subjecting the compound 7 to coupling with the compound 14, deprotecting the coupling product to yield the compound 15, and aromatically cyclizing the compound 15, as shown in Production Process 10. The compound 14 can be synthetically prepared by subjecting the compound 13 to Sonogashira coupling with trimethylsilylacetylene, and detrimethylsilylating the coupling product. The trimethylsilylacetylene for use in Sonogashira coupling is commercially available. The amount of the trimethylsilylacetylene is from 1 to 3 equivalents to the raw material. Catalysts for use herein include, but are not specifically limited to, palladium(II) acetate, dichlorobis(triphenylphosphine)palladium(II), and tetrakis(triphenylphosphine)palladium(0). The amount of the catalyst is about 10% by mole relative to the raw material. Where necessary, an additive such as copper(I) iodide or triphenylphosphine can be added in an amount 1 to 2 times that of the catalyst. Bases for use herein include, but are not specifically limited to, triethylamine, diisopropylamine, and piperidine. Solvents for use herein are not specifically limited, as long as they do not adversely affect the reaction, of which dimethylformamide, tetrahydrofuran, dioxane, diethylene glycol dimethyl ether, toluene, and xylenes are preferred. A reaction temperature is generally from room temperature to the reflux temperature of the solvent.

The detrimethylsilanization can be easily performed by using a fluorine anion or an acid. Such fluorine anions for use herein include, for example, tetrabutylammonium fluoride, hydrogen fluoride, potassium fluoride, and cesium fluoride. Solvents for use herein are not specifically limited, as long as they are inert to the reaction, and include, for example, halogenated hydrocarbons dichloromethane or chloroform, alcohol solvents such as methanol or ethanol, water, diethyl ether, tetrahydrofuran, dioxane, and toluene. A reaction temperature is from −20° C. to the reflux temperature of the solvent. Acids for use herein include, for example, hydrochloric acid, sulfuric acid, and trifluoroacetic acid. Solvents for use herein are not specifically limited, as long as they are inert to the reaction, and include, for example, halogenated hydrocarbons such as dichloromethane or chloroform, alcohol solvents such as methanol or ethanol. A reaction temperature is from −20° C. to the reflux temperature of the solvent.

The amount of the compound 14 in the coupling reaction between the compounds 14 and 7 is from 1 to 2 equivalents to the raw material 7. Catalysts for use herein include, but are not specifically limited to, palladium(II) acetate, dichlorobis(triphenylphosphine)palladium(II), and tetrakis(triphenylphosphine)palladium(0). The amount of the catalyst is about 10% by mole relative to the raw material. Where necessary, an additive such as copper(I) iodide or triphenylphosphine can be added in an amount 1 to 2 times that of the catalyst. Bases for use herein include, but are not specifically limited to, triethylamine, diisopropylamine, and piperidine. Solvents for use herein are not specifically limited, as long as they do not adversely affect the reaction, of which dimethylformamide, tetrahydrofuran, dioxane, diethylene glycol dimethyl ether, toluene, and xylenes are preferred. A reaction temperature is generally from room temperature to the reflux temperature of the solvent.

The protecting group of $T^4$ can be easily deprotected by using an acid or a base. Such acids include, for example, hydrochloric acid, sulfuric acid, and trifluoroacetic acid. Solvents for use herein are not specifically limited, as long as they are inert to the reaction, and include, for example, halogenated hydrocarbons such as dichloromethane or chloroform, alcohol solvents such as methanol or ethanol. A reaction temperature is from −20° C. to the reflux temperature of the solvent. The base is not specifically limited and includes, for example, aqueous sodium hydroxide and aqueous potassium hydroxide. Solvents for use herein are not specifically limited, as long as they are inert to the reaction, and include, for example, alcohol solvents such as methanol or ethanol, ether solvents such as diethyl ether, tetrahydrofuran, dioxane or dimethoxyethane. A reaction temperature is from room temperature to the reflux temperature of the solvent. By performing aromatic cyclization of the compound 15 under the same conditions as in the coupling between the compound 7 and the compound 14, the compound 8 can be produced.

Production Process 11

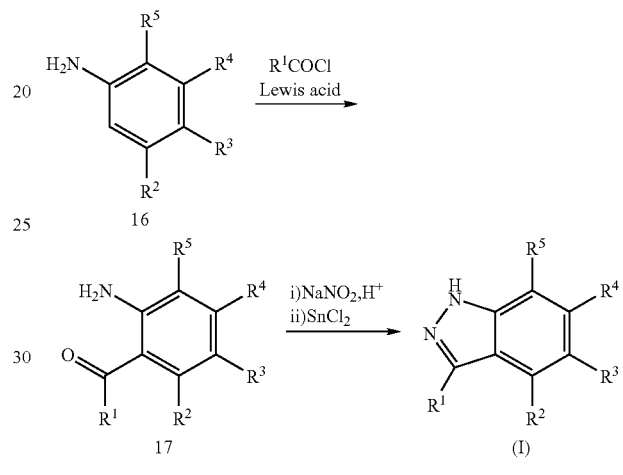

The compound (I) can also be produced by subjecting the aniline 16 and an aryl acid chloride to a Friedel-Crafts reaction to yield the ketone 17, converting the aniline derivative into a diazonium salt, reducing the diazonium salt with tin chloride, and closing the ring of the resulting compound. Lewis acids for use in the Friedel-Crafts reaction for the production of the ketone 17 include, for example, aluminium (III) chloride and ethylaluminum dichloride. Solvents for use herein are preferably halogen-containing solvents such as methylene chloride or chloroform. A reaction temperature is generally from −50° C. to the reflux temperature of the solvent. The ketone 17 can be converted into the diazonium salt by allowing the ketone 17 to react with sodium nitrite in the presence of an acid. Reaction solvents for use herein include, for example, alcohol solvents such as methanol or ethanol, as well as hydrochloric acid, sulfuric acid, and acetic acid. A reaction temperature is generally from 0° C. to room temperature. The diazonium salt can be reduced and the indazole ring can be closed by allowing the diazonium salt to react with tin(II) chloride in the presence of an acid. Reaction solvents for use herein include, for example, alcohol solvents such as methanol or ethanol, as well as hydrochloric acid, sulfuric acid, and acetic acid. A reaction temperature is generally from 0° C. to room temperature.

Practical production processes of 3-arylindazole compounds including production processes for the side chain moiety thereof will be illustrated below, but they are not limited thereto.

Production Process 12

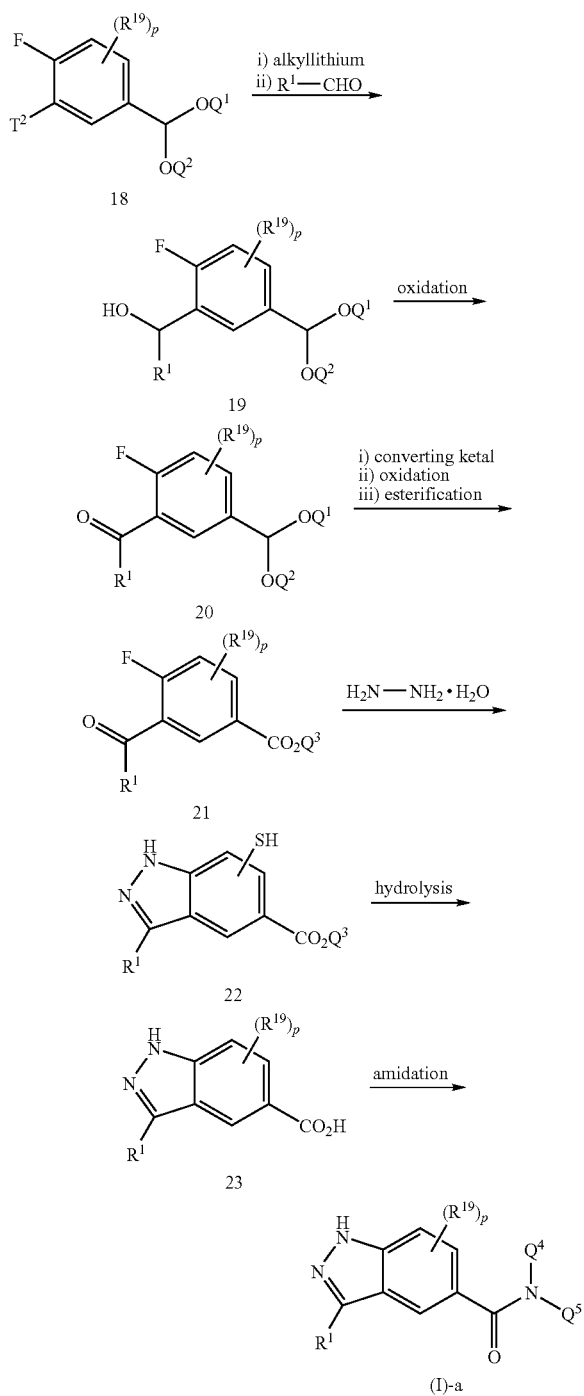

The compound (I)-a can be produced by converting the ortho-halogenofluorobenzene 18 into a lithium aryl, allowing the lithium aryl to react with an aryl aldehyde to yield the alcohol 19, oxidizing the alcohol 19 into the ketone 20, converting the acetal into the ester, treating the ester with hydrazine into the indazole 22, hydrolyzing the indazole 22 into the carboxylic acid 23, and amidating the carboxylic acid 23.

Alkyllithiums for converting the ortho-halogenofluorobenzene 18 into the lithium aryl include, for example, n-butyllithium, sec-butyllithium, tert-butyllithium, and phenyllithium. Where necessary, an additive such as N,N,N',N'-tetramethylethylenediamine or hexamethylphosphoramide can be added. Solvents for use herein are not specifically limited, as long as they are inert to the reaction, and preferred examples thereof are ether solvents such as diethyl ether, tetrahydrofuran, dioxane or dimethoxyethane, as well as benzene and toluene. A reaction temperature is from −78° C. to room temperature.

Oxidizing agents for oxidizing the alcohol 19 include, for example, manganese dioxide, sulfur trioxide-pyridine complex, N-methylmorpholine-N-oxide, and chromic acid oxidizing agents. The oxidation can also be performed by Swern oxidation or Moffat oxidation. Solvents for use herein can be any solvents that are not involved in the reaction and include, for example, halogenated hydrocarbons such as dichloromethane or chloroform, as well as ethyl acetate, acetonitrile, dimethyl sulfoxide, and dimethylformamide. A reaction temperature is generally from −78° C. to the reflux temperature of the solvent.

The ester 21 can be produced by treating with an acid into the aldehyde, oxidizing the aldehyde into the carboxylic acid, and esterifying the carboxylic acid. Acids for use in conversion into the aldehyde include, but are not specifically limited to, p-toluenesulfonic acid, pyridinium p-toluenesulfonate, hydrochloric acid, and sulfuric acid. Solvents for use herein can be any solvents that are not involved in the reaction and include, for example, alcohol solvents such as methanol or ethanol, as well as acetone, and tetrahydrofuran. A reaction temperature is generally from room temperature to the reflux temperature of the solvent. Oxidizing agents for oxidizing the aldehyde into the carboxylic acid include, for example, Jones reagents and sodium chlorite. Solvents for use herein can be any solvents that are not involved in the reaction and include, for example, halogen-containing solvents such as methylene chloride or chloroform, as well as ethyl acetate, dimethylformamide, and dimethyl sulfoxide. A reaction temperature is generally from 0° C. to the reflux temperature of the solvent. The carboxylic acid can be converted into the ester, for example, by allowing the carboxylic acid with an alkyl iodide in the presence of a base or to react with diazomethane. Examples of bases for use herein include sodium hydride, potassium carbonate, and potassium tert-butoxide. A reaction temperature is generally from 0° C. to the reflux temperature of the solvent.

The cyclization of the ester 21 with hydrazine monohydrate can be performed in the absence of, or in the presence of, a solvent. Solvents for use herein are not specifically limited, as long as they are inert to the reaction, and include, for example, ether solvents such as diethyl ether, tetrahydrofuran, dioxane or dimethoxyethane, alcohol solvents such as methanol, ethanol or propanol, as well as pyridine, dimethyl sulfoxide, benzene, and toluene. The amount of the hydrazine monohydrate is from 2 to 20 equivalents to the raw material. A reaction temperature is generally from 0° C. to the reflux temperature of the solvent.

The ester 22 can be easily hydrolyzed by using, for example, aqueous sodium hydroxide or aqueous potassium hydroxide. Solvents for use herein can be any solvents that are not involved to the reaction and include, for example, alcohol solvents such as methanol or ethanol, as well as tetrahydrofuran, dioxane, and other ether solvents. A reaction temperature is generally from 0° C. to the reflux temperature of the solvent.

The carboxylic acid 23 can be amidated by treating with an amine and a condensing agent. Such condensing agents include, for example, dicyclohexylcarbodiimide, diisopropylcarbodiimide, 1-ethyl-3-(3-dimethylaminopropyl)carbodiimide, and 1-ethyl-3-(3-dimethylaminopropyl)carbodiimide hydrochloride. Where necessary, 1-hydroxybenzotriazole and/or N-hydroxysuccinimide can be added. Solvents for use herein can be any solvents that are not involved in the reaction and include, for example, halogen-containing solvents such as methylene chloride or chloroform, ether solvents such as ether or tetrahydrofuran, as well as ethyl acetate, dimethylformamide, and toluene. A reaction temperature is generally from room temperature to the reflux temperature of the solvent.

Production Process 13

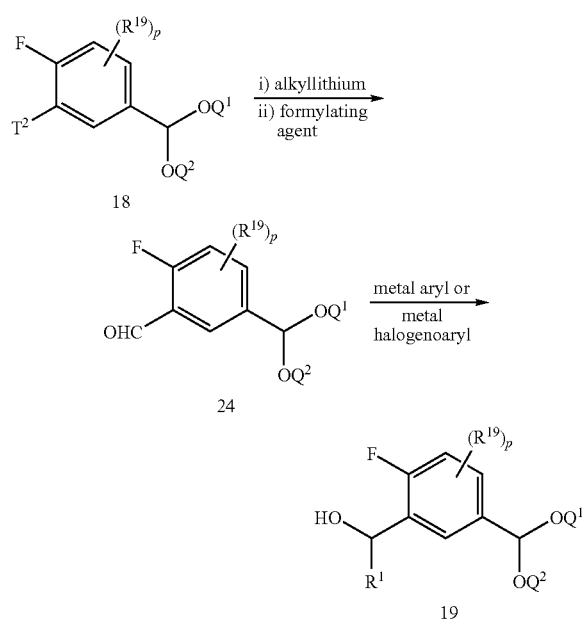

Production Process 14

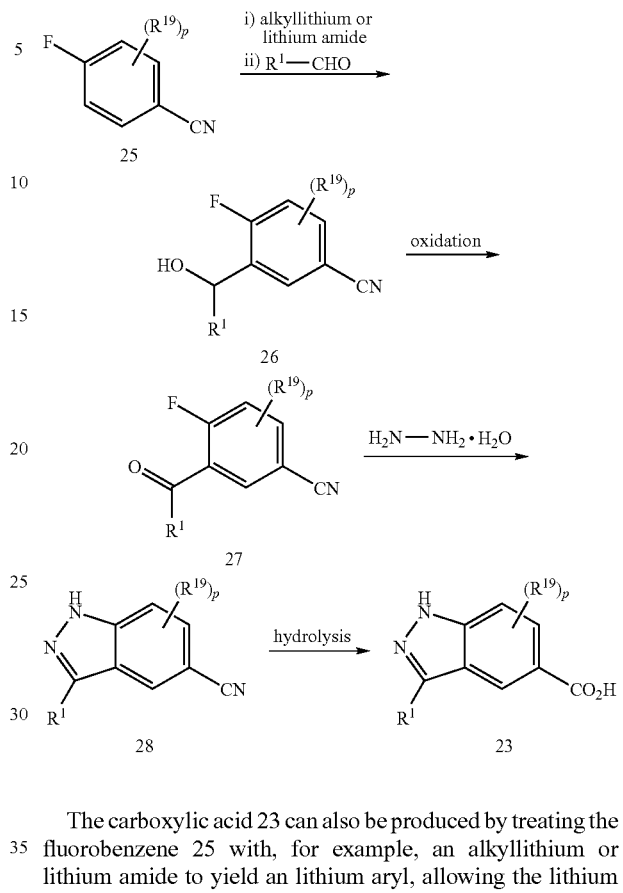

The alcohol 19 can also be produced by converting the ortho-halogenofluorobenzene 18 into a lithium aryl by the procedure of Production Process 12, allowing the lithium aryl to react with a formylation agent to yield the aldehyde 24, and allowing the aldehyde 24 to react with a metal aryl or metal halogenoaryl. Formylation agents for formylation of the lithium aryl prepared from the ortho-halogenofluorobenzene 18 by the procedure of Production Process 12 include, for example, dimethylformamide, N-formylpiperidine, and methylphenylformamide. Reaction solvents for use herein are not specifically limited, as long as they are inert to the reaction, and include, for example, ether solvents such as diethyl ether, tetrahydrofuran, dioxane or dimethoxyethane, as well as benzene and toluene. A reaction temperature is from −78° C. to room temperature. The metal aryl or metal halogenoaryl for the reaction with the aldehyde 24 can be easily prepared by the procedure of Production Process 2. Reaction solvents for use herein are not specifically limited, as long as they are inert to the reaction, and include, for example, ether solvents such as diethyl ether, tetrahydrofuran, dioxane or dimethoxyethane, as well as benzene and toluene. A reaction temperature is from −78° C. to room temperature.

The carboxylic acid 23 can also be produced by treating the fluorobenzene 25 with, for example, an alkyllithium or lithium amide to yield an lithium aryl, allowing the lithium aryl to react with an aryl aldehyde to yield the alcohol 26, oxidizing the alcohol 26 into the ketone 27, treating the ketone 27 with hydrazine to yield the indazole 28, and hydrolyzing the nitrile.

The alkyllithium for converting the fluorobenzene 25 into the lithium aryl includes, for example, n-butyllithium, sec-butyllithium, tert-butyllithium, and phenyllithium. Where necessary, an additive such as N,N,N',N'-tetramethylethylenediamine or hexamethylphosphoramide can be added. The lithium amide includes, for example, lithium diisopropylamide, and lithium 2,2,6,6-tetramethylpiperidide. Solvents for use herein are not specifically limited, as long as they are inert to the reaction, and preferred examples thereof are ether solvents such as diethyl ether, tetrahydrofuran, dioxane or dimethoxyethane, as well as benzene and toluene. A reaction temperature is from −78° C. to room temperature. The compound 28 can be produced by oxidizing the alcohol and closing the indazole ring with the use of hydrazine monohydrate by the procedure of Production Process 12. The nitrile moiety of the compound 28 can be hydrolyzed by using an acid or a base. Such acids include, for example, hydrochloric acid and hydrous sulfuric acid. The reaction can be performed in the absence of, or in the presence of a solvent. Such solvents include, for example, alcohol solvents such as methanol, ethanol or propanol, as well as acetic acid. A reaction temperature is generally from room temperature to the reflux temperature of the solvent. The base includes, for example, sodium hydroxide and potassium hydroxide. Solvents for use herein are not specifically limited, as long as they are inert to the reaction, of which alcohol solvents such as methanol, ethanol or propanol are preferred. A reaction temperature is generally from room temperature to the reflux temperature of the solvent.

Production Process 15

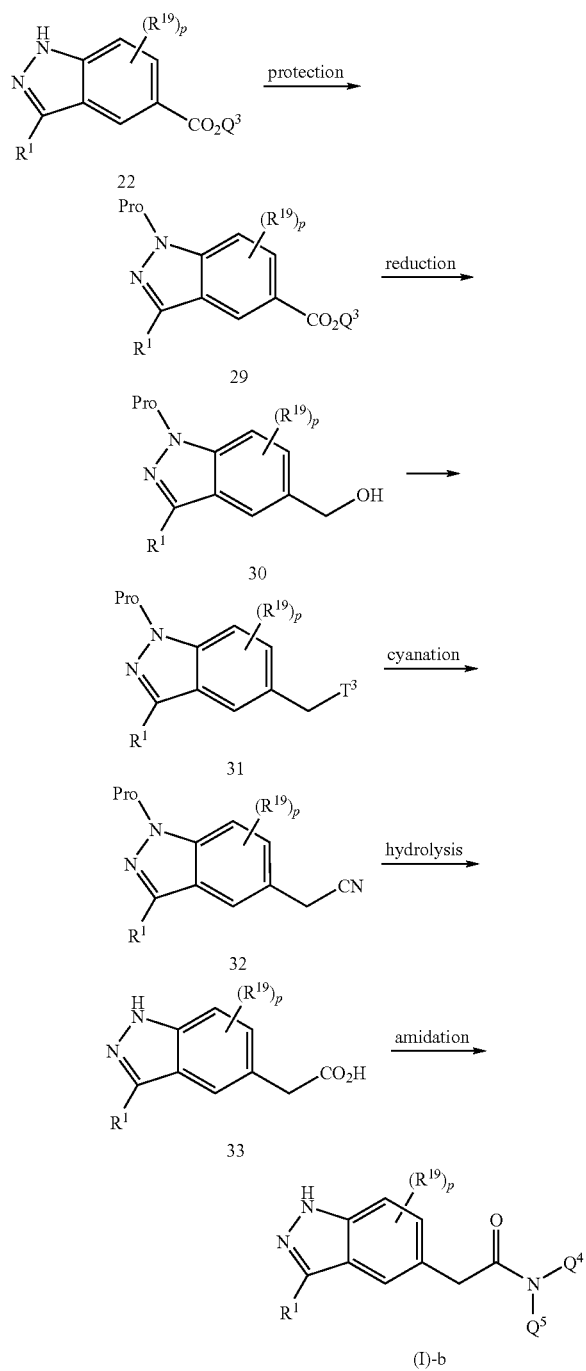

The compound (I)-b can be prepared by protecting the 1-position of the ester 22 produced in Production Process 12 to yield the compound 29, reducing the compound 29 into the alcohol 30, converting the alcohol 30 into a sulfonate or halogen 31, converting the same into the cyano compound 32 and then into the carboxylic acid 33, and amidating the carboxylic acid 33. Protecting groups for protecting the 1-position of the ester 22 include, for example, tert-butyloxycarbonyl group, p-toluenesulfonyl group, triphenylmethyl group, and methoxymethyl group. The tert-butyloxycarbonyl group and p-toluenesulfonyl group can be introduced by allowing the ester 22 to react with di-tert-butyl dicarbonate or p-toluenesulfonyl chloride in the presence of a base. Such bases are not specifically limited, and preferred examples are triethylamine and 4-N,N-dimethylaminopyridine. Solvents for use herein are not specifically limited, as long as they are inert to the reaction and include, for example, ether solvents such as diethyl ether, tetrahydrofuran, dioxane or dimethoxyethane, halogenated hydrocarbons such as dichloromethane or chloroform, as well as pyridine, ethyl acetate, acetonitrile, dimethyl sulfoxide, and dimethylformamide. A reaction temperature is generally from 0° C. to the reflux temperature of the solvent. The triphenylmethyl group and methoxymethyl group can be introduced by allowing the ester 22 to react with chlorotriphenylmethane or chloromethyl methyl ether in the presence of a base. Such bases are not specifically limited, and preferred examples are sodium hydride, potassium tert-butoxide, lithium diisopropylamide, potassium carbonate, and sodium hydroxide. Solvents for use herein are not specifically limited, as long as they are inert to the reaction and include, for example, ether solvents such as diethyl ether, tetrahydrofuran, dioxane or dimethoxyethane, as well as pyridine, ethyl acetate, acetonitrile, dimethyl sulfoxide, and dimethylformamide. A reaction temperature is generally from −20° C. to the reflux temperature of the solvent. Reducing agents for reducing the ester moiety of the compound 29 include, for example, di-iso-butylaluminium hydride, lithium aluminium hydride, and lithium borohydride. Solvents for use herein are not specifically limited, as long as they are inert to the reaction and include, for example, ether solvents such as diethyl ether, tetrahydrofuran, dioxane or dimethoxyethane, as well as benzene and toluene. A reaction temperature is generally from −20° C. to the reflux temperature of the solvent. The alcohol 30 can be converted into the sulfonate by allowing the alcohol 30 to react with a sulfonyl chloride in the presence of a base. Examples of the sulfonyl chloride are methanesulfonyl chloride, and p-toluenesulfonyl chloride. Bases for use herein are not specifically limited and include, for example, triethylamine, 4-dimethylaminopyridine, and sodium hydride. Solvents for use herein are not specifically limited, as long as they are inert to the reaction and include, for example, ether solvents such as diethyl ether, tetrahydrofuran, dioxane or dimethoxyethane, halogen-containing solvents such as methylene chloride or chloroform, as well as pyridine, benzene, toluene, and dimethylformamide. A reaction temperature is from −20° C. to the reflux temperature of the solvent. By performing the reaction in dichloromethane in the presence of triethylamine for a long time, a chloride can be obtained. The sulfonate and chloride can be converted into an iodide by allowing the same to react with about 1.1 equivalent of sodium iodide in acetone at room temperature. The nitrile 32 can be obtained by allowing the sulfonate or halide 31 to react with sodium cyanide or potassium cyanide. Solvents for use herein are not specifically limited, as long as they are inert to the reaction and include, for example, alcohol solvents such as methanol or ethanol, ether solvents such as diethyl ether, tetrahydrofuran, dioxane or dimethoxyethane, as well as dimethylformamide, and dimethyl sulfoxide. A reaction temperature is from −20° C. to the reflux temperature of the solvent. The nitrile 32 can be hydrolyzed by using an acid. Such acids include, for example, hydrochloric acid and hydrous sulfuric acid. The reaction can be performed in the absence of, or in the presence of a solvent. Such solvents include, for example, alcohol solvents such as methanol, ethanol or propanol, as well as acetic acid. A reaction temperature is generally from room temperature to the reflux temperature of the solvent. In this reaction, the protecting group is removed concurrently. By amidating the carboxylic acid 33 by the procedure of Production Process 12, the compound (I)-b can be produced.

Production Process 16

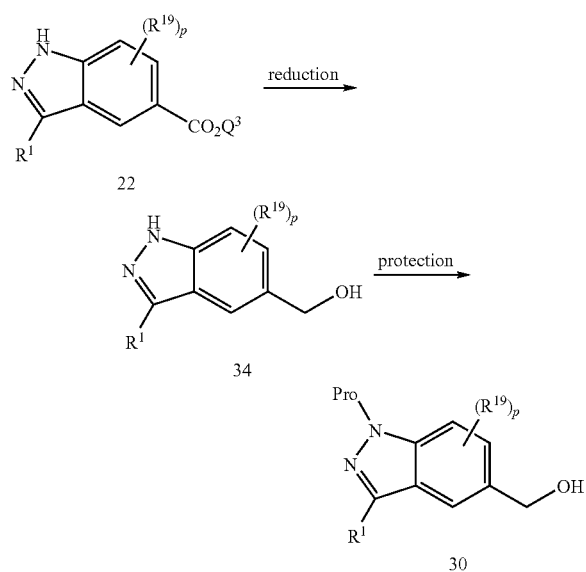

The compound 30 can also be produced by reducing the ester 22 having a non-protected 1-position produced in Production Process 12, and protecting the 1-position. The ester 22 is reduced by the procedure of Production Process 15 to thereby yield the alcohol 34. Then, a protecting group is introduced into the 1-position of the alcohol 34 by the procedure of Production Process 15 to thereby yield the compound 30.

Production Process 17

The compound (I)-c can be produced by oxidizing the alcohol 30 produced in Production Process 15 into the aldehyde 35, subjecting the aldehyde 35 to a Wittig reaction to yield the ester 36, converting the ester 36 into the carboxylic acid 37, and amidating the carboxylic acid 37. Oxidizing agents for oxidizing the alcohol 30 include, for example, manganese dioxide, sulfur trioxide-pyridine complex, N-methylmorpholine-N-oxide, and chromic acid oxidizing agents. The oxidation can also be performed by Swern oxidation or Moffat oxidation. Solvents for use herein can be any solvents that are not involved in the reaction and include, for example, halogenated hydrocarbons such as dichloromethane or chloroform, as well as ethyl acetate, acetonitrile, dimethyl sulfoxide, and dimethylformamide. A reaction temperature is generally from −78° C. to the reflux temperature of the solvent. Reagents for the Wittig reaction of the aldehyde 30 include, for example, triethyl phosphonoacetate, ethyl diphenylphosphonoacetate, and (carbethoxymethyl)triphenylphosphonium bromide. Bases for use herein include, but are not specifically limited to, sodium hydride, sodium hydrogencarbonate, potassium carbonate, sodium hydroxide, potassium tert-butoxide, and benzyltrimethylammonium hydroxide. Solvents for use herein are not specifically limited, as long as they are inert to the reaction and include, for example, ether solvents such as diethyl ether, tetrahydrofuran, dioxane or dimethoxyethane, halogenated hydrocarbons such as dichloromethane or chloroform, as well as ethyl acetate, acetonitrile, toluene, dimethyl sulfoxide, and dimethylformamide. A reaction temperature is generally from 0° C. to room temperature. By hydrolyzing the ester 36 according to the procedure of Production Process 12, the protecting group at the 1-position is concurrently deprotected, and the carboxylic acid 37 can thereby be produced. The compound (I)-c can be produced by amidating the carboxylic acid 37 according to the procedure of Production Process 12.

Production Process 18

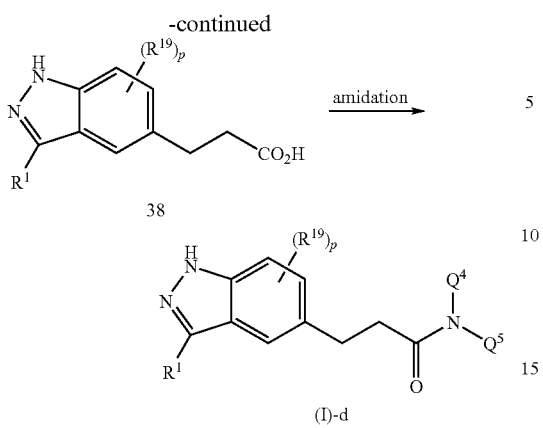

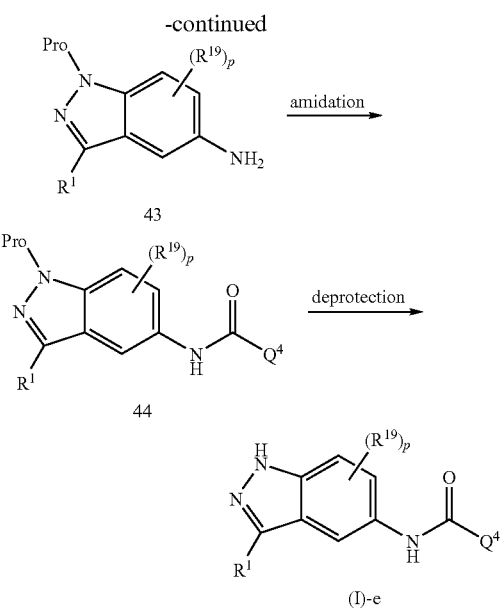

The compound (I)-d can be produced by hydrogenating the carboxylic acid 37 produced in Production Process 17, and amidating the resulting compound. Hydrogenation reagents for the olefin moiety of the carboxylic acid 37 include, but are not specifically limited to, palladium-carbon, platinum oxide, and palladium hydroxide-carbon. The pressure of hydrogen is from 1 to 5 atom. Solvents for use herein are not specifically limited, as long as they are inert to the reaction and include, for example, ether solvents such as diethyl ether, tetrahydrofuran, dioxane or dimethoxyethane, halogenated hydrocarbons such as dichloromethane, chloroform, as well as ethyl acetate, acetonitrile, toluene, and dimethylformamide. A reaction temperature is generally from room temperature to the reflux temperature of the solvent. The compound (I)-d can be produced by amidating the carboxylic acid 38 according to the procedure of Production Process 12.

Production Process 19

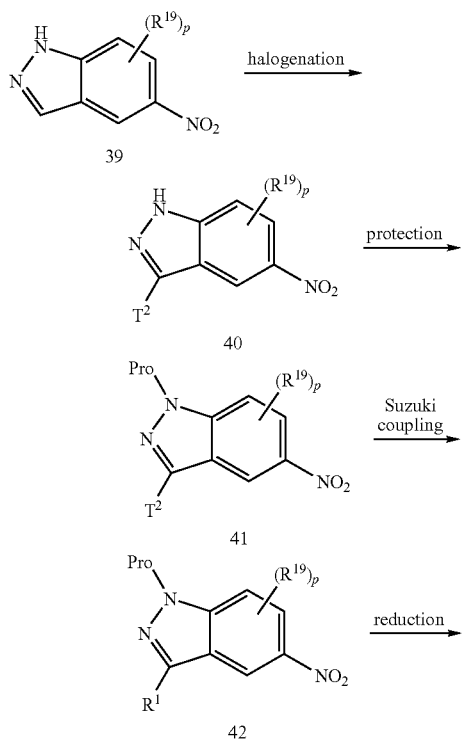

The compound (I)-e can be produced by halogenating the 3-position of the compound 39 into the compound 40, protecting the 1-position of the compound 40 to yield the compound 41, subjecting the compound 41 to Suzuki coupling with an arylboronic acid to yield the compound 42, reducing the compound 42 into the aniline 43, amidating the aniline 43 into the compound 44, and deprotecting the 1-position. Halogenation reagents for the 3-position of the compound 39 include, for example, N-bromosuccinimide, N-iodosuccinimide, N-chlorosuccinimide, and bromine. Where necessary, a radical reaction initiator such as 2,2'-azobisisobutyronitrile and benzoyl peroxide can be added. The amount of the halogenation reagent is from 1.05 to 1.2 equivalents to the raw material. Solvents for use herein are not specifically limited, as long as they are inert to the reaction, and include, for example, halogenated hydrocarbons such as dichloromethane, chloroform or carbon tetrachloride, as well as ethyl acetate, acetonitrile, dimethyl sulfoxide, and dimethylformamide. A reaction temperature is generally from room temperature to the reflux temperature of the solvent. Protecting groups for the 1-position of the compound 40 include, for example, tert-butyloxycarbonyl group, p-toluenesulfonyl group, and triphenylmethyl group. The tert-butyloxycarbonyl group and p-toluenesulfonyl group can be introduced by allowing the compound 40 to react with di-tert-butyl dicarbonate or p-toluenesulfonyl chloride in the presence of a base. Such bases are not specifically limited, and preferred examples thereof are triethylamine and 4-N,N-dimethylaminopyridine. Solvents for use herein are not specifically limited, as long as they are inert in the reaction, and include, for example, ether solvents such as diethyl ether, tetrahydrofuran, dioxane or dimethoxyethane, halogenated hydrocarbons such as dichloromethane or chloroform, as well as pyridine, ethyl acetate, acetonitrile, dimethyl sulfoxide, and dimethylformamide. A reaction temperature is generally from 0° C. to the reflux temperature of the solvent. The triphenylmethyl group can be introduced by allowing the compound 40 to react with chlorotriphenylmethane in the presence of a base. Such bases include, but are not specifically limited to, sodium hydride, potassium tert-butoxide, lithium diisopropylamide, potassium carbonate, and sodium hydroxide. Solvents for use herein are not specifically limited, as long as they are inert to the reaction and include, for example, ether solvents such as diethyl ether, tetrahydrofuran, dioxane or dimethoxyethane, as well as ethyl acetate, acetonitrile, dimethyl sulfoxide, and dimethylformamide. A reaction temperature is from −20° C. to the reflux temperature of the solvent. Among arylboronic acids for use in Suzuki coupling of the compound 41, those commercially available will be purchased, and those not commercially available can be easily prepared according to the procedure of Production Process 3. The amount of the arylboronic acid is from 1 to 3 equivalents to the raw material. Catalysts for use herein include, for example, palladium(II) acetate, dichlorobis(triphenylphosphine)palladium(II), and tetrakis(triphenylphosphine)palladium(0). The amount of the catalyst is about 5% by mole relative to the raw material. Where necessary, a phosphine ligand in an amount of two times by mole that of the catalyst can be added. Such phosphine ligands include, for example, tri-tert-butylphosphine, 2-(di-tert-butylphosphino)biphenyl, 2-(dicyclohexylphosphino)biphenyl, and triphenylphosphine. Examples of bases for use herein are sodium hydrogencarbonate, sodium carbonate, potassium carbonate, cesium carbonate, and potassium fluoride. Solvents for use herein are not specifically limited, as long as they do not adversely affect the reaction, and include, for example, dimethylformamide, N-methylpyrrolidone, tetrahydrofuran, dioxane, diethylene glycol dimethyl ether, and toluene. A reaction temperature is generally from room temperature to the reflux temperature of the solvent. The nitro group of the compound 42 is reduced, for example, by hydrogenation by catalysis of palladium-carbon, palladium hydroxide-carbon, platinum oxide, or Raney's nickel, as well as reduction with tin(II) chloride, and reduction with iron-ammonium chloride. Solvents for use in the hydrogenation are not specifically limited, as long as they do not adversely affect the reaction, and include, for example, alcohol solvents such as methanol or ethanol, halogen-containing solvents such as methylene chloride or chloroform, ether solvents such as tetrahydrofuran or diethyl ether, as well as ethyl acetate, dimethylformamide, and toluene. The amount of the hydrogenation catalyst is from 5% to 20% by weight relative to the raw material. The pressure of hydrogen is generally from 1 to 5 atom. A reaction temperature is generally from room temperature to the reflux temperature of the solvent. Solvents for use in the reduction with tin(II) chloride include, for example, alcohol solvents such as methanol or ethanol, halogenated hydrocarbon solvents such as methylene chloride or chloroform, as well as dimethylformamide, N-methylpyrrolidone, and toluene. A reaction temperature is generally from room temperature to the reflux temperature of the solvent. Solvents for use in the reduction with iron-ammonium chloride are preferably alcohol solvents such as aqueous methanol or aqueous ethanol. The amount of iron is from 3 to 10 equivalents to the raw material. The amount of the ammonium chloride is from 10% to 20% by weight relative to the raw material. A reaction temperature is generally the reflux temperature of the solvent. The aniline 43 can be amidated by treating with a carboxylic acid and a condensing agent. Such condensing agents include, for example, dicyclohexylcarbodiimide, diisopropylcarbodiimide, 1-ethyl-3-(3-dimethylaminopropyl)carbodiimide, and 1-ethyl-3-(3-dimethylaminopropyl)carbodiimide hydrochloride. Where necessary, 1-hydroxybenzotriazole and/or N-hydroxysuccinimide can be added. Solvents for use herein can be any solvents that are not involved in the reaction and include, for example, halogen-containing solvents such as methylene chloride or chloroform, ether solvents such as ether or tetrahydrofuran, as well as ethyl acetate, dimethylformamide, and toluene. A reaction temperature is generally from room temperature to the reflux temperature of the solvent. The aniline 43 can also be amidated by allowing the aniline 43 to react with an acid chloride in the presence of a base. Such bases include, but are not specifically limited to, triethylamine, diisopropylethylamine, and pyridine. Solvents for use herein can be any solvents that are not involved in the reaction and include, for example, halogen-containing solvents such as methylene chloride or chloroform, ether solvents such as ether or tetrahydrofuran, as well as ethyl acetate, and toluene. A reaction temperature is generally from −78° C. to the reflux temperature of the solvent. The tert-butyloxycarbonyl group and triphenylmethyl group as the protecting group of the amide 44 can be easily deprotected or removed by using an acid. Such acids include, for example, hydrochloric acid, sulfuric acid, and trifluoroacetic acid. Where necessary, a radical scavenger such as thiophenol and tri-iso-propylsilane can be added. Solvents for use herein are not specifically limited, as long as they are inert to the reaction, and include, for example, halogenated hydrocarbons such as dichloromethane or chloroform, alcohol solvents such as methanol or ethanol, as well as anisole. A reaction temperature is generally from −20° C. to the reflux temperature of the solvent. The tert-butyloxycarbonyl group and p-toluenesulfonyl group as the protecting agent can be easily deprotected by using a base. Such bases include, but are not specifically limited to, aqueous sodium hydroxide and aqueous potassium hydroxide. Solvents for use herein are not specifically limited, as long as they are inert to the reaction, and include, for example, alcohol solvents such as methanol or ethanol, ether solvents such as diethyl ether, tetrahydrofuran, dioxane or dimethoxyethane. A reaction temperature is from room temperature to the reflux temperature of the solvent.

Production Process 20

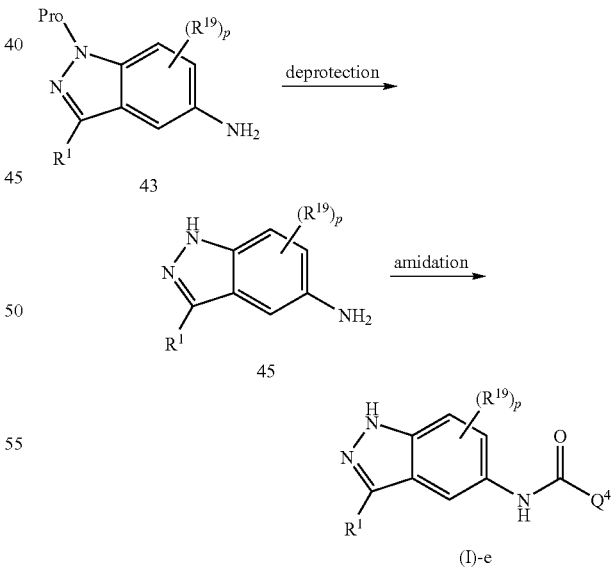

The compound (I)-e can also be produced by deprotecting or removing, by the procedure of Production Process 19, the protecting group of the aniline 43 produced in Production Process 19 to yield the compound 45, and amidating the compound 45 according to the amidation procedure using a condensing agent as in Production Process 19.

Production Process 21

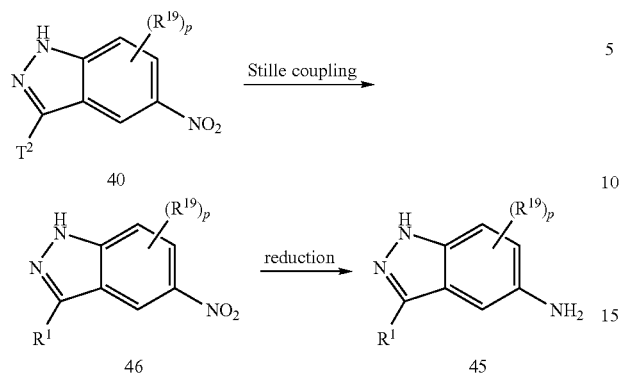

The aniline 45 can also be produced by subjecting the nitro derivative 40 having a non-protected 1-position produced in Production Process 19 to Stille coupling to yield the compound 46, and reducing the nitro group. Among aryltrialkyltins for use in the Stille coupling of the nitro derivative 40, those commercially available will be purchased, and those not commercially available can be easily prepared according to the procedure of Production Process 5. The amount of the aryltrialkyltin is from 1 to 3 equivalents to the raw material. Catalysts for use herein include, for example, palladium(II) acetate, dichlorobis(triphenylphosphine)palladium(II), and tetrakis(triphenylphosphine)palladium(0). The amount of the catalyst is about 5% by mole relative to the raw material. Where necessary, a phosphine ligand in an amount of two times by mole that of the catalyst can be added. Such phosphine ligands include, for example, tri-tert-butylphosphine, 2-(di-tert-butylphosphino)biphenyl, 2-(dicyclohexylphosphino)biphenyl, and triphenylphosphine. Solvents for use herein are not specifically limited, as long as they do not adversely affect the reaction, and include, for example, dimethylformamide, N-methylpyrrolidone, tetrahydrofuran, dioxane, diethylene glycol dimethyl ether, toluene, and xylenes. A reaction temperature is generally from room temperature to the reflux temperature of the solvent. By reducing the nitro derivative 46 according to the procedure of Production Process 19, the aniline 45 can be produced.

Production Process 22

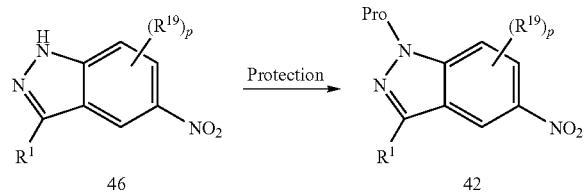

The compound 42 can also be produced by introducing, according to the procedure of Production Process 19, a protecting group into the compound 46 produced in Production Process 21.

Production Process 23

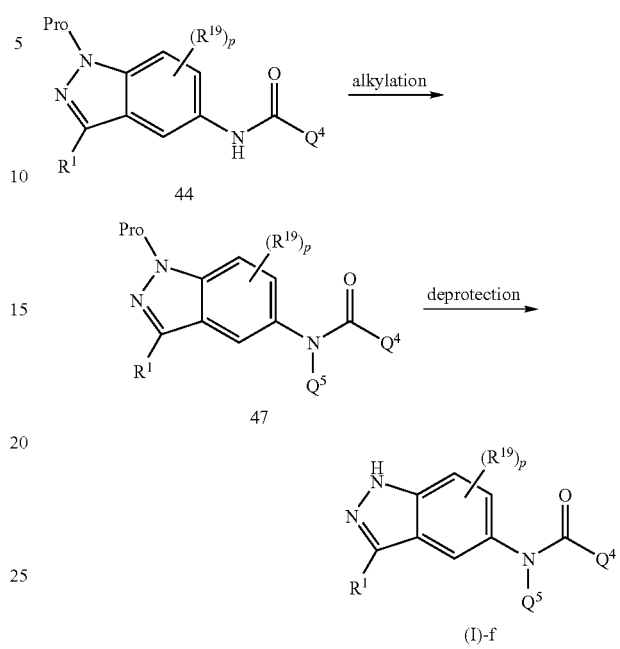

The compound (I)-f can be produced by alkylating the amide 44 produced in Production Process 19 to yield the N-alkylamide 47, and deprotecting the N-alkylamide 47. The amide 44 can be alkylated by allowing the amide 44 to react with a halogenalkyl in the presence of a base. Such bases include, but are not specifically limited to, sodium hydride, potassium carbonate, potassium tert-butoxide, and potassium hydroxide. Solvents for use herein are not specifically limited, as long as they do not adversely affect the reaction, and include, for example, ether solvents such as ether, tetrahydrofuran or dioxane, as well as dimethylformamide, dimethyl sulfoxide, and toluene. A reaction temperature is generally from 0° C. to the reflux temperature of the solvent. By deprotecting the N-alkylamide 47 according to the procedure of Production Process 19, the compound (I)-f can be produced.

Production Process 24

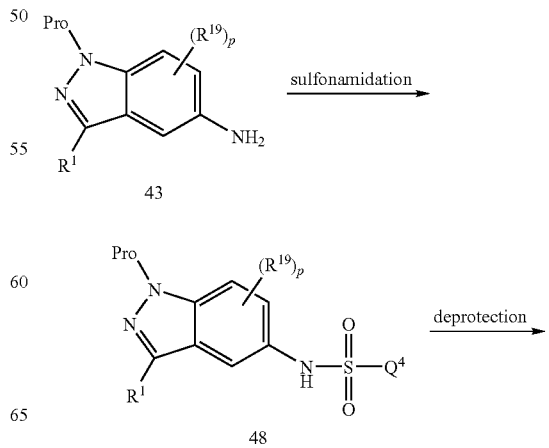

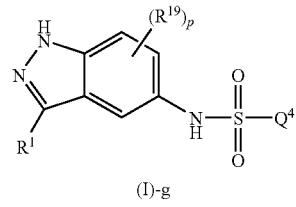

(I)-g

The compound (I)-g can be produced by converting the aniline 43 produced in Production Process 19 into the sulfonamide 48, and deprotecting the sulfonamide 48. The aniline 43 can be converted into the sulfonamide by allowing the aniline 43 to react with a sulfonyl chloride in the presence of a base. Such bases include, but are not specifically limited to, triethylamine, 4-dimethylaminopyridine, potassium carbonate, sodium hydride, and pyridine. The amount of the sulfonyl chloride is from 1.1 to 1.5 equivalents to the raw material. Reaction solvents for use herein are not specifically limited, as long as they do not adversely affect the reaction and include, for example, halogenated hydrocarbons such as dichloromethane or chloroform, ether solvents such as ether, tetrahydrofuran or dioxane, as well as ethyl acetate, acetonitrile, dimethyl sulfoxide, toluene, and dimethylformamide. Among them, ether, tetrahydrofuran, dioxane, and other ether solvents are preferred. A reaction temperature is generally from 0° C. to room temperature. By deprotecting the sulfonamide 48 according to the procedure of Production Process 19, the compound (I)-g can be produced.

Production Process 25

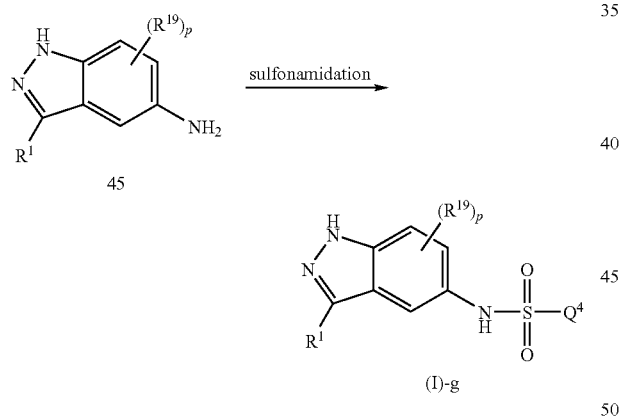

The compound (I)-g can also be produced by converting the aniline 45 having a non-protected 1-position produced in Production Process 21 into a sulfonamide according to the procedure of Production Process 24.

Production Process 26

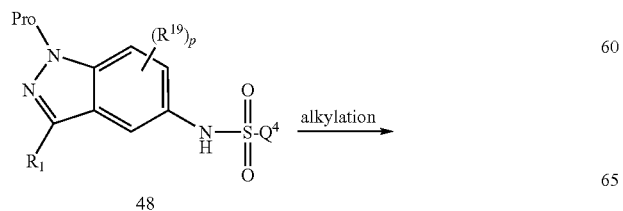

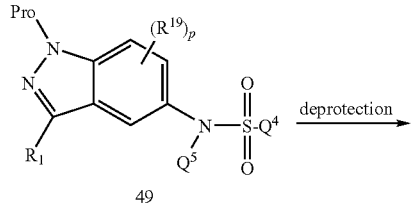

49

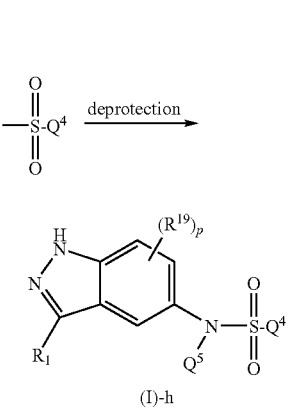

(I)-h

The compound (I)-h can be produced by alkylating the sulfonamide 48 produced in Production Process 24, and deprotecting the resulting compound. The sulfonamide 48 can be alkylated by allowing the sulfonamide 48 to react with a halogenalkyl in the presence of a base. Such bases include, but are not specifically limited to, sodium hydride, potassium carbonate, potassium tert-butoxide, and triethylamine. Solvents for use herein are not specifically limited, as long as they do not adversely affect the reaction, and include, for example, ether solvents such as ether, tetrahydrofuran or dioxane, as well as dimethylformamide, dimethyl sulfoxide, and toluene. A reaction temperature is generally from 0° C. to the reflux temperature of the solvent. By deprotecting the sulfonamide 49 according to the procedure of Production Process 19, the compound (I)-h can be produced.

Production Process 27

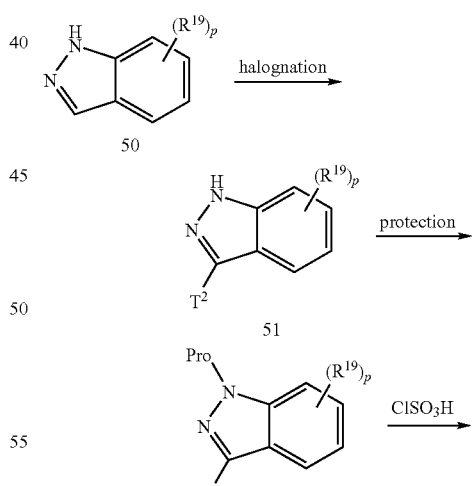

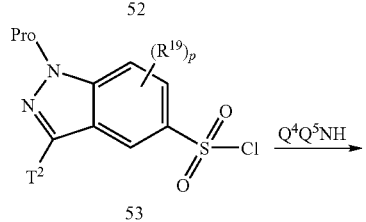

Production Process 28

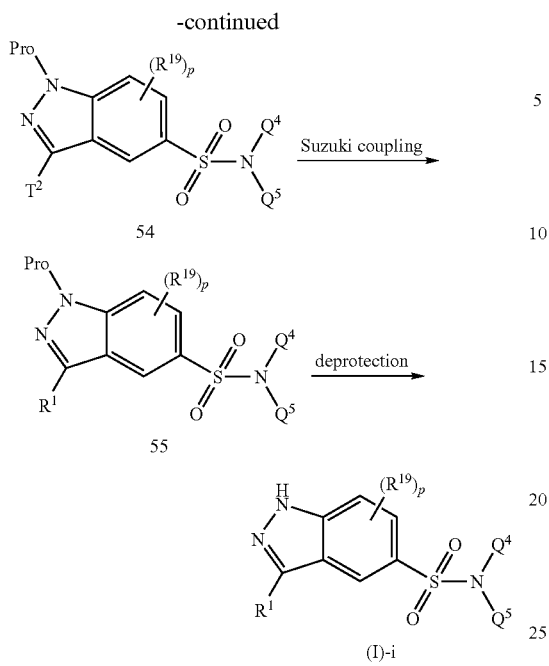

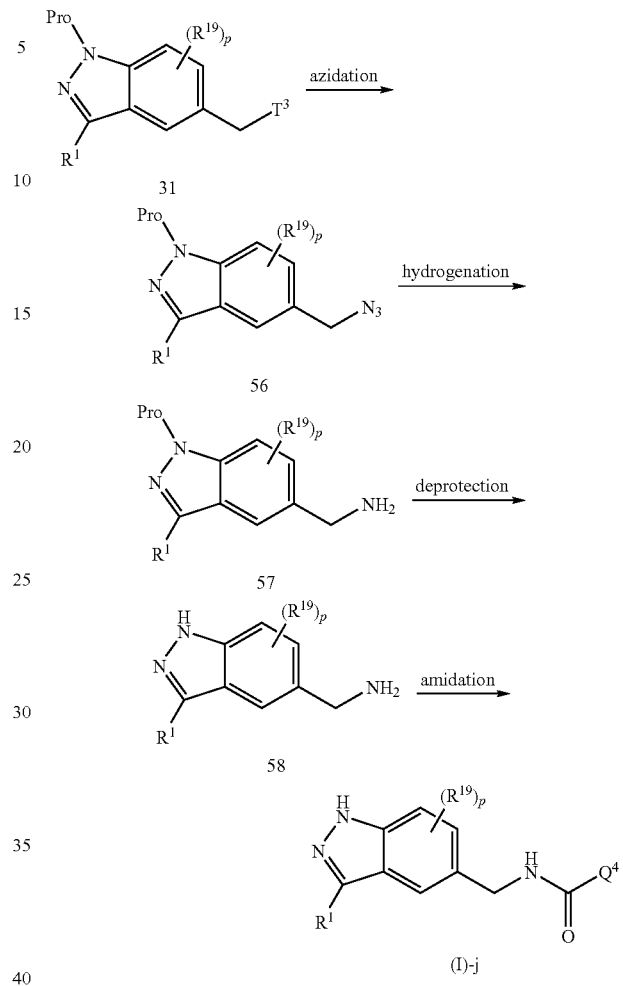

The compound (I)-i can be produced by subjecting the indazole 50 to halogenation and introduction of a protecting group according to the procedure of Production Process 19 to yield the compound 52, allowing the compound 52 to react with chlorosulfuric acid to yield sulfonyl chloride 53, converting the sulfonyl chloride 53 into the sulfonamide 54, subjecting the sulfonamide 54 to Suzuki coupling to yield the compound 55, and deprotecting the compound 55. The sulfonyl chloride 53 can be obtained by allowing the halogenated compound 52 to react with 1 to 2 equivalents of chlorosulfuric acid. Solvents for use herein are not specifically limited, as long as they do not adversely affect the reaction, and include, for example, halogen-containing solvents such as methylene chloride or chloroform. A reaction temperature is generally from 0° C. to room temperature. The sulfonyl chloride 53 can be sulfonamidated by allowing the sulfonyl chloride 53 to react with an amine in the presence of a base. An excess amount of the amine can serve as the base. Alternatively, for example, triethylamine, 4-dimethylaminopyridine, potassium carbonate, and sodium hydride can be added as the base. Reaction solvents for use herein are not specifically limited, as long as they do not adversely affect the reaction, and include, for example, halogenated hydrocarbons such as dichloromethane or chloroform, ether solvents such as ether, tetrahydrofuran or dioxane, as well as ethyl acetate, acetonitrile, dimethyl sulfoxide, toluene, and dimethylformamide. A reaction temperature is generally from 0° C. to room temperature. The sulfonamide 54 is subjected to Suzuki coupling with an arylboronic acid according to the procedure of Production Process 19 to thereby yield the compound 55. The compound 55 is then deprotected according to the procedure of Production Process 19 to thereby yield the compound (I)-i.

The compound (I)-j can be produced by converting the halide or sulfonate produced in Production Process 15 into an azide, reducing the azide into the amine 57, deprotecting the amine 57 to yield the compound 58, and amidating the compound 58. The azide 56 can be obtained by allowing the compound 31 to react with sodium azide or potassium azide. Reaction solvents for use herein are not specifically limited, as long as they do not adversely affect the reaction, and include, for example, alcohol solvents such as methanol or ethanol, ether solvents such as diethyl ether, tetrahydrofuran, dioxane or dimethoxyethane, as well as dimethyl sulfoxide, and dimethylformamide. A reaction temperature is generally from −20° C. to the reflux temperature of the solvent. The azide 56 can be reduced, for example, by hydrogenation by catalysis of palladium-calcium carbonate, palladium-carbon, palladium hydroxide-carbon, platinum oxide, and Raney nickel. Solvents for use in the hydrogenation are not specifically limited, as long as they do not adversely affect the reaction, and include, for example, alcohol solvents such as methanol or ethanol, halogen-containing solvents such as methylene chloride or chloroform, ether solvents such as tetrahydrofuran or diethyl ether, as well as ethyl acetate, dimethylformamide, and toluene. The amount of the hydrogenation catalyst is from 5% to 20% by weight relative to the raw material. The pressure of hydrogen is generally normal pressure (atmospheric pressure) but can be increased up to 5 atm. A reaction temperature is generally from room temperature to the reflux temperature of the solvent. The 1-position of the amine 57 is deprotected according to the procedure of Production Process 3 to thereby yield the compound 58. Then, the compound 58 is amidated according to the procedure of Production Process 19 using a condensing agent to thereby yield the compound (I)-j.

Production Process 29

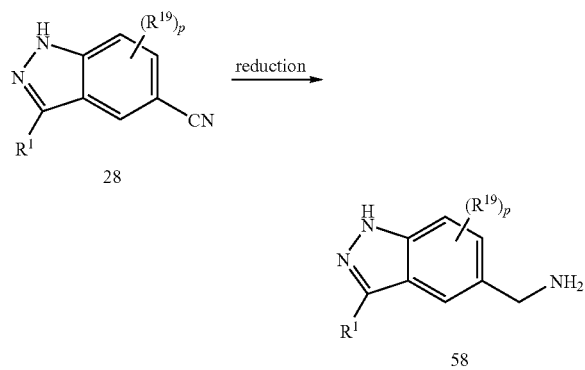

The compound 58 obtained in Production Process 28 can also be produced by reducing the nitrile 28 produced in Production Process 14. Reducing agents for use herein include, for example, sodium borohydride, lithium aluminium hydride, and aluminium hydride. Where necessary, an additive such as aluminium trichloride, boron trifluoride, cobalt chloride, and Raney nickel can be added. Reaction solvents for use herein are not specifically limited, as long as they are inert to the reaction, and include, for example, alcohol solvents such as methanol or ethanol, ether solvents such as diethyl ether, tetrahydrofuran, dioxane or dimethoxyethane. A reaction temperature is from −78° C. to the reflux temperature of the solvent.

Production Process 30

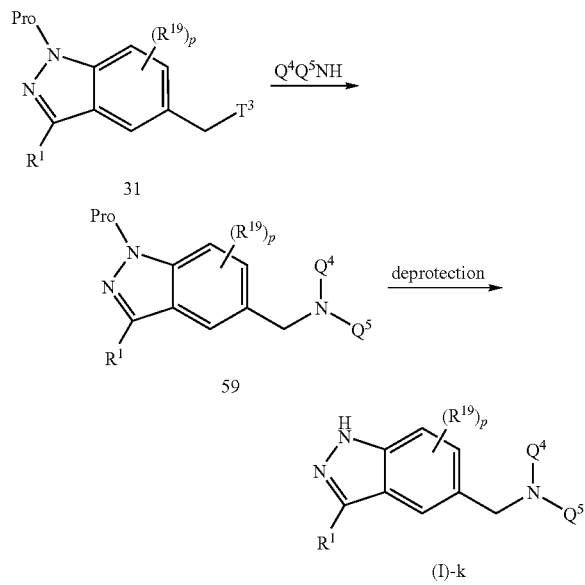

The compound (I)-k can be produced by converting the sulfonate or halide 31 obtained in Production Process 15 into the amine 59, and deprotecting the amine 59. The sulfonate or halide 31 can be aminated to react with an amine in the presence of a base. An excess amount of the amine can serve as the base. Alternatively, a base such as sodium hydride, potassium carbonate, and potassium tert-butoxide can be added. Solvents for use herein are not specifically limited, as long as they do not adversely affect the reaction, and include, for example, alcohol solvents such as methanol or ethanol, halogen-containing solvents such as methylene chloride or chloroform, ether solvents such as tetrahydrofuran or diethyl ether, as well as ethyl acetate, dimethylformamide, dimethyl sulfoxide, and toluene. A reaction temperature is generally from 0° C. to the reflux temperature of the solvent. By deprotecting the amine 59 according to the procedure of Production Process 3, the compound (I)-k can be produced.

Production Process 31

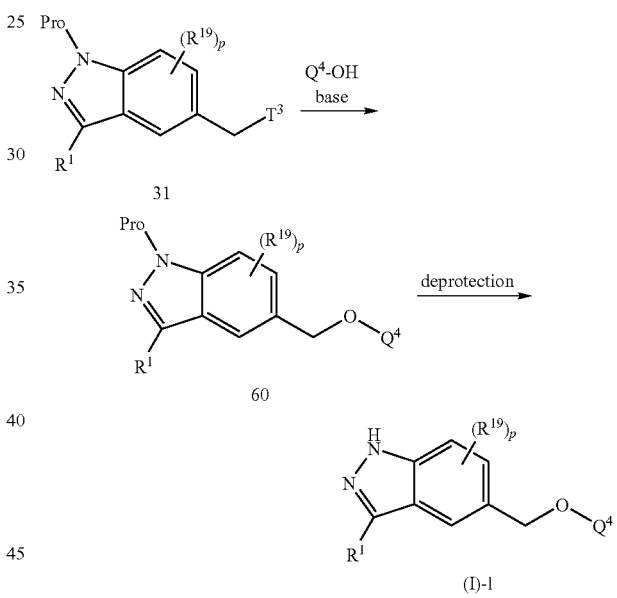

The compound (I)-l can be produced by allowing the sulfonate or halide 31 obtained in Production Process 15 to react with an alcohol in the presence of a base to thereby yield the ether 60, and deprotecting the ether 60. Bases for use in the etherification of the sulfonate or halide 31 include, but are not specifically limited to, sodium hydride, potassium carbonate, potassium tert-butoxide, and silver(I) oxide. Solvents for use herein are not specifically limited, as long as they do not adversely affect the reaction, and include, for example, halogen-containing solvents such as methylene chloride or chloroform, ether solvents such as tetrahydrofuran or diethyl ether, as well as ethyl acetate, dimethylformamide, dimethyl sulfoxide, and toluene. A reaction temperature is generally from 0° C. to the reflux temperature of the solvent. By deprotecting the ether 60 according to the procedure of Production Process 3, the compound (I)-l can be produced.

Production Process 32

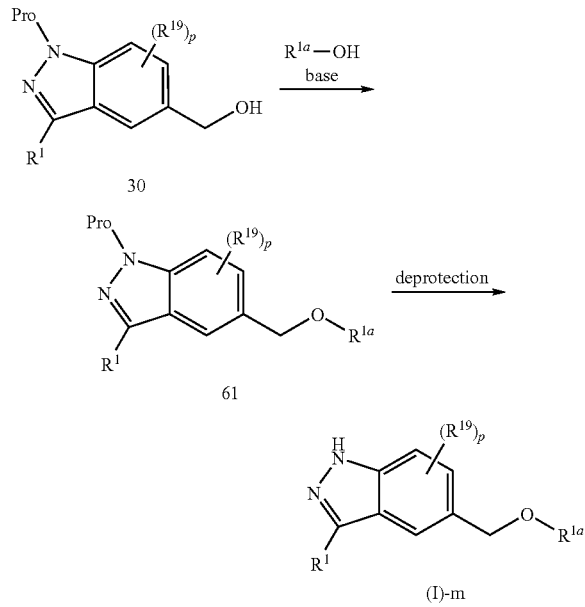

The compound (I)-m can be produced by subjecting the alcohol 30 obtained in Production Process 15 and an aryl alcohol to Mitsunobu reaction to thereby yield the aryl ether 61, and deprotecting the aryl ether 61. The compound 61 can be produced, for example, by allowing the alcohol 30 to react with the aryl alcohol in the presence of triphenylphosphine and diethyl azodicarboxylate or diisopropyl azodicarboxylate. Solvents for use herein are not specifically limited, as long as they do not adversely affect the reaction, and include, for example, halogen-containing hydrocarbons such as methylene chloride or chloroform, ether solvents such as tetrahydrofuran, diethyl ether or dioxane, as well as ethyl acetate, dimethylformamide, and toluene. A reaction temperature is generally from 0° C. to room temperature. By deprotecting the compound 61 according to the procedure of Production Process 3, the compound (I)-m can be produced.

Production Process 33

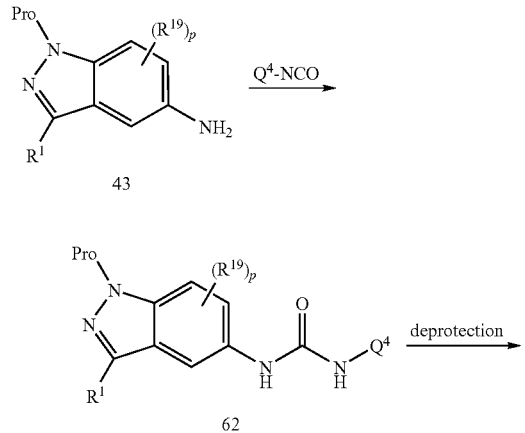

The compound (I)-n can be produced by allowing the aniline 43 obtained in Production Process 19 to react with an isocyanate to yield the urea 62, and deprotecting the urea 62. Solvents for use in the conversion of the aniline 43 into the urea are not specifically limited, as long as they do not adversely affect the reaction, and include, for example, halogen-containing solvents such as methylene chloride or chloroform, ether solvents such as tetrahydrofuran or diethyl ether, as well as ethyl acetate, dimethylformamide, dimethyl sulfoxide, and toluene. A reaction temperature is generally from 0° C. to the reflux temperature of the solvent. By deprotecting the urea 62 according to the procedure of Production Process 19, the compound (I)-n can be produced.

Production Process 34

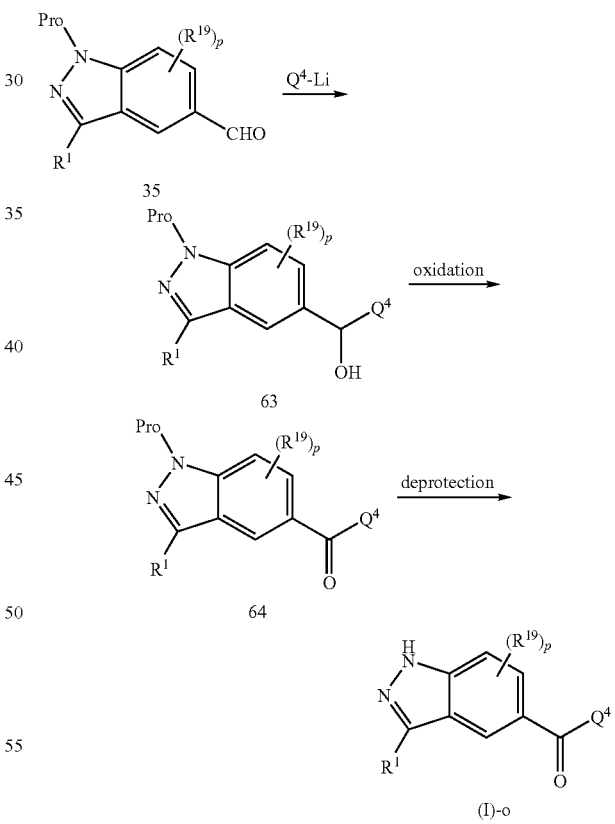

The compound (I)-o can be produced by allowing the aldehyde 35 obtained in Production Process 17 to react with an alkyllithium, a Grignard reagent, a metal aryl, or a metal halogenoaryl to yield the alcohol 63, oxidizing the alcohol 63 into the ketone 64, and deprotecting the ketone 64. The alkyllithium for the reaction of the aldehyde 35 is commercially available. The Grignard reagent can be prepared by using an alkyl halide and magnesium. Among metal aryls or metal halogenoaryls for use herein, those commercially available will be purchased, and those not commercially available can be easily prepared according to the procedure of Production Process 3. Reaction solvents for use herein are not specifically limited, as long as they are inert to the reaction, and include, for example, ether solvents such as diethyl ether, tetrahydrofuran, dioxane or dimethoxyethane, as well as benzene, and toluene. A reaction temperature is from −78° C. to room temperature. Oxidizing agents for oxidizing the alcohol 63 include, for example, manganese dioxide, sulfur trioxide-pyridine complex, N-methylmorpholine-N-oxide, and chromic acid oxidizing agents. The oxidation can also be performed by Swern oxidation or Moffat oxidation. Solvents for use herein can be any solvents that are not involved in the reaction and include, for example, halogenated hydrocarbons such as dichloromethane or chloroform, as well as ethyl acetate, acetonitrile, dimethyl sulfoxide, and dimethylformamide. A reaction temperature is generally from −78° C. to the reflux temperature of the solvent. By deprotecting the ketone 64 according to the procedure of Production Process 3, the compound (I)-o can be produced.

Production Process 35

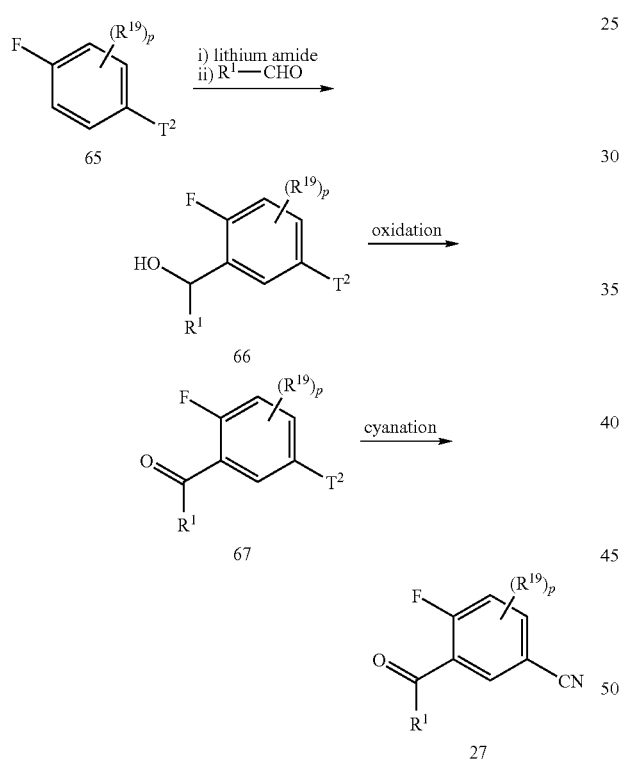

The compound 27 obtained in Production Process 14 can also be produced by treating the fluorobenzene 65 with, for example, lithium amide to yield a lithium aryl, allowing the lithium aryl to react with an aryl aldehyde to yield the alcohol 66, oxidizing the alcohol 66 into a ketone, and replacing $T^2$ a with cyano group.

Lithium amides for converting the fluorobenzene 65 into the lithium aryl include, for example, lithium diisopropylamide, and lithium 2,2,6,6-tetramethylpiperidide. Reaction solvents for use herein are not specifically limited, as long as they are inert to the reaction, and preferred examples thereof are ether solvents such as diethyl ether, tetrahydrofuran, dioxane or dimethoxyethane, as well as benzene, and toluene. A reaction temperature is from −78° C. to room temperature. By oxidizing the alcohol 66 according to the procedure of Production Process 12, the compound 67 can be produced. Reagents for converting the compound 67 into the nitrile 27 include zinc cyanide, lithium cyanide, sodium cyanide, or potassium cyanide in combination with a transition metal catalyst such as tetrakis(triphenylphosphine)palladium, tris(dibenzylideneacetone)dipalladium, dichlorobis(triphenylphosphine)palladium, and palladium diacetate. The reaction may be performed in the presence of a catalytic amount of copper iodide or a phosphine ligand such as triphenylphosphine and 1,1'-bis(diphenylphosphino)ferrocene. Preferred examples of solvents for use herein are dimethylformamide, N-methylpyrrolidone, propionitrile, and acetonitrile. A reaction temperature is preferably within a range from 80° C. to 150° C. The nitrile 27 can also be produced by allowing the compound 67 to react with copper cyanide in a solvent such as dimethylformamide or N-pyrrolidone at a temperature within a range from 140° C. to 200° C.

Production Process 36

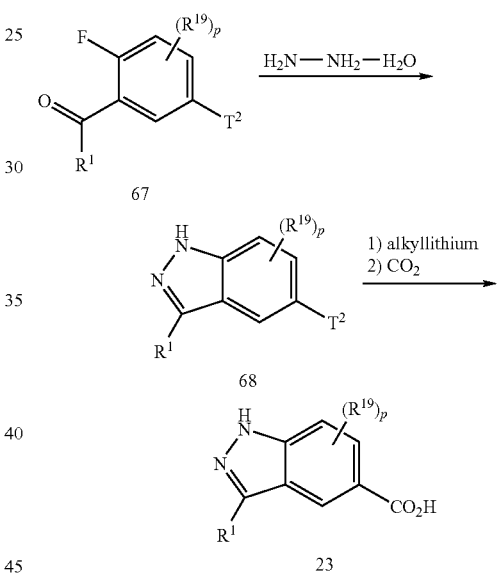

The carboxylic acid 23 obtained in Production Process 12 can also be produced by treating the compound 67 obtained in Production Process 35 with hydrazine to yield the indazole 68, converting the indazole 68 into a lithium aryl with the use of an alkyl lithium, and allowing the lithium aryl to react with carbon dioxide.

By closing the indazole ring of the compound 67 with the use of hydrazine monohydrate according to the procedure of Production Process 12, the indazole 68 can be produced. The alkyllithium for converting the indazole 68 into the lithium aryl includes, for example, n-butyllithium, sec-butyllithium, tert-butyllithium, and phenyllithium. Where necessary, an additive such as N,N,N',N'-tetramethylethylenediamine or hexamethylphosphoramide can be added.

By allowing the lithium aryl to react with carbon dioxide gas or dry ice, the carboxylic acid 23 can be produced. Reaction solvents for use herein are not specifically limited, as long as they are inert to the reaction, and preferred examples thereof are ether solvents such as diethyl ether, tetrahydrofuran, dioxane or dimethoxyethane, as well as benzene, and toluene. A reaction temperature is from −78° C. to room temperature.

Production Process 37

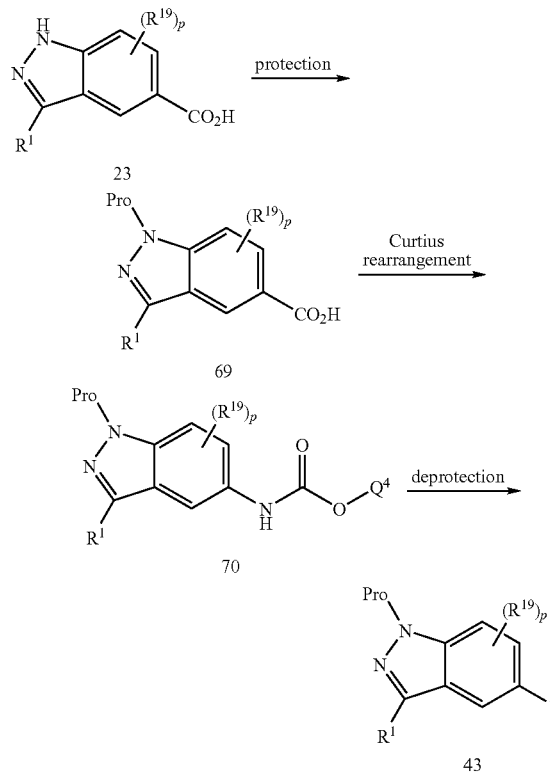

The aniline 43 obtained in Production Process 19 can also be produced by protecting the 1-position of the carboxylic acid 23 obtained in Production Process 12 to yield the compound 69, subjecting the compound 69 to Curtius rearrangement to yield the carbamate 70, and deprotecting the carbamate.

By introducing a protecting group into the 1-position according to the procedure of Production Process 15, the compound 69 can be produced. The compound 69 can be subjected to Curtius rearrangement by treating the compound 69 with, for example, diphenylphosphoryl azide and an amine such as triethylamine or diisopropylethylamine to yield an isocyanate, and allowing the isocyanate to react with an alcohol, or by treating the compound 69 with, for example, thionyl chloride or oxalyl chloride to yield an acid chloride, treating the acid chloride with lithium azide, sodium azide or potassium azide to yield an isocyanate, and allowing the isocyanate to react with an alcohol. The alcohol for use herein is not specifically limited, of which benzyl alcohol and tert-butanol are especially preferred. Solvents for use herein are not specifically limited, as long as they are inert to the reaction, and include, for example, toluene, benzene, tetrahydrofuran, and dioxane. A reaction temperature is generally from room temperature to the reflux temperature of the solvent. A tert-butyloxycarbonyl group as the protecting group of the carbamate 70 can be easily deprotected or removed by using an acid. Such acids include, for example, hydrochloric acid, sulfuric acid, and trifluoroacetic acid. Where necessary, a radical scavenger such as thiophenol or tri-iso-propylsilane can be added. Solvents for use herein are not specifically limited, as long as they are inert in the reaction, and include, for example, halogenated hydrocarbons such as dichloromethane or chloroform, as well as anisole. A benzyloxycarbonyl group as the protecting group can be easily deprotected or removed by hydrogenation. Reagents for use in the hydrogenation include, but are not specifically limited to, palladium-carbon, platinum oxide, and palladium hydroxide-carbon. The pressure of hydrogen is from 1 to 5 atm. Solvents for use herein are not specifically limited, as long as they are inert to the reaction, and include, for example, ether solvents such as diethyl ether, tetrahydrofuran, dioxane or dimethoxyethane, halogenated hydrocarbons such as dichloromethane or chloroform, as well as ethyl acetate, acetonitrile, toluene, and dimethylformamide. A reaction temperature is generally from room temperature to the reflux temperature of the solvent.

Production Process 38

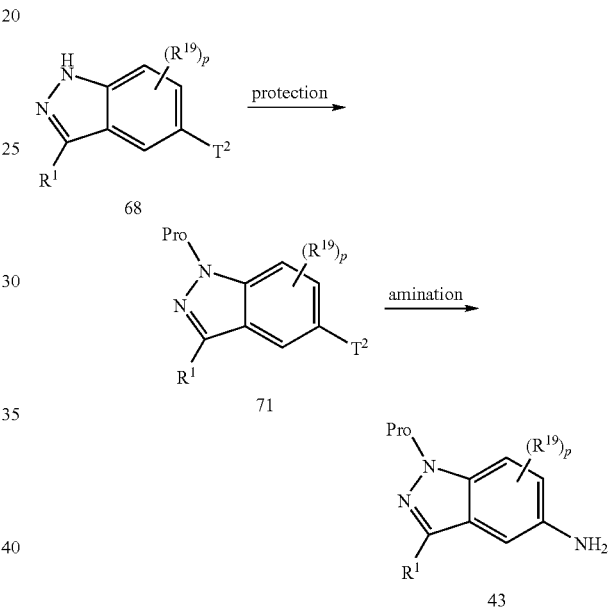

The aniline 43 obtained in Production Process 19 can also be produced by protecting the 1-position of the compound 68 obtained in Production Process 36 to yield the compound 71, and then aminating $T^2$.

By introducing a protecting group into the 1-position of the compound 68 according to the procedure of Production Process 15, the compound 71 can be produced. Palladium catalysts for use in amination of the compound 71 include, for example, tris(dibenzylideneacetone)dipalladium, and palladium diacetate. Phosphine ligands for use herein include, for example, 2,2'-bis(diphenylphosphino)-1,1'-naphthyl, 1,1'-bis(diphenylphosphino)ferrocene, and tri(tert-butyl)phosphine. Bases for use herein include, for example, sodium tert-butoxide, potassium tert-butoxide, and cesium carbonate. An ammonia equivalent for use herein is not specifically limited and is preferably benzophenoneimine. Acids for use in hydrolysis of the resulting imine derivative include, but are not specifically limited to, diluted hydrochloric acid and diluted sulfuric acid. Solvents for use in the reaction are not specifically limited, as long as they are inert to the reaction, and include, for example, toluene, tetrahydrofuran, dioxane, and dimethoxyethane. A reaction temperature is generally from room temperature to 120° C.

Production Process 39

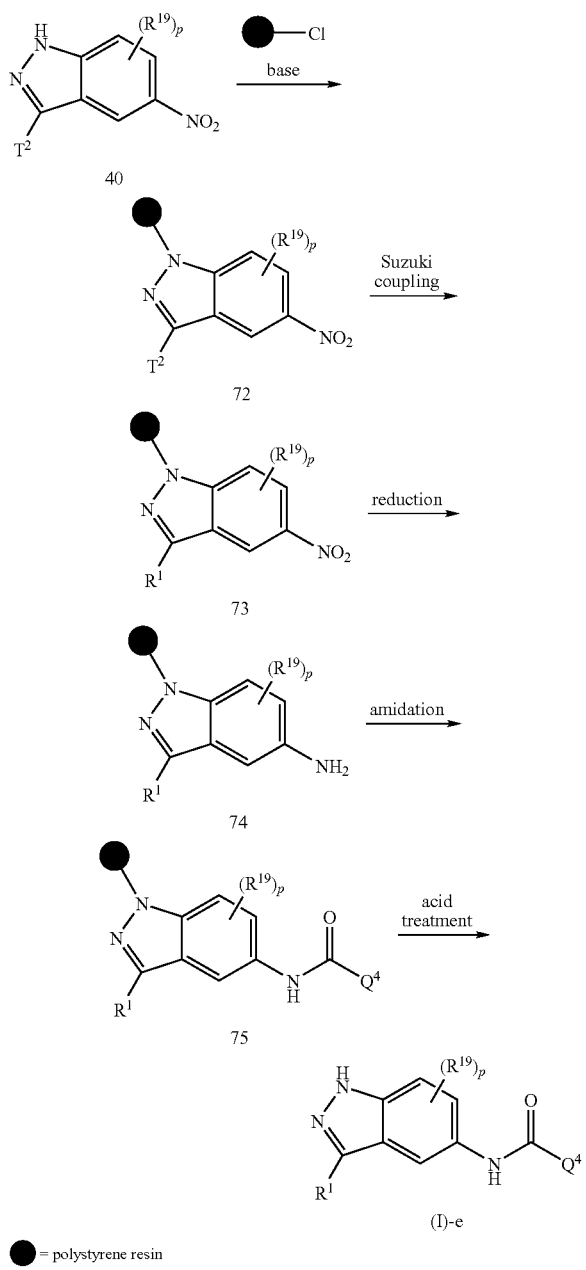

● = polystyrene resin

The compound (I)-e can also be produced by combining, with a resin, the 1-position of the compound 40 obtained in Production Process 19 to yield the compound 72, subjecting the product to Suzuki coupling with an arylboronic acid to yield the compound 73, reducing the product into the aniline 74, amidating the product into the compound 75, and then exciding the target compound from the resin using an acid. Advantages of the synthesis using a resin are that a multitude of a target compound can be synthetically prepared at once, that a purification procedure in each step is not required, as an excess reagent can be removed by washing, and that the resin itself serves as a protecting group. By allowing the compound 40 to react with the resin in the presence of a base, 72 can be obtained. Such bases include, but are not specifically limited to, triethylamine, diisopropylethylamine, 4-N,N-dimethylaminopyridine, sodium hydride, potassium tert-butoxide, and potassium carbonate. Solvents for use herein are not specifically limited, as long as they are inert to the reaction and can hold affinity for the resin, and include, for example, ether solvents tetrahydrofuran or dioxane, as well as dimethyl sulfoxide, dimethylformamide, N-methylpyrrolidone, ethyl acetate, and acetonitrile. A reaction temperature is generally from 0° C. to the reflux temperature of the solvent. Among arylboronic acids for use in Suzuki coupling of the compound 72, those commercially available will be purchased, and those not commercially available can be easily prepared according to the procedure of Production Process 3. The arylboronic acid is used in excess. Catalysts for use herein include, for example, palladium(II) acetate, dichlorobis(triphenylphosphine)palladium(II), and tetrakis(triphenylphosphine)palladium(0). The amount of the catalyst is about 5% by mole relative to the arylboronic acid. Where necessary, a phosphine ligand in an amount of two times by mole that of the catalyst can be added. Such phosphine ligands include, for example, tri-tert-butylphosphine, 2-(di-tert-butylphosphino)biphenyl, 2-(dicyclohexylphosphino)biphenyl, and triphenylphosphine. Bases for use herein include, for example, sodium hydrogencarbonate, sodium carbonate, potassium carbonate, cesium carbonate, and potassium fluoride. Solvents for use herein are not specifically limited, as long as they are inert to the reaction and can hold affinity for the resin, and include, for example, dimethylformamide, N-methylpyrrolidone, tetrahydrofuran, dioxane, and diethylene glycol dimethyl ether. A reaction temperature is generally from room temperature to the reflux temperature of the solvent. The nitro group of the compound 73 can be reduced, for example, by reduction with tin(II) chloride or reduction with iron-ammonium chloride. Solvents for use in the reduction with tin(II) chloride include, for example, alcohol solvents such as methanol or ethanol, dimethylformamide, and N-methylpyrrolidone. A reaction temperature is generally from room temperature to the reflux temperature of the solvent. Solvents for use in the reduction with iron-ammonium chloride are preferably alcohol solvents such as aqueous methanol or aqueous ethanol. The amount of iron is from 3 to 10 equivalents to the raw material. The amount of the ammonium chloride is from 10% to 20% by weight relative to the raw material. A reaction temperature is generally the reflux temperature of the solvent. The aniline 74 can be amidated by treating with a carboxylic acid and a condensing agent. Such condensing agents include, for example, dicyclohexylcarbodiimide, diisopropylcarbodiimide, 1-ethyl-3-(3-dimethylaminopropyl)carbodiimide, and 1-ethyl-3-(3-dimethylaminopropyl)carbodiimide hydrochloride. Where necessary, 1-hydroxybenzotriazole and/or N-hydroxysuccinimide can be added. Solvents for use herein are not specifically limited, as long as they are inert to the reaction and can hold affinity for the resin, and include, for example, ether solvents such as tetrahydrofuran or dioxane, as well as dimethylformamide, N-methylpyrrolidone, and ethyl acetate. A reaction temperature is generally from room temperature to the reflux temperature of the solvent. The compound (I)-e can be easily excided from the resin using an acid. Such acids include, for example, hydrochloric acid, sulfuric acid, and trifluoroacetic acid. Where necessary, a radical scavenger such as thiophenol or tri-iso-propylsilane can be added. Solvents for use herein are not specifically limited, as long as they are inert to the reaction, and include, for example, halogenated hydrocarbons such as dichloromethane or chloroform. A reaction temperature is from room temperature to the reflux temperature of the solvent.

Production Process 40

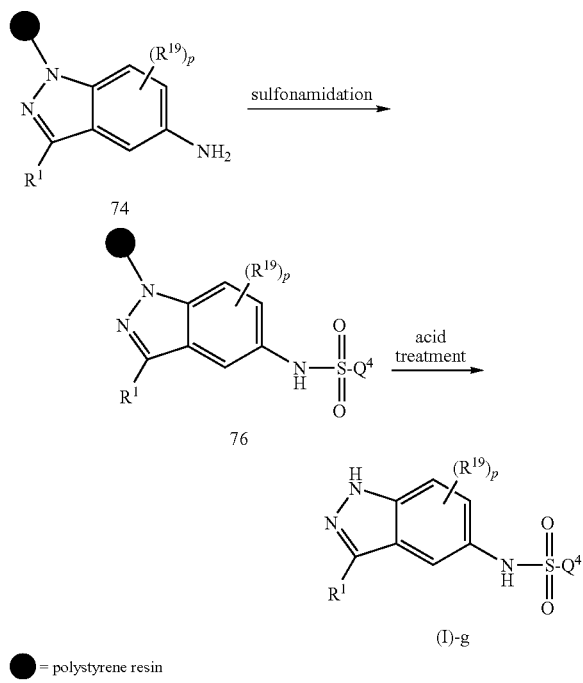

● = polystyrene resin

The compound (I)-g can also be produced by converting the aniline 74 obtained in Production Process 39 into the sulfonamide 76, and then exciding the target compound from the resin using an acid. The aniline 74 can be converted into the sulfonamide by allowing it to react with a sulfonyl chloride in the presence of a base. Such bases include, but are not specifically limited to, triethylamine, 4-dimethylaminopyridine, potassium carbonate, and sodium hydride. The amount of the base is from 0.9 to 1.1 equivalents to the sulfonyl chloride. Reaction solvents for use herein are not specifically limited, as long as they are inert to the reaction and can hold affinity for the resin, and include, for example, ether solvents such as tetrahydrofuran or dioxane, as well as dimethyl sulfoxide, N-methylpyrrolidone, dimethylformamide, ethyl acetate, and acetonitrile. Among them, ether solvents such as tetrahydrofuran or dioxane are preferred. A reaction temperature is generally from 0° C. to room temperature. By exciding from the resin according to the procedure of Production Process 39, the compound (I)-g can be produced.

Material compounds for use in the production of the compounds of the present invention can be in the form of salts and/or hydrates and are not specifically limited as long as they do not adversely affect the reactions. When the compounds (I) according to the present invention are obtained as free compounds, they can be converted into acceptable salts of the above-mentioned compound (I) according to a conventional procedure. Various isomers such as geometrical isomers, optical isomers due to an asymmetric carbon, stereoisomers, and tautomers obtained as the compounds (I) according to the present invention can be purified and isolated according to a conventional separation means. Such separation means include, for example, recrystallization, diastereomeric salt method, enzymatic resolution, and a variety of chromatography such as thin layer chromatography, column chromatography or gas chromatography.

The term "salt(s)" as used in the present description is not specifically limited, as long as it can form a salt with the compound according to the present invention and is pharmacologically acceptable. Preferred examples of the salts are hydrohalides such as hydrofluorides, hydrochlorides, hydrobromides or hydroiodides; salts of inorganic acids, such as sulfates, nitrates, perchlorates, phosphates, carbonates or bicarbonates; salts of organic carboxylic acids, such as acetates, trifluoroacetates, oxalates, maleates, tartrates, fumarates or citrates; salts of organic sulfonic acids, such as methanesulfonates, trifluoromethanesulfonates, ethanesulfonates, benzenesulfonates, toluenesulfonates or camphorsulfonates; salts of amino acids, such as aspartates or glutamates; quaternary amine salts; alkali metal salts such as sodium salts or potassium salts; alkaline earth metal salts such as magnesium salts or calcium salts. More preferred examples of the "pharmacologically acceptable salt(s)" are hydrochlorides, oxalates and trifluoroacetates.

The compounds represented by the formula (I) according to the present invention, a salt thereof or a hydrate of them can be formulated into pharmaceutical preparations according to a conventional procedure. Preferred dosage forms are tablets, powders, fine granules, granules, coated tablets, capsules, syrups, troches, inhalants, suppositories, injections, ointments, ophthalmic ointments, eye drops, nasal drops, ear drops, cataplasms, and lotions. In the formulation, generally used fillers, binders, disintegrators, lubricants, coloring agents, and flavoring agents, as well as stabilizers, emulsifiers, absorbefacients, surfactants, pH adjusting agents, antiseptics, and antioxidants according to necessity can be used. They can be formulated according to a conventional procedure using components generally used as raw materials for pharmaceutical preparations. Examples of such components include (1) animal or vegetable oils such as soybean oil, beef tallow or synthetic glycerides; (2) hydrocarbons such as liquid paraffins, squalane or solid paraffins; (3) ester oils such as octyldodecyl myristate or isopropyl myristate; (4) higher alcohols such as cetostearyl alcohol or behenyl alcohol; (5) silicon resins; (6) silicon oils; (7) surfactants such as polyoxyethylene fatty acid esters, sorbitan fatty acid esters, glycerin fatty acid esters, polyoxyethylene sorbitan fatty acid esters, polyoxyethylene hydrogenated castor oils or polyoxyethylene-polyoxypropylene block copolymers; (8) water-soluble polymers such as hydroxyethyl cellulose, poly (acrylic acid)s, carboxyvinyl polymers, polyethylene glycol, polyvinylpyrrolidone or methylcellulose; (9) lower alcohols such as ethanol or isopropanol; (10) polyhydric alcohols such as glycerol, propylene glycol, dipropylene glycol or sorbitol; (11) sugars such as glucose or sucrose; (12) inorganic powders such as silicic anhydride, magnesium aluminium silicate or aluminium silicate; and (13) purified water.

1) The fillers include, for example, lactose, corn starch, sucrose, glucose, mannitol, sorbitol, crystalline cellulose, and silicon dioxide; 2) the binders include, for example, polyvinyl alcohol, polyvinyl ether, methylcellulose, ethylcellulose, gum arabic, gum tragacanth, gelatin, shellac, hydroxypropyl cellulose, hydroxypropylmethyl cellulose, polyvinylpyrrolidone, polypropylene glycol-polyoxyethylene block polymers, meglumine, calcium citrate, dextrin, and pectin; 3) the disintegrators include, for example, starch, agar, gelatin powder, crystalline cellulose, calcium carbonate, sodium hydrogencarbonate, calcium citrate, dextrin, pectin, and carboxymethylcellulose calcium; 4) the lubricants include, for example, magnesium stearate, talc, polyethylene glycol, silica, and hardened vegetable oils; 5) the coloring agents can be any coloring agents which are approved to add to pharmaceutical preparations; 6) the flavoring agents include, for example, cocoa powder, menthol, aromatic powder, peppermint oil, borneol, and cinnamon powder; 7) the antioxidants can be any antioxidants which are approved to add to pharmaceutical preparations such as ascorbic acid or α-tocopherol.

1) As oral preparations, the compound according to the present invention or the salt thereof is compounded with a filler, and if necessary, a binder, disintegrator, lubricant, coloring agent, flavoring agent, and other components, and the resulting mixture is formulated according to a conventional procedure into a powder, fine granules, granules, tablet, coated tablet, capsule, etc. 2) The tablets and granules can be appropriately coated with, for example, sugar or gelatin, or other according to necessity. 3) Liquid formulations such as syrups, injection preparations or eye droppers can be prepared in a conventional method, by adding a pH adjusting agents, solubilizer, and isotonizing agent, and if necessary, a solubilizing agent, stabilizer, buffer, suspending agent, antioxidant, and other components. The liquid formulations can also be formed into freeze-dried products. The injections can be administered intravenously, subcutaneously and/or intramuscularly. Preferred examples of the suspending agents are methylcellulose, polysorbate 80, hydroxyethyl cellulose, gum arabic, tragacanth powder, sodium carboxymethylcellulose, and polyoxyethylene sorbitan monolaurate; preferred examples of solubilizers are polyoxyethylene hardened caster oil, polysorbate 80, nicotinamide, and polyoxyethylene sorbitan monolaurate; preferred examples of the stabilizers are sodium sulfite, sodium metasulfite, and ether; preferred examples of the preservatives are methyl p-hydroxybenzoate, ethyl p-hydroxybenzoate, sorbic acid, phenol, cresol, and chlorocresol. 4) External preparations can be produced according to a conventional procedure not specifically limited. Base materials for use herein can be any raw materials generally used in, for example, pharmaceutical preparations, quasi drugs, and cosmetics. Such raw materials include, for example, animal or vegetable oils, mineral oils, ester oils, waxes, higher alcohols, fatty acids, silicon oils, surfactants, phospholipids, alcohols, polyhydric alcohols, water-soluble polymers, clay minerals, and purified water. If necessary, any of pH adjusting agents, antioxidants, chelating agents, antiseptics and antimolds, coloring agents, and flavors can be added. In addition, components having differentiation-inducing action, blood-flow accelerators, bactericides, anti-inflammatory agents, cell activators, vitamins, amino acids, humectants, keratolytic agents, and other components can be added according to necessity.

The dose of the pharmaceutical preparation according to the present invention varies depending on the degree of symptom, age, sex, body weight, administration mode, type of the salt, difference in sensibility to the drug, concrete type of the disease, and other factors. Generally, in oral administration, the pharmaceutical preparations may be administered at a daily dose of about 30 µg to about 1000 mg, preferably about 100 µg to about 500 mg, and more preferably about 100 µg to about 100 mg for an adult in one to several divided doses. In injection administration, they may be administered at a daily dose of about 1 to about 3000 µg/kg, and preferably about 3 to about 1000 µg/kg for an adult in one to several divided doses.

The present invention can provide novel indazole compounds. The compounds (I) according to the present invention or the salts thereof have excellent inhibitory action on c-Jun amino-terminal kinases, especially on JNK 3. Accordingly, the compounds (I) according to the present invention or the salts thereof, and pharmaceutical compositions containing the same are useful as therapeutic agents or prophylactic agents for an immunologic disease, inflammatory disease and/or neurodegenerative disease. They are particularly useful as therapeutic agents or prophylactic agents, for example, for acute neurodegenerative diseases such as acute stage of cerebrovascular disorder, head injury, spinal code injury, neuropathy due to hypoxia, and neuropathy due to hypoglycemia; chronic neurodegenerative diseases such as Alzheimer's disease, Parkinson's disease, Huntington's chorea, amyotrophic lateral sclerosis, multiple sclerosis or spinocerebellar degeneration; epilepsy; hepatic encephalopathy; peripheral neuropathy; Parkinsonian syndrome; spastic paralysis; pain; neuralgia; infectious encephalomyelitis; cerebrovascular dementia; or dementia or neurological symptom due to meningitidis.

EXAMPLES

The following production examples, examples, and test examples are indicated by illustration, and the compounds of the present invention are never restricted by the following examples. Those skilled in the art can modify not only the following examples but also the claims according to the present description in various ways to exert the most of the present invention, and such modifications and variations are also included within the scope of the appended claims relating to the present description.

Production Example I-1-a

4-Fluoro-3-[(3-fluorophenyl)(hydroxy)methyl]benzonitrile

In an atmosphere of nitrogen gas, 76.3 ml of 1.56 M solution of n-butyllithium in hexane was added to a solution of 11.1 g of N,N-diisopropylamine in 200 ml tetrahydrofuran under ice-cooling, and the mixture was stirred at the same temperature for 15 minutes. After cooling to −78° C., a solution of 12.1 g of 4-fluorobenzonitrile in 40 ml tetrahydrofuran was added dropwise. After stirring at the same temperature for 45 minutes, 10.6 ml of 3-fluorobenzaldehyde was added dropwise. After stirring at the same temperature for 25 minutes, saturated aqueous ammonium chloride solution was added and the solvent was removed. To the residue was added 150 ml of ethyl acetate, and the mixture was sequentially washed with 1 N hydrochloric acid, water, saturated aqueous sodium hydrogencarbonate solution and brine, dried over anhydrous magnesium sulfate and the solvent was evaporated. The crude product was purified and separated by silica gel column chromatography (ethyl acetate:toluene=3:97 to 1:19), and the resulting crystals were recrystallized from diisopropyl ether-hexane, to give 12.7 g of the title compound as pale yellow needles.

$^1$H-NMR (400 MHz, DMSO-D$_6$) δ 5.97 (1H, d, J=4.4 Hz), 6.40 (1H, d, J=4.4 Hz), 7.09 (1H, td, J=8.4, 2.8 Hz), 7.17 (1H, d, J=8.0 Hz), 7.21 (1H, d, J=10.0 Hz), 7.33-7.44 (2H, m), 7.86 (1H, m), 8.04 (1H, dd, J=2.0, 6.8 Hz).

Production Example I-1-b 3-(3-Fluorophenyl)-1H-5-indazolecarbonitrile

To a solution of 12.5 g of 4-fluoro-3-[(3-fluorophenyl)(hydroxy)methyl]benzonitrile in 200 ml methylene chloride was added 43.8 g of activated manganese dioxide, and the resulting mixture was stirred at room temperature for 10 hours and at 35° C. for further 9 hours. Then, the manganese dioxide was filtered off through Celite. After removing the solvent by distillation, the residue was dissolved in 25 ml of tetrahydrofuran and 25 ml of methanol. 12 ml of hydrazine monohydrate was added, followed by stirring at room temperature for 7 hours. The reaction mixture was added with 150 ml of water, and ice-cooled. Then, the resulting crystals were collected by filtration. The crystals were dried in vacuo, to give 11.6 g of the title compound as yellow crystals.

$^1$H-NMR (400 MHz, DMSO-D$_6$) δ 7.30 (1H, td, J=8.0, 2.8 Hz), 7.58 (1H, td, J=8.0, 6.4 Hz), 7.75 (1H, dd, J=8.8, 1.6 Hz), 7.79 (1H, d, J=8.8 Hz), 7.83 (1H, dd, J=10.4, 2.8 Hz), 7.93 (1H, d, J=8.0 Hz), 8.78 (1H, s), 13.88 (1H, s).

Production Example I-1-c 3-(3-Fluorophenyl)-1H-5-indazolecarboxylic acid

To 10.0 g of 3-(3-fluorophenyl)-1H-5-indazolecarbonitrile were sequentially added 50 ml of glacial acetic acid, 15 ml of water and 12 ml of concentrated sulfuric acid, and the mixture was stirred at 110° C. for 6.5 hours. After standing to cool, the reaction mixture was added with 150 ml of ice-water, and the resulting crystals were collected by filtration. The resulting crystals were dried in vacuo, to give 10.7 g of the title compound as beige orange-pink crystals.

$^1$H-NMR (400 MHz, DMSO-D$_6$) δ 7.28 (1H, dt, J=2.8, 10.1 Hz), 7.61 (1H, dt, J=6.2, 8.2 Hz), 7.67 (1H, d, J=8.8 Hz), 7.72 (1H, ddd, J=1.5, 2.8, 10.1 Hz), 7.82 (1H, d, J=8.2 Hz), 7.97 (1H, d, J=8.8 Hz), 8.63 (1H, s), 12.80-12.95 (1H, bs), 13.67 (1H, s)

Production Example I-2-a 3-(3-Fluorophenyl)-1H-7-indazolecarbonitrile

A total of 637 mg of the title compound as yellow crystals was obtained from 2.42 g of 2-fluorobenzonitrile by the procedures of Production Examples I-1a and I-1b.

$^1$H-NMR (400 MHz, DMSO-D$_6$) δ 7.30 (1H, td, J=8.0, 2.4 Hz), 7.40 (1H, t, J=8.0 Hz), 7.60 (1H, td, J=8.0, 6.8 Hz), 7.77 (1H, d, J=10.0 Hz), 7.87 (1H, d, J=8.0 Hz), 8.02 (1H, d, J=8.0 Hz), 8.49 (1H, d, J=8.0 Hz), 14.32 (1H, s).

Production Example I-2-b 3-(3-Fluorophenyl)-1H-7-indazolecarboxylic acid

A total of 637 mg of the title compound as yellow crystals was obtained from 593 mg of 3-(3-fluorophenyl)-1H-7-indazolecarbonitrile by the procedure of Production Example I-1-c.

$^1$H-NMR (400 MHz, DMSO-D$_6$) δ 7.28 (1H, td, J=8.0, 2.8 Hz), 7.36 (1H, dd, J=7.2, 8.0 Hz), 7.60 (1H, td, J=8.0, 6.8 Hz), 7.76 (1H, dd, J=10.0, 2.8 Hz), 7.87 (1H, d, J=8.0 Hz), 8.05 (1H, d, J=8.0 Hz), 8.39 (1H, d, J=8.0 Hz), 13.40 (1H, s), 13.43 (1H, s).

Production Example I-3-a

3-Fluoro-2-(1,1,1-trimethylsilyl)benzonitrile

To a solution of 5.57 g of N,N-diisopropylamine in 100 ml tetrahydrofuran at −30° C. in an atmosphere of nitrogen gas was added 33 ml of 1.59 M solution of n-butyllithium in hexane, and the mixture was stirred at the same temperature for 25 minutes. After cooling to −78° C., a solution of 6.06 g of 3-fluorobenzonitrile in 9 ml tetrahydrofuran was added dropwise. After stirring at the same temperature for 1 hour, 12.7 ml of chlorotrimethylsilane was added dropwise. After stirring at the same temperature for 1 hour, saturated aqueous ammonium chloride solution was added and the solvent was removed. The residue was added with 130 ml of ethyl acetate, and sequentially washed with water and brine, and dried over anhydrous magnesium sulfate. After filtrating the organic layer through a silica pat, the solvent was evaporated. The crude product was purified and separated by silica gel column chromatography (hexane), to give 6.93 g of the title compound as a pale blue oil.

$^1$H-NMR (400 MHz, CDCl$_3$) δ 0.48 (9H, s), 7.21 (1H, ddd, J=1.2, 8.4, 9.2 Hz), 7.42 (1H, ddd, J=5.6, 7.6, 8.4 Hz), 7.50 (1H, dd, J=1.2, 7.6 Hz).

Production Example I-3-b

3-Fluoro-4-[(3-fluorophenyl)(hydroxy)methyl]-2-(1, 1,1-trimethylsilyl)benzonitrile In an atmosphere of nitrogen gas, 7.0 ml of 1.56 M n-butyllithium in hexane was added to a solution of 1.61 g of 2,2,6,6-tetramethylpiperidine in 20 ml tetrahydrofuran under ice-cooling, and the mixture was stirred at the same temperature for 1 hour. After cooling to −78° C., a solution of 2.0 g of 3-fluoro-2-(1,1,1-trimethylsilyl)benzonitrile in 5 ml tetrahydrofuran was added dropwise. After stirring at the same temperature for 55 minutes, 1.10 ml of 3-fluorobenzaldehyde was added dropwise. After stirring at the same temperature for 1 hour, 1.5 ml of glacial acetic acid was added and the mixture was returned to room temperature. After adding 40 ml of water, the mixture was extracted with diethyl ether. The organic layer was sequentially washed with 1 N hydrochloric acid, water, saturated aqueous sodium hydrogencarbonate solution and brine, dried over anhydrous magnesium sulfate and the solvent was evaporated. The crude product was purified and separated by silica gel column chromatography (ethyl acetate:hexane=1:9), to give 1.35 g of the title compound as a pale yellow viscous oil.

$^1$H-NMR (400 MHz, DMSO-D$_6$) δ 0.40 (9H, s), 5.97 (1H, d, J=4.0 Hz), 6.35 (1H, d, J=4.0 Hz), 7.08 (1H, td, J=8.0, 2.8 Hz), 7.15 (1H, d, J=8.0 Hz), 7.17 (1H, dd, J=8.0, 2.8 Hz), 7.37 (1H, td, J=8.0, 6.0 Hz), 7.72 (1H, d, J=8.0 Hz), 7.76 (1H, t, J=8.0 Hz).

Production Example I-3-c 3-(3-Fluorophenyl)-1H-6-indazolecarbonitrile

To a solution of 1.35 g of 3-fluoro-4-[(3-fluorophenyl)(hydroxy)methyl]-2-(1,1,1-trimethylsilyl)benzonitrile in 30 ml methylene chloride was added 4.5 g of activated manganese dioxide, the mixture was stirred at room temperature for five days, and then the manganese dioxide was filtered off through Celite. After removing the solvent by distillation, the residue was dissolved in 5 ml of tetrahydrofuran and 5 ml of methanol, 1.0 ml of hydrazine monohydrate was added and the mixture was stirred at room temperature for 1 day. The reaction mixture was added with water and extracted with ethyl acetate. The organic layer was sequentially washed with water and brine, dried over anhydrous magnesium sulfate and the solvent was removed. Then, the resulting crystals were suspended in diisopropyl ether, to give 62 mg of the title compound as pale yellow crystals. After concentrating the mother liquor, the residue was purified and separated by silica gel column chromatography (ethyl acetate:toluene=1:9), to give 30 mg of the title compound as yellow crystals.

$^1$H-NMR (400 MHz, DMSO-D$_6$) δ 7.29 (1H, td, J=8.0, 2.8 Hz), 7.54 (1H, dd, J=8.4, 1.2 Hz), 7.59 (1H, td, J=8.0, 6.4 Hz), 7.77 (1H, dd, J=10.4, 2.8 Hz), 7.86 (1H, d, J=8.0 Hz), 8.26 (1H, s), 8.31 (1H, d, J=8.4 Hz), 13.96 (1H, s).

Production Example I-3-d 3-(3-Fluorophenyl)-1H-6-indazolecarboxylic acid

To 92 mg of 3-(3-fluorophenyl)-1H-6-indazolecarbonitrile were sequentially added 1 ml of glacial acetic acid, 0.5 ml of water and 0.4 ml of concentrated sulfuric acid, and the mixture was stirred at 110° C. for 6 hours. After standing to cool, 35 ml of ethyl acetate was added to the reaction mixture. The mixture was sequentially washed with water and brine, dried over anhydrous magnesium sulfate and the solvent was evaporated, to give 94 mg of the title compound as bright yellow crystals.

$^1$H-NMR (400 MHz, DMSO-D$_6$) δ 7.27 (1H, td, J=8.4, 2.4 Hz), 7.59 (1H, td, J=8.0, 6.4 Hz), 7.74-7.81 (2H, m), 7.88 (1H, d, J=8.0 Hz), 8.19 (1H, s), 8.20 (1H, d, J=9.6 Hz), 8.65 (1H, s), 13.14 (1H, s), 13.71 (1H, s).

Production Example I-4-a

[5-(Dimethoxymethyl)-2-fluorophenyl](3-fluorophenyl)methanol

A total of 21.6 g of 3-bromo-4-fluorobenzaldehyde was dissolved in a mixture of 50 ml of methyl orthoformate and 50 ml of methanol, and 0.2 g of p-toluenesulfonic acid monohydrate was added, followed by stirring at room temperature for 1 hour. To the reaction mixture was added aqueous sodium hydrogencarbonate solution, and the mixture was extracted with ethyl acetate. The organic layer was washed with water, dried over anhydrous magnesium sulfate and the solvent was evaporated, to give 24.3 g of 3-bromo-4-fluorobenzaldehyde dimethylacetal as a colorless oil. The product was dissolved in 150 ml of dry tetrahydrofuran. After cooling to −78° C. in an atmosphere of nitrogen gas, 59 ml of a 2.5 M solution of n-butyllithium in hexane was added. After stirring for 30 minutes, 12.7 ml of 3-fluorobenzaldehyde was added and the mixture was heated to room temperature. To the reaction mixture was added aqueous ammonium chloride solution, and the mixture was extracted with ethyl acetate for two times. The organic layer was washed with water, dried over anhydrous magnesium sulfate and the solvent was evaporated. The residue was purified and separated by silica gel column chromatography (ethyl acetate:hexane=1:15), to give 24.3 g of the title compound as a pale yellow oil.

$^1$H-NMR (400 MHz, DMSO-d$_6$) δ 3.20 (3H, s), 3.31 (3H, s), 5.36 (1H, s), 5.93 (1H, d, J=4.4 Hz), 6.19 (1H, d, J=4.4 Hz), 7.00-7.07 (1H, m), 7.07-7.15 (3H, m), 7.25-7.30 (1H, m), 7.30-7.38 (1H, m), 7.56 (1H, dd, J=2.8, 7.4 Hz).

Production Example I-4-b

[5-(Dimethoxymethyl)-2-fluorophenyl](3-fluorophenyl)methanone

In a mixture of 80 ml of dichloromethane and 80 ml of dimethylsulfoxide were dissolved 24.3 g of [5-(dimethoxymethyl)-2-fluorophenyl](3-fluorophenyl)methanol and 27.6 ml of triethylamine, and a suspension of 26.3 g of sulfur trioxide-pyridine complex in 30 ml dimethyl sulfoxide was added, followed by stirring at room temperature for 1 hour. To the reaction mixture was added water, and the mixture was extracted with ethyl acetate for two times. The organic layer was washed with water, dried over anhydrous magnesium sulfate and the solvent was evaporated. The residue was purified and separated by silica gel column chromatography (ethyl acetate:hexane=1:15), to give 18.7 g of the title compound as a colorless oil.

$^1$H-NMR (400 MHz, DMSO-d$_6$) δ 3.25 (6H, s), 5.45 (1H, s), 7.40 (1H, dd, J=8.8, 10.5 Hz), 7.51-7.63 (5H, m), 7.63-7.69 (1H, m).

Production Example I-4-c

The title compound was also synthetically prepared by another procedure as mentioned below. A total of 2.0 g of [5-(dimethoxymethyl)-2-fluorophenyl](3-fluorophenyl)methanol was dissolved in 20 ml of dichloromethane, and the solution was treated with 5 g of manganese dioxide with stirring at room temperature for one day. The reaction mixture was filtrated using a Celite, the solvent was removed by distillation under reduced pressure, to give 2.0 g of the title compound.

Production Example I-4-d

Methyl 4-fluoro-3-(3-fluorobenzoyl)benzoate

A total of 18.7 g of [5-(dimethoxymethyl)-2-fluorophenyl](3-fluorophenyl)methanone was dissolved in 100 ml of tetrahydrofuran, and 5 ml of 5 N hydrochloric acid was added, followed by stirring at room temperature for 1 hour. To the reaction mixture was added saturated aqueous sodium hydrogencarbonate solution, and the mixture was extracted with ethyl acetate for two times. The organic layer was washed with water, dried over anhydrous magnesium sulfate and the solvent was evaporated, to give 15.8 g of 4-fluoro-3-(3-fluorobenzoyl)benzaldehyde as a colorless oil. A total of 13.8 g of this compound was dissolved in 50 ml of dimethyl sulfoxide, and a solution of 15.2 g of sodium chlorite in 50 ml water was added dropwise over 1 hour under ice-cooling. To the reaction mixture was added diluted hydrochloric acid, and the mixture was extracted with ethyl acetate for two times. The organic layer was washed with water, dried over anhydrous magnesium sulfate and the solvent was evaporated. The residue was filtered using diisopropyl ether, to give 12.9 g of 4-fluoro-3-(3-fluorobenzoyl)benzoic acid as a colorless solid. A total of 11.1 g of this compound was dissolved in 50 ml of N,N-dimethylformamide, and 5.8 g of potassium carbonate and 2.9 ml of methyl iodide were added, followed by stirring at room temperature for 12 hours. To the reaction mixture was added water, and the mixture was extracted with ethyl acetate for two times. The organic layer was washed with water, dried over anhydrous magnesium sulfate and the solvent was evaporated. The residue was purified and separated by silica gel column chromatography (ethyl acetate:hexane=1:15), to give 11.5 g of the title compound as a colorless oil.

$^1$H-NMR (400 MHz, CDCl$_3$) δ 3.93 (3H, s), 7.25 (1H, t, J=9.2 Hz), 7.32 (1H, ddt, J=1.2, 2.7, 8.0 Hz), 7.46 (1H, dt, J=5.3, 8.0 Hz), 7.50-7.59 (2H, m), 8.21-7.26 (2H, m).

Production Example I-4-e

Methyl 3-(3-fluorophenyl)-1H-5-indazolecarboxylate

A total of 11.5 g of methyl 4-fluoro-3-(3-fluorobenzoyl)benzoate was dissolved in 40 ml of ethanol, and the reaction mixture was treated with 2.4 ml of hydrazine monohydrate with stirring at room temperature for 12 hours. The reaction mixture was treated with 2 N hydrochloric acid to be acidic and was extracted with two portions of ethyl acetate. The organic layer was washed with water, dried over anhydrous magnesium sulfate and the solvent was evaporated. The residue was recrystallized from hexane-diisopropyl ether, to give 7.0 g of title compound as colorless crystals.

$^1$H-NMR (400 MHz, CDCl$_3$) δ 3.96 (3H, s), 7.16 (1H, t, J=8.3 Hz), 7.48-7.55 (2H, m), 7.70 (1H, d, J=10.0 Hz), 7.79 (1H, d, J=8.8 Hz), 8.12 (1H, d, J=8.8 Hz), 8.77 (1H, s).

Production Example I-4-f 3-(3-Fluorophenyl)-1H-5-indazolecarboxylic acid

A total of 2.1 g of the title compound as a colorless powder was obtained by the procedure of Production Example I-5-b, except from 2.7 g of methyl 3-(3-fluorophenyl)-1H-5-indazolecarboxylate.

The $^1$H-NMR spectrum thereof agrees with that of the compound according to Production Example I-1-c.

Production Example I-5-a

Methyl 3-(2-fluorophenyl)-1H-5-indazolecarboxylate

A total of 1.9 g of the title compound was obtained as a colorless powder by the procedures of Production Examples I-4-a, I-4-c, I-4-d, and I-4-e, except from 3.7 g of 3-bromo-4-fluorobenzaldehyde dimethylacetal produced in Production Example I-4-a and 1.73 ml of 2-fluorobenzaldehyde as starting materials.

$^1$H-NMR (400 MHz, CDCl$_3$) δ 3.95 (3H, s), 7.26-7.32 (1H, m), 7.32 (1H, dt, J=1.7, 7.4 Hz), 7.44-7.51 (1H, m), 7.53 (1H, d, J=8.7 Hz), 7.82 (1H, dt, J=1.7, 7.4 Hz), 8.13 (1H, dd, J=1.6, 8.7 Hz), 8.64 (1H, bs).

Production Example I-5-b 3-(2-Fluorophenyl)-1H-5-indazolecarboxylic acid

A total of 1.6 g of methyl 3-(2-fluorophenyl)-1H-5-indazolecarboxylate was dissolved in 15 ml of a 1:1 solvent mixture of methanol and tetrahydrofuran, 2 ml of 5 N aqueous sodium hydroxide solution was added, followed by heating at 70° C. for 6 hours. After cooling to room temperature, the reaction mixture was added with diluted hydrochloric acid and was extracted with ethyl acetate for two times. The organic layer was washed with water, dried over anhydrous magnesium sulfate and the solvent was evaporated, to give 1.5 g of the title compound as a colorless powder.

$^1$H-NMR (400 MHz, DMSO-d$_6$) δ 7.38 (1H, dt, J=1.2, 7.5 Hz), 7.43 (1H, ddd, J=1.2, 8.3, 10.9 Hz), 7.50-7.57 (1H, m), 7.66 (1H, d, J=8.7 Hz), 7.80 (1H, dd, J=1.9, 7.5 Hz), 7.95 (1H, dd, J=1.2, 8.7 Hz), 8.39 (1H, bs), 13.71 (1H, s).

Production Example I-6-a

Methyl 3-(2-pyridyl)-1H-5-indazolecarboxylate

A total of 1.0 g of the title compound was obtained as a colorless powder by the procedures of Production Examples I-4-a, I-4-c, I-4-d, and I-4-e, except from 3.7 g of 3-bromo-4-fluorobenzaldehyde dimethylacetal produced in Production Example I-4-a and 1.6 ml of 2-pyridinecarboxaldehyde as starting materials.

$^1$H-NMR (400 MHz, CDCl$_3$) δ 3.88 (3H, s), 7.31 (1H, ddd, J=1.8, 5.2, 7.8 Hz), 7.54 (1H, d, J=8.6 Hz), 7.82 (1H, dt, J=1.8, 7.8 Hz), 8.13 (1H, dd, J=1.8, 8.6 Hz), 8.19 (1H, d, J=7.8 Hz), 8.81 (1H, dd, J=1.8, 5.2 Hz), 9.42 (1H, d, J=1.8 Hz).

Production Example I-6-b 3-(2-Pyridyl)-1H-5-indazolecarboxylic acid

A total of 0.8 g of the title compound was obtained as a pale yellow powder by the procedure of Production Example I-5-b, except from 1.0 g of methyl 3-(2-pyridyl)-1H-5-indazolecarboxylate.

$^1$H-NMR (400 MHz, CDCl$_3$) δ 7.39 (1H, ddd, J=1.8, 4.6, 7.5 Hz), 7.64 (1H, d, J=8.5 Hz), 7.91 (1H, dt, J=1.8, 7.5 Hz), 7.95 (1H, dd, J=1.8, 8.5 Hz), 8.18 (1H, d, J=8.5 Hz), 8.77 (1H, dd, J=1.8, 4.6 Hz), 9.25 (1H, s), 13.63 (1H, bs).

Production Example I-7-a

Methyl 3-(3-pyridyl)-1H-5-indazolecarboxylate

A total of 0.88 g of the title compound was obtained as a colorless powder by the procedures of Production Examples I-4-a, I-4-c, I-4-d, and I-4-e, except from 6.5 g of 3-bromo-4-fluorobenzaldehyde dimethylacetal produced in Production Example I-4-a and 2.7 ml of 3-pyridinecarboxaldehyde as starting materials.

$^1$H-NMR (400 MHz, CDCl$_3$) δ 3.96 (3H, s), 7.49 (1H, dd, J=5.1, 7.6 Hz), 7.57 (1H, d, J=9.1 Hz), 8.15 (1H, dd, J=1.0, 9.1 Hz), 8.30 (1H, dt, J=2.0, 7.6 Hz), 8.71 (1H, dd, J=2.0, 5.1 Hz), 8.78 (1H, d, J=1.0 Hz), 9.18 (1H, d, J=2.0 Hz).

Production Example I-7-b 3-(3-Pyridyl)-1H-5-indazolecarboxylic acid

A total of 0.66 g of the title compound was obtained as a pale yellow powder by the procedure of Production Example I-5-b, except from 0.88 g of methyl 3-(3-pyridyl)-1H-5-indazolecarboxylate.

$^1$H-NMR (400 MHz, DMSO-d$_6$) δ 7.58 (1H, dd, J=5.2, 8.0 Hz), 7.68 (1H, d, J=8.8 Hz), 7.98 (1H, dd, J=1.5, 8.8 Hz), 8.34 (1H, dt, J=1.9, 8.0 Hz), 8.62 (1H, s), 8.64 (1H, dd, J=1.9, 5.2 Hz), 9.15 (1H, d, J=1.9 Hz), 12.80-12.95 (1H, bs), 13.73 (1H, s).

Production Example I-8-a

Methyl 3-(2-methoxyphenyl)-1H-5-indazolecarboxylate

A total of 2.2 g of the title compound was obtained as a colorless oil by the procedures of Production Examples I-4-a, I-4-c, I-4-d, and I-4-e, except from 3.7 g of 3-bromo-4-fluorobenzaldehyde dimethylacetal produced in Production Example I-4-a and 2.0 ml of o-anisaldehyde as starting materials.

$^1$H-NMR (400 MHz, CDCl$_3$) δ 3.89 (3H, s), 3.93 (3H, s), 7.11 (1H, d, J=8.3 Hz), 7.13 (1H, t, J=7.5 Hz), 7.47 (1H, dt, J=1.7, 8.7 Hz), 7.50 (1H, d, J=8.3 Hz), 7.68 (1H, dd, J=1.7, 7.5 Hz), 8.07 (1H, dd, J=1.7, 8.7 Hz), 8.58 (1H, s).

Production Example I-8-b 3-(2-Methoxyphenyl)-1H-5-indazolecarboxylic acid

A total of 2.1 g of the title compound was obtained as a colorless powder by the procedure of Production Example I-5-b, except from 2.2 g of methyl 3-(2-methoxyphenyl)-1H-5-indazolecarboxylate.

$^1$H-NMR (400 MHz, DMSO-d$_6$) δ 3.79 (3H, s), 7.07 (1H, dt, J=1.2, 7.1 Hz), 7.20 (1H, d, J=7.4 Hz), 7.46 (1H, ddd, J=1.9, 7.1, 9.1 Hz), 7.53 (1H, d, J=1.9, 7.4 Hz), 7.58 (1H, dd, J=1.2, 9.1 Hz), 7.90 (1H, dd, J=1.6, 9.1 Hz), 8.29 (1H, s), 13.35-13.50 (1H, bs).

Production Example I-9-a

Methyl 3-(2-quinolyl)-1H-5-indazolecarboxylate

A total of 1.3 g of the title compound was obtained as a colorless powder by the procedures of Production Examples I-4-a, I-4-c, I-4-d, and I-4-e, except from 3.7 g of 3-bromo-4-fluorobenzaldehyde dimethylacetal produced in Production Example I-4-a and 2.4 g of 2-quinolinecarboxaldehyde as starting materials.

$^1$H-NMR (400 MHz, CDCl$_3$) δ 4.03 (3H, s), 7.57 (1H, d, J=8.2 Hz), 7.59 (1H, dd, J=1.8, 8.2 Hz), 7.78 (1H, dt, J=1.8, 8.2 Hz), 7.86 (1H, d, J=8.2 Hz), 8.17 (1H, dd, J=1.8, 8.2 Hz), 8.27 (1H, d, J=8.2 Hz), 8.33 (1H, d, J=8.2 Hz), 8.35 (1H, d, J=8.2 Hz), 9.62 (1H, s).

Production Example I-9-b 3-(2-Quinolyl)-1H-5-indazolecarboxylic acid

A total of 1.1 g of the title compound was obtained as a pale yellow powder by the procedure of Production Example I-5-b, except from 1.3 g of methyl 3-(2-quinolyl)-1H-5-indazolecarboxylate.

$^1$H-NMR (400 MHz, DMSO-d$_6$) δ 7.62 (1H, ddd, J=0.9, 6.9, 8.0 Hz), 7.69 (1H, dd, J=0.9, 8.7 Hz), 7.82 (1H, ddd, J=1.5, 6.9, 8.0 Hz), 8.00 (1H, dd, J=1.8, 8.7 Hz), 8.01 (1H, d, J=8.0 Hz), 8.11 (1H, d, J=8.0 Hz), 8.35 (1H, d, J=8.0 Hz), 8.46 (1H, d, J=8.7 Hz), 9.53 (1H, s), 13.80 (1H, s).

Production Example I-10-a

Methyl 3-(3-quinolyl)-1H-5-indazolecarboxylate

A total of 2.1 g of the title compound was obtained as a pale yellow powder by the procedures of Production Examples I-4-a, I-4-c, I-4-d, and I-4-e, except from 4.98 g of 3-bromo-4-fluorobenzaldehyde dimethylacetal produced in Production Example I-4-a and 3.14 g of 3-quinolinecarboxaldehyde as starting materials.

$^1$H-NMR (400 MHz, DMSO-d$_6$) δ 3.90 (3H, s), 7.68 (1H, t, J=7.6 Hz), 7.74 (1H, d, J=8.7 Hz), 7.81 (1H, t, J=7.6 Hz), 8.02 (1H, dd, J=1.6, 8.7 Hz), 8.08 (1H, d, J=7.6 Hz), 8.22 (1H, d, J=7.6 Hz), 8.80 (1H, s), 8.94 (1H, d, J=2.3 Hz), 9.50 (1H, d, J=2.3 Hz).

Production Example I-10-b 3-(3-Quinolyl)-1H-5-indazolecarboxylic acid

A total of 1.9 g of the title compound was obtained as a pale yellow powder by the procedure of Production Example I-5-b, except from 2.1 g of methyl 3-(3-quinolyl)-1H-5-indazolecarboxylate.

$^1$H-NMR (400 MHz, DMSO-d$_6$) δ 7.65 (1H, t, J=7.6 Hz), 7.68 (1H, d, J=8.7 Hz), 7.80 (1H, t, J=7.6 Hz), 8.02 (1H, dd, J=1.4, 8.7 Hz), 8.22 (1H, d, J=7.6 Hz), 8.22 (1H, d, J=7.6 Hz), 8.77 (1H, s), 8.93 (1H, d, J=2.3 Hz), 9.51 (1H, d, J=2.3 Hz), 13.75-13.85 (1H, bs).

Production Example I-11-a

Methyl 3-(4-quinolyl)-1H-5-indazolecarboxylate

A total of 2.00 g of the title compound was obtained as a colorless powder by the procedures of Production Examples I-4-a, I-4-c, I-4-d, and I-4-e, except from 4.98 g of 3-bromo-4-fluorobenzaldehyde dimethylacetal produced in Production Example I-4-a and 3.14 g of 4-quinolinecarboxaldehyde as starting materials.

$^1$H-NMR (400 MHz, DMSO-d$_6$) δ 3.83 (3H, s), 7.64 (1H, t, J=7.6 Hz), 7.80 (1H, d, J=9.2 Hz), 7.83 (1H, t, J=7.6 Hz), 7.83 (1H, d, J=4.3 Hz), 8.03 (1H, dd, J=1.2, 9.2 Hz), 8.14 (1H, d, J=7.6 Hz), 8.38 (1H, d, J=1.2 Hz), 8.39 (1H, d, J=7.6 Hz), 9.07 (1H, d, J=4.3 Hz).

Production Example I-11-b 3-(4-Quinolyl)-1H-5-indazolecarboxylic acid

A total of 1.8 g of the title compound was obtained as a pale yellow powder by the procedure of Production Example I-5-b, except from 2.0 g of methyl 3-(4-quinolyl)-1H-5-indazolecarboxylate.

$^1$H-NMR (400 MHz, DMSO-d$_6$) δ 7.65 (1H, t, J=7.5 Hz), 7.77 (1H, d, J=8.7 Hz), 7.84 (1H, t, J=7.5 Hz), 7.85 (1H, d, J=4.4, Hz), 8.02 (1H, dd, J=1.4, 8.7 Hz), 8.14 (1H, d, J=7.6 Hz), 8.37 (1H, s), 8.43 (1H, d, J=7.6 Hz), 9.08 (1H, d, J=4.4 Hz), 14.00 (1H, s).

Production Example I-12-a

Methyl 3-(2-naphthyl)-1H-5-indazolecarboxylate

A total of 5.70 g of the title compound was obtained as a colorless powder by the procedures of Production Examples I-4-a, I-4-c, I-4-d, and I-4-e, except from 7.50 g of 3-bromo-4-fluorobenzaldehyde dimethylacetal produced in Production Example I-4-a and 5.20 g of 2-naphthylaldehyde as starting materials.

$^1$H-NMR (400 MHz, DMSO-d$_6$) δ 3.88 (3H, s), 7.53-7.60 (2H, m), 7.71 (1H, dd, J=0.9, 8.8 Hz), 7.96-7.99 (1H, m), 8.00 (1H, dd, J=1.3, 8.8 Hz), 8.08 (1H, d, J=8.8 Hz), 8.10-8.13 (m, 1H), 8.12 (1H, dd, J=1.8, 8.8 Hz), 8.51 (bs, 1H), 8.78 (1H, dd, J=0.9, 1.3 Hz).

Production Example I-12-b 3-(2-Naphthyl)-1H-5-indazolecarboxylic acid

A total of 0.9 g of the title compound was obtained as white crystals by the procedure of Production Example I-5-b, except from 1.0 g of methyl 3-(2-naphthyl)-1H-5-indazolecarboxylate.

¹H-NMR (400 MHz, DMSO-D₆) δ 7.34-7.62 (2H, m), 7.70 (1H, d, J=8.8 Hz), 7.96-8.04 (2H, m), 8.10 (1H, d, J=8.8 Hz), 8.12-8.18 (2H, m), 8.55 (1H, s), 8.79 (1H, s), 12.92 (1H, s), 13.66 (1H, s).

Production Example I-13-a 5-(Dimethoxymethyl)-2-fluorobenzaldehyde

A total of 2.49 g of 3-bromo-4-fluorobenzaldehyde dimethylacetal produced in Production Example I-4-a was dissolved in 20 ml of dry tetrahydrofuran. After cooling to −78° C. in an atmosphere of nitrogen gas, 8.5 ml of a 1.56 M solution of n-butyllithium in hexane was added. After stirring for 30 minutes, 1.0 ml of N,N-dimethylformamide was added and the mixture was heated to room temperature. To the reaction mixture was added aqueous ammonium chloride solution, and the mixture was extracted with ethyl acetate for two times. The organic layer was washed with water, dried over anhydrous magnesium sulfate and the solvent was evaporated. The residue was purified and separated by silica gel column chromatography (ethyl acetate:hexane=1:12.5), to give 1.35 g of the title compound as a colorless oil.
¹H-NMR (400 MHz, DMSO-D₆) δ 3.24 (6H, s), 5.45 (1H, s), 7.42 (1H, dd, J=9.0, 10.0 Hz), 7.68-7.75 (1H, m), 7.82 (1H, dd, J=2.0, 7.0 Hz), 10.21 (1H, s).

Production Example I-13-b 1,3-Benzothiazol-2-yl[5-(dimethoxymethyl)-2-fluorophenyl]methanol A total of 1.08 g of benzothiazole was dissolved in 15 ml of dry tetrahydrofuran. After cooling to −78° C. in an atmosphere of nitrogen gas, 6.4 ml of 1.56 M solution of n-butyllithium in hexane was added. After stirring for 5 minutes, 8 ml of a solution of 1.35 g of 5-(dimethoxymethyl)-2-fluorobenzaldehyde in dry tetrahydrofuran was added, followed by stirring for 10 minutes. To the reaction mixture was added aqueous ammonium chloride solution, and the mixture was extracted with ethyl acetate for two times. The organic layer was washed with water, dried over anhydrous magnesium sulfate and the solvent was evaporated. The residue was purified and separated by silica gel column chromatography (ethyl acetate:hexane=3:7), to give 1.8 g of the title compound as a yellow oil.
¹H-NMR (400 MHz, DMSO-d₆) δ 3.20 (6H, s), 5.35 (1H, s), 6.25 (1H, s), 7.11-7.16 (1H, bs), 7.21 (1H, dd, J=8.2, 9.7 Hz), 7.32-7.37 (1H, m), 7.39 (1H, t, J=7.7 Hz), 7.45 (1H, t, J=7.7 Hz), 7.55 (1H, d, J=2.6, 6.7 Hz), 7.88 (1H, d, J=7.7 Hz), 8.08 (1H, d, J=7.7 Hz).

Production Example I-13-c

Methyl 3-(1,3-benzothiazol-2-yl)-1H-5-indazolecarboxylate

A total of 1.05 g of the title compound was obtained as a colorless powder by the procedures of Production Examples I-4-c, I-4-d, and I-4-e, except from 1.8 g of 1,3-benzothiazol-2-yl[5-(dimethoxymethyl)-2-fluorophenyl]methanol as a starting material.
¹H-NMR (400 MHz, CDCl₃) δ 4.02 (3H, s), 7.45 (1H, ddd, J=1.1, 7.2, 8.4 Hz), 7.55 (1H, ddd, J=1.1, 7.2, 8.4 Hz), 7.59 (1H, dd, J=0.9, 8.9 Hz), 7.97 (1H, ddd, J=0.7, 1.1, 8.1 Hz), 8.20 (1H, dd, J=1.4, 8.9 Hz), 8.23 (1H, ddd, J=0.7, 1.1, 8.1 Hz), 9.41 (1H, dd, J=0.9, 1.4 Hz), 10.36-10.48 (1H, bs).

Production Example I-13-d 3-(1,3-Benzothiazol-2-yl)-1H-5-indazolecarboxylic acid A total of 0.95 g of the title compound was obtained as a colorless powder by the procedure of Production Example I-5-b, except from 1.2 g of methyl 3-(1,3-benzothiazol-2-yl)-1H-5-indazolecarboxylate.
¹H-NMR (400 MHz, DMSO-d₆) δ 7.39 (1H, t, J=7.2 Hz), 7.57 (1H, t, J=7.2 Hz), 7.75 (1H, dd, J=0.8, 8.6 Hz), 8.04 (1H, dd, J=1.8, 8.6 Hz), 8.16 (1H, d, J=7.2 Hz), 8.19 (1H, d, J=7.2 Hz), 9.14 (1H, dd, J=0.8, 1.8 Hz), 12.80-13.20 (1H, bs), 14.07 (1H, s).

Production Example I-14-a

3-Bromo-1H-5-indazolecarbonitrile

To a solution of 300 mg of a compound 1H-5-indazolecarbonitrile (synthesized from 4-fluorobenzonitrile according to the procedures described in literature, Tetrahedron Lett., 33, 7499 (1992) and Synthetic commun., 27, 1199 (1997)) in 3 ml dimethylformamide was added 392 mg of N-bromosuccinimide at room temperature, and the mixture was stirred at the same temperature for one day. After removing the solvent by distillation, the residue was added with 25 ml of ethyl acetate. The mixture was sequentially washed with half-saturated aqueous sodium hydrogencarbonate solution, water and brine, dried over anhydrous magnesium sulfate and the solvent was evaporated, to give 440 mg of the title compound as pale red crystals.
¹H-NMR (400 MHz, CDCl₃) δ 7.59 (1H, dd, J=8.4, 0.8 Hz), 7.67 (1H, dd, J=8.4, 1.6 Hz), 8.07 (1H, dd, J=1.6, 0.8 Hz).

Production Example I-14-b tert-Butyl 3-bromo-5-cyano-1H-1-indazolecarboxylate

To a solution of 6.25 g of 3-bromo-1H-5-indazolecarbonitrile in 100 ml tetrahydrofuran at room temperature were added 6.76 g of di-tert-butyl dicarbonate and 516 mg of 4-(dimethylamino)pyridine, and the mixture was stirred at the same temperature overnight. After removing the solvent by distillation, the residue was added with 220 ml of ethyl acetate. The mixture was sequentially washed with diluted hydrochloric acid, water, saturated aqueous sodium hydrogencarbonate solution and brine, dried over anhydrous magnesium sulfate and the solvent was evaporated, to give 8.69 g of the title compound as pale red crystals.
¹H-NMR (400 MHz, CDCl₃) δ 1.73 (9H, s), 7.80 (1H, dd, J=8.8, 1.6 Hz), 8.03 (1H, d, J=1.6 Hz), 8.30 (1H, d, J=8.8 Hz).

Production Example I-14-c 3-(4-Fluorophenyl)-1H-5-indazolecarbonitrile

To a solution of 2.0 g of tert-butyl 3-bromo-5-cyano-1H-1-indazolecarboxylate in 30 ml tetrahydrofuran were added 70 mg of palladium(II) acetate, 218 mg of 2-(dicyclohexylphosphino)biphenyl, 1.19 g of potassium fluoride and 1.30 g of 4-fluorophenylboronic acid, and the mixture was stirred at 50° C. for one day. After removing the solvent by distillation, the residue was diluted with 40 ml of ethyl acetate. The mixture was sequentially washed with water and brine, dried over anhydrous magnesium sulfate and the solvent was evaporated. The residue was dissolved in 25 ml of methylene chloride, and 5 ml of trifluoroacetic acid was added, followed by stirring at room temperature for 1 hour. After removing the solvent by distillation, the residue was diluted with 40 ml of ethyl acetate. The mixture was sequentially washed with saturated aqueous sodium hydrogencarbonate solution and brine, dried over anhydrous magnesium sulfate and the solvent was evaporated. The crude product was purified and separated by silica gel column chromatography (ethyl acetate:toluene=1: 19 to 1:9), to give 1.09 g of the title compound as bright yellow crystals.

$^1$H-NMR (400 MHz, DMSO-D$_6$) δ 7.36 (2H, t, J=8.8 Hz), 7.74 (1H, dd, J=8.8, 1.2 Hz), 7.76 (1H, dd, J=8.8, 1.2 Hz), 8.10 (2H, dd, J=8.8, 5.6 Hz), 8.71 (1H, s), 13.78 (1H, s).

Production Example I-14-d 3-(4-Fluorophenyl)-1H-5-indazolecarboxylic acid

To 1.0 g of 3-(4-fluorophenyl)-1H-5-indazolecarbonitrile were added 5 ml of water, 4 ml of concentrated sulfuric acid and 4 ml of glacial acetic acid, and the mixture was heated under reflux for 3 hours. After standing to cool, 25 ml of ice-cooled water was added. The resulting crystals were collected by filtration. The collected crystals were dissolved in 250 ml of ethyl acetate, sequentially washed with water and brine, and dried over anhydrous magnesium sulfate. After filtrating the organic layer through a silica gel pat, the solvent was evaporated, to give 968 mg of the title compound as bright yellow crystals.

$^1$H-NMR (400 MHz, DMSO-D$_6$) δ 7.41 (2H, t, J=8.8 Hz), 7.66 (1H, d, J=8.8 Hz), 7.95-8.09 (3H, m), 8.63 (1H, s), 12.91 (1H, s), 13.58 (1H, s).

Production Example I-15-a 3-(3-Chlorophenyl)-1H-5-indazolecarbonitrile

A total of 137 mg of the title compound was obtained as white crystals by the procedure of Production Example I-14-c, except from 2.0 g of tert-butyl 3-bromo-5-cyano-1H-1-indazolecarboxylate produced in Production Example I-14-b and 1.46 g of 3-chlorophenylboronic acid.

$^1$H-NMR (400 MHz, CDCl$_3$) δ 7.46 (1H, dt, J=8.0, 1.6 Hz), 7.51 (1H, d, J=8.4 Hz), 7.64 (1H, t, J=8.0 Hz), 7.67 (1H, dd, J=8.4, 1.2 Hz), 7.81 (1H, dt, J=8.0, 1.6 Hz), 7.93 (1H, t, J=1.6 Hz), 8.40 (1H, d, J=1.2 Hz).

Production Example I-15-b 3-(3-Chlorophenyl)-1H-5-indazolecarboxylic acid

A total of 115 mg of the title compound was obtained as beige crystals by the procedure of Production Example I-14-d, except using 135 mg of 3-(3-chlorophenyl)-1H-5-indazolecarbonitrile.

$^1$H-NMR (400 MHz, DMSO-D$_6$) δ 7.53 (1H, dd, J=8.0, 1.6 Hz), 7.62 (1H, td, J=8.0, 1.6 Hz), 7.69 (1H, d, J=8.0 Hz), 7.93-8.05 (3H, m), 8.63 (1H, s), 12.90 (1H, s), 13.71 (1H, s).

Production Example I-16-a

3-[3-(Trifluoromethyl)phenyl]-1H-5-indazolecarbonitrile

A total of 58 mg of the title compound was obtained as white crystals by the procedure of Production Example I-14-c, except using 500 mg of tert-butyl 3-bromo-5-cyano-1H-1-indazolecarboxylate produced in Production Example I-14-b and 442 mg of 3-trifluoromethylphenylboronic acid.

$^1$H-NMR (400 MHz, CDCl$_3$). δ 7.63-7.76 (4H, m), 8.11 (1H, d, J=7.6 Hz), 8.21 (1H, s), 8.40 (1H, s).

Production Example I-16-b

3-[3-(Trifluoromethyl)phenyl]-1H-5-indazolecarboxylic acid

A total of 54 mg of the title compound was obtained as beige crystals by the procedure of Production Example I-14-d, except using 57 mg of 3-[3-(trifluoromethyl)phenyl]-1H-5-indazolecarbonitrile.

$^1$H-NMR (400 MHz, DMSO-D$_6$) δ 7.71 (1H, d, J=8.4 Hz), 7.83 (2H, m), 8.01 (1H, d, J=8.8 Hz), 8.24 (1H, s), 8.32 (1H, m), 8.66 (1H, s), 12.96 (1H, s), 13.77 (1H, s).

Production Example I-17-a

3-Benzo[b]thiophen-2-yl-1H-5-indazolecarbonitrile

To a solution of 600 mg of tert-butyl 3-bromo-5-cyano-1H-1-indazolecarboxylate produced in Production Example I-14-b in 9 ml tetrahydrofuran were added 21 mg of palladium (II) acetate, 57 mg of 2-(di-tert-butylphosphino)biphenyl, 357 mg of potassium fluoride and 498 mg of 2-benzo[b]thiopheneboronic acid, and the mixture was stirred at 50° C. for 1 hour. After removing the solvent by distillation, the residue was dissolved in 2 ml of methylene chloride. 4 ml of trifluoroacetic acid was added and the mixture was stirred at room temperature for one day. After removing the solvent by distillation, the residue was diluted with 50 ml of ethyl acetate. The mixture was sequentially washed with saturated aqueous sodium hydrogencarbonate solution and brine, dried over anhydrous magnesium sulfate and the solvent was evaporated. The crude product was purified and separated by silica gel column chromatography (ethyl acetate:toluene=1: 19), to give 294 mg of the title compound as bright yellow crystals.

$^1$H-NMR (400 MHz, DMSO-D$_6$) δ 7.41 (2H, t, J=7.8 Hz), 7.44 (2H, t, J=7.8 Hz), 7.80 (2H, s), 7.91 (1H, d, J=8.0 Hz), 8.01 (1H, d, J=8.0 Hz), 8.41 (1H, s), 8.99 (1H, s), 13.88 (1H, s).

Production Example I-17-b

3-Benzo[b]thiophen-2-yl-1H-5-indazolecarboxylic acid

To 288 mg of 3-benzo[b]thiophen-2-yl-1H-5-indazolecarbonitrile were added 3 ml of glacial acetic acid, 1 ml of water and 0.8 ml of concentrated sulfuric acid, and the mixture was stirred at 110° C. for 4 hours. After standing to cool, the mixture was added with 120 ml of ethyl acetate, sequentially washed with water and brine, dried over anhydrous magnesium sulfate. After filtering the organic layer through a silica gel pat, the solvent was evaporated, to give 307 mg of the title compound as ocher yellow crystals.

¹H-NMR (400 MHz, DMSO-D₆) δ 7.36-7.48 (2H, m), 7.71 (1H, d, J=8.8 Hz), 7.99-8.07 (3H, m), 8.17 (1H, s), 8.83 (1H, s), 13.72 (1H, s).

Production Example I-18-a 3-(3-Methoxyphenyl)-1H-5-indazolecarbonitrile

A total of 66 mg of the title compound was obtained as bright yellow crystals by the procedure of Production Example I-17-a, except from 200 mg of tert-butyl 3-bromo-5-cyano-1H-1-indazolecarboxylate produced in Production Example I-14-b and 142 mg of 3-methoxyphenylboronic acid.
¹H-NMR (400 MHz, DMSO-D₆) δ 3.87 (3H, s), 7.03 (1H, dd, J=8.0, 2.4 Hz), 7.46 (1H, t, J=8.0 Hz), 7.51 (1H, s), 7.62 (1H, d, J=8.0 Hz), 7.73 (1H, d, J=8.8 Hz), 7.77 (1H, d, J=8.8 Hz), 8.67 (1H, s), 13.76 (1H, s).

Production Example I-18-b 3-(3-Methoxyphenyl)-1H-5-indazolecarboxylic acid

A total of 14 mg of the title compound was obtained as orange crystals by the procedure of Production Example I-17-b, except from 65 mg of 3-(3-methoxyphenyl)-1H-5-indazolecarbonitrile.
¹H-NMR (400 MHz, DMSO-D₆) δ 3.86 (3H, s), 7.04 (1H, dd, J=8.4, 2.4 Hz), 7.50 (1H, t, J=8.0 Hz), 7.54 (1H, s), 7.61 (1H, d, J=8.0 Hz), 7.66 (1H, d, J=8.0 Hz), 7.93 (1H, d, J=8.4 Hz), 8.60 (1H, s), 12.85 (1H, s), 13.44 (1H, s).

Production Example I-19-a

3-Benzo[b]thiophen-3-yl-1H-5-indazolecarbonitrile

A total of 303 mg of the title compound was obtained as light brown crystals by the procedure of Production Example I-17-a, except from 500 mg of tert-butyl 3-bromo-5-cyano-1H-1-indazolecarboxylate produced in Production Example I-14-b and 415 mg of 3-benzo[b]thiopheneboronic acid.
¹H-NMR (400 MHz, DMSO-D₆) δ 7.45-7.55 (2H, m), 7.77 (1H, d, J=8.8 Hz), 7.82 (1H, d, J=8.8 Hz), 8.11 (1H, d, J=7.2 Hz), 8.60 (1H, s), 8.70 (1H, d, J=7.2 Hz), 8.77 (1H, s), 13.85 (1H, s).

Production Example I-19-b

3-Benzo[b]thiophen-3-yl-1H-5-indazolecarboxylic acid

A total of 301 mg of the title compound was obtained as red crystals by the procedure of Production Example I-17-b, except from 300 mg of 3-benzo[b]thiophen-3-yl-1H-5-indazolecarbonitile.
¹H-NMR (400 MHz, DMSO-D₆) δ 7.45-7.55 (2H, m), 7.71 (1H, d, J=8.8 Hz), 8.01 (1H, d, J=8.8 Hz), 8.11 (1H, d, J=7.2 Hz), 8.40 (1H, s), 8.57 (1H, d, J=7.2 Hz), 8.66 (1H, s), 12.89 (1H, s), 13.65 (1H, s).

Production Example I-20-a 3-(5-Acetyl-2-thienyl)-1H-5-indazolecarbonitrile

A total of 94 mg of the title compound was obtained as green crystals by the procedure of Production Example I-17-a, except from 500 mg of tert-butyl 3-bromo-5-cyano-1H-1-indazolecarboxylate produced in Production Example I-14-b and 528 mg of 5-acetyl-2-thiopheneboronic acid.
¹H-NMR (400 MHz, DMSO-D₆) δ 2.59 (3H, s), 7.78 (1H, d, J=8.8 Hz), 7.81 (1H, d, J=8.8 Hz), 8.03 (1H, d, J=4.0 Hz), 8.08 (1H, d, J=4.0 Hz), 8.87 (1H, s), 13.98 (1H, s).

Production Example I-20-b 3-(5-Acetyl-2-thienyl)-1H-5-indazolecarboxylic acid

A total of 85 mg of the title compound was obtained as ocher yellow crystals by the procedure of Production Example I-17-b, except from 94 mg of 3-(5-acetyl-2-thienyl)-1H-5-indazolecarbonitrile.
¹H-NMR (400 MHz, DMSO-D₆) δ 2.59 (3H, s), 7.70 (1H, d, J=8.8 Hz), 7.87 (1H, d, J=3.6 Hz), 8.01 (1H, d, J=8.8 Hz), 8.03 (1H, d, J=3.6 Hz), 8.69 (1H, s), 13.00 (1H, s), 13.82 (1H, s).

Production Example I-21-a 1H-5-Indazolecarboxylic acid

To 867 mg of 1H-5-indazolecarbonitrile used in Production Example I-14-a were added 8 ml of glacial acetic acid, 2.5 ml of water and 2 ml of concentrated sulfuric acid, and the mixture was stirred at 110° C. for 10 hours. After standing to cool, the mixture was added with 50 ml of water, and the resulting crystals were collected by filtration and dried in vacuo, to give 911 mg of the title compound as white crystals.
¹H-NMR (400 MHz, DMSO-D₆) δ 7.59 (1H, dd, J=0.8, 8.8 Hz), 7.91 (1H, dd, J=0.8, 8.8 Hz), 8.24 (1H, s), 8.45 (1H, s), 13.36 (1H, s).

Production Example I-21-b

Methyl 1H-5-Indazolecarboxylate

Under ice-cooling, to a solution of 910 mg of 1H-5-indazolecarboxylic acid in 60 ml tetrahydrofuran was added an excess amount of a solution of diazomethane in diethyl ether, and the mixture was stirred at the same temperature for 1 hour. After removing the solvent by distillation, the residue was added with 50 ml of ethyl acetate, sequentially washed with saturated aqueous sodium hydrogencarbonate solution and brine, dried over anhydrous magnesium sulfate and the solvent was evaporated, to give 923 mg of the title compound as pale yellow crystals.
¹H-NMR (400 MHz, DMSO-D₆) δ 3.87 (3H, s), 7.62 (1H, d, J=8.8 Hz), 7.92 (1H, d, J=8.8 Hz), 8.26 (1H, s), 8.49 (1H, s), 13.42 (1H, s).

Production Example I-21-c 1-(tert-Butyl) 5-methyl 3-bromo-1H-1,5-indazoledicarboxylate A total of 1.43 g of the title compound was obtained as white crystals by the procedure of Production Examples I-14-a and I-14-b, except from 923 mg of methyl 1H-5-indazolecarboxylate.

$^1$H-NMR (400 MHz, DMSO-D$_6$) δ 3.92 (3H, s), 8.19-8.24 (2H, m), 8.26 (1H, dd, J=1.2, 8.8 Hz).

Production Example I-21-d

Methyl 3-benzo[b]furan-2-yl-1H-5-indazolecarboxylate

A total of 281 mg of the title compound was obtained by the procedure of Production Example I-17-a, except from 700 mg of 1-(tert-butyl) 5-methyl 3-bromo-1H-1,5-indazoledicarboxylate and 479 mg of 2-benzo[b]furanboronic acid.

$^1$H-NMR (400 MHz, DMSO-D$_6$) δ 3.93 (3H, s), 7.33 (1H, t, J=7.6 Hz), 7.40 (1H, t, J=8.0 Hz), 7.56 (1H, s), 7.72-7.80 (3H, m), 8.03 (1H, dd, J=1.6, 8.8 Hz), 8.86 (1H, s), 13.91 (1H, s).

Production Example I-21-e

3-Benzo[b]furan-2-yl-1H-5-indazolecarboxylic acid

To a solution of 275 mg of methyl 3-benzo[b]furan-2-yl-1H-5-indazolecarboxylate in 3 ml methanol and 3 ml tetrahydrofuran was added 1.5 ml of 5 N aqueous sodium hydroxide solution, and the mixture was stirred at room temperature for five days. After removing the solvent by distillation, the residue was added with 9 ml of 1 N hydrochloric acid, and the mixture was extracted with 200 ml of ethyl acetate. The organic layer was washed with brine, dried over anhydrous magnesium sulfate and the solvent was evaporated, to give 320 mg of the title compound as pale yellow crystals.

$^1$H-NMR (400 MHz, DMSO-D$_6$) δ 7.32 (1H, t, J=7.2 Hz), 7.39 (1H, t, J=8.0 Hz), 7.54 (1H, s), 7.71 (1H, d, J=8.8 Hz), 7.84-7.79 (2H, m), 8.02 (1H, d, J=8.8 Hz), 8.85 (1H, s), 12.99 (1H, s), 13.85 (1H, s).

Production Example I-22-a

Methyl 3-(3-acetylphenyl)-1H-5-indazolecarboxylate

A total of 92 mg of the title compound was obtained as light brown crystals by the procedure of Production Example I-17-a, except from 355 mg of 1-(tert-butyl) 5-methyl 3-bromo-1H-1,5-indazoledicarboxylate produced in Production Example I-21-c and 246 mg of 3-acetylphenylboronic acid.

$^1$H-NMR (400 MHz, DMSO-D$_6$) δ 2.69 (3H, s), 3.90 (3H, s), 7.73 (1H, d, J=8.8 Hz), 7.75 (1H, t, J=8.0 Hz), 8.01 (1H, dd, J=1.2, 8.8 Hz), 8.06 (1H, dt, J=8.0, 1.2 Hz), 8.25 (1H, dt, J=8.0, 1.2 Hz), 8.50 (1H, t, J=1.2 Hz), 8.68 (1H, d, J=1.2 Hz), 13.75 (1H, s).

Production Example I-22-b 3-(3-Acetylphenyl)-1H-5-indazolecarboxylic acid

A total of 83 mg of the title compound was obtained as yellow crystals by the procedure of Production Example I-21-e, except from 91 mg of methyl 3-(3-acetylphenyl)-1H-5-indazolecarboxylate.

$^1$H-NMR (400 MHz, DMSO-D$_6$) δ 2.68 (3H, s), 7.70 (1H, d, J=8.8 Hz), 7.74 (1H, t, J=8.0 Hz), 7.99 (1H, d, J=8.8 Hz), 8.06 (1H, d, J=8.0 Hz), 8.25 (1H, d, J=8.0 Hz), 8.50 (1H, s), 8.68 (1H, s), 12.93 (1H, s), 13.70 (1H, s).

Production Example I-23-a

3-Phenyl-1H-5-indazolecarbonitrile

To a solution of 300 mg of tert-butyl 3-bromo-5-cyano-1H-1-indazolecarboxylate produced in Production Example I-14-b in 10 ml dimethylformamide were added 376 mg of tri-n-butyl(phenyl)tin and 54 mg of tetrakis(triphenylphosphine)palladium(0), and the mixture was stirred at 150° C. for 45 minutes. After removing the solvent by distillation, the residue was dissolved in 1.5 ml of ethyl acetate and the mixture was adsorbed by 1.5 g of silica gel. The crude product was purified and separated by silica gel column chromatography (ethyl acetate:toluene=3:97 to 1:19) and the resulting amorphous powder was crystallized from diisopropyl ether, to give 117 mg of the title compound as pale yellow crystals.

$^1$H-NMR (400 MHz, DMSO-D$_6$) δ 7.46 (1H, t, J=8.0 Hz), 7.55 (2H, t, J=8.0 Hz), 7.73 (1H, d, J=8.8 Hz), 7.77 (1H, d, J=8.8 Hz), 8.05 (2H, d, J=8.0 Hz), 8.71 (1H, s), 13.76 (1H, s).

Production Example I-23-b

3-Phenyl-1H-5-indazolecarboxylic acid

A total of 110 mg of the title compound was obtained as pale red crystals by the procedure of Production Example I-17-b, except from 116 mg of 3-phenyl-1H-5-indazolecarbonitrile.

$^1$H-NMR (400 MHz, DMSO-D$_6$) δ 7.46 (1H, t, J=8.0 Hz), 7.57 (2H, t, J=8.0 Hz), 7.66 (1H, d, J=8.8 Hz), 7.97 (3H, d, J=8.0 Hz), 8.65 (1H, s), 12.10 (1H, s), 13.56 (1H, s).

Production Example I-24-a tert-Butyl 3-(3-fluorophenyl)-5-(hydroxymethyl)-1H-1-indazolecarboxylate Under ice-cooling, a solution of 10.66 g of 3-(3-fluorophenyl)-1H-5-indazolecarboxylic acid produced in Example I-1-c in 270 ml tetrahydrofuran was added 2.96 g of lithium aluminium hydride, and the mixture was stirred at the same temperature for 30 minutes and then heated under reflux for 7 hours. After ice-cooling again, 0.99 g of lithium aluminium hydride was further added, and the mixture was further heated under reflux for 2 hours. The reaction mixture was ice-cooled, and saturated aqueous ammonium chloride solution was added. Then, 200 ml of 1 N hydrochloric acid was added, and the mixture was extracted with ethyl acetate for two times. The organic layer was washed with brine, and dried over anhydrous magnesium sulfate. After filtrating the organic layer through a silica gel pat, the solvent was evaporated. After the resulting crystals were dissolved in 70 ml of tetrahydrofuran, 7.9 g of di-tert-butyl dicarbonate and 0.44 g of 4-N,N-dimethylaminopyridine were added and the mixture was stirred at room temperature for 1 hour. The reaction mixture was added with 250 ml of ethyl acetate, sequentially washed with 1 N hydrochloric acid, water, saturated aqueous sodium hydrogencarbonate solution and brine, dried over anhydrous magnesium sulfate and the solvent was removed. The residue was recrystallized from ethyl acetate-diisopropyl ether, to give 7.44 g of the title compound as white needles. The mother liquor was concentrated, and the residue was purified and separated by silica gel column chromatography (ethyl acetate:toluene=1:9), to give 1.82 g of the title compound as yellow crystals.

¹H-NMR (400 MHz, DMSO-D₆) δ 1.68 (9H, s), 4.68 (2H, d, J=5.6 Hz), 5.38 (1H, t, J=5.6 Hz), 7.41 (1H, td, J=8.4, 2.4 Hz), 7.60-7.70 (2H, m), 7.75 (1H, d, J=9.2 Hz), 7.85 (1H, d, J=8.0 Hz), 8.04 (1H, s), 8.12 (1H, d, J=8.8 Hz).

Production Example I-24-b tert-Butyl 5-(chloromethyl)-3-(3-fluorophenyl)-1H-1-indazolecarboxylate Under ice-cooling, to a solution of 3.0 g of tert-butyl 3-(3-fluorophenyl)-5-(hydroxymethyl)-1H-1-indazolecarboxylate in 30 ml methylene chloride were added 1.6 ml of triethylamine and 0.78 ml of methanesulfonyl chloride, and the mixture was stirred at room temperature for one day. To the reaction mixture was added 180 ml of ethyl acetate, and the mixture was sequentially washed with water, 1 N hydrochloric acid, water, saturated aqueous sodium hydrogencarbonate solution and brine, dried over anhydrous magnesium sulfate and the solvent was evaporated. The crude product was purified and separated by silica gel column chromatography (toluene), to give 2.74 g of the title compound as yellow crystals.
¹H-NMR (400 MHz, DMSO-D₆) δ 1.69 (9H, s), 4.99 (2H, s), 7.42 (1H, td, J=8.0, 2.4 Hz), 7.67 (1H, td, J=8.0, 6.4 Hz), 7.76 (1H, d, J=8.8 Hz), 7.78 (1H, d, J=8.0 Hz), 7.86 (1H, d, J=8.0 Hz), 8.18 (1H, d, J=8.8 Hz), 8.27 (1H, s).

Production Example I-24-c

2-[3-(3-Fluorophenyl)-1H-5-indazolyl]acetonitrile

To a solution of 1.0 g of tert-butyl 5-(chloromethyl)-3-(3-fluorophenyl)-1H-1-indazolecarboxylate in 5 ml dimethyl sulfoxide was added 204 mg of sodium cyanide, and the mixture was stirred at room temperature for 50 minutes. To the reaction mixture was added 50 ml of ethyl acetate, and after washing with water, the aqueous layer was re-extracted with diethyl ether. The collected organic layer was sequentially washed with water (×2) and brine, dried over anhydrous magnesium sulfate and the solvent was evaporated. The crude product was purified and separated by silica gel column chromatography (ethyl acetate:toluene=1:9), and suspended in diethyl ether-diisopropyl ether, to give 62 mg of the title compound as yellow crystals.
¹H-NMR (400 MHz, DMSO-D₆) δ 4.16 (2H, s), 7.26 (1H, td, J=8.4, 2.4 Hz), 7.42 (1H, d, J=8.8 Hz), 7.59 (1H, td, J=8.0, 6.4 Hz), 7.65 (1H, d, J=8.8 Hz), 7.74 (1H, d, J=10.4 Hz), 7.84 (1H, d, J=8.0 Hz), 8.12 (1H, s), 13.46 (1H, s).

Production Example I-24-d

2-[3-(3-Fluorophenyl)-1H-5-indazolyl]acetic acid 50 mg of 2-[3-(3-fluorophenyl)-1H-5-indazolyl]acetonitrile was suspended in 0.5 ml of water and 0.4 ml of concentrated sulfuric acid, and the suspension was stirred at 95° C. for 2 hours. The reaction mixture was added with 20 ml of ethyl acetate, sequentially washed with water (×2) and brine, dried over anhydrous magnesium sulfate and the solvent was evaporated, to give 48 mg of the title compound as pale red crystals.
¹H-NMR (400 MHz, DMSO-D₆) δ 3.74 (2H, s), 7.24 (1H, td, J=8.4, 2.4 Hz), 7.32 (1H, d, J=8.8 Hz), 7.52-7.62 (2H, m), 7.74 (1H, d, J=10.4 Hz), 7.85 (1H, d, J=8.0 Hz), 7.99 (1H, s), 12.31 (1H, s), 13.33 (1H, s).

Production Example I-25-a tert-Butyl 3-(3-fluorophenyl)-5-formyl-1H-1-indazolecarboxylate A total of 1.5 g of the title compound was obtained as a colorless powder by subjecting 1.7 g of tert-butyl 3-(3-fluorophenyl)-5-(hydroxymethyl)-1H-1-indazolecarboxylate produced in Production Example I-24-a to the oxidation procedure of Production Example I-4-b.
¹H-NMR (400 MHz, CDCl₃) δ 1.75 (9H, s), 7.22 (1H, dt, J=2.5, 10.0 Hz), 7.54 (1H, dt, J=6.1, 8.2 Hz), 7.73 (1H, dd, J=2.5, 10.0 Hz), 7.80 (1H, d, J=10.0 Hz), 8.11 (1H, dd, J=1.5, 8.8 Hz), 8.36 (1H, d, J=8.8 Hz), 8.48 (1H, s), 10.14 (1H, s).

Production Example I-25-b

Ethyl (E)-3-[3-(3-fluorophenyl)-1H-5-indazolyl]-2-propenoate

To a solution of 0.11 ml ethyl diethylphosphonoacetate in 5 ml N,N-dimethylformamide was added 20 mg of sodium hydride (60% oily) under ice-cooling, and the mixture was stirred for 15 minutes. To the reaction mixture was added a solution of 150 mg of tert-butyl 3-(3-fluorophenyl)-5-formyl-1H-1-indazolecarboxylate in 1 ml N,N-dimethylformamide, followed by stirring at room temperature for 30 minutes. To the reaction mixture was added water and the mixture was extracted with ethyl acetate. The organic layer was washed with water, dried over anhydrous magnesium sulfate and the solvent was evaporated. The residue was purified and separated by silica gel column chromatography (ethyl acetate:hexane=1:10), to give 0.16 g of tert-butyl 5-[(E)-3-ethoxy-3-oxo-1-propenyl]-3-(3-fluorophenyl)-1H-1-indazolecarboxylate as a colorless oil. This product was dissolved in 2 ml of tetrahydrofuran, 0.1 ml of 5 N hydrochloric acid was added and the mixture was stirred at room temperature for 1 hour. To the reaction mixture was added saturated aqueous sodium hydrogencarbonate solution, and the mixture was extracted with ethyl acetate for two times. The organic layer was washed with water, dried over anhydrous magnesium sulfate and the solvent was evaporated, to give 0.14 g of the title compound as a colorless powder.
¹H-NMR (400 MHz, DMSO-d₆) δ 1.25 (3H, t, J=7.0 Hz), 4.18 (2H, q, J=7.0 Hz), 6.77 (1H, d, J=16.1 Hz), 7.24 (1H, dt, J=2.4, 8.0 Hz), 7.55 (1H, dt, J=6.4, 8.0 Hz), 7.60 (1H, d, J=8.8 Hz), 7.79-7.84 (1H, m), 7.84 (1H, d, J=8.8 Hz), 7.88 (1H, d, J=16.1 Hz), 7.93 (1H, d, J=8.0 Hz), 8.48 (1H, s), 13.50-13.60 (1H, bs).

Production Example I-25-c (E)-3-[3-(3-Fluorophenyl)-1H-5-indazolyl]-2-propenoic acid To a solution of 0.16 g of ethyl (E)-3-[3-(3-fluorophenyl)-1H-5-indazolyl]-2-propenoate in methanol was added 1 ml of 5 N aqueous sodium hydroxide solution, and the mixture was stirred at room temperature for 30 minutes. The reaction mixture was added with diluted hydrochloric acid to be acidic and was extracted with ethyl acetate for two times. The organic layer was washed with water, dried over anhydrous magnesium sulfate and the solvent was evaporated, to give 90 mg of the title compound as a colorless powder.
¹H-NMR (400 MHz, DMSO-d₆) δ 6.56 (1H, d, J=16.4 Hz), 7.24 (1H, dt, J=2.2, 8.2 Hz), 7.55 (1H, dt, J=6.0, 8.2 Hz), 7.60 (1H, d, J=8.6 Hz), 7.79-7.83 (1H, m), 7.81 (1H, d, J=8.8 Hz), 7.83 (1H, d, J=16.4 Hz), 7.92 (1H, d, J=8.0 Hz), 8.43 (1H, s), 12.15-12.35 (1H, bs), 13.52 (1H, s).

Production Example I-26-a

3-Bromo-5-nitro-1H-indazole

To a solution of 12.4 g of 5-nitro-1H-indazole in 100 ml carbon tetrachloride were added 16.2 g of N-bromosuccinimide and 0.62 g of 2,2'-azobisisobutyronitrile, and the mixture was heated under reflux for 1 hour. The reaction mixture was cooled, and the resulting crystals were filtrated and washed with diethyl ether, to give 24.0 g of the title compound as a pale yellow powder.
$^1$H-NMR (400 MHz, DMSO-d$_6$) δ 7.78 (1H, dd, J=0.5, 9.3 Hz), 8.25 (1H, dd, J=2.1, 9.3 Hz), 8.48 (1H, dd, J=0.5, 2.1 Hz).

Production Example I-26-b tert-Butyl 3-bromo-5-nitro-1H-1-indazolecarboxylate To a solution of 24.0 g of 3-bromo-5-nitro-1H-indazole and 12.2 g of 4-(dimethylamino)pyridine in 50 ml tetrahydrofuran was added dropwise 23 ml of di-tert-butyl carbonate at room temperature. After stirring at room temperature for 30 minutes, the mixture was added with water, acidified by adding diluted hydrochloric acid and extracted with ethyl acetate. The organic layer was washed with water, dried over anhydrous magnesium sulfate and the solvent was evaporated. The residue was purified and separated by silica gel column chromatography (ethyl acetate:hexane=1:10), to give 20.5 g of the title compound as colorless needles.
$^1$H-NMR (400 MHz, CDCl$_3$) δ 1.73 (9H, s), 8.32 (1H, d, J=9.0 Hz), 8.46 (1H, dd, J=2.3, 9.0 Hz), 8.59 (1H, d, J=2.3 Hz).

Production Example I-26-c tert-Butyl 3-(3-fluorophenyl)-5-nitro-1H-1-indazolecarboxylate To a solution of 4.5 g of tert-butyl 3-bromo-5-nitro-1H-1-indazolecarboxylate in 20 ml N,N-dimethylformamide were added 2.8 g of 3-fluorophenylboronic aid, 0.16 g of 2-(di-tert-butylphosphino)biphenyl, 60 mg of palladium acetate and 2.31 g of potassium fluoride, and the mixture was heated at 50° C. for two days. To the reaction mixture was added water and the mixture was extracted with ethyl acetate. The organic layer was washed with water, dried over anhydrous magnesium sulfate and the solvent was evaporated. The residue was purified and separated by silica gel column chromatography (ethyl acetate:hexane=1:15), and then recrystallized from diisopropyl ether-hexane, to give 2.2 g of the title compound as a colorless powder.
$^1$H-NMR (400 MHz, CDCl$_3$) δ 1.76 (9H, s), 7.22-7.28 (1H, m), 7.56 (1H, dt, J=5.9, 8.0 Hz), 7.72 (1H, d, J=9.5 Hz), 7.77 (1H, d, J=8.0 Hz), 8.38 (1H, d, J=9.1 Hz), 8.46 (1H, dd, J=2.0, 9.1 Hz), 8.89 (1H, d, J=2.0 Hz).

Production Example I-26-d tert-Butyl-5-amino-3-(3-fluorophenyl)-1H-1-indazolecarboxylate To a solution of 180 mg of tert-butyl 3-(3-fluorophenyl)-5-nitro-1H-1-indazolecarboxylate in 10 ml tetrahydrofuran was added 100 mg of palladium (5%)-carbon, and the mixture was stirred at room temperature in an atmosphere of hydrogen gas at normal pressure for 3 hours. The reaction mixture was filtrated through Celite and the solvent was evaporated, to give 184 mg of the title compound as a light brown oil.
$^1$H-NMR (400 MHz, CDCl$_3$) δ 1.73 (9H, s), 3.70-3.90 (2H, bs), 6.98 (1H, dd, J=1.9, 8.7 Hz), 7.14 (1H, dt, J=1.9, 8.1 Hz), 7.16 (1H, d, J=1.9 Hz), 7.46 (1H, dt, J=6.0, 8.1 Hz), 7.67 (1H, dt, J=1.9, 9.7 Hz), 7.74 (1H, d, J=8.1 Hz), 7.99 (1H, d, J=8.7 Hz).

Production Example I-27-a

3-Bromo-6-nitro-1H-indazole

To a solution of 5.0 g of 6-nitro-1H-indazole in 50 ml dimethylformamide was added 5.73 g of N-bromosuccinimide at room temperature, and the mixture was stirred at the same temperature for 1 hour. After removing the solvent by distillation, the residue was added with 250 ml of ethyl acetate. The mixture was sequentially washed with half-saturated aqueous sodium hydrogencarbonate solution, water and brine, and dried over anhydrous magnesium sulfate. After filtrating the organic layer through a silica gel pat, the solvent was evaporated and the resulting crystals were suspended in toluene, to give 6.59 g of the title compound as light brown crystals.
$^1$H-NMR (400 MHz, DMSO-D$_6$) δ 7.84 (1H, d, J=8.8 Hz), 8.01 (1H, dd, J=2.0, 8.8 Hz), 8.50 (1H, d, J=2.0 Hz).

Production Example I-27-b 3-(3-Fluorophenyl)-6-nitro-1H-indazole

To a solution of 1.0 g of 3-bromo-6-nitro-1H-indazole in 10 ml N-methylpyrrolidone were added 2.0 g of (3-fluorophenyl)tri-n-butyltin, and 480 mg of tetrakis(triphenylphosphine)palladium(0), and the mixture was stirred at 180° C. for 2 hours. To the reaction mixture was added 60 ml of ethyl acetate. The mixture was sequentially washed with water (×2) and brine, dried over anhydrous magnesium sulfate and the solvent was evaporated. The crude product was purified and separated by silica gel column chromatography (ethyl acetate:toluene=1:49), to give 302 mg of the title compound as orange crystals.
$^1$H-NMR (400 MHz, DMSO-D$_6$) δ 7.30 (1H, td, J=8.8, 2.8 Hz), 7.61 (1H, td, J=8.8, 6.4 Hz), 7.79 (1H, dd, J=8.8, 1.6 Hz), 7.89 (1H, d, J=7.2 Hz), 8.02 (1H, dd, J=8.8, 2.0 Hz), 8.36 (1H, d, J=8.8 Hz), 8.52 (1H, d, J=2.0 Hz), 14.08 (1H, s).

Production Example I-27-c 3-(3-Fluorophenyl)-1H-6-indazolamine

To a solution of 300 mg of 3-(3-fluorophenyl)-6-nitro-1H-indazole in 5 ml methanol and 2.5 ml ethyl acetate was added 60 mg of 20% palladium hydroxide-carbon (water content: 50%), and the mixture was subjected to hydrogenation at room temperature at normal pressure for 7.5 hours. After adding 2.5 ml of ethyl acetate to the reaction mixture, the catalyst was filtered off through Celite. The solvent was evaporated, and the crude product was suspended in ethyl acetate-diisopropyl ether, to give 142 mg of the title compound as white crystals.
$^1$H-NMR (400 MHz, DMSO-D$_6$) δ 5.72 (2H, s), 6.60 (1H, s), 6.62 (1H, d, J=8.8 Hz), 7.18 (1H, td, J=8.4, 2.4 Hz), 7.51 (1H, td, J=8.0, 6.4 Hz), 7.65 (1H, d, J=10.8 Hz), 7.73 (1H, d, J=8.8 Hz), 7.77 (1H, d, J=7.6 Hz), 12.62 (1H, s).

Production Example I-28-a 3-(3-Fluorophenyl)-7-nitro-1H-indazole

A total of 64 mg of the title compound was obtained as purple crystals by the procedures of Production Examples I-27-a and I-27-b, except from 1.13 g of 7-nitro-1H-indazole as a starting material.

$^1$H-NMR (400 MHz, DMSO-D$_6$) δ 7.34 (1H, td, J=8.4, 2.4 Hz), 7.48 (1H, t, J=8.0 Hz), 7.62 (1H, q, j=7.6 Hz), 7.79 (1H, dd, J=10.4, 2.4 Hz), 7.88 (1H, d, J=7.6 Hz), 8.44 (1H, d, J=8.0 Hz), 8.64 (1H, d, J=8.0 Hz), 14.20 (1H, s).

Production Example I-28-b 3-(3-Fluorophenyl)-1H-7-indazolamine

A total of 57 mg of the title compound was obtained as purple crystals by the procedure of Production Example I-27-c, except from 63 mg of 3-(3-fluorophenyl)-7-nitro-1H-indazole as a starting material.

$^1$H-NMR (400 MHz, DMSO-D$_6$) δ 5.43 (2H, s), 6.53 (1H, d, J=7.2 Hz), 6.96 (1H, dd, J=7.2, 8.4 Hz), 7.21 (1H, td, J=8.4, 2.8 Hz), 7.25 (1H, d, J=8.4 Hz), 7.54 (1H, q, J=7.6 Hz), 7.69 (1H, d, J=10.4 Hz), 7.81 (1H, d, J=8.0 Hz), 12.91 (1H, s).

Production Example I-29-a tert-Butyl 3-(2-bromoacetyl)-5-nitro-1H-1-indazolecarboxylate To a solution of 3.0 g of tert-butyl 3-bromo-5-nitro-1H-1-indazolecarboxylate produced in Production Example I-26-b in 20 ml toluene were added 3.2 ml of tributyl(1-ethoxyvinyl)tin and 620 mg of tetrakis(triphenylphosphine)palladium(0), and the mixture was heated at 100° C. in an atmosphere of nitrogen gas for 6 hours. The reaction mixture was cooled to room temperature, and the solvent was evaporated. To the residue was added 20 ml of tetrahydrofuran, 1.56 g of N-bromosuccinimide was added, and the mixture was stirred at room temperature for 1 hour. To the reaction mixture was added aqueous sodium thiosulfate solution, and the mixture was extracted with ethyl acetate. The organic layer was washed with water, dried over anhydrous magnesium sulfate and the solvent was evaporated. The residue was purified and separated by silica gel column chromatography (ethyl acetate:hexane=1:7), to give 0.9 g of the title compound as colorless needles.

$^1$H-NMR (400 MHz, CDCl$_3$) δ 1.78 (9H, s), 4.80 (2H, s), 8.34 (1H, dd, J=0.6, 9.2 Hz), 8.47 (1H, dd, J=2.3, 9.2 Hz), 9.26 (1H, dd, J=0.6, 2.3 Hz).

Production Example I-29-b tert-Butyl 3-(imidazo[1,2-a]pyridin-2-yl)-5-nitro-1H-1-indazolecarboxylate A total of 0.88 g of tert-butyl 3-(2-bromoacetyl)-5-nitro-1H-1-indazolecarboxylate was dissolved in 10 ml of tetrahydrofuran-methanol (1:1), and 240 mg of 2-aminopyridine and 210 mg of sodium hydrogencarbonate were added, followed by heating under reflux for 1 hour. To the reaction mixture was added water, and the mixture was extracted with ethyl acetate. The mixture was washed with water, dried over magnesium sulfate and the solvent was removed. The residue was purified by silica gel column chromatography (ethyl acetate:hexane=1:7), to give 0.38 g of the title compound as a pale yellow powder.

$^1$H-NMR (400 MHz, DMSO-d$_6$) δ 1.69 (9H, s), 7.02 (1H, t, J=6.6 Hz), 7.37 (1H, t, J=6.6 Hz), 7.79 (1H, d, J=7.5 Hz), 8.30 (1H, d, J=7.5 Hz), 8.50 (1H, dd, J=2.3, 7.5 Hz), 8.65 (1H, d, J=6.6 Hz), 8.71 (1H, s), 9.52 (1H, d, J=2.3 Hz).

Production Example I-29-c tert-Butyl 5-amino-3-imidazo[1,2-a]pyridin-2-yl-1H-1-indazolecarboxylate A total of 0.48 g of tert-butyl 3-imidazo[1,2-a]pyridin-2-yl-5-nitro-1H-1-indazolecarboxylate was subjected to treatment by the procedure of Production Example I-26-d, and purified and separated by silica gel column chromatography (ethyl acetate:hexane=1:7), to give 0.11 g of the title compound as a light brown powder.

$^1$H-NMR (400 MHz, CDCl$_3$) δ 1.74 (9H, s), 6.84 (1H, t, J=6.7 Hz), 6.98 (1H, dd, J=2.4, 8.9 Hz), 7.22 (1H, dd, J=6.7, 8.9 Hz), 7.71 (1H, d, J=8.9 Hz), 7.93 (1H, d, J=8.9 Hz), 7.95 (1H, d, J=2.4 Hz), 8.19 (1H, d, J=6.7 Hz), 8.33 (1H, s).

Production Example I-30-a tert-Butyl 5-(azidomethyl)-3-(3-fluorophenyl)-1H-1-indazolecarboxylate To a solution of 600 mg of tert-butyl 5-(chloromethyl)-3-(3-fluorophenyl)-1H-1-indazolecarboxylate produced in Production Example I-24-b in 4 ml dimethyl sulfoxide was added 162 mg of sodium azide, and the mixture was stirred at room temperature for 50 minutes. To the reaction mixture was added 25 ml of diethyl ether. The mixture was sequentially washed with water (×3) and brine, dried over anhydrous magnesium sulfate and the solvent was evaporated, to give 571 mg of the title compound as pale yellow crystals.

$^1$H-NMR (400 MHz, DMSO-D$_6$) δ 1.69 (9H, s), 4.66 (2H, s), 7.42 (1H, td, J=8.0, 2.8 Hz), 7.67 (1H, td, J=8.0, 6.0 Hz), 7.70 (1H, d, J=8.4 Hz), 7.77 (1H, d, J=10.0 Hz), 7.87 (1H, d, J=8.0 Hz), 8.19 (1H, d, J=8.0 Hz), 8.21 (1H, s).

Production Example I-30-b tert-Butyl 5-(aminomethyl)-3-(3-fluorophenyl)-1H-1-indazolecarboxylate To a solution of 550 mg of tert-butyl 5-(azidomethyl)-3-(3-fluorophenyl)-1H-1-indazolecarboxylate in a mixture of 10 ml ethanol and 5 ml tetrahydrofuran was added 110 mg of 5% palladium-calcium carbonate, and the mixture was hydrogenated at room temperature at normal pressure for 1.5 hours. After filtering off the catalyst through Celite, the solvent was evaporated. The crude product was purified and separated by silica gel column chromatography (ethyl acetate:methanol=1:0 to 9:1), to give 427 mg of the title compound as light green crystals.

$^1$H-NMR (400 MHz, DMSO-D$_6$) δ 1.68 (9H, s), 1.99 (2H, s), 3.89 (2H, s), 7.40 (1H, td, J=8.8, 2.8 Hz), 7.64 (1H, d, J=8.4 Hz), 7.65 (1H, td, J=8.0, 6.4 Hz), 7.78 (1H, d, J=10.0 Hz), 7.87 (1H, d, J=8.4 Hz), 8.07 (1H, s), 8.09 (1H, d, J=8.8 Hz).

Production Example I-30-c

[3-(3-Fluorophenyl)-1H-5-indazolyl]methanamine

To a solution of 300 mg of tert-butyl 5-(aminomethyl)-3-(3-fluorophenyl)-1H-1-indazolecarboxylate in 1 ml methylene chloride was added 2 ml of trifluoroacetic acid, and the mixture was stirred at room temperature for 6.5 hours. After removing the solvent by filtration, to the residue was added 20 ml of ethyl acetate. The mixture was sequentially washed with saturated aqueous sodium hydrogencarbonate solution (×2) and brine, dried over anhydrous magnesium sulfate and the solvent was evaporated, to give 188 mg of the title compound as yellow crystals.

$^1$H-NMR (400 MHz, DMSO-D$_6$) δ 3.90 (2H, s), 7.24 (1H, td, J=8.4, 2.4 Hz), 7.40 (1H, d, J=8.4 Hz), 7.55 (1H, d, J=8.4 Hz), 7.57 (1H, td, J=8.0, 6.4 Hz), 7.76 (1H, d, J=10.4 Hz), 7.87 (1H, d, J=8.0 Hz), 8.05 (1H, s), 13.30 (1H, s).

Production Example I-31 tert-Butyl 3-(3-fluorophenyl)-5-(iodomethyl)-1H-1-indazolecarboxylate

To a solution of 500 mg of tert-butyl 5-(chloromethyl)-3-(3-fluorophenyl)-1H-1-indazolecarboxylate produced in Production Example I-24-b in 2.5 ml acetone was added 218 mg of sodium iodide, and the mixture was stirred at room temperature for 2 hours. After filtering off the resulting sodium chloride through Celite, the solvent was evaporated, to give 638 mg of the title compound as bright yellow crystals.

$^1$H-NMR (400 MHz, DMSO-D$_6$) δ 1.68 (9H, s), 4.87 (2H, s), 7.42 (1H, td, J=8.4, 2.8 Hz), 7.67 (1H, td, J=8.0, 6.4 Hz), 7.70-7.78 (2H, m), 7.87 (1H, d, J=8.4 Hz), 8.11 (1H, d, J=8.8 Hz), 8.28 (1H, s).

Production Example I-32-a

Methyl 3-(3-fluorophenyl)-1-trityl-1H-5-indazolecarboxylate

To a solution of 2.43 g of methyl 3-(3-fluorophenyl)-1H-5-indazolecarboxylate produced in Production Example I-4-e in 25 ml tetrahydrofuran was added 720 mg of 60% sodium hydride (oily), and the mixture was stirred under ice-cooling for 10 minutes. Then, 3.26 g of chlorotriphenylmethane was added and the mixture was stirred at the same temperature for 30 minutes and at room temperature for 1 hour. The reaction mixture was ice-cooled, saturated aqueous sodium hydrogencarbonate solution was added, and the mixture was extracted with 100 ml of ethyl acetate. The organic layer was sequentially washed with water and brine, dried over anhydrous magnesium sulfate, and the solvent was evaporated. The residue was crystallized from ethyl acetate-diisopropyl ether, to give 3.48 g of the title compound as white crystals. In addition, the mother liquor was concentrated, and then the residue was crystallized from diisopropyl ether, to give 0.37 g of the title compound as white crystals.

$^1$H-NMR (400 MHz, DMSO-D$_6$) δ 3.85 (3H, s), 6.58 (1H, d, J=8.8 Hz), 7.22 (6H, d, J=6.8 Hz), 7.28-7.40 (10H, m), 7.58-7.64 (2H, m), 7.68 (1H, dd, J=9.2, 1.2 Hz), 7.74 (1H, d, J=7.6 Hz), 8.62 (1H, s).

Production Example I-32-b

[3-(3-Fluorophenyl)-1-trityl-1H-5-indazolyl]methanol

Under ice-cooling, a solution of 3.85 g of methyl 3-(3-fluorophenyl)-1-trityl-1H-5-indazolecarboxylate in 40 ml tetrahydrofuran was added 535 mg of lithium aluminium hydride, and the mixture was stirred at the same temperature for 5 minutes and at room temperature for further 30 minutes. The reaction mixture was ice-cooled, saturated aqueous sodium sulfate solution was added, aluminium hydroxide was precipitated, and the organic layer was decanted. To the residue was added 20 ml of tetrahydrofuran, stirred, and the organic layer was re-decanted twice. The solvent was evaporated from the collected organic layers. The residue was dissolved in 80 ml of ethyl acetate, and then the mixture was sequentially washed with water and brine, dried over anhydrous magnesium sulfate and the solvent was evaporated. The resulting crude crystals were recrystallized from diisopropyl ether, to give 3.37 g of the title compound as white needles.

$^1$H-NMR (400 MHz, DMSO-D$_6$) δ 4.55 (2H, d, J=6.0 Hz), 5.18 (1H, t, J=6.0 Hz), 6.43 (1H, d, J=8.8 Hz), 7.07 (1H, d, J=8.8 Hz), 7.21 (6H, d, J=6.8 Hz), 7.27-7.40 (10H, m), 7.52-7.62 (2H, m), 7.74 (1H, d, J=7.6 Hz), 8.01 (1H, s).

Production Example I-32-c 5-(Chloromethyl)-3-(3-fluorophenyl)-1-trityl-1H-indazole Under ice-cooling, a solution of 1.21 g of [3-(3-fluorophenyl)-1-trityl-1H-5-indazolyl]methanol in 12 ml methylene chloride were added 0.45 ml of triethylamine and 0.23 ml of methanesulfonyl chloride, and the mixture was stirred at room temperature overnight. To the reaction mixture was added 150 ml of ethyl acetate. The mixture was sequentially washed with water, saturated aqueous sodium hydrogencarbonate solution and brine, dried over anhydrous magnesium sulfate and the solvent was evaporated. The resulting crude crystals were recrystallized from diisopropyl ether, to give 1.13 g of the title compound as white crystals.

$^1$H-NMR (400 MHz, DMSO-D$_6$) δ 4.87 (2H, s), 6.49 (1H, d, J=8.8 Hz), 7.18 (1H, d, J=8.8 Hz), 7.21 (6H, d, J=6.8 Hz), 7.25-7.40 (10H, m), 7.56 (1H, td, J=8.0, 7.2 Hz), 7.62 (1H, d, J=10.0 Hz), 7.75 (1H, d, J=7.6 Hz), 8.24 (1H, s).

Production Example I-33 tert-Butyl 5-(hydroxymethyl)-3-(2-naphthyl)-1H-1-indazolecarboxylate

A total of 3.7 g of the title compound was obtained as colorless crystals by the procedure of Production Example I-24-a, except from, as a starting material, 4.1 g of methyl 3-(2-naphthyl)-1H-5-indazolecarboxylate produced in Production Example I-12-a.

$^1$H-NMR (400 MHz, DMSO-d$_6$) δ 1.69 (9H, s), 4.69 (2H, d, J=5.5 Hz), 5.37 (1H, t, J=5.5 Hz), 7.61 (1H, d, J=9.6 Hz), 7.61 (1H, ddd, J=1.3, 3.2, 9.6 Hz), 7.64 (1H, dd, J=1.6, 8.5 Hz), 7.99-8.03 (1H, m), 8.08-8.12 (1H, m), 8.11 (1H, d, J=1.6 Hz), 8.14 (1H, d, J=8.5 Hz), 8.14-8.17 (1H, m), 8.17-8.19 (1H, m), 8.58 (1H, bs).

Production Example I-34

[3-(3-Fluorophenyl)-1-(methoxymethyl)-1H-5-indazolyl]methanol

A total of 1.0 g of methyl 3-(3-fluorophenyl)-1H-5-indazolecarboxylate obtained in Production Example I-4-e was dissolved in 15 ml of N,N-dimethylformamide, and 200 mg of sodium hydride (60% oily) was added under ice-cooling, followed by stirring for 30 minutes. To the reaction mixture was added 0.4 ml of chloromethyl methyl ether, followed by stirring at room temperature for 30 minutes. To the reaction mixture was added water and the mixture was extracted with ethyl acetate for two times. The organic layer was washed with water, dried over anhydrous magnesium sulfate and the solvent was evaporated. The residue was purified and separated by silica gel column chromatography (ethyl acetate:hexane=1:10), to give 0.95 g of methyl 3-(3-fluorophenyl)-1-(methoxymethyl)-1H-5-indazolecarboxylate as colorless needles. This compound was dissolved in 15 ml of tetrahydrofuran, and 8.0 ml of a solution of diisobutylaluminum hydride in toluene was added dropwise at room temperature. While cooling the reaction mixture, water was added. The mixture was acidified with diluted hydrochloric, and extracted with ethyl acetate for two times. The organic layer was washed with sodium hydrogencarbonate and water, dried over anhydrous magnesium sulfate and the solvent was evaporated, to give 0.78 g of the title compound as a colorless oil.

$^1$H-NMR (400 MHz, CDCl$_3$) δ 3.36 (3H, s), 4.85 (2H, d, J=5.0 Hz), 5.76 (2H, s), 7.11 (1H, dt, J=2.8, 8.3 Hz), 7.48 (1H, dt, J=6.5, 8.3 Hz), 7.50 (1H, d, J=8.9 Hz), 7.62 (1H, d, J=8.9 Hz), 7.68 (1H, d, J=10.9 Hz), 7.77 (1H, d, J=8.9 Hz), 8.00 (1H, s).

Production Example I-35-a

3-Bromo-1H-indazole

A total of 1.58 g of the title compound was obtained as beige crystals by the procedure of Production Example I-14-a, except from 1.00 g of 1H-indazole.

$^1$H-NMR (400 MHz, DMSO-D$_6$) δ 7.23 (1H, tt, J=8.0, 1.2 Hz), 7.46 (1H, tt, J=8.0, 1.2 Hz), 7.58 (1H, dd, J=8.0, 1.2 Hz).

Production Example I-35-b 3-(3-Fluorophenyl)-1H-indazole

A total of 42 mg of the title compound was obtained as white crystals by the procedure of Production Example I-27-b, except from 200 mg of 3-bromo-1H-indazole.

$^1$H-NMR (400 MHz, DMSO-D$_6$) δ 7.20-7.28 (2H, m), 7.43 (1H, td, J=8.0, 1.2 Hz) 7.57 (1H, td, J=8.0, 6.0 Hz), 7.61 (1H, dd, J=8.0, 0.8 Hz), 7.75 (1H, ddd, J=10.4, 2.8, 1.2 Hz), 7.86 (1H, ddd, J=8.0, 1.2, 1.2 Hz), 8.10 (1H, dd, J=8.0, 0.8 Hz), 13.37 (1H, s).

Production Example I-36-a 1-(2,2-Diethoxyethoxy)-4-fluorobenzene

To a solution of 10.0 g of 4-fluorophenol and 16.1 ml of bromoacetaldehyde diethylacetal in 100 ml dimethylformaldehyde was added 18.5 g of potassium carbonate at room temperature, and the mixture was stirred at 120° C. for two days. The reaction mixture was filtered through Celite, and the filtrate was diluted with ethyl acetate. The organic layer was sequentially washed with saturated aqueous ammonium chloride solution and brine, dried over anhydrous magnesium sulfate and the solvent was evaporated. The crude product was purified and separated by silica gel column chromatography (ethyl acetate:n-hexane=0:10 to 1:20), to give 17.3 g of the title compound as a colorless oil.

$^1$H-NMR (400 MHz, CDCl$_3$) δ 1.25 (3H, t, J=7.2 Hz), 3.58-3.67 (2H, m), 3.71-3.80 (2H, m), 3.97 (2H, d, J=5.2 Hz), 4.82 (1H, t, J=5.2 Hz), 6.84-6.88 (2H, m), 6.93-6.99 (2H, m).

Production Example I-36-b

5-Fluoro[b]benzofuran

To a solution of 16.0 g of 1-(2,2-diethoxyethoxy)-4-fluorobenzene in 50 ml n-hexane was added 3.2 g of amberlyst 15 at room temperature. After the mixture was treated in a sealed tube at 200° C. for 11 hours, the amberlyst 15 was filtered off. The solvent was evaporated, and the crude product was purified and separated by silica gel column chromatography (n-hexane), to give 4.8 g of the title compound as a colorless oil.

$^1$H-NMR (400 MHz, CDCl$_3$) δ 6.74 (1H, dd, J=1.2, 2.4 Hz), 7.02 (1H, dt, J=2.4, 8.8 Hz), 7.25 (1H, dd, J=2.4, 8.8 Hz), 7.41-7.44 (1H, m), 7.65 (1H, d, J=2.4 Hz).

Production Example I-36-c

5-Fluoro-2-benzo[b]furanboronic acid

In a nitrogen atmosphere, to a solution of 2.0 g of 5-fluorobenzofuran in 150 ml tetrahydrofuran was added 18.5 ml of a 1.59 M solution of n-butyllithium in n-hexane at −78° C., and the mixture was stirred at the same temperature for 10 minutes and at 0° C. for further 10 minutes. At −78° C., 3.7 ml of triethoxyborane was added, and the mixture was stirred for 2 hours while elevating to 0° C. 30 ml of 1 N hydrochloric acid was added, stirred at room temperature for 1 hour, and then the mixture was extracted with ethyl acetate. The extract was washed with brine, dried over anhydrous magnesium sulfate and the solvent was evaporated. The crude product was purified and separated by silica gel column chromatography (ethyl acetate:n-hexane=1:3 to 1:1), to give 525 mg of the title compound as colorless crystals.

$^1$H-NMR (400 MHz, CDCl$_3$) δ 7.09 (1H, dt, J=2.4, 8.8 Hz), 7.29 (1H, dd, J=2.4, 8.8 Hz), 7.33 (1H, s), 7.44 (1H, dd, J=4.0, 8.8 Hz).

Production Example I-36-d

3-Iodo-5-nitro-1H-indazole

To a solution of 17.0 g of 5-nitroindazole in 100 ml dimethylformamide was added 24.6 g of N-iodosuccinimide at room temperature, and the mixture was stirred at 80° C. for 7 hours. After standing to cool, to the reaction mixture were added 150 ml of water and 200 ml of diethyl ether, and the resulting crystals were collected by filtration. The crystals were sequentially washed with water, isopropanol and diethyl ether, to give 27.5 g of the title compound as colorless crystals.

$^1$H-NMR (400 MHz, DMSO-D$_6$) δ 7.74 (1H, d, J=9.2 Hz), 8.23 (1H, dd, J=2.4, 9.2 Hz), 8.30 (1H, d, J=2.4 Hz), 12.01 (1H, brs).

Production Example I-36-e

3-Iodo-5-nitro-1-trityl-1H-indazole

To a solution of 27.5 g of 3-iodo-5-nitro-1H-indazole in 300 ml tetrahydrofuran at 0° C. in an atmosphere of nitrogen gas was added 6.1 g of 60% sodium hydride, and the mixture was stirred at the same temperature for 10 minutes. To the mixture was added 39.8 g of trityl chloride, followed by stirring at room temperature for 1 hour. Water was added and the mixture was diluted with ethyl acetate. The organic layer was sequentially washed with saturated aqueous ammonium chloride solution and brine, dried over anhydrous magnesium sulfate and the solvent was evaporated. The resulting crude crystals were washed with diethyl ether, to give 48:5 g of the title compound as colorless crystals.

$^1$H-NMR (400 MHz, DMSO-D$_6$) δ 6.42 (1H, d, J=9.2 Hz), 7.13-7.32 (15H, m), 7.89 (1H, ddd, J=0.4, 2.4, 9.2 Hz), 8.44 (1H, d, J=2.4 Hz).

Production Example I-36-f 3-(5-Fluoro[b]benzofuran-2-yl)-5-nitro-1-trityl-1H-indazole A total of 255 mg of the title compound was obtained as pale yellow crystals by the procedure of Production Example I-26-c, except from 500 mg of 3-iodo-5-nitro-1-trityl-1H-indazole and 178 mg of 5-fluoro-2-benzo[b]furanboronic acid.

$^1$H-NMR (400 MHz, CDCl$_3$) δ 6.49 (1H, dd, J=0.8, 9.2 Hz), 7.08 (1H, dt, J=2.4, 9.2 Hz), 7.15-7.36 (17H, m), 7.59 (1H, dd, J=4.0, 9.2 Hz), 7.90 (1H, dd, J=2.4, 9.2 Hz), 9.25 (1H, dd, J=0.8, 2.4 Hz).

Production Example I-36-g 3-(5-Fluoro[b]benzofuran-2-yl)-1-trityl-1H-indazol-5-ylamine A total of 178 mg of the title compound was obtained as colorless crystals by the procedure of Production Example I-26-d, except from 250 mg of 3-(5-fluorobenzo[b]furan-2-yl)-5-nitro-1-trityl-1H-indazole as a starting material.

$^1$H-NMR (400 MHz, CDCl$_3$) δ 3.67 (2H, brs), 6.25 (1H, dd, J=0.8, 9.2 Hz), 6.49 (1H, dd, J=2.4, 9.2 Hz), 6.97 (1H, dt, J=2.4, 9.2 Hz), 7.02 (1H, d, J=0.8 Hz), 7.20 (1H, dd, J=2.4, 9.2 Hz), 7.20-7.31 (15H, m), 7.45 (1H, d, J=2.4 Hz), 7.47 (1H, dd, J=4.0, 9.2 Hz).

Example I-1

N5-(3-Pyridylmethyl)-3-(4-fluorophenyl)-1H-5-indazolecarboxamide

To a solution of 150 mg of 3-(4-fluorophenyl)-1H-5-indazolecarboxylic acid produced in Production Example I-14 in 2.5 ml dimethylformamide were added a solution of 70 mg of 3-picolylamine in 0.5 ml dimethylformamide and 124 mg of 1-ethyl-3-(3-dimethylaminopropyl)carbodiimide hydrochloride (=WSC.HCl), and the mixture was stirred at room temperature for four days. After removing the solvent by distillation, the residue was dissolved in 25 ml of ethyl acetate. The mixture was sequentially washed with water and brine, dried over anhydrous magnesium sulfate and the solvent was removed. The resulting crude crystals were recrystallized from ethyl acetate-diisopropyl ether, to give 109 mg of the title compound as pale yellow crystals.

$^1$H-NMR (400 MHz, DMSO-D$_6$) δ 4.55 (1H, d, J=5.6 Hz), 7.34-7.44 (3H, m), 7.65 (1H, d, J=8.8 Hz), 7.75 (1H, d, J=7.2 Hz), 7.96 (1H, d, J=8.8 Hz), 8.07 (2H, dd, J=5.6, 8.8 Hz), 8.46 (1H, d, J=8.0 Hz), 8.58 (1H, s), 8.61 (1H, s), 9.23 (1H, t, J=5.6 Hz), 13.49 (1H, s).

Example I-2

N5-(3-Pyridylmethyl)-3-(3-chlorophenyl)-1H-5-indazolecarboxamide

A total of 36 mg of the title compound was obtained as white needles by the procedure of Example I-1, except from 60 mg of 3-(3-chlorophenyl)-1H-5-indazolecarboxylic acid produced in Production Example I-15 and 35 mg of 3-picolylamine.

$^1$H-NMR (400 MHz, DMSO-D$_6$) δ 4.56 (1H, d, J=5.6 Hz), 7.36 (1H, dd, J=4.8, 8.0 Hz), 7.51 (1H, d, J=8.0 Hz), 7.61 (1H, t, J=8.0 Hz), 7.66 (1H, d, J=8.8 Hz), 7.76 (1H, d, J=8.0 Hz), 7.97 (1H, d, J=8.0 Hz), 8.02 (1H, s), 8.03 (1H, d, J=8.8 Hz), 8.46 (1H, dd, J=1.6, 4.8 Hz), 8.59 (1H, d J=1.6 Hz), 8.62 (1H, s), 9.26 (1H, t, J=5.6 Hz), 13.62 (1H, s).

Example I-3

N5-(3-Pyridylmethyl)-3-[3-(trifluoromethyl)phenyl]-1H-5-indazolecarboxamide

A total of 28 mg of the title compound was obtained as white crystals by the procedure of Example I-1, except from 53 mg of 3-[3-(trifluoromethyl)phenyl]-1H-5-indazolecarboxylic acid produced in Production Example I-16 and 28 mg of 3-picolylamine.

$^1$H-NMR (400 MHz, DMSO-D$_6$) δ 4.56 (2H, d, J=6.0 Hz), 7.37 (1H, dd, J=4.8, 8.0 Hz), 7.69 (1H, d, J=8.8 Hz), 7.76 (1H, d, J=8.0 Hz), 7.79-7.87 (2H, m), 7.98 (1H, d, J=8.8 Hz), 8.28 (1H, s), 8.38 (1H, d, J=6.0 Hz), 8.46 (1H, d, J=4.8 Hz), 8.59 (1H, s), 8.64 (1H, s), 9.26 (1H, t, J=6.0 Hz), 13.69 (1H, s).

Example I-4

N5-(3-Pyridylmethyl)-3-(3-methoxyphenyl)-1H-5-indazolecarboxamide

A total of 8 mg of the title compound was obtained as a white amorphous powder by the procedure of Example I-1, except from 14 mg of 3-(3-methoxyphenyl)-1H-5-indazolecarboxylic acid produced in Production Example I-18 and 12 mg of 3-picolylamine.

$^1$H-NMR (400 MHz, DMSO-D$_6$) δ 4.56 (2H, d, J=5.6 Hz), 7.02 (1H, d, J=8.0 Hz), 7.37 (1H, dd, J=4.8, 7.6 Hz), 7.48 (1H, t, J=8.0 Hz), 7.53 (1H, s), 7.62 (1H, d, J=8.4 Hz), 7.64 (1H, d, J=8.0 Hz), 7.75 (1H, d, J=7.6 Hz), 7.95 (1H, d, J=8.4 Hz), 8.46 (1H, d, J=4.8 Hz), 8.58 (1H, s), 8.62 (1H, s), 9.26 (1H, t, J=5.6 Hz), 13.49 (1H, s).

Example I-5

N5-[(1S)-1-(Hydroxymethyl)-2-methylpropyl]-3-(3-fluorophenyl)-1H-5-indazolecarboxamide A total of 50 mg of the title compound was obtained as a colorless powder by the procedure of Example I-1, except from 150 mg of 3-(3-fluorophenyl)-1H-5-indazolecarboxylic acid produced in Production Example I-4 and 1.2 ml of 0.5 M solution of valinol in acetonitrile as starting materials.

$^1$H-NMR (400 MHz, DMSO-d$_6$) δ 0.90 (3H, d, J=8.0 Hz), 0.92 (3H, d, J=8.0 Hz), 1.88-2.00 (1H, m), 3.48-3.60 (2H, m), 3.78-3.87 (1H, m), 4.55-4.66 (1H, m), 7.23-7.30 (1H, m), 7.56-7.65 (1H, m), 7.62 (1H, d, J=8.4 Hz), 7.80 (1H, d, J=10.1 Hz), 7.86-7.96 (2H, m), 8.15 (1H, d, J=8.4 Hz), 8.54 (1H, s)

Example I-6

N5-[(1R)-2-Hydroxy-1-phenylethyl]-3-(3-fluorophenyl)-1H-5-indazolecarboxamide

A total of 20 mg of the title compound was obtained as a colorless powder by the procedure of Example I-1, except from 50 mg of 3-(3-fluorophenyl)-1H-5-indazolecarboxylic acid produced in Production Example I-4 and 30 mg of R(−)-2-phenylglycinol as starting materials.

$^1$H-NMR (400 MHz, DMSO-d$_6$) δ 3.64-3.79 (2H, m), 4.88 (1H, t, J=6.0 Hz), 5.12 (1H, dt, J=5.7, 8.2 Hz), 7.19-7.24 (1H, m), 7.28 (1H, dt, J=2.4, 8.2 Hz), 7.29-7.34 (2H, m), 7.38-7.42 (2H, m), 7.61 (1H, dt, J=6.3, 8.2 Hz), 7.64 (1H, d, J=8.9 Hz), 7.80 (1H, d, J=10.1 Hz), 7.90 (1H, d, J=7.7 Hz), 7.95 (1H, d, J=8.9 Hz), 8.61 (1H, s), 8.84 (1H, d, J=8.2 Hz), 13.57 (1H, s)

Example I-7

N5-[(1S)-2-Hydroxy-1-phenethyl]-3-benzo[b]thiophen-3-yl-1H-5-indazolecarboxamide To a solution of 50 mg of 3-benzo[b]thiophen-3-yl-1H-5-indazolecarboxylic acid produced in Production Example I-19 in 4 ml dimethylformamide were added 28 mg of (2S)-2-amino-2-phenyl-1-ethanol, 39 mg of 1-hydroxybenzotriazole monohydrate, and 49 mg of 1-ethyl-3-(3-dimethylaminopropyl)carbodiimide hydrochloride, and the mixture was stirred at room temperature for five days. To the reaction mixture was added 40 ml of ethyl acetate, and the mixture was sequentially washed with water, 1 N hydrochloric acid, water, saturated aqueous sodium hydrogencarbonate solution and brine, dried over anhydrous magnesium sulfate and the solvent was removed. The resulting crude crystals were recrystallized from ethyl acetate-diethyl ether, to give 46 mg of the title compound as pale red crystals.

$^1$H-NMR (400 MHz, DMSO-D$_6$) δ 3.66-3.81 (2H, m) 5.00 (1H, t, J=5.6 Hz), 5.16 (1H, td, J=8.0, 5.6 Hz), 7.24 (1H, t, J=7.6 Hz), 7.33 (2H, t, J=7.6 Hz), 7.42 (2H, d, J=7.6 Hz), 7.45-7.55 (2H, m), 7.68 (1H, d, J=8.8 Hz), 7.99 (1H, d, J=8.4 Hz), 8.11 (1H, d, J=8.8 Hz), 8.50 (1H, s), 8.65-8.70 (2H, m), 8.81 (1H, d, J=8.0 Hz), 13.55 (1H, s).

Example I-8

N5-[1-(Hydroxymethyl)cyclopentyl]-3-(3-fluorophenyl)-1H-5-indazolecarboxamide

A total of 16 mg of the title compound was obtained as a colorless powder by the procedure of Example I-7, except from 180 mg of 3-(3-fluorophenyl)-1H-5-indazolecarboxylic acid produced in Production Example I-4 and 115 mg of 1-amino-1-cyclopentanemethanol as starting materials.

$^1$H-NMR (400 MHz, DMSO-d$_6$) δ 1.51-1.60 (2H, m), 1.63-1.72 (2H, m), 1.72-1.80 (2H, m), 1.97-2.07 (2H, m), 3.60 (2H, d, J=6.1 Hz), 4.87 (1H, t, J=6.1 Hz), 7.26 (1H, dt, J=2.7, 8.7 Hz), 7.59 (1H, dt, J=6.3, 7.9 Hz), 7.59 (1H, d, J=8.6 Hz), 7.80 (1H, ddd, J=1.6, 2.7, 10.5 Hz), 7.94 (1H, s), 8.49 (1H, s), 13.51 (1H, s)

Example I-9

N5-(2-Hydroxy-2-phenylethyl)-3-(3-fluorophenyl)-1H-5-indazolecarboxamide

A total of 75 mg of the title compound was obtained as a colorless powder by the procedure of Example I-7, except from 180 mg of 3-(3-fluorophenyl)-1H-5-indazolecarboxylic acid produced in Production Example I-4 and 137 mg of 2-amino-1-phenylethanol as starting materials.

$^1$H-NMR (400 MHz, DMSO-d$_6$) δ 3.30-3.37 (1H, m), 3.51 (1H, ddd, J=4.6, 5.8, 13.2 Hz), 4.80 (1H, dd, J=4.6, 8.3 Hz), 5.56 (1H, d, J=4.6 Hz), 7.21-7.26 (1H, m), 7.28 (1H, dt, J=2.4, 8.4 Hz), 7.30-7.35 (2H, m), 7.36-7.40 (2H, m), 7.60 (1H, dt, J=6.3, 8.4 Hz), 7.62 (1H, d, J=9.2 Hz), 7.81 (1H, d, J=10.4 Hz), 7.90 (1H, d, J=9.2 Hz), 7.90 (1H, d, J=8.4 Hz), 8.54 (1H, s), 8.76 (1H, d, J=5.8 Hz), 13.54 (1H, bs)

Example I-10

N5-(2-Hydroxypropyl)-3-(3-fluorophenyl)-1H-5-indazolecarboxamide

A total of 60 mg of the title compound was obtained as a colorless oily substance by the procedure of Example I-7, except from 180 mg of 3-(3-fluorophenyl)-1H-5-indazolecarboxylic acid produced in Production Example I-4 and 0.08 ml of 1-amino-2-propanol as starting materials.

$^1$H-NMR (400 MHz, CDCl$_3$) δ 1.29 (3H, d, J=5.0 Hz), 3.38 (1H, ddd, J=4.9, 7.4, 14.0 Hz), 3.73 (1H, ddd, J=3.0, 6.5, 14.0 Hz), 4.06-4.13 (1H, m), 6.75-6.81 (1H, m), 7.14 (1H, dt, J=2.5, 8.1 Hz), 7.49 (1H, dt, J=6.2, 8.1 Hz), 7.55 (1H, d, J=8.8 Hz), 7.68 (1H, ddd, J=1.4, 2.5, 9.7 Hz), 7.76 (1H, d, J=8.1 Hz), 7.86 (1H, dd, J=1.8, 8.8 Hz), 8.49 (1H, d, J=1.8 Hz)

Example I-11

N5-[1-(4-Chlorophenyl)-2-hydroxyethyl]-3-(3-fluorophenyl)-1H-5-indazolecarboxamide A total of 55 mg of the title compound was obtained as a colorless powder by the procedure of Example I-7, except from 180 mg of 3-(3-fluorophenyl)-1H-5-indazolecarboxylic acid produced in Production Example I-4 and 112 mg of 2-amino-2-(4-chlorophenyl)-1-ethanol as starting materials.

$^1$H-NMR (400 MHz, CDCl$_3$) δ 4.03 (1H, dd, J=5.4, 11.4 Hz), 4.07 (1H, dd, J=4.1, 11.4 Hz), 5.30 (1H, ddd, J=4.1, 5.4, 11.4 Hz), 7.02 (1H, d, J=7.0 Hz), 7.14 (1H, dt, J=2.3, 8.0 Hz), 7.36 (4H, s), 7.49 (1H, dt, J=6.0, 8.0 Hz), 7.56 (1H, d, J=8.7 Hz), 7.68 (1H, ddd, J=1.5, 2.3, 9.9 Hz), 7.76 (1H, d, J=8.0 Hz), 7.87 (1H, dd, J=1.7, 8.7 Hz), 8.55 (1H, d, J=1.7 Hz)

Example I-12

N5-{2-Hydroxy-1-[4-(trifluoromethyl)phenyl]ethyl}-3-(3-fluorophenyl)-1H-5-indazolecarboxamide A total of 80 mg of the title compound was obtained as a colorless powder by the procedure of Example I-7, except from 162 mg of 3-(3-fluorophenyl)-1H-5-indazolecarboxylic acid produced in Production Example I-4 and 130 mg of 2-amino-2-[4-(trifluoromethyl)phenyl]-1-ethanol as starting materials.

$^1$H-NMR (400 MHz, DMSO-d$_6$) δ 3.66-3.83 (2H, m), 5.07 (1H, t, J=5.5 Hz), 5.12-5.22 (1H, m), 7.28 (1H, dt, J=2.5, 8.7 Hz), 7.58-7.68 (2H, m), 7.65 (2H, d, J=8.2 Hz), 7.69 (2H, d, J=8.2 Hz), 7.80 (1H, bd, J=10.5 Hz), 7.90 (1H, d, J=8.7 Hz), 7.94 (1H, d, J=8.8 Hz), 8.62 (1H, s), 8.94 (1H, d, J=7.8 Hz), 13.58 (1H, s)

Example I-13

N5-(2,3-Dihydroxypropyl)-3-(3-fluorophenyl)-1H-5-indazolecarboxamide

A total of 40 mg of the title compound was obtained as a colorless oily substance by the procedure of Example I-7, except from 180 mg of 3-(3-fluorophenyl)-1H-5-indazolecarboxylic acid produced in Production Example I-4 and 0.08 ml of 3-amino-1,2-propanediol as starting materials.

$^1$H-NMR (400 MHz, CDCl$_3$) δ 3.17-3.24 (1H, m), 3.24-3.40 (2H, m), 3.40-3.57 (1H, m), 3.62-3.70 (1H, m), 4.59 (1H, bs), 4.86 (1H, bs), 7.27 (1H, dt, J=2.2, 8.4 Hz), 7.60 (1H, dt, J=6.3, 8.4 Hz), 7.63 (1H, d, J=9.0 Hz), 7.81 (1H, d, J=10.1 Hz), 7.91 (1H, d, J=8.4 Hz), 7.93 (1H, d, J=9.0 Hz), 8.59 (1H, s), 8.65 (1H, t, J=5.6 Hz)

Example I-14

N5-[1-(2-Fluorophenyl)-2-hydroxyethyl]-3-(3-fluorophenyl)-1H-5-indazolecarboxamide A total of 51 mg of the title compound was obtained as a colorless powder by the procedure of Example I-7, except from 180 mg of 3-(3-fluorophenyl)-1H-5-indazolecarboxylic acid produced in Production Example I-4 and 155 mg of 2-(2-fluorophenyl)glycinol as starting materials.

$^1$H-NMR (400 MHz, CDCl$_3$) δ 3.66 (1H, dd, J=5.3, 11.0 Hz), 3.72 (1H, dd, J=8.0, 11.0 Hz), 5.10 (1H, t, J=6.0 Hz), 5.41 (1H, ddd, J=5.3, 8.0, 8.1 Hz), 7.13-7.19 (2H, m), 7.25-7.31 (2H, m), 7.50 (1H, dt, J=2.4, 7.9 Hz), 7.62 (1H, dt, J=6.3, 7.9 Hz), 7.64 (1H, d, J=8.9 Hz), 7.80 (1H, ddd, J=1.6, 2.4, 10.5 Hz), 7.90 (1H, d, J=7.9 Hz), 7.94 (1H, dd, J=1.6, 9.0 Hz), 8.62 (1H, s), 8.90 (1H, d, J=8.1 Hz)

Example I-15

N3-[3-(3-Fluorophenyl)-1H-5-indazolyl]nicotinamide

To a solution of 100 mg of tert-butyl 5-amino-3-(3-fluorophenyl)-1H-1-indazolecarboxylate produced in Production Example I-26 and 0.1 ml of triethylamine in 5 ml tetrahydrofuran was added 55 mg of nicotinic acid chloride hydrochloride, and the mixture was stirred at room temperature for two days. After the completion of the reaction, the reaction mixture was treated with 5 N hydrochloric acid by the procedure of Production Example I-25-b, to give 62 mg of the title compound as a colorless powder.

$^1$H-NMR (400 MHz, DMSO-d$_6$) δ 7.24 (1H, dt, J=2.4, 8.3 Hz), 7.55-7.63 (3H, m), 7.69 (1H, ddd, J=1.7, 2.4, 10.2 Hz), 7.79 (1H, s), 7.80 (1H, d, J=8.3 Hz), 8.32 (1H, dt, J=1.9, 8.1 Hz), 8.57 (1H, s), 8.76 (1H, dd, J=1.9, 5.0 Hz), 9.14 (1H, d, J=2.4 Hz) 10.53 (1H, s), 13.39 (1H, s)

Example I-16

N1-[3-(3-Fluorophenyl)-1H-5-indazolyl]-2-(2-thienyl)acetamide

A total of 20 mg of the title compound was obtained as a colorless powder by the procedure of Example I-15, except from 120 mg of tert-butyl 5-amino-3-(3-fluorophenyl)-1H-1-indazolecarboxylate produced in Production Example I-26 and 0.05 ml of 2-thiopheneacetic acid chloride as starting materials.

$^1$H-NMR (400 MHz, DMSO-d$_6$) δ 4.01 (2H, s), 7.06-7.13 (3H, m), 7.34 (1H, dd, J=1.8, 4.6 Hz), 7.38 (1H, dd, J=1.6, 8.6 Hz), 7.41 (1H, bs), 7.45 (1H, d, J=8.6 Hz), 7.47 (1H, dt, J=6.0, 7.8 Hz), 7.64 (1H, d, J=9.9 Hz), 7.72 (1H, d, J=7.8 Hz), 8.20 (1H, d, J=1.6 Hz)

Example I-17

N1-[3-(3-Fluorophenyl)-1H-5-indazolyl]-2-(4-pyridyl)acetamide

A solution of 50 mg of tert-butyl 5-amino-3-(3-fluorophenyl)-1H-1-indazolecarboxylate produced in Production Example I-26, 26 mg of 4-pyridylacetic acid hydrochloride and 0.05 ml of triethylamine in 5 ml tetrahydrofuran was added 37 mg of 1,1'-carbonyldiimidazole as a condensing agent at room temperature. After the completion of the reaction, the reaction mixture was treated with 5 N hydrochloric acid by the procedure of Production Example I-25-b, to give 11 mg of the title compound as a colorless powder.

$^1$H-NMR (400 MHz, DMS-d$_6$) δ 3.73 (2H, s), 7.15 (1H, dd, J=1.8, 9.1 Hz), 7.20-7.27 (1H, m), 7.30 (2H, d, J=8.8 Hz), 7.48 (2H, d, J=8.8 Hz), 7.55-7.60 (5H, m), 10.03 (1H, bs), 13.35 (1H, s)

Example I-18

N-[3-(3-Fluorophenyl)-1H-5-indazolyl]methanesulfonamide

A solution of 50 mg of tert-butyl 5-amino-3-(3-fluorophenyl)-1H-1-indazolecarboxylate produced in Production Example I-26 in 2 ml tetrahydrofuran were added 30 μl of triethylamine and 15 μl of methanesulfonyl chloride, and the mixture was stirred at room temperature for 10 hours. The reaction mixture was diluted with water and was extracted with ethyl acetate. The organic layer was sequentially washed with 1 N hydrochloric acid, water, saturated aqueous sodium hydrogencarbonate solution and brine, dried over anhydrous magnesium sulfate and the solvent was removed. The resulting crude crystals were recrystallized from ethyl acetate-diethyl ether, to give 26 mg of the title compound as a colorless powder.

$^1$H-NMR (400 MHz, DMSO-d$_6$) δ 2.92 (3H, s), 7.24 (1H, dt, J=2.7, 8.8 Hz), 7.33 (1H, dd, J=1.8, 8.8 Hz), 7.57 (1H, t, J=7.5 Hz), 7.59 (1H, d, J=8.8 Hz), 7.65 (1H, d, J=10.4 Hz), 7.78 (1H, d, J=7.5 Hz), 7.86 (1H, d, J=1.8 Hz), 13.40 (1H, bs)

Example I-19

N1-[3-(3-Fluorophenyl)-1H-5-indazolyl]-2,2,2-trifluoro-1-ethanesulfonamide

A total of 26 mg of the title compound was obtained as a colorless powder by the procedure of Example I-18, except from 50 mg of tert-butyl 5-amino-3-(3-fluorophenyl)-1H-1-indazolecarboxylate produced in Production Example I-26 and 0.02 ml of 2,2,2-trifluoro-1-ethanesulfonyl chloride as starting materials.

$^1$H-NMR (400 MHz, DMSO-d$_6$) δ 4.48 (2H, q, J=10.0 Hz), 7.24 (1H, dt, J=2.6, 8.0 Hz), 7.31 (1H, dd, J=1.8, 8.9 Hz), 7.58 (1H, dt, J=5.8, 8.0), 7.61 (1H, d, J=8.9 Hz), 7.67 (1H, ddd, J=1.5, 2.6, 10.1 Hz), 7.76 (1H, d, J=8.0 Hz), 7.87 (1H, d, J=1.8 Hz), 10.29 (1H, bs), 13.42 (1H, s)

Example I-20

N1-[3-(3-Fluorophenyl)-1H-5-indazolyl]-4-methyl-1-benzenesulfonamide

A total of 35 mg of the title compound was obtained as a colorless powder by the procedure of Example I-18, except from 50 mg of tert-butyl 5-amino-3-(3-fluorophenyl)-1H-1-indazolecarboxylate produced in Production Example I-26 and 30 mg of p-toluenesulfonyl chloride as starting materials.

$^1$H-NMR (400 MHz, DMSO-d$_6$) δ 2.28 (3H, s), 7.15 (1H, dd, J=1.8, 9.1 Hz), 7.20-7.27 (1H, m), 7.30 (2H, d, J=8.8 Hz), 7.48 (2H, d, J=8.8 Hz), 7.55-7.60 (5H, m), 10.03 (1H, bs), 13.35 (1H, s)

Example I-21

N4-[3-(3-Fluorophenyl)-1H-5-indazolyl]-4-morpholinecarboxamide

A total of 30 mg of the title compound was obtained as a colorless powder by the procedure of Example I-18, except from 50 mg of tert-butyl 5-amino-3-(3-fluorophenyl)-1H-1-indazolecarboxylate produced in Production Example I-26 and 30 mg of 4-morpholinecarbonyl chloride as starting materials.

$^1$H-NMR (400 MHz, DMSO-d$_6$) δ 3.40-3.47 (4H, m), 3.58-3.63 (4H, m), 7.21 (1H, dt, J=2.7, 8.5 Hz), 7.48 (1H, d, J=8.8 Hz), 7.53 (1H, dd, J=1.4, 8.8), 7.56 (1H, dt, J=6.5, 8.0 Hz), 7.65 (1H, ddd, J=1.6, 2.7, 10.7 Hz), 7.76 (1H, d, J=8.0 Hz), 8.14 (1H, d, J=1.4 Hz), 8.59 (1H, s), 13.21 (1H, s)

Example I-22

N1-[(1R)-2-Hydroxy-1-phenylethyl]-(E)-3-[3-(3-fluorophenyl)-1H-5-indazolyl]-2-propenamide A total of 11 mg of the title compound was obtained as a colorless powder by the procedure of Example I-7, except from 50 mg of (E)-3-[3-(3-fluorophenyl)-1H-5-indazolyl]-2-propenoic acid produced in Production Example I-25 and 18 mg of S(+)-2-phenylglycinol as starting materials.

$^1$H-NMR (400 MHz, DMSO-d$_6$) δ 3.61 (2H, t, J=5.5 Hz), 4.93 (1H, t, J=5.5 Hz), 4.98 (1H, dt, J=5.5, 8.1 Hz), 6.81 (1H, d, J=15.6 Hz), 7.20-7.25 (1H, m), 7.24 (1H, dt, J=2.6, 8.6 Hz), 7.28-7.36 (4H, m), 7.56 (1H, dt, J=6.0, 7.9 Hz), 7.55 (1H, dt, J=7.9, 6.2 Hz), 7.62 (1H, d, J=15.6 Hz), 7.63 (1H, d, J=9.0 Hz), 7.65 (1H, d, J=9.0 Hz), 7.78 (1H, ddd, J=1.6, 2.3, 10.7 Hz), 7.89 (1H, d, J=7.9 Hz), 8.30 (1H, s), 8.44 (1H, d, J=8.1 Hz), 13.50 (1H, s)

Example I-23 a; 3-(3-Fluorophenyl)-5-{[(3S)tetrahydro-3-furanyloxy]methyl}-1-trityl-1H-indazole To a solution of 40 mg of (S)-3-hydroxytetrahydrofuran in tetrahydrofuran was added 15 mg of 60% sodium hydride (oily) in an atmosphere of nitrogen gas, and the mixture was stirred at room temperature for 15 minute. To the reaction mixture were added 150 mg of 5-(chloromethyl)-3-(3-fluorophenyl)-1-trityl-1H-indazole produced in Production Example I-32 and 45 mg of sodium iodide, followed by stirring at room temperature for five days. After adding water to the reaction mixture, it was extracted with 20 ml of ethyl acetate. The organic layer was sequentially washed with half-saturated aqueous sodium chloride solution and brine, dried over anhydrous magnesium sulfate and the solvent was evaporated. The resulting crude product was purified and separated by silica gel column chromatography (ethyl acetate:toluene=0:1 to 1:9), to give 84 mg of the title compound as a white amorphous powder.

$^1$H-NMR (400 MHz, DMSO-D$_6$) δ 1.90-1.97 (2H, m), 3.63-3.77 (4H, m), 4.19-4.25 (1H, m), 4.50 (1H, d, J=15.6 Hz), 4.52 (1H, d, J=15.6 Hz), 6.46 (1H, d, J=8.8 Hz), 7.09 (1H, d, J=8.8 Hz), 7.17-7.40 (16H, m), 7.56 (1H, td, J=8.0, 6.4 Hz), 7.59 (1H, d, J=10.0 Hz), 7.75 (1H, d, J=8.0 Hz), 8.04 (1H, s).

b: 3-(3-Fluorophenyl)-5-{[(3S)tetrahydro-3-furanyloxy]methyl}-1H-indazole

To a solution of 82 mg of 3-(3-fluorophenyl)-5-{[(3S)tetrahydro-3-furanyloxy]methyl}-1-trityl-1H-indazole in 1.6 ml methylene chloride were added 0.05 ml of triisopropylsilane and 0.4 ml of trifluoroacetic acid, and the mixture was stirred at room temperature for 20 minutes. To the reaction mixture was added ethyl acetate. The mixture was sequentially washed with saturated aqueous sodium hydrogencarbonate solution (×2) and brine, dried over anhydrous magnesium sulfate and the solvent was evaporated. Then, the resulting crude product was purified and separated by silica gel column chromatography (ethyl acetate:toluene=1:4), to give 36 mg of the title compound as a viscous colorless oil.

$^1$H-NMR (400 MHz, DMSO-D$_6$) δ 1.93-2.01 (2H, m), 3.64-3.81 (4H, m), 4.21-4.28 (1H, m), 4.59 (1H, d, J=15.6 Hz), 4.62 (1H, d, J=15.6 Hz), 7.24 (1H, td, J=8.0, 2.4 Hz), 7.40 (1H, d, J=8.4 Hz), 7.58 (1H, td, J=8.0, 6.4 Hz), 7.59 (1H, d, J=8.4 Hz), 7.74 (1H, ddd, J=10.4, 1.6, 2.4 Hz), 7.86 (1H, d, J=8.0 Hz), 8.04 (1H, s), 13.38 (1H, s).

Example I-24

N-Ethyl-N'-[3-(3-fluorophenyl)-1H-5-indazolyl]urea

To a solution of 50 mg of tert-butyl 5-amino-3-(3-fluorophenyl)-1H-1-indazolecarboxylate produced in Production Example I-26 in 5 ml tetrahydrofuran was added 0.015 ml of ethyl isocyanate, and the mixture was stirred at room temperature for 2 hours. After the completion of the reaction, to the reaction mixture was added with 1 ml of 5 N hydrochloric acid and the mixture was stirred for further 1 hour. To the reaction mixture was added an aqueous sodium hydrogencarbonate solution, and the mixture was extracted with ethyl acetate. The extract was sequentially washed with water, dried over anhydrous magnesium sulfate and the solvent was evaporated. To the residue was added diisopropyl ether, and the mixture was filtered, to give 28 mg of the title compound as a colorless powder.

$^1$H-NMR (400 MHz, DMSO-d$_6$) δ 1.05 (3H, t, J=6.5 Hz), 3.11 (2H, dq, J=5.6, 6.5 Hz), 6.06 (1H, t, J=5.6 Hz), 7.21 (1H, dt, J=2.9, 8.6 Hz), 7.30 (1H, dd, J=1.7, 8.9), 7.46 (1H, d, J=8.9 Hz), 7.56 (1H, dt, J=6.0, 8.1 Hz), 7.64 (1H, ddd, J=1.4, 2.9, 10.6 Hz), 7.74 (1H, d, J=8.6 Hz), 8.22 (1H, s), 8.48 (1H, s), 13.17 (1H, s)

Example I-25 a; [3-(3-Fluorophenyl)-1-(methoxymethyl)-1H-5-indazolyl](2-thienyl)methanol

A total of 700 mg of 3-(3-fluorophenyl)-1-(methoxymethyl)-1H-5-indazolylcarboxaldehyde was obtained as a colorless oil, by subjecting 780 mg of [3-(3-fluorophenyl)-1-

(methoxymethyl)-1H-5-indazolyl]methanol produced in Production Example I-34 to the oxidation procedure of Production Example I-4-c.

A solution of 0.15 ml of thiophene in dry tetrahydrofuran was cooled to −78° C. in an atmosphere of nitrogen gas, 1.8 ml of a 2.5 M solution of n-butyllithium in hexane was added dropwise, and the mixture was stirred at −20° C. for 1 hour. The reaction mixture was cooled again to −78° C., and a solution of 0.35 g of the above-obtained 3-(3-fluorophenyl)-1-(methoxymethyl)-1H-5-indazolylcarboxaldehyde in 4 ml dry tetrahydrofuran was added to the reaction mixture, followed by heating to room temperature. To the reaction mixture was added an aqueous ammonium chloride solution, and the mixture was extracted with ethyl acetate. The organic layer was washed with water, dried over anhydrous magnesium sulfate and the solvent was evaporated. The residue was purified and separated by silica gel column chromatography (ethyl acetate:hexane=1:6), to give 90 mg of the title compound as a colorless oil.

$^1$H-NMR (400 MHz, CDCl$_3$) δ 3.37 (3H, s), 5.74 (2H, s), 6.24 (1H, s), 6.92 (1H, dd, J=1.0, 3.4 Hz), 6.95 (1H, dd, J=3.4, 4.8 Hz), 7.11 (1H, dt, J=2.7, 8.2 Hz), 7.28 (1H, dd, J=1.0, 4.8 Hz), 7.48 (1H, dt, J=6.5, 8.2 Hz), 7.54 (1H, dd, J=1.9, 9.0 Hz), 7.60 (1H, d, J=9.0 Hz), 7.69 (1H, ddd, J=1.2, 2.7, 9.9 Hz), 7.76 (1H, dt, J=1.2, 8.2 Hz), 8.12 (1H, d, J=1.9 Hz)

b; [3-(3-Fluorophenyl)-1H-5-indazolyl](2-thienyl)methanone

A total of 90 mg of [3-(3-fluorophenyl)-1-(methoxymethyl)-1H-5-indazolyl](2-thienyl)methanol was oxidized by the procedure of Production Example I-4-c, to give 85 mg of [3-(3-fluorophenyl)-1-(methoxymethyl)-1H-5-indazolyl](2-thienyl)methanone as a colorless powder. This compound was dissolved in 3 ml of tetrahydrofuran, and 1 ml of 5 N hydrochloric acid was added, followed by heating under reflux for one day. To the reaction mixture was added aqueous sodium hydrogencarbonate solution and the mixture was extracted with ethyl acetate. The organic layer was washed with water, dried over anhydrous magnesium sulfate and the solvent was evaporated. The residue was purified and separated by silica gel column chromatography (ethyl acetate:hexane=1:5), to give 30 mg of the title compound as colorless needles.

By treating 17 mg of [3-(3-fluorophenyl)-1-(hydroxymethyl)-1H-5-indazolyl](2-thienyl)methanone, a by-product formed by incomplete deprotection in the above reaction, with concentrated aqueous ammonia solution in methanol, 11 mg of the title compound was further obtained.

$^1$H-NMR (400 MHz, CDCl$_3$) δ 7.15 (1H, dt, J=2.6, 8.4 Hz), 7.21 (1H, dd, J=3.8, 4.9 Hz), 7.50 (1H, dt, J=6.6, 8.0 Hz), 7.64 (1H, d, J=8.9 Hz), 7.67-7.72 (1H, m), 7.71 (1H, dd, J=1.0, 3.8 Hz), 7.74-7.79 (1H, m), 7.76 (1H, dd, J=1.0, 4.9 Hz), 8.02 (1H, dd, J=1.4, 8.9 Hz), 8.61 (1H, d, J=1.4 Hz)

Example I-26 a; tert-Butyl 3-(3-fluorophenyl)-5-[hydroxy(phenyl)methyl]-1H-1-indazolecarboxylate A total of 30 mg of the title compound was obtained as a colorless oil by the procedure of Production Example I-25-a, except from 160 mg of tert-butyl 3-(3-fluorophenyl)-5-formyl-1H-1-indazolecarboxylate produced in Production Example I-25-a and 0.58 ml of a 1.04 N solution of phenyllithium in cyclohexane as starting materials.

$^1$H-NMR (400 MHz, CDCl$_3$) δ 1.73 (9H, s), 6.02 (1H, bs), 6.24 (1H, s), 7.17 (1H, ddt, J=1.3, 2.7, 8.5 Hz), 7.25-7.30 (1H, m), 7.32-7.37 (2H, m), 7.37-7.41 (2H, m), 7.49 (1H, dt, J=6.3, 7.8 Hz), 7.51 (1H, dd, J=1.5, 8.6 Hz), 7.72 (1H, ddd, J=1.7, 2.7, 9.7 Hz), 7.88 (1H, dd, J=1.3, 7.8 Hz), 8.06 (1H, d, J=1.5 Hz), 8.13 (1H, d, J=8.6 Hz)

b; [3-(3-Fluorophenyl)-1H-5-indazolyl](phenyl)methanone

A total of 30 mg of tert-butyl 3-(3-fluorophenyl)-5-[hydroxy(phenyl)methyl]-1H-1-indazolecarboxylate as a starting material was oxidized by the procedure of Production Example I-4-c, was treated with 5 N hydrochloric acid by the procedure of Production Example I-25-b, to give 4 mg of the title compound as a colorless powder.

$^1$H-NMR (400 MHz, DMS-d$_6$) δ 7.25 (1H, ddt, J=0.7, 2.7, 8.6 Hz), 7.52-7.59 (3H, m), 7.64-7.70 (1H, m), 7.69 (1H, ddd, J=1.4, 2.7, 10.4 Hz), 7.74 (1H, dd, J=0.7, 8.6 Hz), 7.75-7.80 (3H, m, 7.83 (1H, dd, J=1.5, 8.6 Hz), 8.38 (1H, dd, J=0.7, 1.5 Hz)

Example I-27 a; (E)-3-(Dimethylamino)-1-(1H-3-indazolyl)-2-propen-1-one

A total of 5.0 g of 1H-indazole as a starting material was subjected to bromination and tert-butoxycarbonylation by the procedures of Production Examples I-26-a and I-26-b, was acetylated at the 3-position by the procedure of Production Example I-29-a, to give 2.5 g of tert-butyl 3-acetyl-1H-1-indazolecarboxylate. A total of 1.5 g of this product was treated with 5 N hydrochloric acid by the procedure of Production Example I-25-b and thereby yielded 860 mg of 1-(1H-3-indazolyl)ethanone. A solution of 240 mg of this product and 0.4 ml of N,N-dimethylformamide dimethylacetal in 5 ml toluene was heated under reflux for 9 hours. The solvent was evaporated, and the residue was purified and separated by silica gel column chromatography (ethyl acetate:hexane=2:1), to give 88 mg of the title compound as a colorless powder.

$^1$H-NMR (400 MHz, DMSO-d$_6$) δ 2.88 (3H, bs), 3.13 (3H, bs), 6.08 (1H, d, J=13.1 Hz), 7.19 (1H, t, J=7.6 Hz), 7.36 (1H, t, J=7.6 Hz), 7.56 (1H, d, J=7.6 Hz), 7.72 (1H, d, J=13.1 Hz), 8.26 (1H, d, J=7.6 Hz), 13.37 (1H, s)

b; 4-(1H-3-Indazolyl)-2-pyrimidinamine

A total of 20 mg of metallic sodium was dissolved in 5 ml of dry ethanol. To the resulting solution were added 76 mg of guanidine hydrochloride and 85 mg of (E)-3-(dimethylamino)-1-(1H-3-indazolyl)-2-propen-1-one, followed by heating under reflux for 12 hours. To the reaction mixture was added aqueous ammonium chloride solution, and the mixture was extracted with ethyl acetate. The organic layer was washed with water, dried over anhydrous magnesium sulfate and the solvent was evaporated. The residue was purified and separated by silica gel column chromatography (ethyl acetate:hexane=7:5), to give 55 mg of the title compound as a colorless powder.

$^1$H-NMR (400 MHz, DMSO-d$_6$) δ 6.69 (2H, bs), 7.22 (1H, t, J=7.9 Hz), 7.24 (1H, d, J=5.3 Hz), 7.40 (1H, t, J=7.9 Hz), 7.58 (1H, d, J=7.9 Hz), 8.26 (1H, d, J=5.3 Hz), 8.67 (1H, d, J=7.9 Hz)

The compounds according to Examples I-28 to I-100 were synthesized by the following Synthesis Process I-A.

Synthesis Process I-A

A total of 96 pieces of a polystyrene resin (SunPhase Polystyrene D-Seriese, Trityl™) labeled with TRANSTEM™ was left stand in 100 ml of a 10% solution of acetyl chloride in methylene chloride for 3 hours. After removing the solution, the residue was washed with three portions of methylene chloride and dried in vacuo. The resin was heated in a solution of 15 g of 3-bromo-5-nitro-1H-indazole produced in Production Example I-26-a and diisopropylamine in 150 ml N-methylpyrrolidone at 80° C. for 4 hours. After removing the solution, the resin was sequentially washed with N-methylpyrrolidone, ethanol, water, methanol and tetrahydrofuran, and dried in vacuo.

The resulting resin was divided among 8 groups (each 12 pieces) according to its label and was added to 15 ml of a solution of 0.5 M boronic acid in N-methylpyrrolidone of eight types previously prepared, respectively. Each reaction mixture was treated with 1.5 ml of a 0.5 M solution of 2-(di-tert-butylphosphino)biphenyl in N-methylpyrrolidone, 1.8 ml of a 8 M aqueous solution of potassium fluoride, and a catalytic amount of palladium(II) acetate by heating at 80° C. for 12 hours. After removing the solution, the resin was washed according to the above procedure and was dried under reduced pressure. The resin was heated in 150 ml of a 2 M solution of stannic chloride in N-methylpyrrolidone at 80° C. for 4 hours. After removing the solution, the resin was washed according to the above procedure and was dried in vacuo.

The resin was further divided among 12 groups (each 8 pieces) according to its label and was added to 15 ml of a solution of 0.5 M carboxylic acid in N-methylpyrrolidone of twelve types previously prepared, respectively. To each well were sequentially added 1.15 g of 1-hydroxybenzotriazole monohydrate, 1.2 ml of 1-ethyl-3-(3-dimethylaminopropyl) carbodiimide (=WSC) and 2.0 ml of diisopropylethylamine. In a sulfonamide compound, a sulfonyl chloride reagent and diisopropylethylamine were added in tetrahydrofuran. The mixture was subjected to sonication for 1 hour and was left stand at room temperature for one day. After removing the solution, the resin was washed according to the above procedure and was dried under reduced pressure. The resin was placed in each of 96-well pin plate according to its label.

A mixture solution of 0.5 ml of trifluoroacetic acid, 0.1 ml of triisopropylsilane, and 0.5 ml of dichloromethane previously prepared was added to the resin in each of the 96-well plate, and the mixture was subjected to sonication for 10 minutes and was left stand for 30 minutes. This procedure was repeated twice, and the resin was washed with 1 ml of dimethylformamide. Next, nitrogen gas was blown to the acid-treated wells, and each residue was dissolved in a dimethylformamide solution obtained in washing procedure, was purified and separated by LC-MS (developing solvent, (eluent); 0.1% solution of trifluoroacetic acid in acetonitrile:0.1% aqueous solution of trifluoroacetic acid=1:99 to 100:0/20 minute-cycle, flow rate; 20 ml/min, column; YMC Combiprep ODS-AM, 20 mmΦ×50 mm (Long)), to give the following compounds.

Example I-28

2-(5-{[2-(1,1-Dioxo-1l$^6$,4-thiazinan-4-yl)acetyl]amino}-1H-3-indazolyl)benzoic acid MS (ESI) m/z 429 MH$^+$ Example I-29

N7-[3-(2,3-Dihydro-1H-5-indolyl)-1H-5-indazolyl]bicyclo[4.2.0]octa-1(6),2,4-triene-7-carboxamide MS (ESI) m/z 381 MH$^+$ Example I-30

N1-[3-(8-Quinolyl)-1H-5-indazolyl]-2,4-dichlorobenzamide

MS (ESI) m/z 433 M$^+$

Example I-31

N1-{3-[4-(Methylsulfonyl)phenyl]-1H-5-indazolyl}-2-(2,4-dichlorophenyl)acetamide MS (ESI) m/z 474 M$^+$ Example I-32

N1-(3-Benzo[b]thiophen-2-yl-1H-5-indazolyl)-1-cyclopentanecarboxamide

MS (ESI) m/z 362 MH$^+$

Example I-33

N7-(3-Benzo[b]thiophen-2-yl-1H-5-indazolyl)-2,3-dihydrobenzo[b]furan-7-carboxamide MS (ESI) m/z 412 MH$^+$ Example I-34

N1-(3-Benzo[b]thiophen-2-yl-1H-5-indazolyl)-3-(2-thienyl)propanamide

MS (ESI) m/z 404 MH$^+$

Example I-35

N1-(3-Benzo[b]thiophen-2-yl-1H-5-indazolyl)-(E)-3-cyclopropyl-2-propenamide

MS (ESI) m/z 360 MH$^+$

Example I-36

N1-[3-(2-Naphthyl)-1H-5-indazolyl]-1-cyclopropanecarboxamide

MS (ESI) m/z 328 MH$^+$

Example I-37

N2-[3-(2-Naphthyl)-1H-5-indazolyl]-2-thiophenecarboxamide

MS (ESI) m/z 370 MH$^+$

Example I-38

N1-[3-(2-Naphthyl)-1H-5-indazolyl]-8-hydroxyoctanamide

MS (ESI) m/z 402 MH$^+$

Example I-39

N1-(3-{3-[(Cyclopropylcarbonyl)amino]phenyl}-1H-5-indazolyl)-1-cyclopropanecarboxamide MS (ESI) m/z 361 MH$^+$

Example I-40

N1-3-[4-(Benzyloxy)phenyl]-1H-5-indazolyl3-oxo-1-cyclopentanecarboxamide

MS (ESI) m/z 426 MH$^+$

Example I-41

N1-[3-(2-Naphthyl)-1H-5-indazolyl]-4-(hydroxymethyl)benzamide

MS (ESI) m/z 394 MH$^+$

Example I-42

N1-[3-(2-Naphthyl)-1H-5-indazolyl]-4-methoxy-1-cyclohexanecarboxamide

MS (ESI) m/z 400 MH$^+$

Example I-43

N1-[3-(2-Naphthyl)-1H-5-indazolyl]-2-hydroxy-3-phenylpropanamide

MS (ESI) m/z 408 MH$^+$

Example I-44

N1-(3-Benzo[b]thiophen-2-yl-1H-5-indazolyl)-trans-4-hydroxy-1-cyclohexanecarboxamide MS (ESI) m/z 392 MH$^+$

Example I-45

N1-(3-Benzo[b]furan-2-yl-1H-5-indazolyl)-2-(3-pyridyl)acetamide

MS (ESI) m/z 369 MH$^+$

Example I-46

N1-(3-Benzo[b]furan-2-yl-1H-5-indazolyl)-2-(3-thienyl)acetamide

MS (ESI) m/z 374 MH$^+$

Example I-47

N2-(3-Benzo[b]furan-2-yl-1H-5-indazolyl)-1,2,3,4-tetrahydro-2-naphthalenecarboxamide MS (ESI) m/z 408 MH$^+$

Example I-48

N2-(3-Benzo[b]furan-2-yl-1H-5-indazolyl)-2-furamide

MS (ESI) m/z 344 MH$^+$

Example I-49

N3-(3-Benzo[b]furan-2-yl-1H-5-indazolyl)-3-furamide

MS (ESI) m/z 344 MH$^+$

Example I-50

N1-(3-Benzo[b]furan-2-yl-1H-5-indazolyl)-2-hydroxy-2-phenylacetamide

MS (ESI) m/z 384 MH$^+$

Example I-51

N1-[3-(4-Acetylphenyl)-1H-5-indazolyl]-2-(2-pyridyl)acetamide

MS (ESI) m/z 371 MH$^+$

Example I-52

N1-[3-(4-Acetylphenyl)-1H-5-indazolyl]-2-(3,4-dimethoxyphenyl)acetamide

MS (ESI) m/z 430 MH$^+$

Example I-53

N1-[3-(2-Naphthyl)-1H-5-indazolyl]-4-oxopentanamide

MS (ESI) m/z 358 MH$^+$

Example I-54

N1-(3-Benzo[b]thiophen-2-yl-1H-5-indazolyl)-3-methoxypropanamide

MS (ESI) m/z 352 MH$^+$

Example I-55

N3-(3-Benzo[b]thiophen-2-yl-1H-5-indazolyl)tetrahydro-3-furancarboxamide

MS (ESI) m/z 364 MH$^+$

Example I-56

N1-(3-Benzo[b]furan-2-yl-1H-5-indazolyl)-3-oxo-1-indancaroxamide

MS (ESI) m/z 408 MH$^+$

Example I-57

N1-[3-(4-Acetylphenyl)-1H-5-indazolyl]-3-phenoxypropanamide

MS (ESI) m/z 400 MH$^+$

Example I-58

N1-[3-(2-Naphthyl)-1H-5-indazolyl]-3-hydroxy-2-(hydroxymethyl)-2-methylpropanamide MS (ESI) m/z 376 MH$^+$

Example I-59

N1-[3-(2-Naphthyl)-1H-5-indazolyl]-2-(2-oxocyclopentyl)acetamide

MS (ESI) m/z 384 MH+

Example I-60

N2-(3-Benzo[b]thiophen-2-yl-1H-5-indazolyl)-(2S)-5-oxotetrahydro-1H-2-pyrrolecarboxamide MS (ESI) m/z 377 MH+

Example I-61

N2-(3-Benzo[b]thiophen-2-yl-1H-5-indazolyl)-(2R)-5-oxotetrahydro-1H-2-pyrrolecarboxamide MS (ESI) m/z 377 MH+

Example I-62

N2-(3-Benzo[b]furan-2-yl-1H-5-indazolyl)tetrahydro-2-furancarboxamide

MS (ESI) m/z 348 MH+

Example I-63

N3-(3-Benzo[b]furan-2-yl-1H-5-indazolyl)-2,2-dimethyl-5-oxotetrahydro-3-furancarboxamide MS (ESI) m/z 390 MH+

Example I-64

N-(3-Phenyl-1H-5-indazolyl)methanesulfonamide

MS (ESI) m/z 288 MH+

Example I-65

4-({[3-(3-Fluorophenyl)-1H-5-indazolyl]amino}sulfonyl)benzoic acid

MS (ESI) m/z 412 MH+

Example I-66

N1-[5-({[3-(3-Fluorophenyl)-1H-5-indazolyl]amino}sulfonyl)-4-methyl-1,3-thiazol-2-yl]acetamide MS (ESI) m/z 446 MH+

Example I-67

N2-[3-(4-Methoxyphenyl)-1H-5-indazolyl]-4-(phenylsulfonyl)-2-thiphenesulfonamide MS (ESI) m/z 526 MH+

Example I-68

N2-[3-(1,3-Benzodioxol-5-yl)-1H-5-indazolyl]-2-propanesulfonamide

MS (ESI) m/z 360 MH+

Example I-69

N1-[3-(2-Thienyl)-1H-5-indazolyl]-3,5-di(trifluoromethyl)-1-benzenesulfonamide

MS (ESI) m/z 492 MH+

Example I-70

N,N-Dimethyl-N'-{3-[4-(trifluoromethyl)phenyl]-1H-5-indazolyl}sulfamide

MS (ESI) m/z 385 MH+

Example I-71

N2-{3-[3,5-Di(trifluoromethyl)phenyl]-1H-5-indazolyl}-5-(2-pyridyl)-2-thiophenesulfonamide MS (ESI) m/z 569 MH+

Example I-72

N2-[3-(2,4-Dichlorophenyl)-1H-5-indazolyl]-2-furamide

MS (ESI) m/z 372 MH+

Example I-73

N1-[3-(3-Ethoxyphenyl)-1H-5-indazolyl]-3-hydroxy-3-methylpentanamide

MS (ESI) m/z 368 MH+

Example I-74

N1-(3-Dibenzo[b,d]furan-4-yl-1H-5-indazolyl)-1-cyclopropanecaroxamide

MS (ESI) m/z 368 MH+

Example I-75

N1-{3-[4-(tert-butyl)phenyl]-1H-5-indazolyl}-1-phenyl-1-cyclopropanecarboxamide

MS (ESI) m/z 410 MH+

Example I-76

N1-[3-(2-Naphthyl)-1H-5-indazolyl]-3-hydroxy-2,2-dimethylpropanamide

MS (ESI) m/z 360 MH+

Example I-77

N1-{3-[3-Fluoro-4-(phenyl)phenyl]-2-oxo-2-phenylacetamide

MS (ESI) m/z 436 MH+

Example I-78

N1-{3-[4-(trifluoromethoxy)phenyl]-1H-5-indazolyl}-4-(dimethylamino)benzamide

MS (ESI) m/z 441 MH+

Example I-79

N1-[3-(4-Phenoxyphenyl)-1H-5-indazolyl]-3-hydroxy-3-methylbutanamide

MS (ESI) m/z 402 MH$^+$

Example I-80

N1-[3-(3,4-Dichlorophenyl)-1H-5-indazolyl]-(1S,2S)-2-phenylcyclopropane-1-carboxamide MS (ESI) m/z 422 M$^+$

Example I-81

N7-[3-(3-Acetylphenyl)-1H-5-indazolyl]bicyclo[4.2.0]octa-1(6),2,4-triene-7-carboxamide MS (ESI) m/z 382 MH$^+$

Example I-82

N4-[3-(3-Acetylphenyl)-1H-5-indazolyl]isonicotinamide

MS (ESI) m/z 357 MH$^+$

Example I-83

N1-[3-(3-Acetylphenyl)-1H-5-indazolyl]-(2R)-2-amino-2-cyclohexylethanamide

MS (ESI) m/z 391 MH$^+$

Example I-84

N1-[3-(5-Acetyl-2-thienyl)-1H-5-indazolyl]-1-cyclobutanecarboxamide

MS (ESI) m/z 340 MH$^+$

Example I-85

N1-[3-(4-Biphenyl)-1H-5-indazolyl]-1-phenyl-1-cyclopentanecarboxamide

MS (ESI) m/z 458 MH$^+$

Example I-86

N3-[3-(3-Biphenyl)-1H-5-indazolyl]-1,2,3,4-tetrahydro-3-isoquinolinecarboxamide

MS (ESI) m/z 445 MH$^+$

Example I-87

N1-{3-[3,5-Di(trifluoromethyl)phenyl]-1H-5-indazolyl}-(2R)-2-amino-3,3-diphenylpropanamide MS (ESI) m/z 569 MH$^+$

Example I-88

N1-(3-Benzo[b]furan-2-yl-1H-5-indazolyl)-(2R)-2-amino-3,3-dimethylbutanamide

MS (ESI) m/z 363 MH$^+$

Example I-89

N1-(3-Benzo[b]furan-2-yl-1H-5-indazolyl)-(2R)-2-amino-3-(benzyloxy)propanamide

MS (ESI) m/z 427 MH$^+$

Example I-90

N1-(3-Benzo[b]thiophen-2-yl-1H-5-indazolyl)-(2R)-2-amino-3-phenylpropanamide

MS (ESI) m/z 413 MH$^+$

Example I-91

N1-(3-Benzo[b]thiophen-2-yl-1H-5-indazolyl)-(2R)-2-amino-3-methylbutanamide

MS (ESI) m/z 365 MH$^+$

Example I-92

N2-[3-(2-Thienyl)-1H-5-indazolyl]-2-pyridinecarboxamide

MS (ESI) m/z 321 MH$^+$

Example I-93

N1-[3-(2-Furyl)-1H-5-indazolyl]-3-hydroxy-2-phenylpropanamide

MS (ESI) m/z 348 MH$^+$

Example I-94

N-[3-(2-Naphthyl)-1H-5-indazolyl]methanesulfonamide

MS (ESI) m/z 338 MH$^+$

Example I-95

N1-[3-(2-Naphthyl)-1H-5-indazolyl]acetamide

MS (ESI) m/z 302 MH$^+$

Example I-96

N1-{3-[2-(trifluoromethyl)phenyl]-1H-5-indazolyl}-2-(1,3-benzodioxol-5-yl)acetamide MS (ESI) m/z 440 MH$^+$

Example I-97

N1-[3-(3-Thienyl)-1H-5-indazolyl]-2-methoxyacetamide

MS (ESI) m/z 288 MH$^+$

Example I-98

N1-[3-(1H-2-Pyrrolyl)-1H-5-indazolyl]-(3S)-3-hydroxy-3-phenylpropanamide

MS (ESI) m/z 347 MH$^+$

Example I-99

N1-[3-(2,4-Dimethoxy-5-pyrimidinyl)-1H-5-indazolyl]-2-(2-thienyl)acetamide

MS (ESI) m/z 396 MH$^+$

Example I-100

N1-[3-(3-Pyridyl)-1H-5-indazolyl]-(3R)-3-hydroxy-3-phenylpropanamide

MS (ESI) m/z 359 MH$^+$

The compounds according to Examples I-101 to I-107 were synthesized by the following Synthesis Process I-B.

Synthesis Process I-B

The resin was subjected to the procedures of Synthesis Process I-A till the treatment with stannic chloride and was divided among two groups (each 48 pieces) according to the label, followed by amidation with a 0.5 M solution of any of two amino acids having an amino group protected by Fmoc group in N-methylpyrrolidone. Each of the resin was washed and was treated with N-methylpyrrolidone solution containing 20% piperidine to thereby remove the Fmoc group.

The resulting resin was divided among twelve groups (each 8 pieces), ten groups of which were treated with any of 0.5 M solution of five alkyl bromides in N-methylpyrrolidone and cesium carbonate for alkylation of the amide group. Then, the resin was subjected to an acid treatment according to the procedure of Synthesis Process I-A, was separated and purified by LC-MS according to the procedure of Synthesis Process I-A, to give the following compounds.

Example I-101

N2-[3-Benzo[b]furan-2-yl-1H-5-indazolyl]-(2S)-tetrahydro-1H-2-pyrrolecarboxamide MS (ESI) m/z 347 MH$^+$

Example I-102

N2-[3-(5-Acetyl-2-thienyl)-1H-5-indazolyl]-(2S)-1-benzyltetrahydro-1H-2-pyrrolecarboxamide MS (ESI) m/z 445 MH$^+$

Example I-103

N2-[3-(3-Ethoxyphenyl)-1H-5-indazolyl]-(2S)-1-[3-(trifluoromethyl)benzyl]tetrahydro-1H-2-pyrrolecarboxamide MS (ESI) m/z 509 MH$^+$

Example I-104

N4-[3-(2-Naphthyl)-1H-5-indazolyl]-4-piperidinecarboxamide

MS (ESI) m/z 371 MH$^+$

Example I-105

N4-[3-Benzo[b]thiophen-2-yl-1H-5-indazolyl]-1-benzyl-4-piperidinecarboxamide

MS (ESI) m/z 467 MH$^+$

Example I-106

N4-[3-(4-Acetylphenyl)-1H-5-indazolyl]-1-(2,4-difluorobenzyl)-4-piperidinecarboxamide MS (ESI) m/z 489 MH$^+$

Example I-107

Methyl {3-[4-({[3-(1-naphthyl)-1H-5-indazolyl]amino}carbonyl)piperidino]methyl}benzoate MS (ESI) m/z 519 MH$^+$ The compounds according to Examples I-108 to I-156 were synthesized by the following Synthesis Process I-C.

Synthesis Process I-C

A solution of 180 mg of each indazolecarboxylic acid produced in Production Examples I-1 to I-25 in 6 ml dimethylformamide was pipetted into several test tubes in an amount of 0.5 ml each, each of which was treated with 1.1 equivalents of any of various amines. The reaction mixture was sequentially treated with 0.065 ml of a 1 M solution of 1-hydroxybenzotriazole monohydrate in dimethylformamide, 0.130 ml of a 1 M solution of 1-ethyl-3-(3-dimethylaminopropyl)carbodiimide (=WSC) in dimethylformamide, and 0.05 ml of diisopropylamine, the mixture was subjected to sonication for 10 minutes and was left stand for one day. Each of the reaction mixtures was separated and purified by LC-MS under the conditions of Synthesis Process I-A and thereby yielded the test compounds.

Example I-108

[3-(3-Fluorophenyl)-1H-5-indazolyl](morpholino)methanone

MS (ESI) m/z 326 MH$^+$

Example I-109

[3-(3-Fluorophenyl)-1H-5-indazolyl](4-methylpiperazino)methanone

MS (ESI) m/z 339 MH$^+$

Example I-110

[3-(3-Fluorophenyl)-1H-5-indazolyl](4-hydroxy-4-phenylpiperidino)methanone

MS (ESI) m/z 416 MH$^+$

Example I-111

N5-(3-morpholinopropyl)-3-(3-fluorophenyl)-1H-5-indazolecarboxamide

MS (ESI) m/z 383 MH$^+$

Example I-112

N5-[(1S)-1-(Hydroxymethyl)-3-methylbutyl]-3-(3-fluorophenyl)-1H-5-indazolecarboxamide MS (ESI) m/z 342 MH$^+$

Example I-113

N5-[(1S)-2-Hydroxy-1-(1H-1-indazolylmethyl)ethyl]-3-(3-fluorophenyl)-1H-5-indazolecarboxamide MS (ESI) m/z 380 MH$^+$

Example I-114

N5-[(1S)-1-Benzyl-2-hydroxyethyl]-3-(3-fluorophenyl)-1H-5-indazolecarboxamide

MS (ESI) m/z 390 MH$^+$

Example I-115

N5-[(1S)-1-(Hydroxymethyl)propyl]-3-(3-fluorophenyl)-1H-5-indazolecarboxamide

MS (ESI) m/z 328 MH$^+$

Example I-116

N5-[(1R)-1-(Hydroxymethyl)propyl]-3-(3-fluorophenyl)-1H-5-indazolecarboxamide

MS (ESI) m/z 328 MH$^+$

Example I-117

N5-(2-Piperidinoethyl)-3-(3-fluorophenyl)-1H-5-indazolecarboxamide

MS (ESI) m/z 367 MH$^+$

Example I-118

N5-(trans-4-Hydroxycyclohexyl)-3-(3-fluorophenyl)-1H-5-indazolecarboxamide

MS (ESI) m/z 354 MH$^+$

Example I-119

N5-[2-(2-Hydroxyethoxy)ethyl]-3-(3-fluorophenyl)-1H-5-indazolecarboxamide

MS (ESI) m/z 344 MH$^+$

Example I-120

N5-Ethyl-N-5-(2-hydroxyethyl)-3-(3-fluorophenyl)-1H-5-indazolecarboxamide

MS (ESI) m/z 328 MH$^+$

Example I-121

N5-[4-(Aminosulfonyl)benzyl]-3-(2-methoxyphenyl)-1H-5-indazolecarboxamide

MS (ESI) m/z 437 MH$^+$

Example I-122

N5-[(1R,2R)-2-(Hydroxymethyl)cyclohexyl]-3-(2-fluorophenyl)-1H-5-indazolecarboxamide MS (ESI) m/z 368 MH$^+$

Example I-123

N5-[(1R,2R)-2-Hydroxycyclohexyl]-3-(2-quinolyl)-1H-5-indazolecarboxamide

MS (ESI) m/z 387 MH$^+$

Example I-124

N5-[(1-(Methoxymethyl)propyl]-3-(2-quinolyl)1H-5-indazolecarboxamide

MS (ESI) m/z 375 MH$^+$

Example I-125

N5-[4-(Methylsulfonyl)benzyl]-3-(2-quinolyl)-1H-5-indazolecarboxamide

MS (ESI) m/z 457 MH$^+$

Example I-126

N5-[(1R,2S)-2-(Hydroxymethyl)cyclohexyl]-3-(3-quinolyl)-1H-5-indazolecarboxamide MS (ESI) m/z 401 MH$^+$

Example I-127

N5-[2-(1H-3-Indolyl)ethyl]-3-(4-quinolyl)-1H-5-indazolecarboxamide

MS (ESI) m/z 368 MH$^+$

Example I-128

N5-(5-Hydroxypentyl)-3-(-(1,3-benzothiazol-2-yl)-1H-5-indazolecarboxamide

MS (ESI) m/z 381 MH$^+$

Example I-129

N5-Cyclopropyl-3-phenyl-1H-5-indazolecarboxamide

MS (ESI) m/z 278 MH$^+$

Example I-130

N5-[2-(Acetylamino)ethyl]-3-(2-naphthyl)-1H-5-indazolecarboxamide

MS (ESI) m/z 373 MH$^+$

Example I-131

N5-(3-Pyridylmethyl)-3-(5-acetyl2-thienyl)-1H-5-indazolecarboxamide

MS (ESI) m/z 377 MH$^+$

Example I-132

N5-[(1S)-2-Amino-1-methyl-2-oxoethyl]-3-(3-acetylphenyl)-1H-5-indazolecarboxamide MS (ESI) m/z 373 M+Na$^+$

Example I-133

N6-(3-Methoxybenzyl)-3-(3-fluorophenyl)-1H-6-indazolecarboxamide

MS (ESI) m/z 376 MH$^+$

Example I-134

N7-[3-(1H-1-Imidazolyl)propyl]-3-(3-fluorophenyl)-1H-7-indazolecarboxamide

MS (ESI) m/z 364 MH$^+$

Example I-135

N1-Cyclopropyl-2-[3-(3-fluorophenyl)-1H-5-indazolyl]acetamide

MS (ESI) m/z 310 MH$^+$

Example I-136

N1-(3-Methoxyphenethyl)-2-[3-(3-fluorophenyl)-1H-5-indazolyl]acetamide

MS (ESI) m/z 404 MH$^+$

Example I-137

N5-[3-(2-Oxotetrahydro-1H-1-pyrrolyl)propyl]-3-benzo[b]thiophen-2-yl-1H-5-indazolecarboxamide MS (ESI) m/z 419 MH$^+$

Example I-138

N5-[2-(2-Thienyl)ethyl]-3-benzo[b]thiophen-2-yl-1H-5-indazolecarboxamide

MS (ESI) m/z 404 MH$^+$

Example I-139

N5-(2-Phenoxyethyl)-3-benzo[b]furan-2-yl-1H-5-indazolecarboxamide

MS (ESI) m/z 398 MH$^+$

Example I-140

N5-(3-Tetrahydro-1H-1-pyrrolylpropyl)-3-benzo[b]furan-2-yl-1H-5-indazolecarboxamide MS (ESI) m/z 389 MH$^+$

Example I-141

N5-[2-(1H-3-Indolyl)ethyl]-3-(2-naphthyl)-1H-5-indazolecarboxamide

MS (ESI) m/z 431 MH$^+$

Example I-142

N5-(2,3-Dihydro-1H-2-indenyl)-3-(3-fluorophenyl)-1H-5-indazolecarboxamide

MS (ESI) m/z 372 MH$^+$

Example I-143

N5-Cyclopropyl-3-(3-fluorophenyl)-1H-5-indazolecarboxamide

MS (ESI) m/z 296 MH$^+$

Example I-144

N5-(2-Furylmethyl)-3-(3-fluorophenyl)-1H-5-indazolecarboxamide

MS (ESI) m/z 336 MH$^+$

Example I-145

N5-Tetrahydro-2-furanylmethyl-3-(3-fluorophenyl)-1H-5-indazolecarboxamide

MS (ESI) m/z 340 MH$^+$

Example I-146

N5-(2-Morpholinoethyl)-3-(3-fluorophenyl)-1H-5-indazolecarboxamide

MS (ESI) m/z 369 MH$^+$

Example I-147

N5-(2,3-Dihydro-1,4-benzodioxin-6-yl)-3-(3-fluorophenyl)-1H-5-indazolecarboxamide MS (ESI) m/z 390 MH$^+$

Example I-148

N5-[(2R)-3,4-Dihydro-2H-2-chromenylmethyl]-3-(2-pyridyl)-1H-5-indazolecarboxamide MS (ESI) m/z 385 MH$^+$

Example I-149

N5-[1-(Methoxymethyl)propyl]-3-(2-pyridyl)-1H-5-indazolecarboxamide

MS (ESI) m/z 325 MH$^+$

Example I-150

N5-(1,3-Benzodioxol-5-ylmethyl)-3-(3-pyridyl)-1H-5-indazolecarboxamide

MS (ESI) m/z 373 MH$^+$

Example I-151

N5-Cyclopropylmethyl-3-(2-naphthyl)-1H-5-indazolecarboxamide

MS (ESI) m/z 342 MH$^+$

Example I-152

N5-[(3R)-2-Oxotetrahydro-1H-3-furanyl]-3-(2-naphthyl)-1H-5-indazolecarboxamide

MS (ESI) m/z 372 MH$^+$

Example I-153

N5-[2-(2-Puryl)-2-oxoethyl]-3-(2-naphthyl)-1H-5-indazolecarboxamide

MS (ESI) m/z 396 MH$^+$

Example I-154

N5-[2-((1,3-Thiazol-2-yl)ethyl]-3-(2-naphthyl)-1H-5-indazolecarboxamide

MS (ESI) m/z 399 MH$^+$

Example I-155

N5-(2-Ethoxyethyl)-3-(3-fluorophenyl)-1H-5-indazolecarboxamide

MS (ESI) m/z 328 MH$^+$

Example I-156

N5-[(3S)-2-Oxotetrahydro-1H-3-furanyl]-3-(2-quinolyl)-1H-5-indazolecarboxamide

MS (ESI) m/z 373 MH$^+$

The compounds according to Examples I-157 to I-162 were synthesized by the following Synthesis Process I-D.

Synthesis Process I-D

Each of the amines produced in Production Examples I-27, I-28 and I-30 was dissolved in dimethylformamide to a concentration of 5 mg/ml and each 1 ml of the solution was pipetted into test tubes. The solution was mixed with 0.05 ml of a 0.5 M solution of any of carboxylic acids, 0.025 ml of a 1 M solution of 1-hydroxybenzotriazole monohydrate in dimethylformamide, and 0.05 ml of a 1 M solution of 1-ethyl-3-(3-dimethylaminopropyl)carbodiimide (=WSC) in dimethylformamide, each of which had been prepared, and the mixture was stirred at room temperature overnight. A sulfonamide compound was allowed to react with methanesulfonyl chloride in tetrahydrofuran in the presence of triethylamine. Each of the reaction mixtures was separated and purified by LC-MS under the conditions of Synthesis Process I-A, to give the following compounds.

Example I-157

Benzyl N-((1S)-2-{[3-(3-fluorophenyl)-1H-6-indazolyl]amino}-1-methyl-2-oxoethyl)carbamate MS (ESI) m/z 433 MH$^+$

Example I-158

N1-[3-(3-Fluorophenyl)-1H-7-indazolyl]-3-phenoxybenzamide

MS (ESI) m/z 424 MH$^+$

Example I-159

N1-{[3-(3-Fluorophenyl)-1H-5-indazolyl]methyl}-1-cyclopropanecarboxamide

MS (ESI) m/z 310 MH$^+$

Example I-160

N1-{[3-(3-Fluorophenyl)-1H-5-indazolyl]methyl}-3-methoxybenzamide

MS (ESI) m/z 376 MH$^+$

Example I-161

N1-{[3-(3-Fluorophenyl)-1H-5-indazolyl]methyl}-3-phenoxypropanamide

MS (ESI) m/z 390 MH$^+$

Example I-162

N3-{[3-(3-Fluorophenyl)-1H-5-indazolyl]methyl}tetrahydro-3-furancarboxamide

MS (ESI) m/z 340 MH$^+$

The compounds according to Examples I-163 to I-166 were synthesized by according to following Synthesis Process I-E.

Synthesis Process I-E

Each of the amines produced in Production Examples I-29 and I-36 was dissolved in dimethylformamide to a concentration of 20 mg/ml and each 0.5 ml of the solution was pipetted into test tubes. The solution was sequentially mixed with 0.08 ml of a 0.5 M solution of any of carboxylic acids in dimethylformamide, 0.1 ml of a 0.5 M solution of 1-hydroxybenzotriazole monohydrate in dimethylformamide, 0.1 ml of a 1 M solution of 1-ethyl-3-(3-dimethylaminopropyl)carbodiimide in dimethylformamide, and 0.05 ml of diisopropylethylamine, each of which had been prepared, and the mixture was left stand for one day. The reaction mixture in the test tube was diluted with water, was extracted with two portions of ethyl acetate and was air-dried by blowing nitrogen gas to remove the solvent. The resulting residue was treated with 1 ml of a 1:1 mixture of trifluoroacetic acid and dichloromethane containing 10% triethylsilane by standing still for 1 hour. The reaction mixture was air-dried by blowing nitrogen gas, and residue was dissolved in 0.5 ml of N,N-dimethylformamide. Each of the solutions was separated and purified by LC-MS by the procedure of Synthesis Process I-A, to give the following compounds.

Example I-163

N1-(3-Imidazo[1,2-a]pyridin-2-yl-1H-5-indazolyl)-2-(3-thienyl)acetamide

MS (ESI) m/z 374 MH$^+$

Example I-164

N2-(3-Imidazo[1,2-a]pyridin-2-yl-1H-5-indazolyl)-1,2,3,4-tetrahydronaphthalene-2-carboxamide MS (ESI) m/z 408 MH$^+$

Example I-165

Cyclopropanecarboxylic acid [3-(fluorobenzo[b]furan-2-yl)-1H-indazol-5-yl]amide

MS (ESI) m/z 336 MH$^+$

Example I-166

5-Oxo-pyrrolidine-(2S)-2-carboxylic acid [3-(fluorobenzo[b]furan-2-yl)-1H-indazol-5-yl]amide MS (ESI) m/z 379 MH$^+$ The compounds according to Examples I-167 and I-168 were synthesized by following Synthesis Process I-F.

Synthesis Process I-F

As a starting material, 0.19 g of tert-butyl 3-(2-naphthyl)-5-(hydroxymethyl)-1H-1-indazolecarboxylate produced in Production Example I-33 was subjected to the procedures of Production Example I-30a and I-30b, to give 0.15 g of tert-butyl 5-(aminomethyl)-3-(2-naphthyl)-1H-1-indazolecarboxylate as a colorless oil. The compound was allowed to react with any of carboxylic acids and was then treated with an acid according to the procedure of Synthesis Process I-E. Each of the reaction mixtures was separated and purified by LC-MS under the conditions of Synthesis Process I-A, to give the following compounds.

Example I-167

N1-{[3-(2-Naphthyl)-1H-5-indazolyl]methyl}-3-methoxypropanamide

MS (ESI) m/z 360 MH$^+$

Example I-168

N1-{[3-(2-Naphthyl)-1H-5-indazolyl]methyl}-2-(3-thienyl)acetamide

MS (ESI) m/z 398 MH$^+$

The compound according to Examples I-169 to I-171 were synthesized by following Synthesis Process I-G.

Synthesis Process I-G

To an ice-cold solution of 373 mg of tert-butyl 5-(hydroxymethyl)-3-(2-naphthyl)-1H-1-indazolecarboxylate produced in Production Example I-33 in 10 ml dry tetrahydrofuran were added dropwise 0.17 ml of triethylamine and 0.09 ml of methanesulfonyl chloride, and the mixture was stirred for 20 minutes. Each 1 ml of the reaction mixture was pipetted into test tubes, each of which was treated with 0.4 ml of a 1 M solution of any of amines in dimethylformamide with stirring for one day. The suspended reaction mixture was diluted with a small amount of water and was filtrated through a membrane filter. Each of the reaction mixtures was separated and purified by LC-MS under the conditions of Synthesis Process I-A and thereby yielded the following test compounds.

Example I-169

4-{[3-(2-Naphthyl)-1H-5-indazolyl]methyl}morpholine

MS (ESI) m/z 344 MH$^+$

Example I-170

5-(2,3-Dihydro-1H-1-indolylmethyl)-3-(2-naphthyl)-1H-indazole

MS (ESI) m/z 376 MH$^+$

Example I-171

5-{[4-(2-Methoxyphenyl)piperazino]methyl}-3-(2-naphthyl)-1H-indazole

MS (ESI) m/z 449 MH$^+$

The compound according to Examples I-172 and I-173 were synthetically prepared by following Synthesis Process I-H.

Synthesis Process I-H

Into test tubes were pipetted 15 mg of tert-butyl 5-(hydroxymethyl)-3-(2-naphthyl)-1H-1-indazolecarboxylate produced in Production Example I-33 and 0.5 ml of tetrahydrofuran, each of which was treated with 1 equivalent of any of phenols. Each of the mixtures was further treated with 15 mg of triphenylphosphine and 0.02 ml of a 40% solution of diethyl azodicarboxylate in toluene by standing still for one week. Each of the reaction mixtures was separated and purified by LC-MS under the conditions of Synthesis Process I-A, the solvent was removed by blowing nitrogen gas, and the residue was treated with 1 ml of a 1:1 mixture solution of trifluoroacetic acid and dichloromethane containing 10% triethylsilane by standing still for 1 hour. The solvent in the reaction mixture was removed by blowing nitrogen gas, the resulting residue was dissolved in 0.5 ml of N,N-dimethylformamide, was separated and purified by LC-MS under the conditions of Synthesis Process I-A and thereby yielded the following compounds.

Example I-172

5-[(3-Methoxyphenoxy)methyl]-3-(2-naphthyl)-1H-indazole

MS (ESI) m/z 381 MH$^+$

Example I-173

7-[3-(2-Naphthyl)-1H-5-indazolyl]methoxy-2H-2-chromenone

MS (ESI) m/z 419 MH$^+$

Production Example II-1-a
1-Bromo-4-fluoro-2-methoxy-benzene

A total of 10 g of 2-bromo-5-fluoro-phenol was dissolved in 105 ml of N,N-dimethylformamide, 10.9 g of potassium carbonate and 4.9 ml of iodomethane were added under ice-cooling, and the mixture was stirred at room temperature for 3 hours. Water was added to the reaction mixture, followed by extracting with diethyl ether. The resulting organic layer was washed with brine, dried over magnesium sulfate and the solvent was evaporated, to give 9.75 g of the title compound as a yellow oil.

$^1$H-NMR (400 MHz, CDCl$_3$) δ 3.88 (3H, s), 6.59 (1H, td, J=8.4, 2.8 Hz), 6.65 (1H, dd, J=10.4, 2.8 Hz), 7.47 (1H, dd, J=8.4, 6.0 Hz)

Production Example II-1-b (5-Bromo-2-fluoro-4-methoxy-phenyl)-(3-fluoro-phenyl)-methanone A total of 716 mg of aluminium chloride was suspended in 24.4 ml of dichloromethane and was then mixed with 0.65 ml of 3-fluorobenzoyl chloride and 1 g of 1-bromo-4-fluoro-2-methoxy-benzene obtained in Production Example II-1-a under stirring at −60° C. The mixture was raised in temperature to room temperature over 2.5 hours and was stirred for further 3 hours. Water was added to the reaction mixture under ice-cooling, followed by extracting with diethyl ether. The resulting organic layer was washed with saturated aqueous sodium hydrogencarbonate solution and brine, dried over magnesium sulfate and the solvent was evaporated. The residue was purified and separated by silica gel column chromatography (ethyl acetate:hexane=1:10), to give 856 mg of the title compound as white crystals.

$^1$H-NMR (400 MHz, CDCl$_3$) δ 3.98 (3H, s), 6.69 (1H, d, J=11.6 Hz), 7.27-7.58 (4H, m), 7.83 (1H, d, J=7.2 Hz)

Production Example II-1-c

4-Fluoro-5-(3-fluoro-benzoyl)-2-methoxy-benzonitrile

A total of 856 mg of (5-bromo-2-fluoro-4-methoxy-phenyl)-(3-fluoro-phenyl)-methanone obtained in Production Example II-1-b was dissolved in 13.1 ml of N,N-dimethylformamide, 185 mg of zinc cyanide, 13.6 mg of tris(dibenzylideneacetone)dipalladium and 17.4 mg of 1,1'-bis(diphenylphosphino)ferrocene were added thereto, and the mixture was stirred at 120° C. in an atmosphere of nitrogen gas for 7 hours. After cooling to room temperature, water was added to the reaction mixture and the mixture was extracted with diethyl ether. The resulting organic layer was washed with brine, dried over magnesium sulfate and the solvent was evaporated. The residue was purified and separated by silica gel column chromatography (ethyl acetate:hexane=1:2), to give 203 mg of the title compound as pale yellow crystals.

$^1$H-NMR (400 MHz, CDCl$_3$) δ 4.03 (3H, s), 6.78 (1H, d, J=11.6 Hz), 7.30-7.37 (1H, m), 7.42-7.56 (3H, m), 7.89 (1H, d, J=7.6 Hz)

Production Example II-1-d 3-(3-Fluoro-phenyl)-6-methoxy-1H-indazole-5-carbonitrile A total of 203 mg of 4-fluoro-5-(3-fluoro-benzoyl)-2-methoxy-benzonitrile obtained in Production Example II-1-c was dissolved in 3 ml of tetrahydrofuran and 3 ml of methanol, 7.4 ml of hydrazine monohydrate was added at room temperature under stirring, and the mixture was stirred at room temperature for 14 hours. Then, water was added and the mixture was extracted with ethyl acetate. The resulting organic layer was washed with 1 N hydrochloric acid, saturated aqueous sodium hydrogencarbonate solution and brine, dried over magnesium sulfate and the solvent was evaporated. The resulting crystals were washed with diethyl ether, to give 172 mg of the title compound as pale yellow crystals.

$^1$H-NMR (400 MHz, CD$_3$OD) δ 4.01 (3H, s), 7.14 (1H, s), 7.18 (1H, td, J=8.4, 2.8 Hz), 7.54 (1H, td, J=8.4, 6.0 Hz), 7.62-7.68 (1H, m), 7.76 (1H, J=8.4 Hz), 8.37 (1H, s)

Production Example II-1-e 3-(3-Fluoro-phenyl)-6-methoxy-1H-indazole-5-carboxylic acid A total of 172 mg of 3-(3-fluoro-phenyl)-6-methoxy-1H-indazole-5-carbonitrile obtained in Production Example II-1-d was dissolved in 2 ml of acetic acid, 0.7 ml of water and 0.5 ml of sulfuric acid, followed by stirring at 110° C. for 18 hours. After cooling to room temperature, water was added to the reaction mixture. The resulting crystals were washed with water, to give 159 mg of the title compound as light pink crystals.

$^1$H-NMR (400 MHz, CD$_3$OD) δ 3.99 (3H, s), 7.12 (1H, s), 7.14-7.20 (1H, m), 7.55 (1H, td, J=8.0, 6.0 Hz), 7.61-7.67 (1H, m), 7.76 (1H, d, J=8.0 Hz), 8.53 (1H, s)

Production Example II-2-a (3-Bromo-6-fluoro-2-methoxy-phenyl)-(3-fluoro-phenyl)-methanol A total of 1.64 ml of diisopropylamine was dissolved in 27 ml of tetrahydrofuran, 6.8 ml of a 1.57 M solution of n-butyllithium in hexane was added at −50° C. under stirring, and the mixture was stirred at −30° C. for 30 minutes. After cooling to −60° C., 2 g of 1-bromo-4-fluoro-2-methoxy-benzene obtained in Production Example II-1-a was added and the mixture was stirred at −60° C. for 1 hour. Then, 1.55 ml of 3-fluoro-benzaldehyde was added, followed by stirring for 1 hour. Saturated aqueous ammonium chloride solution was added to the reaction mixture, and the mixture was extracted with diethyl ether. The resulting organic layer was washed with brine, dried over magnesium sulfate and the solvent was evaporated, to give 2.4 g of the title compound as a yellow-brown oil.

$^1$H-NMR (400 MHz, CDCl$_3$) δ 3.52 (3H, s), 3.56 (1H, d, J=10.4 Hz), 6.16 (1H, d, J=11.6 Hz), 6.86 (1H, t, J=8.8 Hz), 6.92-6.99 (1H, m), 7.07-7.16 (2H, m), 7.30 (1H, td, J=8.0, 6.0 Hz), 7.51 (1H, dd, J=8.8, 6.0 Hz)

Production Example II-2-b (3-Bromo1-6-fluoro-2-methoxy-phenyl)-(3-fluoro-phenyl)-methanone A total of 2.4 g of (3-bromo-6-fluoro-2-methoxy-phenyl)-(3-fluoro-phenyl)-methanol obtained in Production Example II-2-a was dissolved in 24.3 ml of dichloromethane. Under ice-cooling and stirring, 1.28 g of 1-methylmorpholine-N-oxide, 3.65 g of powdery 4A molecular sieve and 128 mg of tetrapropylammonium perruthenate were added, followed by stirring at room temperature for 3 hours. Isopropyl alcohol was added to the reaction mixture and then the mixture was filtered through Celite. The resulting filtrate was evaporated, and the residue was purified and separated by silica gel column chromatography (ethyl acetate:hexane=1:8), to give 2.07 g of the title compound as a pale yellow oil.

$^1$H-NMR (400 MHz, CDCl$_3$) δ 3.80 (3H, s), 6.86 (1H, dd, J=8.8, 8.0 Hz), 7.29-7.36 (1H, m), 7.42-7.50 (1H, m), 7.54-7.61 (2H, m), 7.66 (1H, dd, J=8.8, 5.6 Hz)

Production Example II-2-c

5-Bromo-3-(3-fluoro-phenyl)-4-methoxy-1H-indazole

A total of 0.703 g of the title compound was obtained as pale yellow crystals by the procedure of Production Example II-1-d, except using 0.959 g of (3-bromo1-6-fluoro-2-methoxy-phenyl)-(3-fluoro-phenyl)-methanone obtained in Production Example II-2-b.

$^1$H-NMR (400 MHz, CDCl$_3$) δ 3.51 (3H, s), 7.10-7.17 (1H, m), 7.17 (1H, d, J=8.8 Hz), 7.45 (1H, td, J=8.0, 6.0 Hz), 7.56 (1H, d, J=8.8 Hz), 7.69-7.75 (1H, m), 7.77 (1H, d, J=8.0 Hz)

Production Example II-2-d

3-(3-Fluoro-phenyl)-4-methoxy-1H-indazole-5-carboxylic acid

A total of 230 mg of 5-bromo-3-(3-fluoro-phenyl)-4-methoxy-1H-indazole obtained in Production Example II-2-c was dissolved in 4.78 ml of tetrahydrofuran, and 0.99 ml of a 1.59 M solution of n-butyllithium in hexane was added under stirring at −78° C. After stirring at −78° C. for 30 minutes, dry ice was added. After stirring at the same temperature for 10 minutes, saturated aqueous ammonium chloride solution was added. The mixture was extracted with ethyl acetate, and the resulting organic layer was washed with brine, dried over magnesium sulfate and the solvent was evaporated. The residue was purified and separated by silica gel column chromatography (ethyl acetate:hexane=1:1), to give 41.1 mg of the title compound.

$^1$H-NMR (400 MHz, CD$_3$OD) δ 3.55 (3H, s), 7.14-7.21 (1H, m), 7.36 (1H, d, J=8.8 Hz), 7.50 (1H, td, J=8.0, 6.0 Hz), 7.60-7.65 (1H, m), 7.72 (1H, d, J=8.0 Hz), 7.88 (1H, d, J=8.8 Hz)

Production Example II-3-a

2,4-Difluoro-3-{(3-fluoro-phenyl)-hydroxymethyl}-benzonitrile

A total of 9.35 g of the title compound was obtained as a yellow oil by the procedure of Production Example II-2-a, except from 5 g of 2,4-difluoro-benzonitrile.

$^1$H-NMR (400 MHz, CDCl$_3$) δ 6.30 (1H, s), 6.98-7.18 (4H, m), 7.33 (1H, td, J=8.0, 6.0 Hz), 7.58-7.65 (1H, m)

Production Example II-3-b

2,4-Difluoro-3-(3-fluoro-benzoyl)-benzonitrile

A total of 6.29 g of the title compound was obtained as pale yellow crystals by the procedure of Production Example II-2-b, except from 9.35 g of 2,4-difluoro-3-{(3-fluoro-phenyl)-hydroxymethyl}-benzonitrile obtained in Production Example II-3-a.

$^1$H-NMR (400 MHz, CDCl$_3$) δ 7.19 (1H, t, J=8.0 Hz), 7.36-7.44 (1H, m), 7.52 (1H, td, J=8.0, 6.0 Hz), 7.55-7.60 (2H, m), 7.78-7.86 (1H, m)

Production Example II-3-c

4-Fluoro-3-{(3-fluoro-phenyl)-1H-indazole-5-carbonitrile

A total of 479 mg of the title compound was obtained as pale yellow crystals by the procedure of Production Example II-1-d, except from 952 mg of 2,4-difluoro-3-{(3-fluoro-benzoyl)-benzonitrile obtained in Production Example II-3-b.

$^1$H-NMR (400 MHz, CD$_3$OD) δ 7.17-7.23 (1H, m), 7.49-7.66 (4H, m), 7.70-7.75 (1H, m)

Production Example II-3-d

4-Fluoro-3-{(3-fluoro-phenyl)-1H-indazole-5-carboxylic acid

A total of 246 mg of the title compound was obtained as pale gray crystals by the procedure of Production Example II-1-e, except from 220 mg of 4-fluoro-3-{(3-fluoro-phenyl)-1H-indazole-5-carbonitrile obtained in Production Example II-3-c.

$^1$H-NMR (400 MHz, CD$_3$OD) 7.14-7.21 (1H, m), 7.39 (1H, d, J=8.8 Hz), 7.51 (1H, td, J=8.0, 6.0 Hz), 7.57-7.64 (1H, m), 7.68-7.73 (1H, m), 7.96 (1H, dd, J=8.8, 6.4 Hz)

Production Example II-4-a

(5-Bromo-2-fluoro-4-methyl-phenyl)-(3-fluoro-phenyl)-methanol

A total of 11.6 g of the title compound was obtained as a pale yellow oil by the procedure of Production Example II-2-a, except from 5.98 g of 2-bromo-5-fluoro-toluene.

$^1$H-NMR (400 MHz, CDCl$_3$) δ 2.36 (3H, s), 6.06 (1H, s), 6.93 (1H, d, J=11.2 Hz), 6.96-7.00 (1H, m), 7.08-7.18 (1H, m), 7.31 (1H, td, J=8.0, 6.0 Hz), 7.63 (1H, d, J=7.2 Hz)

Production Example II-4-b

(5-Bromo1-2-fluoro-4-methyl-phenyl)-(3-fluoro-phenyl)-methanone

A total of 6.63 g of the title compound was obtained as a yellow oil by the procedure of Production Example II-2-b, except from 11.6 g of (5-bromo-2-fluoro-4-methyl-phenyl)-(3-fluoro-phenyl)-methanol obtained in Production Example II-4-a.

$^1$H-NMR (400 MHz, CDCl$_3$) δ 2.48 (3H, s), 7.08 (1H, d, J=10.4 Hz), 7.28-7.35 (1H, m), 7.46 (1H, td, J=8.0, 5.6 Hz), 7.49-7.60 (2H, m), 7.73 (1H, d, J=6.4 Hz)

Production Example II-4-c

5-Bromo-3-(3-fluoro-phenyl)-6-methyl-1H-indazole

A total of 1.57 g of the title compound was obtained as white crystals by the procedure of Production Example II-1-d, except from 2.42 g of (5-bromo1-2-fluoro-4-methyl-phenyl)-(3-fluoro-phenyl)-methanone obtained in Production Example II-4-b.

$^1$H-NMR (400 MHz, CDCl$_3$) δ 2.56 3H, s), 7.09-7.16 (1H, m), 7.40 (1H, s), 7.49 (1H, td, J=8.0, 6.0 Hz), 7.62-7.68 (1H, m), 7.70-7.75 (1H, m), 8.21 (1H, s), 10.10 (1H, brs)

Production Example II-4-d

3-(3-Fluoro-phenyl)-6-methyl-1H-indazole-5-carboxylic acid

A total of 195 mg of the title compound was obtained as pale brown crystals by the procedure of Production Example II-2-d, except from 670 mg of 5-bromo-3-(3-fluoro-phenyl)-6-methyl-1H-indazole obtained in Production Example II-4-c.

$^1$H-NMR (400 MHz, CD$_3$OD) δ 2.71 (3H, s), 7.12-7.20 (1H, m), 7.41 (1H, s), 7.50-7.81 (4H, m), 8.61 (1H, s)

Production Example II-5-a

1,5-Dibromo-2,4-difluorobenzene

A total of 1.6 g of 1-bromo-2,4-difluorobenzene was suspended in 8.29 ml of sulfuric acid, and 1.62 g of N-bromo-succinimide was added under ice-cooling. After stirring at room temperature for 17 hours, the reaction mixture was poured onto ice-water and extracted with ethyl acetate. The resulting organic layer was washed with saturated aqueous sodium hydrogencarbonate solution and brine, dried over magnesium sulfate and the solvent was evaporated. The residue was purified and separated by silica gel column chromatography (hexane), to give 2.18 g of the title compound as a pale yellow oil.

$^1$H-NMR (400 MHz, CDCl$_3$) δ 6.99 (1H, t, J=8.0 Hz), 7.77 (1H, t, J=6.8 Hz)

Production Example II-5-b (5-Bromo-2,4-difluoro-phenyl)-(3-fluoro-phenyl)-methanol A total of 2.02 g of 1,5-dibromo-2,4-difluorobenzene obtained in Production Example II-5-a was dissolved in 38 ml of diethyl ether, and 4.9 ml of a 1.58 M solution of n-butyllithium in hexane was added under stirring at −70° C. After stirring for 1 hour, 4.9 ml of m-fluorobenzaldehyde was added and the mixture was stirred for 15 minutes. Saturated aqueous ammonium chloride solution was added to the reaction mixture, followed by extracting with ethyl acetate. The resulting organic layer was washed with brine, dried over magnesium sulfate and the solvent was evaporated. The residue was purified and separated by silica gel column chromatography (ethyl acetate:hexane=1:10), to give 0.96 g of the title compound.

$^1$H-NMR (400 MHz, CDCl$_3$) δ 6.07 (1H, d, J=3.2 Hz), 6.87 (1H, dd, J=9.6, 8.4 Hz), 6.95-7.04 (1H, m), 7.07-7.18 (2H, m), 7.33 (1H, td, J=8.4, 6.0 Hz), 7.73 (1H, t, J=8.0 Hz)

Production Example II-5-c (5-Bromo-2,4-difluoro-phenyl)-(3-fluoro-phenyl)-methanone A total of 8.34 g of the title compound was obtained by the procedure of Production Example II-2-b, except from 17.0 g of (5-bromo-2,4-difluoro-phenyl)-(3-fluoro-phenyl)-methanol obtained in Production Example II-5-b.

$^1$H-NMR (400 MHz, CDCl$_3$) δ 7.02 (1H, t, J=8.4 Hz), 7.30-7.64 (4H, m), 7.82 (1H, t, J=7.6 Hz)

Production Example II-5-d 2,4-Difluoro-5-(3-fluoro-benzoyl)-benzonitrile

A total of 1.63 g of the title compound was obtained as yellow-brown crystals by the procedure of Production Example II-1-c, except from 4.03 g of (5-bromo-2,4-difluoro-phenyl)-(3-fluoro-phenyl-methanone obtained in Production Example II-5-c.

$^1$H-NMR (400 MHz, CDCl$_3$) δ 7.13 (1H, t, J=8.8 Hz), 7.34-7.56 (4H, m), 7.93 (1H, t, J=7.2 Hz)

Production Example II-5-e

6-Fluoro-3-(3-fluoro-phenyl)-1H-indazole-5-carbonitrile

A total of 0.982 g of the title compound was obtained as pale yellow crystals by the procedure of Production Example I-1-d, except from 1.63 g of 2,4-difluoro-5-(3-fluoro-benzoyl)-benzonitrile obtained in Production Example II-5-d.

$^1$H-NMR (400 MHz, DMSO-D$_6$) δ 7.26-7.36 (1H, m), 7.50-7.63 (1H, m), 7.73 (1H, d, J=10.0 Hz), 7.80-7.86 (1H, m), 7.91 (1H, d, J=8.0 Hz), 8.88 (1H, d, J=6.0 Hz)

Production Example II-5-f

6-Fluoro-3-(3-fluoro-phenyl)-1H-indazole-5-carboxylic acid

A total of 415 mg of the title compound was obtained as pale yellow crystals by the procedure of Production Example II-1-e, except from 653 mg of 6-fluoro-3-(3-fluoro-phenyl)-1H-indazole-5-carbonitrile obtained in Production Example II-5-e.

$^1$H-NMR (400 MHz, DMSO-D$_6$) δ 7.27-7.35 (1H, m), 7.49 (1H, d, J=11.2 Hz), 7.63 (1H, td, J=8.0, 6.0 Hz), 7.70-7.76 (1H, m), 7.82 (1H, d, J=8.0 Hz)

Production Example II-6

3-(3-Fluoro-phenyl)-6-hydroxy-1H-indazole-5-carboxylic acid

A total of 96.2 mg of 3-(3-fluoro-phenyl)-6-methoxy-1H-indazole-5-carboxylic acid obtained in Production Example II-1-e was dissolved in 3.36 ml of dichloromethane, 4.0 ml of a 1.0 M solution of boron tribromide in dichloromethane was added under ice-cooling, and the mixture was stirred at room temperature for 1.5 hours. Water was added to the reaction mixture, followed by extracting with ethyl acetate. The resulting organic layer was washed brine, dried over magnesium sulfate and the solvent was evaporated, to give 84.1 mg of the crude product of the title compound.

$^1$H-NMR (400 MHz, CD$_3$OD) δ 6.93 (1H, s), 7.13-7.23 (1H, m), 7.50-7.79 (3H, m), 8.63 (1H, s)

Production Example II-7-a

2-Amino-4-fluoro-benzoic acid ethyl ester

A total of 10 g of 2-amino-4-fluoro-benzoic acid was dissolved in 129 ml of ethanol, 6.45 ml of sulfuric acid was added and the mixture was heated under reflux for 11 hours. After cooling to room temperature, the solvent was evaporated to about half. Water was added and the mixture was extracted with ethyl acetate. The resulting organic layer was washed with saturated aqueous sodium hydrogencarbonate solution and brine, dried over magnesium sulfate and the solvent was evaporated. The residue was purified and separated by silica gel column chromatography (ethyl acetate:hexane=1:5), to give 7.57 g of the title compound as a pale yellow oil.

$^1$H-NMR (400 MHz, CDCl$_3$) δ 1.38 (3H, t, J=6.8 Hz), 4.32 (2H, q, J=6.8 Hz), 5.88 (2H, brs), 6.28-6.38 (2H, m), 7.88 (1H, dd, J=8.8, 6.8 Hz)

Production Example II-7-b

2-Acetylamino-4-fluoro-benzoic acid ethyl ester

A total of 3.84 g of 2-amino-4-fluoro-benzoic acid ethyl ester obtained in Production Example II-7-a was dissolved in 50 ml of pyridine, 1.64 ml of acetyl chloride was added under ice-cooling, and the mixture was stirred for 1 hours. The reaction mixture was diluted with water and was extracted with diethyl ether. The resulting organic layer was washed with 1 N hydrochloric acid and brine, dried over magnesium sulfate, and then evaporated, to give 4.0 g of the title compound.

$^1$H-NMR (400 MHz, CDCl$_3$) δ 1.41 (3H, t, J=6.8 Hz), 2.14 (3H, s), 4.38 (2H, q, J=6.8 Hz), 6.73-6.81 (1H, m), 8.06 (1H, dd, J=8.8, 6.4 Hz), 8.53 (1H, dd, J=12.0, 2.4 Hz), 11.3 (1H, brs)

Production Example II-7-c

2-Acetylamino-4-fluoro-5-iodo-benzoic acid ethyl ester

A total of 3.12 g of silver sulfate was suspended in 45 ml of sulfuric acid, 5 ml of water was added, and the mixture was stirred at room temperature for 15 minutes. 1 ml of iodine monochloride was added, followed by stirring at room temperature for 1 hour. The mixture was filtered, and to 44 ml of the filtrate was added 2 g of 2-acetylamino-4-fluoro-benzoic acid ethyl ester obtained in Production Example II-7-b under ice-cooling, and the mixture was stirred for 1 hour. The reaction mixture was poured onto ice-water and was extracted with ethyl acetate. The resulting organic layer was washed with saturated aqueous sodium hydrogencarbonate solution and brine, dried over magnesium sulfate and the solvent was evaporated. The residue was purified and separated by silica gel column chromatography (ethyl acetate:hexane=1:5), to give 2.9 g of the title compound as white crystals.

$^1$H-NMR (400 MHz, CDCl$_3$) δ 1.43 (3H, t, J=6.8 Hz), 2.24 (3H, s), 4.39 (2H, q, J=6.8 Hz), 8.41 (1H, d, J=7.2 Hz), 8.59 (1H, d, J=11.2 Hz

Production Example II-7-d

2-Acetylamino-4-fluoro-5-(3-fluoro-benzoyl)-benzoic acid ethyl ester

A total of 812 mg of 2-acetylamino-4-fluoro-5-iodo-benzoic acid ethyl ester obtained in Production Example II-7-c was dissolved in 13.9 ml of anisole, and 956 mg of potassium carbonate, 356 mg of 3-fluorophenyl-boronic acid and 49 mg of bis(triphenylphosphine)palladium dichloride were added. After replacing the inside atmosphere of the reaction system with carbon monoxide gas, the mixture was stirred at 80° C. in an atmosphere of carbon monoxide (normal pressure) for 14 hours. After cooling to room temperature and replacing the inside atmosphere of the reaction system with nitrogen gas, water was added and the mixture was extracted with ethyl acetate. The resulting organic layer was washed with brine, dried over magnesium sulfate and the solvent was evaporated. The residue was purified and separated by silica gel column chromatography (ethyl acetate:hexane=1:5), to give 234 mg of the title compound as pale yellow crystals.

$^1$H-NMR (400 MHz, CDCl$_3$) δ 1.43 (3H, t, J=6.8 Hz), 2.27 (3H, s), 4.41 (2H, q, J=6.8 Hz), 7.05-7.12 (1H, m), 7.20-7.46 (3H, m), 8.15 (1H, d, J=8.8 Hz), 8.64 (1H, d, J=13.6 Hz)

Production Example II-7-e

6-Acetylamino-3-(3-fluoro-phenyl)-1H-indazole-5-carboxylic acid ethyl ester

A total of 160 mg of the title compound was obtained as pale yellow crystals by the procedure of Production Example II-1-d, except from 234 mg of 2-acetylamino-4-fluoro-5-(3-fluoro-benzoyl)-benzoic acid ethyl ester obtained in Production Example II-7-d.

$^1$H-NMR (400 MHz, CDCl$_3$) δ 1.47 (3H, t, J=6.8 Hz), 2.32 (3H, s), 4.46 (2H, q, J=6.8 Hz), 7.12-7.19 (1H, m), 7.51 (1H, td, J=8.0, 6.0 Hz), 7.64-7.70 (1H, m), 7.75 (1H, d, J=8.0 Hz), 8.79 (1H, s), 8.99 (1H, s)

Production Example II-7-f

6-Acetylamino-3-(3-fluoro-phenyl)-1H-indazole-5-carboxylic acid

A total of 160 mg of 6-acetylamino-3-(3-fluoro-phenyl)-1H-indazole-5-carboxylic acid ethyl ester obtained in Production Example II-7-e was dissolved in 3 ml of ethanol and 1 ml of 5 N aqueous sodium hydroxide solution, and the solution was stirred at 50° C. for 2 hours. After cooling to room temperature, 1 N hydrochloric acid was added and the mixture was extracted with ethyl acetate. The resulting organic layer was washed with brine, dried over magnesium sulfate and the solvent was evaporated, to give 155 mg of the title compound as pale yellow crystals.

$^1$H-NMR (400 MHz, CD$_3$OD) δ 2.24 (3H, s), 7.14-7.21 (1H, m), 7.56 (1H, td, J=8.0, 6.0 Hz), 7.63-7.68 (1H, m), 7.77 (1H, d, J=8.0 Hz), 8.79-8.85 (2H, m)

Production Example II-8-a

4-Fluoro-3-[(3-fluorophenyl)-hydroxymethyl]-5-methoxybenzonitrile

To a solution of 15.0 g of 4-fluoro-3-methoxybenzonitrile and 21.8 ml of N,N,N',N',N"-pentamethyldiethylenetriamine in 300 ml tetrahydrofuran was added 65.5 ml of a 1.59 M solution of n-butyllithium in hexane at −78° C. in an atmosphere of nitrogen gas, followed by stirring at the same temperature for 1 hour. At the same temperature, 10.5 ml of 3-fluorobenzaldehyde was added dropwise, followed by stirring at the same temperature for 1 hour. Then, water was added and the mixture was extracted with diethyl ether. The organic layer was washed with saturated aqueous ammonium chloride solution and brine, dried over anhydrous magnesium sulfate and the solvent was evaporated. The crude product was purified and separated by silica gel column chromatography (ethyl acetate:n-hexane=1:10 to 1:3), to give 7.1 g of the title compound as a colorless oil.

$^1$H-NMR (400 MHz, CDCl$_3$) δ 2.55 (1H, brs), 3.89 (3H, s), 6.13 (1H, s), 6.98 (1H, dt, J=2.0, 8.0 Hz), 7.10 (1H, d, J=8.0 Hz), 7.12 (1H, dd, J=2.0, 8.0 Hz), 7.16 (1H, d, J=8.0 Hz), 7.31 (1H, dt, J=5.6, 8.0 Hz), 7.50 (1H, dd, J=2.0, 5.6 Hz)

Production Example II-8-b

4-Fluoro-3-(3-fluorobenzoyl)-5-methoxybenzonitrile

To a solution of 7.0 g of 4-fluoro-3-[(3-fluorophenyl)-hydroxymethyl]-5-methoxybenzonitrile in 70 ml toluene was added 11.1 g of activated manganese dioxide at room temperature. After stirring at 60° C. for one day, the manganese dioxide was filtered off through Celite. The solvent was removed and the crude product was purified and separated by silica gel column chromatography (ethyl acetate:n-hexane=1:3), to give 640 mg of the title compound as colorless crystals.

¹H-NMR (400 MHz, CDCl₃) δ 3.99 (3H, s), 7.35 (1H, dt, J=1.2, 5.6 Hz), 7.37 (1H, dd, J=2.0, 8.0 Hz), 7.42 (1H, dd, J=2.0, 5.6 Hz), 7.48 (1H, dt, J=5.6, 8.0 Hz), 7.51-7.58 (2H, m)

Production Example II-8-c 3-(3-Fluorophenyl)-7-methoxy-1H-indazole-5-carbonitrile To a solution of 640 mg of 4-fluoro-3-(3-fluorobenzoyl)-5-methoxybenzonitrile in 6 ml ethanol was added 3 ml of hydrazine monohydrate at room temperature, followed by stirring at 70° C. for one day. The reaction mixture was evaporated, and the resulting crystals were collected by filtration. The crystals were sequentially washed with ethanol and diethyl ether, to give 590 mg of the title compound as colorless crystals.

¹H-NMR (400 MHz, DMSO-D₆) δ 4.03 (3H, s), 7.23-7.29 (1H, m), 7.25 (1H, d, J=1.2 Hz), 7.55 (1H, dt, J=6.4, 8.0 Hz), 7.78 (1H, ddd, J=1.2, 2.4, 6.4 Hz), 7.88 (1H, dt, J=1.2, 8.0 Hz), 8.31 (1H, d, J=1.2 Hz Production Example II-8-d 3-(3-Fluorophenyl)-7-methoxy-1H-indazole-5-carboxylic acid To 450 mg of 3-(3-fluorophenyl)-7-methoxy-1H-indazole-5-carbonitrile were sequentially added 6 ml of glacial acetic acid, 2 ml of water and 2 ml of concentrated sulfuric acid, followed by stirring at 100° C. for one day. After standing to cool, water was added to the reaction mixture and the resulting crystals were collected by filtration. The crystals were sequentially washed with isopropanol and diethyl ether, to give 428 mg of the title compound as colorless crystals.

¹H-NMR (400 MHz, DMSO-D₆) δ 4.03 (3H, s), 7.27 (1H, dt, J=2.4, 8.0 Hz), 7.37 (1H, s), 7.60 (1H, dt, J=6.4, 8.0 Hz), 7.69 (1H, ddd, J=1.2, 2.4, 6.4 Hz), 7.80 (1H, d, J=8.0 Hz), 8.24 (1H, s)

Production Example II-9-a (5-Bromo-2-fluoro-3-methylphenyl)-(3-fluorophenyl)methanol In an atmosphere of nitrogen gas, 74.1 ml of a 1.57 M solution of n-butyllithium in hexane was added to a solution of 16.3 ml of N,N-diisopropylamine in 400 ml tetrahydrofuran at 0° C., and the mixture was stirred at the same temperature for 30 minutes. After cooling to −78° C., a solution of 20.0 g of 5-bromo-2-fluorotoluene in 40 ml tetrahydrofuran was added dropwise. After stirring at the same temperature for 1 hour, 11.2 ml of 3-fluorobenzaldehyde was added dropwise and the mixture was stirred at the same temperature for 3 hours. The reaction mixture was neutralized with 1 N hydrochloric acid and diluted with ethyl acetate. The organic layer was washed with brine, dried over anhydrous magnesium sulfate, and the solvent was evaporated. The crude product was purified and separated by silica gel column chromatography (ethyl acetate:n-hexane=1:20), to give 20.6 g of the title compound as a colorless oil.

¹H-NMR (400 MHz, CDCl₃) δ 2.23 (3H, s), 2.34 (1H, d, J=4.0 Hz), 6.06 (1H, d, J=4.0 Hz), 6.98 (1H, dt, J=2.4, 8.0 Hz), 7.12 (1H, d, J=8.0 Hz), 7.17 (1H, d, J=8.0 Hz), 7.25 (1H, d, J=6.0 Hz), 7.31 (1H, dt, J=6.0, 8.0 Hz), 7.50 (1H, dd, J=2.4, 6.0 Hz)

Production Example II-9-b

5-Bromo-3-(3-fluorophenyl)-7-methyl-1H-indazole

To a solution of 20.0 g of (5-bromo-2-fluoro-3-methylphenyl)-(3-fluorophenyl)methanol in 200 ml toluene was added 16.7 g of activated manganese dioxide at room temperature. After stirring at 80° C. for 2 hours, the manganese dioxide was filtered off through Celite. After removing the solvent by distillation, to a solution of the residue in 100 ml of ethanol was added 15.5 ml of hydrazine monohydrate at room temperature and the mixture was heated under reflux for one day. The reaction mixture was evaporated and diluted with ethyl acetate. The organic layer was sequentially washed with saturated aqueous ammonium chloride solution and brine, dried over anhydrous magnesium sulfate, and the solvent was evaporated. A solution of the residue in 20 ml pyridine was stirred in a sealed tube at 200° C. for 10 hours. After cooling, the reaction mixture was evaporated, the residue was dissolved in ethyl acetate and 5 N hydrochloric acid, and the aqueous layer was extracted with ethyl acetate. The collected organic layer was washed with brine, dried over anhydrous magnesium sulfate, and the solvent was evaporated. The resulting crystals were washed with ethyl acetate, to give 11.3 g of the title compound as colorless crystals.

¹H-NMR (400 MHz, DMSO-D₆) δ 2.58 (3H, s), 7.15 (1H, ddd, J=0.8, 2.4, 8.0 Hz), 7.33 (1H, dd, J=0.8, 1.6 Hz), 7.53 (1H, dt, J=6.0, 8.0 Hz), 7.61 (1H, ddd, J=1.6, 2.4, 6.0 Hz), 7.72 (1H, ddd, J=0.8, 1.6, 8.0 Hz), 8.31 (1H, dd, J=0.8, 1.6 Hz)

Production Example II-9-c

5-Bromo-3-(3-fluorophenyl)-7-methyl-1-trityl-1H-indazole

To a solution of 2.56 g of 5-bromo-3-(3-fluorophenyl)-7-methyl-1H-indazole in 30 ml of dimethylformamide was added 0.50 g of sodium hydride at room temperature, and the mixture was stirred at the same temperature for 15 minutes. At the same temperature, 2.34 g of triphenylmethane chloride was added and the mixture was stirred at the same temperature for one day. Water was added to the reaction mixture and the mixture was diluted with ethyl acetate. The organic layer was sequentially washed with saturated aqueous ammonium chloride solution and brine, dried over anhydrous magnesium sulfate, and the solvent was evaporated. The crude product was purified and separated by silica gel column chromatography (ethyl acetate:n-hexane=1:10) and the resulting crystals were washed with diethyl ether, to give 1.94 g of the title compound as colorless crystals.

¹H-NMR (400 MHz, CDCl₃) δ 1.43 (3H, s), 7.01 (1H, ddd, J=0.8, 2.4, 8.0 Hz), 7.08 (1H, dd, J=0.8, 1.6 Hz), 7.10-7.32 (15H, m), 7.37 (1H, dt, J=6.0, 8.0 Hz), 7.41 (1H, ddd, J=1.6, 2, 4, 6.0 Hz), 7.54 (1H, ddd, J=0.8, 1.6, 8.0 Hz), 8.07 (1H, dd, J=0.8, 1.6 Hz)

Production Example II-9-d 3-(3-Fluorophenyl)-7-methyl-1H-indazole-5-carbonitrile To a solution of 1.5 g of 5-bromo-3-(3-fluorophenyl)-7-methyl-1-trityl-1H-indazole in 15 ml dimethylformamide were added 0.64 g of zinc cyanide and 0.32 g of tetrakis(triphenylphosphine)palladium(0) at room temperature, and the mixture was stirred at 100° C. for one day. At the same temperature, 0.32 g of tetrakis(triphenylphosphine)palladium(0) was added and the mixture was stirred at 130° C. for one day. The reaction mixture was diluted with ethyl acetate, and the organic layer was sequentially washed with saturated aqueous ammonium chloride solution and brine, dried over anhydrous magnesium sulfate, and the solvent was evaporated. The crude product was purified and separated by silica gel column chromatography (ethyl acetate:n-hexane=1:10 to 1:1) and the resulting crystals were washed with diethyl ether, to give 431 mg of the title compound as colorless crystals.

$^1$H-NMR (400 MHz, DMSO-D$_6$) δ 2.57 (3H, s), 7.26 (1H, dd, J=2.4, 8.0 Hz), 7.53 (1H, s), 7.56 (1H, dt, J=6.0, 8.0 Hz), 7.79 (1H, dt, J=2.4, 6.0 Hz), 7.89 (1H, d, J=8.0 Hz), 8.55 (1H, s)

Production Example II-9-e 3-(3-Fluorophenyl)-7-methyl-1H-indazole-5-carboxylic acid To 430 mg of 3-(3-fluorophenyl)-7-methyl-1H-indazole-5-carbonitrile were sequentially added 6.0 ml of glacial acetic acid, 2.0 ml of water and 2.0 ml of concentrated sulfuric acid, followed by stirring at 100° C. for one day. After standing to cool, the reaction mixture was diluted with 20 ml of water, and the resulting crystals were collected by filtration. The crystals were sequentially washed with water and diethyl ether, to give 360 mg of the title compound as colorless crystals.

$^1$H-NMR (400 MHz, DMSO-D$_6$) δ 2.58 (3H, s), 7.27 (1H, dd, J=2.4, 8.0 Hz), 7.61 (1H, q, J=8.0 Hz), 7.71 (1H, dd, J=2.4, 8.0 Hz), 7.76 (1H, s), 7.81 (1H, d, J=8.0 Hz), 8.46 (1H, s)

Production Example II-10-a (3-Bromo-6-fluoro-2-methoxy-phenyl)-naphthalen-2-yl-methanol In an atmosphere of nitrogen gas, 2.38 ml of a 2.66 M solution of n-butyllithium in hexane was added to a solution of 0.64 g of N,N-diisopropylamine in 9 ml tetrahydrofuran at −78° C. After stirring at the same temperature for 1 hour, 1.18 g of 1-bromo-4-fluoro-2-methoxy-benzene obtained in Production Example II-1-a was added dropwise. After stirring at the same temperature for 1 hour and 20 minutes, a solution of 0.99 g of 2-naphthoaldehyde in 4 ml tetrahydrofuran was added dropwise. After stirring at the same temperature for 1 hour and 20 minutes, water was added under ice-cooling and the mixture was extracted with diethyl ether for two times. The extract was sequentially washing with water and brine, dried over anhydrous magnesium sulfate and the solvent was evaporated. The crude product was purified and separated by silica gel column chromatography, to give 1.72 g of the title compound as a pale yellow oil.

$^1$H-NMR (400 MHz, CDCl$_3$) δ 3.46 (3H, s), 3.68 (1H, d, J=10.8 Hz), 6.35 (1H, d, J=10.8 Hz), 6.88 (1H, t, J=8.8 Hz), 7.42-7.53 (4H, m), 7.80-7.85 (4H, m)

Production Example II-10-b (3-Bromo-6-fluoro-2-methoxy-phenyl)-naphthalen-2-yl-methanone To a solution of 1.72 g of (3-bromo-6-fluoro-2-methoxy-phenyl)-naphthalen-2-yl-methanol in 34.4 ml methylene chloride was added 5.16 g of activated manganese dioxide, followed by stirring at room temperature for 17 hours. Then, the manganese dioxide was filtered off through Celite. The solvent was removed by distillation, to give 1.63 g of the title compound as a yellow oil.

$^1$H-NMR (400 MHz, CDCl$_3$) δ 3.80 (3H, s), 6.91 (1H, dd, J=8.0, 8.8 Hz), 7.51-7.55 (1H, m), 7.59-7.68 (2H, m), 7.87-7.93 (3H, m), 8.02 (1H, dd, J=1.6, 8.4 Hz), 8.20 (1H, bs)

Production Example II-10-c

5-Bromo-4-methoxy-3-naphthalen-2-yl-1H-indazole

A total of 1.63 g of (3-bromo-6-fluoro-2-methoxy-phenyl)-naphthalen-2-yl-methanone was dissolved in 15 ml of pyridine, 2.2 ml of hydrazine monohydrate was added, followed by stirring at 100° C. for 6 hours. Water was added to the reaction mixture, and then it was extracted with ethyl acetate for two times. The organic layer was sequentially washed with 1 N hydrochloric acid, water, saturated aqueous sodium hydrogencarbonate solution and brine, dried over anhydrous magnesium sulfate and the solvent was removed by distillation. Then, the resulting crystals were washed with hexane once and dried in vacuo, to give 0.923 g of the title compound as brown crystals.

$^1$H-NMR (400 MHz, CD$_3$OD) δ 3.39 (3H, s), 7.31 (1H, d, J=8.8 Hz), 7.52-7.58 (3H, m), 7.91-8.03 (4H, m), 8.40 (1H, bs)

ESI-MS: m/z=351, 353 (M−H)$^-$

Production Example II-10-d

4-Methoxy-3-naphthalen-2-yl-1H-indazole-5-carboxylic acid

In an atmosphere of nitrogen gas, 2.94 ml of a 2.66 M solution of n-butyllithium in hexane was added to a solution of 0.923 g of 5-bromo-4-methoxy-3-naphthalen-2-yl-1H-indazole in 26 ml tetrahydrofuran at −78° C. After stirring at the same temperature for 1 hour and 15 minutes, carbon dioxide gas was bubbled into the reaction mixture at the same temperature for 10 minutes. After stirring at the same temperature for further 15 minutes, the mixture was stirred at room temperature for 20 minutes. Saturated aqueous ammonium chloride solution was added and the mixture was extracted ethyl acetate for two times. The organic layer was washed with brine once, dried over anhydrous magnesium sulfate and the solvent was evaporated. The resulting crystals were washed with one portion of a 1:1 solvent of hexane:diethyl ether, and dried in vacuo, to give 0.586 g of the title compound as brown crystals.

$^1$H-NMR (400 MHz, CD$_3$OD) δ 3.48 (3H, s), 7.36 (1H, d, J=8.8 Hz), 7.51-7.55 (2H, m), 7.88-8.02 (5H, m), 8.39 (1H, bs)

ESI-MS: m/z=317 (M−H)$^-$

Production Example II-11-a

3-Bromo-6-fluoro-2-methoxy-benzaldehyde

In an atmosphere of nitrogen gas, 18.7 ml of a 2.66 M solution of n-butyllithium in hexane was added to a solution of 5 g of N,N-diisopropylamine in 89 ml tetrahydrofuran at −78° C. After stirring at the same temperature for 1 hour and 10 minutes, 9.27 g of 1-bromo-4-fluoro-2-methoxy-benzene obtained in Production Example II-1-a was added dropwise. After stirring at the same temperature for 1.5 hours, 5.52 ml of N-formylpiperidine was added dropwise. After stirring at the same temperature for 25 minutes, 9 ml of acetic acid was added at the same temperature, water was added at room temperature, and the mixture was extracted with diethyl ether for three times. The extract was sequentially washed with 0.2 N hydrochloric acid, water and brine, dried over anhydrous magnesium sulfate and the solvent was evaporated. The crude product was purified and separated by silica gel column chromatography, to give 5.65 g of the title compound as pale yellow crystals.

$^1$H-NMR (400 MHz, CDCl$_3$) δ 3.97 (3H, s), 6.90 (1H, dd, J=9.0, 9.6 Hz), 7.76 (1H, dd, J=5.6, 9.0 Hz), 10.35 (1H, s)

Production Example II-11-b

Benzo[b]furan-2-yl-(3-bromo-6-fluoro-2-methoxy-phenyl)-methanol

In an atmosphere of nitrogen gas, 3.56 ml of a 2.66 M solution of n-butyllithium in hexane was added to a solution of 1.12 g of 2,3-benzofuran in 10 ml tetrahydrofuran at −78° C. After stirring at the same temperature for 10 minutes, the mixture was stirred under ice-cooling for 15 minutes and was then stirred at −78° C. for 8 minutes. Then, a solution of 2 g of 3-bromo-6-fluoro-2-methoxy-benzaldehyde in 3.5 ml tetrahydrofuran was added dropwise at the same temperature. After stirring at the same temperature for 30 minutes, saturated aqueous ammonium chloride solution was added at the same temperature. Water was added at room temperature and the mixture was extracted with diethyl ether for two times. The organic layer was sequentially washed with water and brine, dried over anhydrous magnesium sulfate and the solvent was evaporated. The crude product was purified and separated by silica gel column chromatography, to give 2 g of the title compound as a yellow oil.

$^1$H-NMR (400 MHz, CDCl$_3$) δ 3.74-3.78 (4H, m), 6.28 (1H, d, J=10.4 Hz), 6.647-6.652 (1H, m), 6.86 (1H, t, J=9.2 Hz), 7.18-7.26 (2H, m), 7.40-7.43 (1H, m), 7.51-7.54 (2H, m)

Production Example II-11-c

Benzo[b]furan-2-yl-(3-bromo-6-fluoro-2-methoxy-phenyl)-methanone

A total of 1.93 g of the title compound was obtained as a yellow oil by the procedure of Production Example II-10-b, except from 2 g of benzo[b]furan-2-yl-(3-bromo-6-fluoro-2-methoxy-phenyl)-methanol.

$^1$H-NMR (400 MHz, CDCl$_3$) δ 3.86 (3H, s), 6.90 (1H, dd, J=8.0, 8.8 Hz), 7.29-7.33 (1H, m), 7.37 (1H, bs), 7.48-7.53 (1H, m), 7.58-7.61 (1H, m), 7.64-7.69 (2H, m)

Production Example II-11-d

3-Benzo[b]furan-2-yl-5-bromo-4-methoxy-1H-indazole

A total of 1.38 g of the title compound was obtained as brown crystals by the procedure of Production Example II-10-c, except from 1.93 g of benzo[b]furan-2-yl-(3-bromo-6-fluoro-2-methoxy-phenyl)-methanone.

$^1$H-NMR (400 MHz, CD$_3$OD) δ 3.86 (3H, s), 7.25-7.37 (3H, m), 7.53 (1H, d, J=1.2 Hz), 7.57-7.61 (2H, m), 7.69-7.71 (1H, m)

ESI-MS: m/z=341, 343 (M−H)$^-$

Production Example II-11-e

3-Benzo[b]furan-2-yl-4-methoxy-1H-indazole-5-carboxylic acid

A total of 0.2 g of the title compound was obtained as brown crystals by the procedure of Production Example II-10-d, except from 0.69 g of 3-benzo[b]furan-2-yl-5-bromo-4-methoxy-1H-indazole.

$^1$H-NMR (400 MHz, CD$_3$OD) δ 3.48 (3H, s), 7.36 (1H, d, J=8.8 Hz), 7.51-7.55 (2H, m), 7.88-8.02 (5H, m), 8.39 (1H, bs

ESI-MS: m/z=307 (M−H).

Production Example II-12-a

Benzo[b]thiophen-2-yl-(3-bromo-6-fluoro-2-methoxy-phenyl)-methanol

A total of 2.14 g of the title compound was obtained as an orange oil by the procedure of Production Example II-11-b, except from 2 g of 3-bromo-6-fluoro-2-methoxy-benzaldehyde obtained in Production Example II-11-a and benzo[b]thiophene.

$^1$H-NMR (400 MHz, CDCl$_3$) δ 3.66 (3H, s), 4.05 (1H, d, J=11.2 Hz), 6.38 (1H, d, J=11.2 Hz), 6.88 (1H, t, J=9.2 Hz), 6.97-6.98 (1H, m), 7.26-7.33 (2H, m), 7.54 (1H, dd, J=6.0, 8.8 Hz), 7.64-7.66 (1H, m), 7.77-7.79 (1H, m)

Production Example II-12-b

Benzo[b]thiophen-2-yl-(3-bromo-6-fluoro-2-methoxy-phenyl)-methanone

A total of 2.04 g of the title compound was obtained as an orange oil by the procedure of Production Example II-10-b, except from 2.14 g of benzo[b]thiophen-2-yl-(3-bromo-6-fluoro-2-methoxy-phenyl)-methanol.

$^1$H-NMR (400 MHz, CDCl$_3$) δ 3.85 (3H, s), 6.91 (1H, dd, J=7.6, 8.8 Hz), 7.37-7.41 (1H, m), 7.46-7.50 (1H, m), 7.64-7.68 (2H, m), 7.81-7.84 (1H, m), 7.88-7.90 (1H, m)

Production Example II-12-c

3-Benzo[b]thiophen-2-yl-5-bromo-4-methoxy-1H-indazole

A total of 1.42 g of the title compound was obtained as black-green crystals by the procedure of Production Example II-10-c, except from 2.04 g of benzo[b]thiophen-2-yl-(3-bromo-6-fluoro-2-methoxy-phenyl)-methanone.

$^1$H-NMR (400 MHz, CD$_3$OD) δ 3.76 (3H, s), 7.29 (1H, d, J=8.8 Hz), 7.33-7.39 (2H, m), 7.58 (1H, d, J=8.8 Hz), 7.86-7.88 (2H, m), 8.10 (1H, bs)

ESI-MS: m/z=357, 359 (M−H)$^-$

Production Example II-12-d

3-Benzo[b]thiophen-2-yl-4-methoxy-1H-indazole-5-carboxylic acid

A total of 0.64 g of the title compound was obtained as black-green crystals by the procedure of Production Example II-10-d, except from 1.42 g of 3-benzo[b]thiophen-2-yl-5-bromo-4-methoxy-1H-indazole.

$^1$H-NMR (400 MHz, CD$_3$OD) δ 3.84 (3H, s), 7.33-7.39 (3H, m), 7.86-7.90 (3H, m), 8.14 (1H, bs)

ESI-MS: m/z=323 (M−H)$^-$

Production Example II-13-a

2,4-Difluoro-3-formyl-benzonitrile

In an atmosphere of nitrogen gas, 66 ml of a 1.6 M solution of n-butyllithium in hexane was added to an ice-cold solution of 11.1 g of N,N-diisopropylamine in 100 ml tetrahydrofuran, and the mixture was stirred at the same temperature for 20 minutes. After cooling to −78° C., a solution of 13.9 g of 2,4-difluorobenzonitrile in 15 ml tetrahydrofuran was added dropwise. After stirring at the same temperature for 10 minutes, 8.6 ml of dimethylformamide was added dropwise and the mixture was stirred at the same temperature for 15 minutes. After adding 20 ml of glacial acetic acid to the reaction mixture, 200 ml of water was added and the mixture was extracted with diethyl ether for two times. The organic layer was sequentially washed with 0.2 N hydrochloric acid and brine, dried over anhydrous magnesium sulfate and the solvent was evaporated. The resulting crude crystals were triturated with diethyl ether-n-hexane, to give 8.61 g of the title compound as bright yellow crystals.

$^1$H-NMR (400 MHz, DMSO-$d_6$) δ 7.53 (1H, t, J=8.8 Hz), 8.33 (1H, ddd, J=6.0, 7.2, 8.8 Hz), 10.17 (1H, s)

Production Example II-13-b

4-Fluoro-1H-indazole-5-carbonitrile

A total of 8.55 g of 2,4-difluoro-3-formyl-benzonitrile obtained in Production Example II-13-a was dissolved in 40 ml of tetrahydrofuran and 40 ml of methanol, and 5.1 ml of hydrazine monohydrate was added, followed by stirring at room temperature for three days and was further stirred at 50° C. for 3 hours and at 70° C. for 3 hours. The reaction mixture was added with 150 ml of ice-water, 300 ml of ethyl acetate and 100 ml of tetrahydrofuran were added, and unnecessary matters were filtered off. The organic layer was sequentially washed with water and brine, dried over anhydrous magnesium sulfate and the solvent was evaporated. The crude product was purified and separated by silica gel column chromatography (ethyl acetate:toluene=1:9 to 1:4), to give 509 mg of the title compound as bright yellow crystals. In addition, a portion with impurities was purified again by silica gel column chromatography (ethyl acetate:n-hexane=1:4 to 1:0), to give 1.80 g of the title compound as bright yellow crystals.

$^1$H-NMR (400 MHz, DMSO-$d_6$) δ 7.58 (1H, d, J=8.8 Hz), 7.70 (1H, dd, J=6.0, 8.8 Hz), 8.45 (1H, s), 13.94 (1H, s)

Production Example II-13-c

4-Fluoro-1H-indazolecarboxylic acid methyl ester

To 1.65 g of 4-fluoro-1H-indazole-5-carbonitrile obtained in Production Example II-13-b were added 8 ml of glacial acetic acid, 8 ml of water and 16 ml of concentrated sulfuric acid, and the mixture was stirred at 110° C. for 4 hours. After standing to cool, 150 mg of ice-water was added, and the precipitated carboxylic acid was collected by filtration. Under ice-cooling, to a solution of the resulting carboxylic acid in 12 ml dimethylformamide and 40 ml tetrahydrofuran was added an excess amount of a solution of diazomethane in diethyl ether, and the mixture was stirred at the same temperature for 45 minutes. The solvent was evaporated, and the residue was dissolved in 100 ml of ethyl acetate. The mixture was sequentially washed with saturated aqueous sodium hydrogencarbonate solution, water and brine, dried over anhydrous magnesium sulfate and the solvent was evaporated, to give 1.98 g of the title compound as bright yellow crystals.

$^1$H-NMR (400 MHz, DMSO-$d_6$) δ 3.87 (3H, s), 7.45 (1H, d, J=8.8 Hz), 7.82 (1H, dd, J=6.8, 8.8 Hz), 8.36 (1H, s), 13.70 (1H, s)

Production Example II-13-d

3-Bromo-4-fluoro-1H-5-indazolecarboxylic acid methyl ester

To a solution of 2.2 g of 4-fluoro-1H-5-indazolecarboxylic acid methyl ester obtained in Production Example II-13-c in 20 ml dimethylformamide was added 2.12 g of N-bromosuccinimide at room temperature, and the mixture was stirred at the same temperature for 1 hour. After removing the solvent by distillation, 120 ml of ethyl acetate was added to the residue. The mixture was sequentially washed with half-saturated aqueous sodium hydrogencarbonate solution, water and brine, dried over anhydrous magnesium sulfate and the solvent was evaporated, to give 3.0 g of the title compound as bright yellow crystals.

$^1$H-NMR (400 MHz, DMSO-$d_6$) δ 3.88 (3H, s), 7.48 (1H, d, J=8.8 Hz), 7.85 (1H, dd, J=6.4, 8.8 Hz), 14.00 (1H, s)

Production Example II-13-e

3-Bromo-4-fluoro-1-trityl-1H-indazole-5-carboxylic acid methyl ester

Under ice-cooling, to a solution of 2.99 g of 3-bromo-4-fluoro-1H-5-indazolecarboxylic acid methyl ester obtained in Production Example II-13-d in 30 ml tetrahydrofuran was added 526 mg of 60% sodium hydride, and the mixture was stirred for 25 minutes. Then, 3.21 g of triphenylmethyl chloride was added and the mixture was stirred at the same temperature for 15 minutes and further stirred at room temperature for 45 minutes. The reaction mixture was ice-cooled again, saturated aqueous sodium hydrogencarbonate solution was added and the mixture was extracted with 100 ml of ethyl acetate. The organic layer was sequentially washed with water (×2) and brine, dried over anhydrous magnesium sulfate and the solvent was evaporated. The crude product was purified and separated by silica gel column chromatography (ethyl acetate:hexane=1:9), and the resulting crystals were recrystallized from diisopropyl ether, to give 1.73 g of the title compound as white needles.

$^1$H-NMR (400 MHz, DMSO-$d_6$) δ 3.83 (3H, s), 6.30 (1H, d, J=8.8 Hz), 7.12-7.20 (6H, m), 7.30-7.40 (9H, m), 7.55 (1H, dd, J=6.8, 8.8 Hz)

Production Example II-13-f

3-Benzo[b]thiophen-2-yl-4-fluoro-1H-5-indazolecarboxylic acid methyl ester

To a solution of 515 mg of 3-bromo-4-fluoro-1-trityl-1H-indazole-5-carboxylic acid methyl ester obtained in Production Example II-13-e in 7.5 ml dimethylformamide were sequentially added 267 mg of 2-benzo[b]thipheneboronic acid, 1 ml of an aqueous solution of 291 mg of potassium fluoride, 30 mg of 2-(di-tert-butylphosphino)biphenyl and 12 mg of palladium(II) acetate, and the mixture was stirred at 55° C. for 1 hour. The reaction mixture was ice-cooled, and then the precipitated crystals were collected by filtration. The resulting crystals were dissolved in a mixture solution of ethyl acetate and tetrahydrofuran, and the mixture was sequentially washed with water, half-saturated aqueous sodium hydrogencarbonate solution and brine, dried over anhydrous magnesium sulfate and the solvent was evaporated, to give 504 mg of a crude coupling product. A total of 350 mg of the resulting crude coupling product was suspended in 4 ml of methylene chloride, 2 ml of trifluoroacetic acid and 0.1 ml of triisopropylsilane were added, and the mixture was stirred at room temperature for 15 minutes. To the reaction mixture was added saturated aqueous sodium hydrogencarbonate solution and it was extracted with 50 ml of ethyl acetate. The organic layer was sequentially washed with saturated aqueous sodium hydrogencarbonate solution and brine, dried over anhydrous magnesium sulfate and the solvent was evaporated. The crude product was purified and separated by silica gel column chromatography (ethyl acetate:toluene=1:9), to give 154 mg of the title compound as pale yellow crystals.

$^1$H-NMR (400 MHz, DMSO-D$_6$) δ 3.91 (3H, s), 7.38-7.45 (2H, m), 7.52 (1H, d, J=8.8 Hz), 7.91 (1H, dd, J=6.8, 8.8 Hz), 7.96-8.03 (2H, m), 8.05 (1H, s), 14.01 (1H, s).

Production Example II-13-g

3-Benzo[b]thiophen-2-yl-4-fluoro-1H-5-indazolecarboxylic acid

To a solution of 152 mg of 3-benzo[b]thiophen-2-yl-4-fluoro-1H-5-indazolecarboxylic acid methyl ester obtained in Production Example II-13-f in a mixture of 2 ml of tetrahydrofuran and 2 ml of methanol was added 1 ml of 5 N aqueous sodium hydroxide solution, and the mixture was stirred at 55° C. for 2.5 hours. After standing to cool, 5.5 ml of 1 N hydrochloric acid was added and the mixture was extracted with ethyl acetate. The organic layer was sequentially washed with water and brine, dried over anhydrous magnesium sulfate and the solvent was evaporated. The crude product was recrystallized from tetrahydrofuran-ethyl acetate, to give 104 mg of the title compound as pale red crystals.

$^1$H-NMR (400 MHz, DMSO-D$_6$) δ 7.36-7.43 (2H, m), 7.47 (1H, d, J=8.8 Hz), 7.88 (1H, dd, J=6.4, 8.8 Hz), 7.95-8.00 (2H, m), 8.03 (1H, s), 13.16 (1H, s).

Production Example II-14-a

4-Fluoro-3-naphthalen-2-yl-1H-5-indazolecarboxylic acid methyl ester

By the procedure of Production Example II-13-f, 495 mg of a Suzuki coupling product was obtained from 515 mg of 3-bromo-4-fluoro-1-trityl-1H-indazole-5-carboxylic acid methyl ester obtained in Production Example II-13-e and 258 mg of n-naphthaleneboronic acid. A total of 350 mg of the coupling product was subjected to deprotection (on trityl group) by the procedure of Production Example II-13-f, to give 154 mg of the title compound as bright yellow crystals.

$^1$H-NMR (400 MHz, DMSO-D$_6$) δ 3.88 (3H, s), 7.52 (1H, d, J=8.8 Hz), 7.56-7.62 (2H, m), 7.89 (1H, dd, J=6.4, 8.0 Hz), 7.96-8.10 (4H, m) 8.39 (1H, s), 13.94 (1H, s)

Production Example II-14-b

4-Fluoro-3-naphthalen-2-yl-1H-5-indazolecarboxylic acid

A total of 63 mg of the title compound was obtained as bright yellow crystals by the procedure of Production Example II-13-g, except using 152 mg of 4-fluoro-3-naphthalen-2-yl-1H-5-indazolecarboxylic acid methyl ester produced in Production Example II-14-a.

$^1$H-NMR (400 MHz, DMSO-D$_6$) δ 7.49 (1H, d, J=8.8 Hz), 7.55-7.61 (2H, m), 7.88 (1H, dd, J=6.4, 8.8 Hz), 7.96-8.08 (4H, m), 8.39 (1H, s), 13.08 (1H, s), 13.88 (1H, s).

Production Example II-15-a

3-Benzo[b]furan-2-yl-1H-5-indazolecarboxylic acid methyl ester

A total of 123 mg of the title compound was obtained as bright yellow crystals by the procedure of Production Example II-13-f, except from 308 mg of 3-bromo-4-fluoro-1-trityl-1H-indazole-5-carboxylic acid methyl ester produced in Production Example II-13-e and 145 mg of 2-benzo[b]furanboronic acid.

$^1$H-NMR (400 MHz, DMSO-D$_6$) δ 3.91 (3H, s), 7.32 (1H, t, J=7.6 Hz), 7.39 (1H, dd, J=7.6, 8.4 Hz), 7.51 (1H, s), 7.54 (1H, d, J=8.8 Hz), 7.69 (1H, d, J=8.4 Hz), 7.78 (1H, d, J=7.6 Hz), 7.91 (1H, dd, J=6.4, 8.8 Hz), 14.15 (1H, s)

Production Example II-15-b

3-Benzo[b]furan-2-yl-1H-5-indazolecarboxylic acid

A total of 115 mg of the title compound was obtained as bright yellow crystals by the procedure of Production Example II-13-f, except from 121 mg of 3-benzo[b]furan-2-yl-1H-5-indazolecarboxylic acid methyl ester obtained in Production Example II-15-a.

$^1$H-NMR (400 MHz, DMSO-D$_6$) δ 7.32 (1H, t, J=7.6 Hz), 7.39 (1H, dd, J=7.6, 8.0 Hz), 7.50 (1H, s), 7.50 (1H, d, J=8.8 Hz), 7.69 (1H, d, J=8.0 Hz), 7.76 (1H, d, J=7.6 Hz), 7.90 (1H, dd, J=6.8, 8.8 Hz), 13.18 (1H, s), 14.09 (1H, s)

Production Example II-16-a

Benzo[b]thiophen-2-yl-(5-bromo-2,4-difluorophenyl)methanone

As a raw material, 17.7 g of 1,5-dibromo-2,4-difluorobenzene obtained in Production Example II-5-a was subjected to lithiation with n-butyllithium by the procedure of Production Example II-5-b, was subjected to formylation with N,N-dimethylformamide, to give 10.7 g of 5-bromo-2,4-difluorobenzaldehyde. This compound was allowed to react with benzothiophene by the procedure of Production Example II-12-a to yield an alcohol, and then the alcohol was oxidized by the procedure of Production Example II-10-b, to give 9.7 g of the title compound as a colorless oil.

$^1$H-NMR (400 MHz, CDCl$_3$) δ 7.07 (1H, t, J=8.6 Hz), 7.44 (1H, t, J=8.4 Hz), 7.52 (1H, t, J=8.4 Hz), 7.77 (1H, s), 8.65 (1H, d, J=6.6 Hz), 13.50-13.60 (1H, bs).

Production Example II-16-b 5-(Benzo[b]thiophen-2-carbonyl)-2,4-difluoro-benzonitrile A total of 1.46 g of the title compound was obtained as pale yellow crystals by the procedure of Production Example II-1-c, except from 2.98 g of benzo[b]thiophen-2-yl-(5-bromo-2,4-difluorophenyl)methanone.

$^1$H-NMR (400 MHz, CDCl$_3$) δ 7.16 (1H, t, J=8.8 Hz), 7.44 (1H, t, J=8.0 Hz), 7.53 (1H, t, J=8.0 Hz), 7.73 (1H, s), 7.88 (1H, d, J=8.0 Hz), 7.91 (1H, d, J=8.0 Hz).

Production Example II-16-c

3-Benzo[b]thiophen-2-yl-6-fluoro-1H-indazole-5-carbonitrile

A total of 1.08 g of the title compound was obtained as pale yellow crystals by the procedure of Production Example II-10-c, except from 1.46 g of 5-(benzo[b]thiophen-2-carbonyl)-2,4-difluoro-benzonitrile.

$^1$H-NMR (400 MHz, DMSO-d$_6$) δ 7.37-7.45 (2H, m), 7.74 (1H, d, J=10.0 Hz), 7.86-7.91 (1H, m), 7.97-8.01 (1H, m), 8.39 (1H, s), 9.06 (1H, d, J=6.0 Hz).

Production Example II-16-d

3-Benzo[b]thiophen-2-yl-6-fluoro-1H-indazole-5-carboxylic acid

A total of 600 mg of 3-benzo[b]thiophen-2-yl-6-fluoro-1H-indazole-5-carbonitrile obtained in Production Example II-16-c was hydrolyzed by the procedure of Production Example II-1-e, to give 310 mg of the title compound as a light brown powder.

$^1$H-NMR (400 MHz, DMSO-d$_6$) δ 7.36-7.43 (2H, m), 7.50 (1H, d, J=10.9 Hz), 7.97-8.02 (2H, m), 8.16 (1H, s), 8.73 (1H, d, J=6.9 Hz), 13.15-13.30 (1H, bs), 13.69 (1H, s).

Production Example II-17-a

(5-Bromo-2,4-difluorophenyl)naphthalene-2-yl-methanone

A total of 13.6 g of 1,5-dibromo-2,4-difluorobenzene obtained in Production Example II-5-a as a raw material was subjected to lithiation with n-butyllithium by the procedure of Production Example II-5-b. This compound was treated with 2-naphthoaldehyde to yield an alcohol, the alcohol was oxidized by the procedure of Production Example II-10-b, to give 13.5 g of the title compound as a colorless oil.

$^1$H-NMR (400 MHz, CDCl$_3$) δ 7.51-7.59 (2H, m), 7.63 (1H, d, J=9.0 Hz), 7.93-7.96 (1H, m), 8.02 (1H, d, J=8.4 Hz), 8.14-8.18 (1H, m), 8.15 (1H, dd, J=1.6, 8.4 Hz), 8.56 (1H, d, J=1.6 Hz), 8.61 (1H, d, J=6.5 Hz), 13.45-13.65 (1H, bs).

Production Example II-17-b

2,4-Difluoro-5-(naphthalene-2-carbonyl)-benzonitrile

A total of 2.3 g of the title compound was obtained as a colorless powder by the procedure of Production Example II-1-c, except from 3.76 g of (5-bromo-2,4-difluorophenyl)naphthalene-2-yl-methanone.

$^1$H-NMR (400 MHz, CDCl$_3$) δ 7.15 (1H, t, J=8.8 Hz), 7.60 (1H, t, J=7.8 Hz), 7.67 (1H, t, J=7.8 Hz), 7.91-7.97 (4H, m), 7.97 (1H, t, J=7.0 Hz), 8.19 (1H, s).

Production Example II-17-c

6-Fluoro-3-naphthalen-2-yl-1H-indazole-5-carbonitrile

A total of 2.1 g of 2,4-difluoro-5-(naphthalene-2-carbonyl)-benzonitrile was allowed to react with hydrazine monohydrate by the procedure of Production Example II-10-c and thereby yielded 1.6 g of the title compound as a colorless powder.

$^1$H-NMR (400 MHz, DMSO-d$_6$) δ 7.53-7.61 (2H, m), 7.72 (1H, d, J=9.6 Hz), 7.93-7.98 (1H, m), 8.03 (1H, d, J=8.5 Hz), 8.14-8.19 (1H, m), 8.18 (1H, d, J=8.5 Hz), 8.65 (1H, s), 9.03 (1H, d, J=6.0 Hz), 13.83-13.97 (1H, bs)

Production Example II-17-d

6-Fluoro-3-naphthalen-2-yl-1H-indazole-5-carboxylic acid

A total of 700 mg of 6-fluoro-3-naphthalen-2-yl-1H-indazole-5-carbonitrile obtained in Production Example II-17-c was hydrolyzed by the procedure of Production Example II-1-e and thereby yielded 610 mg of the title compound as a colorless powder.

$^1$H-NMR (400 MHz, DMSO-d$_6$) δ 7.47 (1H, d, J=11.3 Hz), 7.53-7.60 (2H, m), 7.94-7.99 (1H, m), 8.07 (1H, d, J=8.6 Hz), 8.09-8.14 (1H, m), 8.11 (1H, d, J=8.6 Hz), 8.50 (1H, s), 8.67 (1H, d, J=7.2 Hz), 13.05-13.25 (1H, bs), 13.62 (1H, s).

Production Example II-18-a

5-Bromo-3-(3-fluoro-phenyl)-4-methoxy-1-trityl-1H-indazole

A total of 530 mg of 5-bromo-3-(3-fluoro-phenyl)-4-methoxy-1H-indazole obtained in Production Example II-2-c was dissolved in 8.3 ml of dimethylformamide, and 99 mg of sodium hydride (60% content) was added under ice-cooling and stirring. After stirring for 15 minutes, 483 mg of triphenylmethyl chloride was added. After stirring at room temperature for 1 hour, saturated aqueous ammonium chloride solution was added and the mixture was extracted with ethyl acetate. The resulting organic layer was washed with brine, dried over magnesium sulfate and the solvent was evaporated.

The crude product was purified and separated by silica gel column chromatography (ethyl acetate:hexane=1:8), to give 998 mg of the title compound as pale yellow crystals.

$^1$H-NMR (400 MHz, CDCl$_3$) δ 3.54 (3H, s), 6.16 (1H, d, J=8.8 Hz), 7.01-7.08 (1H, m), 7.11 (1H, d, J=8.8 Hz), 7.16-7.40 (16H, m), 7.64-7.69 (1H, m), 7.74 (1H, d, J=8.0 Hz).

Production Example II-18-b

3-(3-Fluoro-phenyl)-4-methoxy-1-trityl-1H-indazol-5-ylamine

A total of 810 mg of 5-bromo-3-(3-fluoro-phenyl)-4-methoxy-1-trityl-1H-indazole obtained in Production Example II-18-a was dissolved in 7.2 ml of toluene, 194 mg of sodium t-butoxide, 0.29 ml of benzophenoneimine, 135 mg of 2,2'-bis(diphenylphosphino)-1,1'-binaphthyl and 74.5 mg of tris(dibenzylideneacetone)bispalladium were added, and the mixture was stirred at 80° C. in an atmosphere of nitrogen gas for 8 hours. The reaction mixture was cooled to room temperature, and diethyl ether was added. The mixture was filtrated through Celite, and the filtrate was evaporated. The resulting residue was dissolved in 7.2 ml of tetrahydrofuran and 0.36 ml of 2 N hydrochloric acid was added, followed by stirring at room temperature for 3 hours. Saturated aqueous sodium hydrogencarbonate solution was added to the reaction mixture and the mixture was extracted with diethyl ether. The resulting organic layer was washed with brine, dried over magnesium sulfate and the solvent was evaporated. The residue was purified and separated by silica gel column chromatography (ethyl acetate:hexane=1:3), to give 426 mg of the title compound as reddish brown crystals.

$^1$H-NMR (400 MHz, CDCl$_3$) δ 3.46 (3H, s), 6.11 (1H, d, J=8.8 Hz), 6.55 (1H, d, J=8.8 Hz), 6.96-7.04 (1H, m), 7.20-7.62 (16H, m), 7.68-7.74 (1H, m), 7.76 (1H, d, J=8.0 Hz).

Production Example II-19-a

4-Fluoro-3-(3-fluoro-phenyl)-1-trityl-1H-indazole-5-carboxylic acid

A total of 1.29 g of the title compound was obtained as an ocher yellow amorphous substance by the procedure of Production Example II-18-a, except from 1.25 g of 4-fluoro-3-(3-fluoro-phenyl)-1H-indazole-5-carboxylic acid obtained in Production Example II-3-d.

$^1$H-NMR (400 MHz, CD$_3$OD) δ 6.34 (1H, d, J=9.2 Hz), 7.08-7.16 (1H, m), 7.16-7.37 (16H, m), 7.38-7.67 (3H, m).

Production Example II-19-b

{4-Fluoro-3-(3-fluoro-phenyl)-1-trityl-1H-indazol-5-yl}-carbamic acid benzyl ester A total of 1.29 g of 4-fluoro-3-(3-fluoro-phenyl)-1-trityl-1H-indazole-5-carboxylic acid obtained in Production Example II-19-a was dissolved in 12.5 ml of toluene. Under stirring at room temperature, 0.38 ml of triethylamine and 0.566 ml of diphenylphosphoryl azide were added, and the mixture was stirred at room temperature for 2 hours and at 120° C. for further 1.5 hours. To the reaction mixture was added 0.776 ml of benzyl alcohol, followed by stirring at 120° C. for 1.5 hours. After cooling to room temperature, the reaction mixture was added with water, and extracted with ethyl acetate. The resulting organic layer was washed with brine, dried over magnesium sulfate and the solvent was evaporated. The residue was purified and separated by silica gel column chromatography (ethyl acetate:hexane 1:5), to give 652 mg of the title compound as an ocher yellow oil.

$^1$H-NMR (400 MHz, CDCl$_3$) δ 5.19 (2H, s), 6.23 (1H, d, J=9.2 Hz), 6.70-7.71 (26H, m

Production Example II-19-c

4-Fluoro-3-(3-fluoro-phenyl)-1-trityl-1H-indazol-5-yl-amine

A total of 652 mg of {4-fluoro-3-(3-fluoro-phenyl)-1-trityl-1H-indazol-5-yl}-carbamic acid benzyl ester obtained in Production Example II-19-b was dissolved in 20 ml of methanol, 652 mg of 10% palladium-carbon, and the mixture was subjected to catalytic hydrogenation at room temperature at normal pressure. After stirring for 4 hours, the mixture was filtered through Celite, and the filtrate was evaporated. The residue was purified and separated by silica gel column chromatography (ethyl acetate:hexane=1:5), to give 297 mg of the title compound.

$^1$H-NMR (400 MHz, CDCl$_3$) δ 3.54 (2H, brs), 6.09 (1H, d, J=8.8 Hz), 6.56 (1H, t, J=8.8 Hz), 6.96-7.40 (17H, m), 7.51 (1H, d, J=10.4 Hz), 7.69 (1H, d, J=7.6 Hz)

Production Example II-20-a

6-Fluoro-3-(3-fluoro-phenyl)-1-trityl-1H-indazole-5-carboxylic acid

A total of 496 mg of the title compound was obtained as ocher yellow crystals by the procedure of Production Example II-18-a, except from 352 mg of 6-fluoro-3-(3-fluoro-phenyl)-1H-indazole-5-carboxylic acid obtained in Production Example II-5-f.

$^1$H-NMR (400 MHz, CDCl$_3$) δ 6.13 (1H, d, J=12.8 Hz), 6.96-7.78 (19H, m), 8.73 (1H, d, J=10.4 Hz).

Production Example II-20-b

{6-Fluoro-3-(3-fluoro-phenyl)-1-trityl-1H-indazol-5-yl}-carbamic acid benzyl ester A total of 760 mg (crude purified product) was obtained by the procedure of Production Example II-19-b, except from 496 mg of 6-fluoro-3-(3-fluoro-phenyl)-1H-indazole-5-carboxylic acid obtained in Production Example II-20-a.

$^1$H-NMR (400 MHz, CDCl$_3$) δ 5.24 (2H, s) 6.09 (1H, d, J=12.0 Hz), 6.80-6.86 (1H, brs), 7.00-7.07 (1H, m), 7.14-7.46 (22H, m), 7.54-7.60 (1H, m), 7.65-7.73 (1H, m)

Production Example II-20-c

6-Fluoro-3-(3-fluoro-phenyl)-1-trityl-1H-indazol-5-yl-amine

A total of 185 mg of the title compound was obtained as pale yellow crystals by the procedure of Production Example II-19-c, except from 760 mg of {6-fluoro-3-(3-fluoro-phenyl)-1-trityl-1H-indazol-5-yl}-carbamic acid benzyl ester obtained in Production Example II-20-b.

$^1$H-NMR (400 MHz, CDCl$_3$) δ 3.65 (2H, brs), 6.06 (1H, d, J=12.0 Hz), 6.97-7.05 (1H, m), 7.16-7.44 (17H, m), 7.54 (1H, d, J=6.0 Hz), 7.63 (1H, d, J=7.2 Hz)

Production Example II-21

4-Bromo-3-(3-fluoro-phenyl)-1-trityl-1H-indazol-5-yl-amine

A total of 1.04 g of 3-(3-fluoro-phenyl)-1-trityl-1H-indazol-5-ylamine was dissolved in 22.3 ml of dichloromethane, and 375 mg of sodium hydrogencarbonate was added. Under ice-cooling and stirring, a solution of 0.12 ml of bromine in 50 ml dichloromethane was added dropwise over 50 minutes. After stirring for 2 hours while ice-cooling, saturated aqueous sodium thiosulfate solution and the mixture was extracted with diethyl ether. The resulting organic layer was washed with brine, dried over magnesium sulfate and the solvent was evaporated. The residue was purified and separated by silica gel column chromatography (ethyl acetate:hexane=1:5), to give 1.18 g of the title compound as a white foam.

$^1$H-NMR (400 MHz, CDCl$_3$) δ 3.97 (2H, brs), 6.31 (1H, d, J=8.8 Hz), 6.52 (1H, d, J=8.8 Hz), 7.02-7.09 (1H, m), 7.18-7.43 (18H, m).

Production Example II-22-a

5-Bromo-3-(3-fluoro-phenyl)-6-methoxy-1H-indazole

A total of 2.68 g of the title compound was obtained as pale yellow crystals by the procedure of Production Example II-1-d, except from 5.05 g of (5-bromo-2-fluoro-4-methoxy-phenyl)-(3-fluoro-phenyl)-methanone obtained in Production Example II-1-b.

$^1$H-NMR (400 MHz, CDCl$_3$) δ 3.94 (3H, s), 6.85 (1H, s), 7.09-7.16 (1H, m), 7.48 (1H, td, J=8.0, 6.0 Hz), 7.61-7.66 (1H, m), 7.68-7.74 (1H, m), 8.17 (1H, s).

Production Example II-22-b

5-Bromo-3-(3-fluoro-phenyl)-6-methoxy-1-trityl-1H-indazole

A total of 1.64 g of the title compound was obtained as pale yellow crystals by the procedure of Production Example II-18-a, except from 914 mg of 5-bromo-3-(3-fluoro-phenyl)-6-methoxy-1H-indazole obtained in Production Example II-22-a.

$^1$H-NMR (400 MHz, CDCl$_3$) δ 3.38 (3H, s), 5.74 (1H, s), 7.00-7.06 (1H, m), 7.14-7.36 (15H, m), 7.40 (1H, td, J=8.0, 6.0 Hz), 7.55 (1H, d, J=10.4 Hz), 7.65 (1H, d, J=8.0 Hz), 8.15 (1H, s)

Production Example II-22-c

3-(3-Fluoro-phenyl)-6-methoxy-1-trityl-1H-indazol-5-ylamine

A total of 526 mg of the title compound was obtained as an ocher yellow amorphous substance by the procedure of Production Example II-18-b, except from 674 mg of 5-bromo-3-(3-fluoro-phenyl)-6-methoxy-1-trityl-1H-indazole obtained in Production Example II-22-b.

$^1$H-NMR (400 MHz, CDCl$_3$) δ 3.37 (3H, s), 3.77 (2H, brs), 5.65 (1H, s), 6.95-7.02 (1H, m), 7.17-7.40 (17H, m), 7.57 (1H, d, J=10.4 Hz), 7.67 (1H, d, J=8.0 Hz)

Production Example II-23

3-(3-Fluoro-phenyl)-7-methyl-1-trityl-1H-indazol-5-ylamine

To a solution of 2.0 g of 5-bromo-3-(3-fluorophenyl)-7-methyl-1-trityl-1H-indazole obtained in Production Example II-9-c in 20 ml toluene at room temperature were added 0.73 g of benzophenoneimine, 95 mg of tris(dibenzylideneacetone)(chloroform)dipalladium(0), 0.17 g of 2,2'-bis(diphenylphosphino)-1,1'-binaphthyl and 0.53 g of sodium tert-butyrate, and the mixture was heated under reflux for one day. The mixture was diluted with water and ethyl acetate, and the organic layer was sequentially washed with saturated aqueous ammonium chloride solution and brine, dried over anhydrous magnesium sulfate, and the solvent was evaporated. The residue was dissolved in 30 ml of tetrahydrofuran, 10 ml of 5 N hydrochloric acid was added at room temperature, and the mixture was stirred at the same temperature for 30 minutes. The reaction mixture was neutralized with 5 N aqueous sodium hydroxide solution and was extracted with ethyl acetate. The organic layer was washed with brine, dried over anhydrous magnesium sulfate, and the solvent was evaporated. The crude product was purified and separated by silica gel column chromatography (ethyl acetate:n-hexane=1:10 to 1:3), and the resulting obtained crystals were washed with diethyl ether, to give 0.86 g of the title compound as colorless crystals.

$^1$H-NMR (400 MHz, CDCl$_3$) δ 1.38 (3H, s), 3.61 (2H, brs), 6.45 (1H, dd, J=2.4, 0.8 Hz), 6.95 (1H, dt, J=0.8, 8.0 Hz), 7.12-7.31 (16H, m), 7.32 (1H, dt, J=6.0, 8.0 Hz), 7.43 (1H, ddd, J=1.2, 2.4, 10.4 Hz), 7.55 (1H, dt, J=1.2, 8.0 Hz)

Production Example II-24-a

3-Benzo[b]thiophen-2-yl-5-bromo-6-fluoro-1H-indazole

A total of 5.7 g of benzo[b]thiophen-2-yl-(5-bromo-2,4-difluorophenyl)methanone obtained in Production Example II-16-a was allowed to react with hydrazine monohydrate by the procedure of Production Example II-10-c and thereby yielded 0.6 g of the title compound as a colorless powder.

$^1$H-NMR (400 MHz, DMSO-d$_6$) δ 7.34-7.43 (2H, m), 7.65 (1H, d, J=8.8 Hz), 7.90 (1H, bd, J=7.6 Hz), 7.97 (1H, bd, J=7.6 Hz), 8.28 (1H, s), 8.65 (1H, d, J=6.6 Hz), 13.50-13.60 (1H, bs).

Production Example II-24-b

3-Benzo[b]thiophen-2-yl-5-bromo-6-fluoro-1-trityl-1H-indazole

A total of 350 mg of the title compound was obtained as pale yellow crystals by the procedure of Production Example II-18-a, except from 269 mg of 3-benzo[b]thiophen-2-yl-5-bromo-6-fluoro-1H-indazole.

$^1$H-NMR (400 MHz, CDCl$_3$) δ 6.12 (1H, d, J=9.6 Hz), 7.18-7.38 (15H, m), 7.73-7.84 (5H, m), 8.27 (1H, d, j=6.4 Hz).

Production Example II-24-c

3-Benzo[b]thiophen-2-yl-6-fluoro-1-trityl-1H-indazol-5-ylamine

A total of 280 mg of the title compound was obtained as pale yellow crystals by the procedure of Production Example II-1-c, except from 350 mg of 3-benzo[b]thiophen-2-yl-5-bromo-6-fluoro-1-trityl-1H-indazole.

$^1$H-NMR (400 MHz, DMSO-d$_6$) δ 5.88 (1H, d, J=12.4 Hz), 7.12-7.42 (17H, m), 7.47 (1H, d, J=8.4 Hz), 7.82 (1H, s), 7.86 (1H, d, J=6.8 Hz), 7.93 (1H, d, J=6.8 Hz).

Production Example II-25-a

5-Bromo-6-fluoro-3-naphthalen-2-yl-1H-indazole

A total of 7.0 g of (5-bromo-2,4-difluorophenyl)naphthalene-2-yl-methanone obtained in Production Example II-17-a was allowed to react with hydrazine monohydrate by the procedure of Production Example II-10-c and thereby yielded 1.5 g of the title compound as a colorless powder.

$^1$H-NMR (400 MHz, DMSO-d$_6$) δ 7.51-7.59 (2H, m), 7.63 (1H, d, J=9.0 Hz), 7.93-7.96 (1H, m), 8.02 (1H, d, J=8.4 Hz), 8.14-8.18 (1H, m), 8.15 (1H, dd, J=1.6, 8.4 Hz), 8.56 (1H, d, J=1.6 Hz), 8.61 (1H, d, J=6.5 Hz), 13.45-13.65 (1H, bs).

Production Example II-25-b

5-Bromo-6-fluoro-3-naphthalen-2-yl-1-trityl-1H-indazole

A total of 1.22 g of the title compound was obtained as white crystals by the procedure of Production Example II-18-a, except from 811 mg of 5-bromo-6-fluoro-3-naphthalen-2-yl-1H-indazole.

$^1$H-NMR (400 MHz, CDCl$_3$) δ 6.17 (1H, d, J=10.0 Hz), 7.21-7.35 (15H, m), 7.45-7.54 (2H, m), 7.81-7.97 (4H, m), 8.26-8.31 (2H, m).

Production Example II-25-c

6-Fluoro-3-naphthalen-2-yl-1-trityl-1H-indazol-5-ylamine

A total of 970 mg of the title compound was obtained as pale yellow crystals by the procedure of Production Example II-1-c, except from 1.22 g of 5-bromo-6-fluoro-3-naphthalen-2-yl-1-trityl-1H-indazole.

$^1$H-NMR (400 MHz, DMSO-d$_6$) δ 5.94 (1H, d, J=12.0 Hz), 7.20-7.40 (15H, m), 7.47-7.59 (3H, m), 7.86-8.00 (4H, m), 8.31 (1H, s).

Production Example II-26

C-{3-(3-Fluoro-phenyl)-6-methoxy-1H-indazol-5-yl}-methylamine

A total of 71 mg of lithium aluminium hydride was suspended in 4.7 ml of tetrahydrofuran, 249 mg of aluminium chloride was added under ice-cooling, and the mixture was stirred for 10 minutes. To the reaction mixture was added 50 mg of 3-(3-fluoro-phenyl)-6-methoxy-1H-indazole-5-carbonitrile obtained in Production Example II-1-d, followed by stirring at room temperature for 3 hours. The reaction mixture was ice-cooled, 27% aqueous ammonia was added and the mixture was filtrated through Celite. The filtrate was evaporated, and the residue was purified and separated by silica gel column chromatography (NH silica gel) (ethyl acetate), to give 108 mg of the title compound.

$^1$H-NMR (400 MHz, CD$_3$OD) δ 4.02 (3H, s), 4.25 (2H, s), 7.10-7.19 (2H, m), 7.54 (1H, td, 8.0, 6.0 Hz), 7.63-7.69 (1H, m), 7.78 (1H, d, 8.0 Hz)

Production Example II-27-a

4-Fluoro-3-(3-fluoro-benzoyl)-2-methoxy-benzonitrile

A total of 399 mg of the title compound was obtained as a pale yellow oil by the procedure of Production Example II-1-c, except from 2.07 g of (3-bromo1-6-fluoro-2-methoxy-phenyl)-(3-fluoro-phenyl)-methanone obtained in Production Example II-2-b.

$^1$H-NMR (400 MHz, CDCl$_3$) δ 4.00 (3H, s), 7.01 (1H, t, J=8.0 Hz), 7.32-7.76 (5H, m).

Production Example II-27-b

3-(3-Fluoro-phenyl)-4-methoxy-1H-indazole-5-carbonitrile

A total of 364 mg of the title compound was obtained as pale yellow crystals by the procedure of Production Example II-1-d, except from 399 mg of 4-fluoro-3-(3-fluoro-benzoyl)-2-methoxy-benzonitrile obtained in Production Example II-27-a.

$^1$H-NMR (400 MHz, CDCl$_3$) δ 3.94 (3H, s), 7.13-7.29 (2H, m), 7.47 (1H, td, J=8.0, 6.0 Hz), 7.52 (1H, d, J=8.8 Hz), 7.61-7.66 (1H, m), 7.67-7.72 (1H, m).

Production Example II-27-c

C-{3-(3-Fluoro-phenyl)-4-methoxy-1H-indazol-5-yl}-methylamine

A total of 25.8 mg of the title compound was obtained by the procedure of Production Example II-26, except from 50 mg of 3-(3-fluoro-phenyl)-4-methoxy-1H-indazole-5-carbonitrile obtained in Production Example II-27-b.

$^1$H-NMR (400 MHz, CD$_3$OD) δ 3.92 (5H, s), 7.10-7.18 (1H, m), 7.31 (1H, d, J=8.4 Hz), 7.43 (1H, d, J=8.4 Hz), 7.44-7.80 (3H, m). 7.47 (1H, td, J=8.0, 6.0 Hz), 7.52 (1H, d, J=8.8 Hz), 7.61-7.66 (1H, m), 7.67-7.72 (1H, m).

Production Example II-28

C-{6-Fluoro-3-(3-fluoro-phenyl)-1H-indazol-5-yl}-methylamine

A total of 120 mg of the title compound was obtained as ocher yellow crude crystals by the procedure of Production Example II-26, except from 100 mg of 6-fluoro-3-(3-fluoro-phenyl)-1H-indazole-5-carbonitrile obtained in Production Example II-5-e.

$^1$H-NMR (400 MHz, CD$_3$OD) δ 4.34 (2H, s), 7.08-7.24 (1H, m), 7.42 (1H, d, J=10.6 Hz), 7.56 (1H, td, J=8.0, 6.0 Hz), 7.67-7.74 (1H, m), 7.80-7.85 (1H, m), 8.26 (1H, d, J=7.2 Hz)

Production Example II-29

C-(3-Benzo[b]thiophen-2-yl-6-fluoro-1H-indazol-5-yl)-methylamine

A total of 394 mg of the title compound was obtained as yellow crude crystals by the procedure of Production Example II-26, except from 300 mg of 3-benzo[b]thiophen-2-yl-6-fluoro-1H-indazole-5-carbonitrile obtained in Production Example II-16-c.

$^1$H-NMR (400 MHz, DMSO-d$_6$) δ 4.23 (2H, s), 7.37-7.46 (2H, m), 7.53 (1H, d, J=10.4 Hz), 7.89 (1H, d, J=7.2 Hz), 8.00 (1H, d, J=7.2 Hz), 8.23 (1H, s), 8.62 (1H, d, J=7.2 Hz).

Production Example II-30

C-(3-Benzo[b]thiophen-2-yl-6-fluoro-1H-indazol-5-yl)-methylamine

A total of 495 mg of the title compound was obtained by the procedure of Production Example II-26, except from 300 mg of 6-fluoro-3-naphthalen-2-yl-1H-indazole-5-carbonitrile obtained in Production Example II-17-c.

$^1$H-NMR (400 MHz, DMSO-d$_6$) δ 4.23 (2H, s), 7.51 (1H, d, J=10.0 Hz), 7.52-7.64 (2H, m), 7.97 (1H, d, J=8.8 Hz), 8.05 (1H, d, J=8.8 Hz), 8.14-8.21 (2H, m), 8.62 (1H, d, J=7.2 Hz), 8.65 (1H, s).

Production Example II-31-a

(6-Bromo-2,3-difluorophenyl)trimethylsilyl

In an atmosphere of nitrogen gas, 66.0 ml of a 1.57 M solution of n-butyllithium in hexane was added to a solution of 18.2 ml of N,N-diisopropylamine in 200 ml tetrahydrofuran at 0° C., and the mixture was stirred at the same temperature for 10 minutes. After cooling to −78° C., a solution of 20.0 g of 1-bromo-3,4-difluorobenzene in 100 ml tetrahydrofuran was added dropwise. After stirring at the same temperature for 30 minutes, 32.9 ml of chlorotrimethylsilane was added dropwise. The temperature was gradually raised to room temperature and the mixture was stirred for one day. The reaction mixture was diluted with water and ethyl acetate. The organic layer was washed with brine, dried over anhydrous magnesium sulfate, and the solvent was evaporated. The crude product was purified and separated by silica gel column chromatography (n-hexane), to give 20.3 g of the title compound as a colorless oil.

$^1$H-NMR (400 MHz, CDCl$_3$) δ 0.47 (9H, s), 6.99 (1H, dt, J=9.6, 8.8 Hz), 7.27 (1H, ddd, J=2.0, 4.0, 8.8 Hz).

Production Example II-31-b (5-Bromo-2,3-difluorophenyl)-(3-fluorophenyl)methanone A total of 5.0 g of (6-bromo-2,3-difluorophenyl)trimethylsilyl was allowed to react with 3-fluoro-benzaldehyde by the procedure of Production Example II-2-a. The resulting crude product was dissolved in 50 ml of dimethylformamide and 5 ml of water, cesium fluoride was added at room temperature, and the mixture was stirred at the same temperature for 3 hours. The reaction mixture was diluted with ethyl acetate, and the organic layer was sequentially washed with saturated aqueous ammonium chloride solution and brine, dried over anhydrous magnesium sulfate, and the solvent was evaporated. The resulting crude product was oxidized by the procedure of Production Example II-8-b, to give 4.52 g of the title compound as a colorless oil.

$^1$H-NMR (400 MHz, CDCl$_3$) δ 7.34 (1H, ddt, J=1.2, 2.4, 8.0 Hz), 7.43 (1H, td, J=2.4, 5.2 Hz), 7.48 (1H, dt, J=5.2, 8.0 Hz), 7.50-7.58 (4H, m).

Production Example II-31-c 3,4-Difluoro-5-(3-fluorobenzoyl)benzonitrile

A total of 3.5 g of the title compound was obtained as a pale yellow oil by the procedure of Production Example II-9-d, except from 4.5 g of (5-bromo-2,3-difluorophenyl)-(3-fluorophenyl)methanone.

$^1$H-NMR (400 MHz, CDCl$_3$) δ 7.38 (1H, ddd, J=1.2, 2.4, 8.0 Hz), 7.47-7.55 (3H, m), 7.63-7.71 (2H, m).

Production Example II-31-d

7-Fluoro-3-(3-fluorophenyl)-1H-indazole-5-carbonitrile

A total of 3.2 g of the title compound was obtained as colorless crystals by the procedure of Production Example II-1-d, except from 3.5 g of 3,4-difluoro-5-(3-fluorobenzoyl)benzonitrile.

$^1$H-NMR (400 MHz, CD$_3$OD) δ 7.20 (1H, dd, J=2.0, 8.0 Hz), 7.49 (1H, dd, J=1.2, 10.4 Hz), 7.56 (1H, dt, J=6.0, 8.0 Hz), 7.69 (1H, td, J=2.0, 10.4 Hz), 7.78 (1H, d, J=8.0 Hz), 8.33 (1H, d, J=1.2 Hz).

Production Example II-31-e

7-Fluoro-3-(3-fluorophenyl)-1H-indazole-5-carboxylic acid

A total of 2.1 g of the title compound was obtained as colorless crystals by the procedure of Production Example II-1-e, except from 3.2 g of 7-fluoro-3-(3-fluorophenyl)-1H-indazole-5-carbonitrile.

$^1$H-NMR (400 MHz, DMSO-D$_6$) δ 7.31 (1H, ddd, J=1.2, 2.4, 8.0 Hz), 7.62 (1H, dt, J=6.0, 8.0 Hz), 7.70 (1H, dd, J=1.2, 11.6 Hz), 7.72 (1H, ddd, J=1.2, 2.4, 10.0 Hz), 7.81 (1H, dt, J=1.2, 8.0 Hz), 8.44 (1H, d, J=1.2 Hz).

Production Example II-32-a (5-Bromo-2,3-difluorophenyl)naphthalen-2-ylmethanone

A total of 5.5 g of the title compound was obtained as colorless crystals by the procedure of Production Example II-31-a, except from 5.0 g of (6-bromo-2,3-difluorophenyl)trimethylsilyl.

$^1$H-NMR (400 MHz, CDCl$_3$) δ 7.48 (1H, td, J=2.0, 8.8 Hz), 7.52-7.59 (2H, m), 7.64 (1H, dt, J=1.2, 8.0 Hz), 7.88-7.98 (4H, m), 8.23 (1H, s).

Production Example II-32-b 3,4-Difluoro-5-(naphthalen-2-carbonyl)benzonitrile

A total of 2.94 g of the title compound was obtained as colorless crystals by the procedure of Production Example II-9-d, except from 5.5 g of (5-bromo-2,3-difluorophenyl)naphthalen-2-ylmethanone.

$^1$H-NMR (400 MHz, CDCl$_3$) δ 7.58 (1H, dt, J=1.2, 8.0 Hz), 7.64-7.72 (3H, m), 7.90-7.96 (4H, m), 8.19 (1H, s).

Production Example II-32-c

7-Fluoro-3-naphthalen-2-yl-1H-indazole-5-carbonitrile

A total of 2.60 g of the title compound was obtained as colorless crystals by the procedure of Production Example II-1-d, except from 2.94 g of 3,4-difluoro-5-(naphthalen-2-carbonyl)benzonitrile.

$^1$H-NMR (400 MHz, CD$_3$OD) δ 7.48-7.56 (3H, m), 7.88-7.93 (1H, m), 7.98-8.11 (3H, m), 8.44 (1H, s), 8.47 (1H, d, J=0.8 Hz).

Production Example II-32-d

7-Fluoro-3-naphthalen-2-yl-1H-indazole-5-carboxylic acid

To 1.0 g of 7-fluoro-3-naphthalen-2-yl-1H-indazole-5-carbonitrile were sequentially added 5.0 ml of glacial acetic acid, 5.0 ml of water and 10.0 ml of concentrated sulfuric acid, and the mixture was stirred at 120° C. for one day. After standing to cool, 20 ml of water was added to the reaction mixture and the resulting crystals were collected by filtration. The crystals were sequentially washed with water and diethyl ether, to give 1.0 g of the title compound as colorless crystals.

$^1$H-NMR (400 MHz, DMSO-D$_6$) δ 7.55-7.60 (2H, m), 7.71 (1H, dd, J=0.8, 11.2 Hz), 7.96-7.99 (1H, m), 8.08-8.14 (3H, m), 8.51 (1H, s), 8.59 (1H, d, J=0.8 Hz).

Production Example II-33-a

3-Benzo[b]thiophen-2-yl-4-fluoro-1-trityl-1H-5-indazolecarboxylic acid

To a solution of 149 mg of the coupling product (3-benzo[b]thiophen-2-yl-4-fluoro-1-trityl-1H-5-indazolecarboxylic acid methyl ester) obtained in Production Example II-13-f in a solvent mixture of 4 ml of tetrahydrofuran and 1 ml of methanol was added 0.5 ml of 5 N aqueous sodium hydroxide solution, and the mixture was stirred at 50° C. for 2 hours. To the reaction mixture was added 3 ml of 1 N hydrochloric acid and the mixture was extracted with 20 ml of ethyl acetate. The organic layer was sequentially washed with water and brine, dried over anhydrous magnesium sulfate, and the solvent was evaporated, to give 145 mg of the title compound as yellow crystals.

$^1$H-NMR (400 MHz, DMSO-D$_6$) δ 6.29 (1H, dd J=1.2, 8.8 Hz), 7.14-7.23 (6H, m), 7.27-7.42 (11H, m), 7.55 (1H, t, J=8.8 Hz), 7.91-7.97 (2H, m), 8.02 (1H, s), 13.19 (1H, s).

Production Example II-33-b

{3-Benzo[b]thiophen-2-yl-4-fluoro-1-trityl-1H-indazol-5-yl}carbamic acid benzyl ester A total of 73 mg of the title compound was obtained as a colorless viscous oil by the procedure of Production Example II-19-b, except from 143 mg of 3-benzo[b]thiophen-2-yl-4-fluoro-1-trityl-1H-5-indazolecarboxylic acid obtained in Production Example II-33-a.

$^1$H-NMR (400 MHz, DMSO-D$_6$) δ 5.14 (2H, s), 6.23 (1H, d, J=8.8 Hz), 7.13-7.45 (23H, m), 7.89-7.99 (3H, m), 9.43 (1H, s).

Production Example II-33-c

3-Benzo[b]thiophen-2-yl-4-fluoro-1-trityl-1H-indazol-5-ylamine

A total of 52 mg of the title compound was obtained as bright yellow crystals by the procedure of Production Example II-19-c, except from 68 mg of {3-benzo[b]thiophen-2-yl-4-fluoro-1-trityl-1H-indazol-5-yl}carbamic acid benzyl ester produced in Production Example II-33-b.

$^1$H-NMR (400 MHz, DMSO-D$_6$) δ 5.00 (2H, s), 6.00 (1H, d, J=8.8 Hz), 6.69 (1H, t, J=8.8 Hz), 7.10-7.40 (17H, m), 7.83-7.93 (3H, m)

Production Example II-34-a

4-Fluoro-3-naphthalen-2-yl-1-trityl-1H-5-indazolecarboxylic acid

A total of 127 mg of the title compound was obtained as yellow crystals by the procedure of Production Example II-33-a, except from 139 mg of the coupling product (4-fluoro-3-naphthalen-2-yl-1-trityl-1H-5-indazolecarboxylic acid methyl ester) produced in Production Example II-14-a.

$^1$H-NMR (400 MHz, DMSO-D$_6$) δ 6.34 (1H, dd, J=0.8, 8.8 Hz), 7.18-7.40 (16H, m), 7.50-7.60 (2H, m), 7.84 (1H, d, J=8.4 Hz), 7.93-8.08 (3H, m), 8.30 (1H, s), 13.09 (1H, s)

Production Example II-34-b

{4-Fluoro-3-naphthalen-2-yl-1-trityl-1H-indazol-5-yl}carbamic acid benzyl ester

A total of 54 mg of the title compound was obtained as a colorless viscous oil by the procedure of Production Example II-19-b, except from 125 mg of 4-fluoro-3-naphthalen-2-yl-1-trityl-1H-5-indazolecarboxylic acid obtained in Production Example II-34-a.

$^1$H-NMR (400 MHz, DMSO-D$_6$) 5.11 (2H, s), 6.27 (1H, d, J=8.8 Hz), 7.20-7.45 (2H, m), 7.52-7.58 (2H, m), 7.83 (1H, d, J=8.4 Hz), 7.92-8.00 (3H, m), 8.26 (1H, s), 9.35 (1H, s).

Production Example II-34-c

4-Fluoro-3-naphthalen-2-yl-1-trityl-1H-indazol-5-ylamine

A total of 41 mg of the title compound was obtained as pale red crystals by the procedure of Production Example II-19-c, except from 54 mg of {4-fluoro-3-naphthalen-2-yl-1-trityl-1H-indazol-5-yl}carbamic acid benzyl ester produced in Production Example II-34-b.

$^1$H-NMR (400 MHz, DMSO-D$_6$) δ 4.92 (2H, s), 6.07 (1H, d, J=8.8 Hz), 6.70 (1H, t, J=8.8 Hz), 7.20-7.40 (15H, m), 7.51-7.58 (2H, m), 7.86 (1H, d, J=8.8 Hz), 7.91-7.98 (3H, m) 8.28 (1H, s)

Production Example II-35-a

1-Bromo-4-fluoro-2-propoxy-benzene

A total of 5 g of 2-bromo-5-fluoro-phenol was dissolved in 66 ml of N,N-dimethylformamide. Under ice-cooling, 5.42 g of potassium carbonate and 3.07 ml of iodopropane were added, and the mixture was stirred at room temperature for 10 hours. Water was added to the reaction mixture, followed by extracting with diethyl ether. The resulting organic layer was washed with brine, dried over magnesium sulfate and the solvent was evaporated, to give 8.29 g of the title compound as a yellow oil.

$^1$H-NMR (400 MHz, CDCl$_3$) δ 1.08 (3H, t, J=7.2 Hz), 1.80-1.93 (2H, m), 3.95 (2H, t, J=6.0 Hz), 6.54 (1H, td, J=8.8, 2.4 Hz), 6.61 (1H, dd, J=10.8, 2.4 Hz), 7.44 (1H, dd, J=8.8, 6.0 Hz)

Production Example II-35-b

Benzo[b]furan-2-yl-(3-bromo-6-fluoro-2-propoxy-phenyl)-methanol

A total of 5.59 g of the title compound was obtained as a pale yellow oil by the procedure of Production Example II-2-a, except from 3 g of 1-bromo-4-fluoro-2-propoxy-benzene.

$^1$H-NMR (400 MHz, CDCl$_3$) δ 0.96 (3H, t, J=7.2 Hz), 1.80-1.93 (2H, m), 3.95 (2H, t, J=6.4 Hz), 6.29 (1H, d, J=9.2 Hz), 6.84 (1H, t, J=9.2 Hz), 7.16-7.76 (6H, m)

Production Example II-35-c

Benzo[b]furan-2-yl-(3-bromo-6-fluoro-2-propoxy-phenyl)-methanone

A total of 1.46 g of the title compound was obtained as a yellow oil by the procedure of Production Example II-2-b, except from 5.59 g of benzo[b]furan-2-yl-(3-bromo-6-fluoro-2-propoxy-phenyl)-methanol.

$^1$H-NMR (400 MHz, CDCl$_3$) δ 0.86 (3H, t, J=7.2 Hz), 1.61-1.72 (2H, m), 3.96 (2H, t, J=6.8 Hz), 6.87 (1H, t, J=9.2 Hz), 7.29-7.70 (6H, m)

Production Example II-35-d

3-Benzo[b]furan-2-yl-5-bromo-4-propoxy-1H-indazole

A total of 801 mg of the title compound was obtained as pale yellow crystals by the procedure of Production Example II-10-c, except from 1.46 g of benzo[b]furan-2-yl-(3-bromo-6-fluoro-2-propoxy-phenyl)-methanone.
$^1$H-NMR (400 MHz, DMSO-D$_6$) δ 0.92 (3H, t, J=7.2 Hz), 1.65-1.78 (2H, m), 3.77 (2H, t, J=6.4 Hz), 7.28 (1H, t, J=7.2 Hz), 7.33-7.38 (1H, m), 7.36 (1H, d, J=8.8 Hz), 7.44 (1H, s), 7.59 (1H, d, J=8.8 Hz), 7.64 (1H, d, J=8.8 Hz), 7.72 (1H, d, J=8.8 Hz)

Production Example II-35-e

3-Benzo[b]furan-2-yl-4-propoxy-1H-indazole-5-carboxylic acid

A total of 45 mg of the title compound was obtained by the procedure of Production Example II-10-d, except from 326 mg of 3-benzo[b]furan-2-yl-5-bromo-4-propoxy-1H-indazole.
$^1$H-NMR (400 MHz, CD$_3$OD) δ 0.86 (3H, t, J=7.2 Hz), 1.70-1.81 (2H, m), 3.95 (2H, t, J=7.2 Hz), 7.27 (1H, t, J=7.6 Hz), 7.32-7.38 (2H, m), 7.53 (1H, s), 7.58 (1H, d, J=7.6 Hz), 7.68 (1H, d, J=7.6 Hz), 7.89 (1H, d, J=8.8 Hz)

Production Example II-36-a

7-Fluoro-3-(3-fluorophenyl)-1-trityl-1H-indazole-5-carboxylic acid

A total of 1.4 g of the title compound was obtained as colorless crystals by the procedure of Production Example II-9-c, except from 1.0 g of 7-fluoro-3-(3-fluorophenyl)-1H-indazole-5-carboxylic acid obtained in Production Example II-31-e.
$^1$H-NMR (400 MHz, DMSO-D$_6$) δ 7.10-7.13 (5H, m), 7.25-7.35 (1H, m), 7.45 (1H, d, J=12.0 Hz), 7.53 (1H, d, J=8.0 Hz), 7.59 (1H, dt, J=6.4, 8.0 Hz), 7.69 (1H, d, J=8.0 Hz), 8.44 (1H, d, J=1.2 Hz).

Production Example II-36-b

7-Fluoro-3-(3-fluorophenyl)-1-trityl-1H-indazol-5-ylamine

To a solution of 1.0 g of 7-fluoro-3-(3-fluorophenyl)-1-trityl-1H-indazole-5-carboxylic acid in 20 ml toluene at room temperature were added 0.40 ml of triethylamine and 0.46 ml of diphenylphosphoryl azide, the mixture was stirred at the same temperature for 2 hours and at 120° C. for 1.5 hours. To the reaction mixture was added 1.0 ml of benzyl alcohol, followed by stirring at 120° C. for 1.5 hours. After cooling to room temperature, water was added to the reaction mixture was and the mixture was extracted with ethyl acetate. The organic layer was washed with saturated aqueous sodium chloride solution, dried over magnesium sulfate, and the solvent was evaporated. To a solution of the resulting crude product in a solvent mixture of 20 ml of methanol and 10 ml of tetrahydrofuran was added 1.0 g of 10% palladium-carbon at room temperature, and the mixture was subjected to catalytic hydrogenation at the same temperature and at normal atmospheric pressure. After stirring for 4 hours, the reaction mixture was filtrated through Celite, the filtrate was evaporated, and the residue was purified and separated by silica gel column chromatography (ethyl acetate:hexane=1:5), to give 540 mg of the title compound.
$^1$H-NMR (400 MHz, DMSO-D$_6$) δ 5.19 (2H, d, J=8.4 Hz), 6.33 (1H, dd, J=1.6, 14.0 Hz), 6.95 (1H, d, J=1.6 Hz), 7.08-7.41 (16H, m), 7.42 (1H, ddd, J=1.2, 1.6, 10.0 Hz), 7.49 (1H, dt, J=6.0, 10.0 Hz), 7.56 (1H, d, J=8.0 Hz).

Production Example II-37-a 7-Fluoro-3-naphthalen-2-yl-1-trityl-1H-indazole-5-carboxylic acid A total of 840 mg of the title compound was obtained as colorless crystals by the procedure of Production Example II-9-c, except from 500 mg of 7-fluoro-3-naphthalen-2-yl-1H-indazole-5-carboxylic acid obtained in Production Example II-32-d.
$^1$H-NMR (400 MHz, DMSO-D$_6$) δ 7.14-7.36 (15H, m), 7.46 (1H, dd, J=1.2, 12.4 Hz), 7.55-7.58 (2H, m), 7.85 (1H, dd, J=2.0, 8.8 Hz), 7.92-7.96 (1H, m), 8.03 (1H, d, J=1.2, 8.8 Hz), 8.06-8.09 (1H, m), 8.41 (1H, s), 8.56 (1H, d, J=1.2 Hz).

Production Example II-37-b

7-Fluoro-3-naphthalen-2-yl-1-trityl-1H-indazol-5-ylamine

A total of 320 mg of the title compound was obtained as colorless crystals by the procedure of Production Example II-36-b, except from 870 mg of 7-fluoro-3-naphthalen-2-yl-1-trityl-1H-indazole-5-carboxylic acid.
$^1$H-NMR (400 MHz, DMSO-D$_6$) δ 5.18 (2H, d, J=8.4 Hz), 6.36 (1H, dd, J=1.6, 9.6 Hz), 7.11 (1H, d, J=1.6 Hz), 7.22-7.33 (15H, m), 7.50 (1H, dt, J=1.2, 6.8 Hz), 7.54 (1H, dt, J=1.2, 6.8 Hz), 7.80 (1H, dd, J=1.2, 8.8 Hz), 7.88-7.97 (3H, m), 8.27 (1H, s).

Production Example II-38-a (4-Methoxy-3-naphthalen-2-yl-1-trityl-1H-indazol-5-yl)-carbamic acid benzyl ester 493 mg of 4-methoxy-3-naphthalen-2-yl-1H-indazole-5-carboxylic acid obtained in Production Example II-10-d was dissolved in 10 ml of dimethylformamide. Under ice-cooling and stirring, 136 mg of sodium hydride (content 60%) was added thereto. After stirring for 15 minutes, 454 mg of triphenylmethyl chloride was added. After stirring at room temperature for 2 hours, the reaction mixture was diluted with saturated aqueous ammonium chloride solution and was extracted with ethyl acetate. The resulting organic layer was washed with brine, dried over magnesium sulfate and the solvent was evaporated. The residue was purified and separated by silica gel column chromatography (chloroform:methanol=20:1), to give 728 mg of a trityl derivative as an ocher yellow amorphous substance. The resulting compound was dissolved in 10 ml of toluene, and 0.27 ml of triethylamine and 0.28 ml of diphenylphosphoryl azide were added to the solution at room temperature under stirring. The mixture was stirred at room temperature for 2 hours and at 120° C. for further 1.5 hours. 0.67 ml of benzyl alcohol was added thereto, followed by stirring at 120° C. for 1.5 hours. After cooling to room temperature, water was added thereto and the mixture was extracted with ethyl acetate. The resulting organic layer was washed with brine, dried over magnesium sulfate and the solvent was evaporated. The residue was purified and separated by silica gel column chromatography (ethyl acetate:hexane=1:4), to give 466 mg of the title compound as an ocher yellow oil.
$^1$H-NMR (400 MHz, CDCl$_3$) δ 3.38 (3H, s), 5.20 (2H, s), 6.29 (1H, d, J=9.6 Hz), 7.17-7.49 (23H, m), 7.84-7.90 (3H, m), 8.02 (1H, d, J=7.2 Hz), 8.44 (1H, s).

Production Example II-38-b

4-Methoxy-3-naphthalen-2-yl-1-trityl-1H-indazol-5-ylamine 466 mg of (4-methoxy-3-naphthalen-2-yl-1-trityl-1H-indazol-5-yl)-carbamic acid benzyl ester obtained in Production Example II-38-a was dissolved in 20 ml of a 1:1 solvent mixture of ethyl acetate and methanol. 300 mg of 10% palladium-carbon was added and the mixture was subjected to catalytic hydrogenation at room temperature and normal atmospheric pressure. The reaction mixture was filtered through Celite, and the solvent was removed, to give 252 mg of the title compound.

$^1$H-NMR (400 MHz, DMSO-D$_6$) δ 3.37 (3H, s), 6.21 (1H, d, J=8.8 Hz), 6.81 (1H, d, J=9.2 Hz), 7.06 (1H, t, J=7.6 Hz), 7.18-7.61 (17H, m), 7.97-8.01 (3H, m), 8.46 (1H, s).

Production Example II-39-a

(3-Benzo[b]thiophen-2-yl-4-methoxy-1-trityl-1H-indazol-5-yl)carbamic acid benzyl ester 548 mg of 3-benzo[b]thiophen-2-yl-4-methoxy-1H-indazole-5-carboxylic acid obtained in Production Example II-12-d was dissolved in 10 ml of dimethylformamide. Under ice-cooling and stirring, 149 mg of sodium hydride (content 60%) was added and the mixture was stirred for 15 minutes. Then, 495 mg of triphenylmethyl chloride was added and the mixture was stirred at room temperature for 2 hours. Then, saturated aqueous ammonium chloride solution was added and the mixture was extracted with ethyl acetate. The resulting organic layer was washed with saturated aqueous sodium chloride solution, dried over magnesium sulfate and the solvent was evaporated. The residue was purified and separated by silica gel column chromatography (chloroform:methanol=20:1), to give 854 mg of a trityl derivative as an ocher yellow amorphous substance. The resulting compound was dissolved in 10 ml of toluene, 0.32 ml of triethylamine and 0.36 ml of diphenylphosphoryl azide were added, followed by stirring at room temperature for 2 hours and at 120° C. for 1.5 hours. Then, 0.78 ml of benzyl alcohol was added, followed by stirring at 120° C. for 1.5 hours. After cooling to room temperature, water was added and the mixture was extracted with ethyl acetate. The resulting organic layer was washed with brine, dried over magnesium sulfate and the solvent was evaporated. The residue was purified and separated by silica gel column chromatography (ethyl acetate:hexane=1:4), to give 939 mg of the title compound as an ocher yellow oil.

$^1$H-NMR (400 MHz, CDCl$_3$) δ 3.70 (3H, s), 5.20 (2H, s), 6.23 (1H, d, J=9.2 Hz), 7.21-7.39 (23H, m), 7.78 (2H, d, J=8.4 Hz), 8.01 (1H, s).

Production Example II-39-b

3-Benzo[b]thiophen-2-yl-4-methoxy-1-trityl-1H-indazol-5-ylamine

A total of 939 mg of (3-benzo[b]thiophen-2-yl-4-methoxy-1-trityl-1H-indazol-5-yl)-carbamic acid benzyl ester obtained in Production Example II-39-a was dissolved in 20 ml of a 2:1 solvent mixture of ethyl acetate and methanol. 300 mg of 20% palladium hydroxide-carbon was added thereto, and the mixture was subjected to catalytic hydrogenation at room temperature and at normal atmospheric pressure in the presence of. The reaction mixture was filtrated through Celite, and the solvent was removed, to give 458 mg of the title compound.

$^1$H-NMR (400 MHz, DMSO-D$_6$) δ 3.63 (3H, s), 6.02 (1H, d, J=8.8 Hz), 6.68 (1H, d, J=8.8 Hz), 7.00 (1H, t, J=7.2 Hz), 7.10-7.36 (16H, m), 7.87 (2H, t, J=8.0 Hz), 8.07 (1H, s).

Production Example II-40

C-(7-Fluoro-3-naphthalen-2-yl-1H-indazol-5-yl)methylamine

A total of 260 mg of the title compound was obtained as colorless crystals by the procedure of Production Example II-26, except from 280 mg of 7-fluoro-3-naphthalen-2-yl-1H-indazole-5-carbonitrile obtained in Production Example II-32-c.

$^1$H-NMR (400 MHz, DMSO-D$_6$) δ 3.86 (2H, s), 7.28 (1H, d, J=12.0 Hz), 7.50-7.60 (2H, m), 7.95 (1H, d, J=8.4 Hz), 7.98 (1H, s), 8.03 (1H, d, J=8.4 Hz), 8.10 (1H, d, J=8.4 Hz), 8.16 (1H, dd, J=1.6, 8.4 Hz), 8.54 (1H, s).

Production Example II-41-a

5-Bromo-2-fluoro-4-methoxy-benzaldehyde 8.4 g of 1-bromo-4-fluoro-2-methoxy-benzene obtained in Production Example II-1-a was dissolved in 200 ml of dichloromethane. 21 ml of titanium tetrachloride and 5.6 ml of dichloromethyl methyl ether were added at 0° C. in nitrogen atmosphere, followed by stirring at room temperature for 4.5 hours. Then, the reaction mixture was gradually poured onto ice-water, and extracted with diethyl ether for two times. The organic layer was sequentially washed with each one portion of water, saturated aqueous sodium hydrogencarbonate solution and water, dried over magnesium sulfate and the solvent was evaporated, to give 9.44 g of the title compound as white crystals.

$^1$H-NMR (400 MHz, CDCl$_3$) δ 3.97 (3H, s), 6.67 (1H, d, J=12.0 Hz), 8.05 (1H, d, J=7.6 Hz), 10.15 (1H, s)

Production Example II-41-b

4-Fluoro-5-formyl-2-methoxy-benzonitrile 5.33 g of 5-bromo-2-fluoro-4-methoxy-benzaldehyde was dissolved in 73 ml of 1-methyl-2-pyrrolidone, 2.46 g of copper cyanide was added under stirring at 180° C. for 5.5 hours. After cooling to room temperature, water was added to the reaction mixture. The mixture was extracted with ethyl acetate and filtered through Celite. Then, the resulting organic layer was washed with water and brine, dried over magnesium sulfate and the solvent was evaporated. The residue was purified and separated by silica gel column chromatography, to give 0.983 g of the title compound as pale yellow crystals.

$^1$H-NMR (400 MHz, CDCl$_3$) δ 4.03 (3H, s), 6.76 (1H, d, J=12.0 Hz), 8.14 (1H, d, J=7.2 Hz), 10.17 (1H, s)

Production Example II-41-c

6-Methoxy-1H-indazole-5-carbonitrile

A total of 0.915 g of the title compound was obtained as pale yellow crystals by the procedure of Production Example II-1-d, except from 0.983 g of 4-fluoro-5-formyl-2-methoxy-benzonitrile.

¹H-NMR (400 MHz, CD₃OD) δ 3.99 (3H, s), 7.10 (1H, s), 8.06 (1H, s), 8.15 (1H, s).

Production Example II-41-d

3-Bromo-6-methoxy-1H-indazole-5-carbonitrile

A total of 1.2 g of the title compound was obtained as yellow crystals by the procedure of Production Example II-13-d, except from 0.915 g of 6-methoxy-1H-indazole-5-carbonitrile.

¹H-NMR (400 MHz, CD₃OD) δ 4.00 (3H, s), 7.10 (1H, s), 7.97 (1H, s)

Production Example II-41-e

3-Bromo-6-methoxy-1-trityl-1H-indazole-5-carbonitrile

A total of 2.41 g of the title compound was obtained as brown crystals by the procedure of Production Example II-9-c, except from 1.2 g of 3-bromo-6-methoxy-1H-indazole-5-carbonitrile.

¹H-NMR (400 MHz, CDCl₃) δ 3.36 (3H, s), 5.60 (1H, s), 7.14-7.17 (5H, m), 7.24-7.32 (10H, m), 7.81 (1H, s)

Production Example II-41-f

6-Methoxy-3-naphthalen-2-yl-1-trityl-1H-indazole-5-carbonitrile

A total of 249 mg of the title compound (a Suzuki coupling product) was obtained as white crystals by the procedure of Production Example II-13-f, except from 600 mg of 3-bromo-6-methoxy-1-trityl-1H-indazole-5-carbonitrile and 260 mg of 2-naphthaleneboronic acid.

¹H-NMR (400 MHz, CDCl₃) δ 3.39 (3H, s), 5.73 (1H, s), 7.14-7.33 (16H, m), 7.49-7.53 (2H, m), 7.84-7.95 (3H, m), 8.28 (1H, s), 8.38 (1H, s)

Production Example II-41-g

6-Methoxy-3-naphthalen-2-yl-1H-indazole-5-carboxylic acid

A total of 104.3 mg of the title compound was obtained as brown crystals by the procedure of Production Example II-1-e, except from 249 mg of 6-methoxy-3-naphthalen-2-yl-1-trityl-1H-indazole-5-carbonitrile.

¹H-NMR (400 MHz, CD₃OD) δ 4.02 (3H, s), 7.15 (1H, s), 7.53-7.58 (2H, m), 7.91-7.94 (1H, m), 8.00-8.06 (3H, m), 8.41 (1H, s), 8.66 (1H, s)

ESI-MS: m/z=319 (M+H)⁺

Production Example II-42-a

3-Benzo[b]thiophen-2-yl-6-methoxy-1-trityl-1H-indazole-5-carbonitrile

A total of 292.5 mg of the title compound (a Suzuki coupling product) was obtained as white crystals by the procedure of Production Example II-13-f, except from 600 mg of 3-bromo-6-methoxy-1-trityl-1H-indazole-5-carbonitrile obtained in Production Example II-41-e and 269 mg of 2-benzo[b]thiopheneboronic acid.

¹H-NMR (400 MHz, CDCl₃) δ 3.37 (3H, s), 5.69 (1H, s), 7.14-7.89 (20H, m), 8.34 (1H, s)

Production Example II-42-b

3-Benzo[b]thiophen-2-yl-6-methoxy-1H-indazole-5-carboxylic acid

A total of 133.6 mg of the title compound was obtained as brown crystals by the procedure of Production Example II-1-e, except from 292.5 mg of 3-benzo[b]thiophen-2-yl-6-methoxy-1-trityl-1H-indazole-5-carbonitrile.

¹H-NMR (400 MHz, CD₃OD) δ 4.00 (3H, s), 7.12 (1H, s), 7.34-7.40 (2H, m), 7.88-7.92 (2H, m), 7.95 (1H, s), 8.69 (1H, s)

ESI-MS: m/z=325 (M+H)⁺

Production Example II-43-a

3-Benzo[b]furan-2-yl-4-fluoro-1-trityl-1H-5-indazolecarboxylic acid

A total of 146 mg of the title compound was obtained as bright yellow crystals by the hydrolysis procedure of Production Example II-33-a, except from 152 mg of 3-benzo[b]furan-2-yl-4-fluoro-1-trityl-1H-5-indazolecarboxylic acid methyl ester obtained in the coupling reaction of Production Example II-15-a.

¹H-NMR (400 MHz, DMSO-D₆) δ 6.36 (1H, d J=8.8 Hz), 7.18-7.40 (17H, m), 7.44 (1H, s), 7.56 (1H, dd, J=7.2, 8.8 Hz), 7.63 (1H, d, J=8.0 Hz), 7.74 (1H, d, J=7.6 Hz), 13.19 (1H, s).

Production Example II-43-b

{3-Benzo[b]furan-2-yl-4-fluoro-1-trityl-1H-indazol-5-yl}carbamic acid benzyl ester A total of 26 mg of the title compound was obtained as a white amorphous powder by the procedure of Production Example II-19-b, except from 144 mg of 3-benzo[b]furan-2-yl-4-fluoro-1-trityl-1H-5-indazolecarboxylic acid obtained in Production Example II-43-a.

¹H-NMR (400 MHz, DMSO-D₆) δ 5.12 (2H, s), 6.28 (1H, d, J=9.2 Hz), 7.16-7.44 (24H, m), 7.60 (1H, d, J=8.4 Hz), 7.73 (1H, d, J=8.0 Hz), 9.40 (1H, s).

Production Example II-43-c

3-Benzo[b]furan-2-yl-4-fluoro-1-trityl-1H-indazol-5-ylamine

A total of 24 mg of the title compound was obtained as a pale yellow viscous oily substance by the procedure of Production Example II-19-c, except from 26 mg of {3-benzo[b]furan-2-yl-4-fluoro-1-trityl-1H-indazol-5-yl}carbamic acid benzyl ester obtained in Production Example II-43-b.

¹H-NMR (400 MHz, DMSO-D₆) δ 4.99 (2H, s), 6.06 (1H, d, J=8.8 Hz), 6.69 (1H, t, J=8.8 Hz), 7.14-7.41 (18H, m), 7.57 (1H, d, J=8.0 Hz), 7.69 (1H, d, J=7.6 Hz)

Typical synthesis processes for the compounds according to the examples will be illustrated below.

Synthesis Process II-A

Each of the carboxylic acids produced in Production Examples II was dissolved in dimethylformamide and was pipetted into test tubes. To each test tube were sequentially added 1.2 equivalents of a 1 M solution of various of amines in dimethylformamide, 1.2 equivalents of a 1 M solution of 1-hydroxybenzotriazole monohydrate in dimethylformamide, 4 equivalents of diisopropylethylamine, and 2 equivalents of 1-ethyl-3-(3-dimethylaminopropyl)carbodiimide hydrochloride (i.e., WSC.HCl), each of which had been previously prepared. The mixture was stirred at room temperature overnight. The reaction mixture was purified and separated by LC-MS (developing solvent; acetonitrile solution containing 0.1% trifluoroacetic acid:aqueous solution containing 0.1% trifluoroacetic acid=20:80 to 80:20, 10 minute-cycle, flow rate; 30 ml/min, column; YMC Combiprep ODS-AM, 20 mmΦ×50 mm (Long)), to give the compounds according to Examples.

Synthesis Process II-B

Each of the amines produced in Production Examples II was dissolved in dimethylformamide and was pipetted into test tubes. To each test tube were sequentially added 1.2 equivalents of a 1 M solution of any of carboxylic acids in dimethylformamide, 1.2 equivalents of a 1 M solution of 1-hydroxybenzotriazole monohydrate in dimethylformamide, 4 equivalents of diisopropylethylamine and 2 equivalents of 1-ethyl-3-(3-dimethylaminopropyl)carbodiimide hydrochloride (i.e., WSC.HCl), each of which had been previously prepared. The mixture was stirred at room temperature overnight. The reaction mixture was diluted with water and was extracted with ethyl acetate. The extract was air-dried by blowing nitrogen gas to remove the solvent, and the residue was treated with a 1:5 mixture solution of trifluoroacetic acid and dichloromethane, and the mixture was stirred at room temperature overnight. The reaction mixture was air-dried by blowing nitrogen gas to remove the solvent, and the residue was dissolved in dimethylformamide. Each was purified and separated by LC-MS under the same conditions as in Synthesis Process II-A and thereby yielded the compounds according to Examples.

Synthesis Process II-C

Each of the amines produced in Production Examples II was dissolved in dimethylformamide and was pipetted into test tubes. To each test tube were sequentially added 1.2 equivalents of a 1 M solution of any of carboxylic acids in dimethylformamide, 1.2 equivalents of a 1 M solution of 1-hydroxybenzotriazole monohydrate in dimethylformamide, 4 equivalents of diisopropylethylamine and 2 equivalents of 1-ethyl-3-(3-dimethylaminopropyl)carbodiimide hydrochloride (i.e., WSC.HCl), each of which had been previously prepared. The mixture was stirred at room temperature overnight. Each mixture was purified and separated by LC-MS under the same conditions as in Synthesis Process II-A, to give the compounds according to Examples.

Synthesis Process II-D

Each of the amines produced in Production Examples II was dissolved in dichloromethane and was pipetted into test tubes (1 ml each). To each test tube were sequentially added 3 equivalents of triethylamine and 2 equivalents of any of sulfonyl chlorides, and the mixture was stirred at room temperature overnight. The reaction mixture was treated with 0.2 ml of trifluoroacetic acid under stirring at room temperature overnight. The reaction mixture was air-dried by blowing nitrogen gas, and the residue was dissolved in dimethylformamide. Each was purified and separated by LC-MS under the same conditions as in Synthesis Process II-A, to give the compounds according to Examples.

Synthesis Process II-E

Each of the amines produced in Production Examples II was dissolved in 1 ml of dichloromethane. Each solution was treated with 0.2 ml of trifluoroacetic acid under stirring at room temperature overnight. The reaction mixture was air-dried by blowing nitrogen gas, and the residue was dissolved in dimethylformamide. Each was purified and separated by LC-MS under the same conditions as in Synthesis Process II-A, to give the compounds according to Examples.

The compounds according to Examples II-1 to II-152 were synthesized by Synthesis Process II-A using the carboxylic acids produced in Production Examples II-1 to II-17.

Example II-1

3-(3-Fluoro-phenyl)-6-methoxy-1H-indazole-5-carboxylic acid (furan-2-ylmethyl)-amide MS (ESI) m/z 366 MH$^+$ Example II-2

3-(3-Fluoro-phenyl)-6-methoxy-1H-indazole-5-carboxylic acid (2-acetylamino-ethyl)-amide MS (ESI) m/z 371 MH$^+$ Example II-3

3-(3-Fluoro-phenyl)-6-methoxy-1H-indazole-5-carboxylic acid [(1S)-1-hydroxymethyl-2-methyl-propyl]-amide MS (ESI) m/z 372 MH$^+$ Example II-4

3-(3-Fluoro-phenyl)-6-methoxy-1H-indazole-5-carboxylic acid (pyridin-3-ylmethyl)-amide MS (ESI) m/z 377 MH$^+$ Example II-5

3-(3-Fluoro-phenyl)-4-methoxy-1H-indazole-5-carboxylic acid (furan-2-ylmethyl)-amide MS (ESI) m/z 366 MH$^+$ Example II-6

3-(3-Fluoro-phenyl)-4-methoxy-1H-indazole-5-carboxylic acid (2-acetylamino-ethyl)-amide MS (ESI) m/z 371 MH$^+$ Example II-7

3-(3-Fluoro-phenyl)-4-methoxy-1H-indazole-5-carboxylic acid [(1S)-1-hydroxymethyl-2-methyl-propyl]-amide MS (ESI) m/z 372 MH$^+$ Example II-6

3-(3-Fluoro-phenyl)-4-methoxy-1H-indazole-5-carboxylic acid (pyridin-3-ylmethyl)-amide MS (ESI) m/z 377 MH$^+$

Example II-9

3-(3-Fluoro-phenyl)-4-methoxy-1H-indazole-5-carboxylic acid cyclopropylamide

MS (ESI) m/z 326 MH$^+$

Example II-10

3-(3-Fluoro-phenyl)-6-methoxy-1H-indazole-5-carboxylic acid cyclopropylamide

MS (ESI) m/z 326 MH$^+$

Example II-11

4-Fluoro-3-(3-fluoro-phenyl)-1H-indazole-5-carboxylic acid cyclopropylamide

MS (ESI) m/z 314 MH$^+$

Example II-12

4-Fluoro-3-(3-fluoro-phenyl)-1H-indazole-5-carboxylic acid (2-acetylamino-ethyl)-amide MS (ESI) m/z 359 MH$^+$

Example II-13

4-Fluoro-3-(3-fluoro-phenyl)-1H-indazole-5-carboxylic acid (2-dimethylamino-ethyl)-amide MS (ESI) m/z 345 MH$^+$

Example II-14

3-(3-Fluoro-phenyl)-6-hydroxy-1H-indazole-5-carboxylic acid cyclopropylamide

MS (ESI) m/z 312 MH$^+$

Example II-15

3-(3-Fluoro-phenyl)-6-hydroxy-1H-indazole-5-carboxylic acid (furan-2-ylmethyl)-amide MS (ESI) m/z 352 MH$^+$

Example II-16

3-(3-Fluoro-phenyl)-6-hydroxy-1H-indazole-5-carboxylic acid (2-acetylamino-ethyl)-amide MS (ESI) m/z 357 MH$^+$

Example II-17

3-(3-Fluoro-phenyl)-6-hydroxy-1H-indazole-5-carboxylic acid (pyridin-3-ylmethyl)-amide MS (ESI) m/z 363 MH$^+$

Example II-18

3-(3-Fluoro-phenyl)-6-hydroxy-1H-indazole-5-carboxylic acid (2-dimethylamino-ethyl)-amide MS (ESI) m/z 343 MH$^+$

Example II-19

3-(3-Fluoro-phenyl)-6-hydroxy-1H-indazole-5-carboxylic acid (1H-imidazol-4-ylmethyl)-amide MS (ESI) m/z 352 MH$^+$

Example II-20

6-Fluoro-3-(3-fluoro-phenyl)-1H-indazole-5-carboxylic acid (furan-2-ylmethyl)-amide MS (ESI) m/z 354 MH$^+$

Example II-21

6-Fluoro-3-(3-fluoro-phenyl)-1H-indazole-5-carboxylic acid (2-acetylamino-ethyl)-amide MS (ESI) m/z 359 MH$^+$

Example II-22

6-Fluoro-3-(3-fluoro-phenyl)-1H-indazole-5-carboxylic acid (pyridin-3-ylmethyl)-amide MS (ESI) m/z 365 MH$^+$

Example II-23

6-Fluoro-3-(3-fluoro-phenyl)-1H-indazole-5-carboxylic acid (2-dimethylamino-ethyl)-amide MS (ESI) m/z 345 MH$^+$

Example II-24

6-Fluoro-3-(3-fluoro-phenyl)-1H-indazole-5-carboxylic acid (1H-imidazol-4-ylmethyl)-amide MS (ESI) m/z 354 MH$^+$

Example II-25

6-Fluoro-3-(3-fluoro-phenyl)-1H-indazole-5-carboxylic acid cyclopropylamide

MS (ESI) m/z 314 MH$^+$

Example II-26

3-(3-Fluoro-phenyl)-4-methoxy-1H-indazole-5-carboxylic acid 3-methoxy-benzylamide MS (ESI) m/z 406 MH$^+$

Example II-27

6-Fluoro-3-(3-fluoro-phenyl)-1H-indazole-5-carboxylic acid 3-methoxy-benzylamide MS (ESI) m/z 394 MH$^+$

Example II-28

3-(3-Fluoro-phenyl)-6-methyl-1H-indazole-5-carboxylic acid 3-methoxy-benzylamide MS (ESI) m/z 390 MH$^+$

Example II-29

4-Fluoro-3-(3-fluoro-phenyl)-1H-indazole-5-carboxylic acid 3-methoxy-benzylamide MS (ESI) m/z 394 MH$^+$

Example II-30

3-(3-Fluoro-phenyl)-4-methoxy-1H-indazole-5-carboxylic acid [3-(2-oxo-pyrrolidin-1-yl)-propyl]-amide MS (ESI) m/z 411 MH$^+$

Example II-31

3-(3-Fluoro-phenyl)-6-methyl-1H-indazole-5-carboxylic acid [3-(2-oxo-pyrrolidin-1-yl)-propyl]-amide MS (ESI) m/z 395 MH$^+$

Example II-32

4-Fluoro-3-(3-fluoro-phenyl)-1H-indazole-5-carboxylic acid [3-(2-oxo-pyrrolidin-1-yl)-propyl]-amide MS (ESI) m/z 399 MH$^+$

Example II-33

3-(3-Fluoro-phenyl)-6-methyl-1H-indazole-5-carboxylic acid (2-thiophen-2-yl-ethyl)-amide MS (ESI) m/z 380 MH$^+$

Example II-34

4-Fluoro-3-(3-fluoro-phenyl)-1H-indazole-5-carboxylic acid (2-thiophen-2-yl-ethyl)-amide MS (ESI) m/z 384 MH$^+$

Example II-35

4-Fluoro-3-(3-fluoro-phenyl)-1H-indazole-5-carboxylic acid (tetrahydrofuran-2-ylmethyl)-amide MS (ESI) m/z 358 MH$^+$

Example II-36

4-Fluoro-3-(3-fluoro-phenyl)-1H-indazole-5-carboxylic acid (2-ethoxy-ethyl)-amide MS (ESI) m/z 346 MH$^+$

Example II-37

3-(3-Fluoro-phenyl)-6-methyl-1H-indazole-5-carboxylic acid (2-ethoxy-ethyl)-amide MS (ESI) m/z 342 MH$^+$

Example II-38

3-(3-Fluoro-phenyl)-6-methyl-1H-indazole-5-carboxylic acid cyclopropylmethyl-amide MS (ESI) m/z 324 MH$^+$

Example II-39

3-(3-Fluoro-phenyl)-6-methyl-1H-indazole-5-carboxylic acid (2-methylsulfanyl-ethyl)-amide MS (ESI) m/z 344 MH$^+$

Example II-40

4-Fluoro-3-(3-fluoro-phenyl)-1H-indazole-5-carboxylic acid (2-methylsulfanyl-ethyl)-amide MS (ESI) m/z 348 MH$^+$

Example II-41

3-(3-Fluoro-phenyl)-6-methyl-1H-indazole-5-carboxylic acid [(1S)-1-carbamoyl-ethyl]-amide MS (ESI) m/z 341 MH$^+$

Example II-42

4-Fluoro-3-(3-fluoro-phenyl)-1H-indazole-5-carboxylic acid [(1S)-1-carbamoyl-ethyl]-amide MS (ESI) m/z 345 MH$^+$

Example II-43

3-(3-Fluoro-phenyl)-6-methyl-1H-indazole-5-carboxylic acid [(1S)-2-hydroxy-1-phenyl-ethyl]-amide MS (ESI) m/z 390 MH$^+$

Example II-44

4-Fluoro-3-(3-fluoro-phenyl)-1H-indazole-5-carboxylic acid [(1S)-2-hydroxy-1-phenyl-ethyl]-amide MS (ESI) m/z 394 MH$^+$

Example II-45

3-(3-Fluoro-phenyl)-6-methyl-1H-indazole-5-carboxylic acid (2-thiazol-2-yl-ethyl)-amide MS (ESI) m/z 381 MH$^+$

Example II-46

4-Fluoro-3-(3-fluoro-phenyl)-1H-indazole-5-carboxylic acid (2-thiazol-2-yl-ethyl)-amide MS (ESI) m/z 385 MH$^+$

Example II-47

3-(3-Fluoro-phenyl)-6-methyl-1H-indazole-5-carboxylic acid [(3R)-2-oxo-tetrahydrofuran-3-yl]-amide MS (ESI) m/z 354 MH$^+$

Example II-48

4-Fluoro-3-(3-fluoro-phenyl)-1H-indazole-5-carboxylic acid [(3R)-2-oxo-tetrahydrofuran-3-yl]-amide MS (ESI) m/z 358 MH$^+$

Example II-49

3-(3-Fluorophenyl)-7-methoxy-1H-indazole-5-carboxylic acid cyclopropylamide

MS (ESI) m/z 326 MH$^+$

Example II-50

3-(3-Fluorophenyl)-7-methoxy-1H-indazole-5-carboxylic acid (2-methylsulfanylethyl)amide MS (ESI) m/z 360 MH$^+$

Example II-51

3-(3-Fluorophenyl)-7-methoxy-1H-indazole-5-carboxylic acid [(1S)-1-hydroxymethyl-2-methyl-propyl]amide MS (ESI) m/z 372 MH$^+$

Example II-52

3-(3-Fluorophenyl)-7-methoxy-1H-indazole-5-carboxylic acid [tetrahydrofuran-(2S)-2-ylmethyl]amide MS (ESI) m/z 370 MH$^+$

Example II-53

3-(3-Fluorophenyl)-7-methoxy-1H-indazole-5-carboxylic acid [tetrahydrofuran-(2R)-2-ylmethyl]amide MS (ESI) m/z 370 MH$^+$

Example II-54

3-(3-Fluorophenyl)-7-methoxy-1H-indazole-5-carboxylic acid (furan-2-ylmethyl)amide MS (ESI) m/z 366 MH$^+$

Example II-55

3-(3-Fluorophenyl)-7-methoxy-1H-indazole-5-carboxylic acid (5-methylfuran-2-ylmethyl)amide MS (ESI) m/z 380 MH$^+$

Example II-56

3-(3-Fluorophenyl)-7-methoxy-1H-indazole-5-carboxylic acid (thiophen-2-ylmethyl)amide MS (ESI) m/z 382 MH$^+$

Example II-57

3-(3-Fluorophenyl)-7-methoxy-1H-indazole-5-carboxylic acid (benzo[b]furan-2-ylmethyl)amide MS (ESI) m/z 416 MH$^+$

Example II-58

3-(3-Fluorophenyl)-7-methyl-1H-indazole-5-carboxylic acid cyclopropylamide

MS (ESI) m/z 310 MH$^+$

Example II-59

3-(3-Fluorophenyl)-7-methyl-1H-indazole-5-carboxylic acid (2-methylsulfanylethyl)amide MS (ESI) m/z 344 MH$^+$

Example II-60

3-(3-Fluorophenyl)-7-methyl-1H-indazole-5-carboxylic acid [(1S)-1-hydroxymethyl-2-methyl-propyl]amide MS (ESI) m/z 356 MH$^+$

Example II-61

3-(3-Fluorophenyl)-7-methyl-1H-indazole-5-carboxylic acid [tetrahydrofuran-(2S)-2-ylmethyl]amide MS (ESI) m/z 354 MH$^+$

Example II-62

3-(3-Fluorophenyl)-7-methyl-1H-indazole-5-carboxylic acid [tetrahydrofuran-(2R)-2-ylmethyl]amide MS (ESI) m/z 354 MH$^+$

Example II-63

3-(3-Fluorophenyl)-7-methyl-1H-indazole-5-carboxylic acid (furan-2-ylmethyl)amide MS (ESI) m/z 350 MH$^+$

Example II-64

3-(3-Fluorophenyl)-7-methyl-1H-indazole-5-carboxylic acid (5-methylfuran-2-ylmethyl)amide MS (ESI) m/z 364 MH$^+$

Example II-65

3-(3-Fluorophenyl)-7-methyl-1H-indazole-5-carboxylic acid (thiophen-2-ylmethyl)amide MS (ESI) m/z 366 MH$^+$

Example II-66

3-(3-Fluorophenyl)-7-methyl-1H-indazole-5-carboxylic acid (benzo[b]furan-2-ylmethyl)amide MS (ESI) m/z 400 MH$^+$

Example II-67

4-Methoxy-3-naphthalen-2-yl-1H-indazole-5-carboxylic acid (2-thiophen-2-yl-ethyl)-amide MS (ESI) m/z 428 MH$^+$

Example II-68

4-Methoxy-3-naphthalen-2-yl-1H-indazole-5-carboxylic acid (2-methylsulfanyl-ethyl)-amide MS (ESI) m/z 392 MH$^+$

Example II-69

4-Methoxy-3-naphthalen-2-yl-1H-indazole-5-carboxylic acid [(1S)-1-carbamoyl-ethyl]-amide MS (ESI) m/z 389 MH$^+$

Example II-70

4-Methoxy-3-naphthalen-2-yl-1H-indazole-5-carboxylic acid [(1S)-2-hydroxy-1-phenyl-ethyl]-amide MS (ESI) m/z 438 MH$^+$

Example II-71

4-Methoxy-3-naphthalen-2-yl-1H-indazole-5-carboxylic acid (2-thiazol-2-yl-ethyl)-amide MS (ESI) m/z 429 MH$^+$

Example II-72

4-Methoxy-3-naphthalen-2-yl-1H-indazole-5-carboxylic acid [(3R)-2-oxo-tetrahydrofuran-3-yl]-amide MS (ESI) m/z 402 MH$^+$

Example II-73

4-Methoxy-3-naphthalen-2-yl-1H-indazole-5-carboxylic acid (tetrahydrofuran-2-ylmethyl)-amide MS (ESI) m/z 402 MH$^+$

Example II-74

4-Methoxy-3-naphthalen-2-yl-1H-indazole-5-carboxylic acid (2-ethoxy-ethyl)-amide MS (ESI) m/z 390 MH$^+$

Example II-75

4-Methoxy-3-naphthalen-2-yl-1H-indazole-5-carboxylic acid cyclopropylmethyl-amide MS (ESI) m/z 372 MH$^+$

Example II-76

4-Methoxy-3-naphthalen-2-yl-1H-indazole-5-carboxylic acid (furan-2-ylmethyl)-amide MS (ESI) m/z 398 MH$^+$

Example II-77

4-Methoxy-3-naphthalen-2-yl-1H-indazole-5-carboxylic acid (5-methyl-furan-2-ylmethyl)-amide MS (ESI) m/z 412 MH$^+$

Example II-78

4-Methoxy-3-naphthalen-2-yl-1H-indazole-5-carboxylic acid cyclopropyl-amide

MS (ESI) m/z 358 MH$^+$

Example II-79

4-Methoxy-3-naphthalen-2-yl-1H-indazole-5-carboxylic acid 3-methoxy-benzylamide

MS (ESI) m/z 438 MH$^+$

Example II-80

4-Methoxy-3-naphthalen-2-yl-1H-indazole-5-carboxylic acid [3-(2-oxo-pyrrolidin-1-yl)-propyl]-amide MS (ESI) m/z 443 MH$^+$

Example II-81

4-Methoxy-3-naphthalen-2-yl-1H-indazole-5-carboxylic acid [(1S)-1-hydroxymethyl-2-methyl-propyl]-amide MS (ESI) m/z 404 MH$^+$

Example II-82

4-Methoxy-3-naphthalen-2-yl-1H-indazole-5-carboxylic acid (furan-3-ylmethyl)-amide MS (ESI) m/z 398 MH$^+$

Example II-83

4-Methoxy-3-naphthalen-2-yl-1H-indazole-5-carboxylic acid (pyridin-2-ylmethyl)-amide MS (ESI) m/z 409 MH$^+$

Example II-84

4-Methoxy-3-naphthalen-2-yl-1H-indazole-5-carboxylic acid (thiophen-2-ylmethyl)-amide MS (ESI) m/z 414 MH$^+$

Example II-85

3-Benzo[b]furan-2-yl-4-methoxy-1H-indazole-5-carboxylic acid (2-thiophen-2-yl-ethyl)-amide MS (ESI) m/z 418 MH$^+$

Example II-86

3-Benzo[b]furan-2-yl-4-methoxy-1H-indazole-5-carboxylic acid (2-methylsulfanyl-ethyl)-amide MS (ESI) m/z 382 MH$^+$

Example II-87

3-Benzo[b]furan-2-yl-4-methoxy-1H-indazole-5-carboxylic acid [(1S)-1-carbamoyl-ethyl]-amide MS (ESI) m/z 379 MH$^+$

Example II-88

3-Benzo[b]furan-2-yl-4-methoxy-1H-indazole-5-carboxylic acid [(1S)-2-hydroxy-1-phenyl-ethyl]-amide MS (ESI) m/z 428 MH$^+$

Example II-89

3-Benzo[b]furan-2-yl-4-methoxy-1H-indazole-5-carboxylic acid (2-thiazol-2-yl-ethyl)-amide MS (ESI) m/z 419 MH$^+$

Example II-90

3-Benzo[b]furan-2-yl-4-methoxy-1H-indazole-5-carboxylic acid [(3R)-2-oxo-tetrahydrofuran-3-yl]-amide MS (ESI) m/z 392 MH$^+$

Example II-91

3-Benzo[b]furan-2-yl-4-methoxy-1H-indazole-5-carboxylic acid (tetrahydrofuran-2-ylmethyl)-amide MS (ESI) m/z 392 M$^+$

Example II-92

3-Benzo[b]furan-2-yl-4-methoxy-1H-indazole-5-carboxylic acid (2-ethoxy-ethyl)-amide MS (ESI) m/z 380 MH$^+$

Example II-93

3-Benzo[b]furan-2-yl-4-methoxy-1H-indazole-5-carboxylic acid cyclopropylmethyl-amide MS (ESI) m/z 362 MH$^+$

Example II-94

3-Benzo[b]furan-2-yl-4-methoxy-1H-indazole-5-carboxylic acid (furan-2-ylmethyl)-amide MS (ESI) m/z 388 MH$^+$

Example II-95

3-Benzo[b]furan-2-yl-4-methoxy-1H-indazole-5-carboxylic acid (5-methyl-furan-2-ylmethyl)-amide MS (ESI) m/z 402 MH$^+$

Example II-96

3-Benzo[b]furan-2-yl-4-methoxy-1H-indazole-5-carboxylic acid cyclopropylamide

MS (ESI) m/z 348 MH$^+$

Example II-97

3-Benzo[b]furan-2-yl-4-methoxy-1H-indazole-5-carboxylic acid 3-methoxy-benzylamide MS (ESI) m/z 428 MH$^+$

Example II-98

3-Benzo[b]furan-2-yl-4-methoxy-1H-indazole-5-carboxylic acid [3-(2-oxo-pyrrolidin-1-yl)-propyl]-amide MS (ESI) m/z 433 MH$^+$

Example II-99

3-Benzo[b]furan-2-yl-4-methoxy-1H-indazole-5-carboxylic acid [(1S)-1-hydroxymethyl-2-methyl-propyl]-amide MS (ESI) m/z 394 MH$^+$

Example II-100

3-Benzo[b]furan-2-yl-4-methoxy-1H-indazole-5-carboxylic acid (furan-3-ylmethyl)-amide MS (ESI) m/z 388 MH$^+$

Example II-101

3-Benzo[b]furan-2-yl-4-methoxy-1H-indazole-5-carboxylic acid (pyridin-2-ylmethyl)-amide MS (ESI) m/z 399 MH$^+$

Example II-102

3-Benzo[b]furan-2-yl-4-methoxy-1H-indazole-5-carboxylic acid (thiophen-2-ylmethyl)-amide MS (ESI) m/z 404 MH$^+$

Example II-103

3-Benzo[b]thiophen-2-yl-4-methoxy-1H-indazole-5-carboxylic acid (2-thiophen-2-yl-ethyl)-amide MS (ESI) m/z 434 MH$^+$

Example II-104

3-Benzo[b]thiophen-2-yl-4-methoxy-1H-indazole-5-carboxylic acid (2-methylsulfanyl-ethyl)-amide MS (ESI) m/z 398 MH$^+$

Example II-105

3-Benzo[b]thiophen-2-yl-4-methoxy-1H-indazole-5-carboxylic acid [(1S)-1-carbamoyl-ethyl]-amide MS (ESI) m/z 395 MH$^+$

Example II-106

3-Benzo[b]thiophen-2-yl-4-methoxy-1H-indazole-5-carboxylic acid [(1S)-2-hydroxy-1-phenyl-ethyl]-amide MS (ESI) m/z 444 MH$^+$

Example II-107

3-Benzo[b]thiophen-2-yl-4-methoxy-1H-indazole-5-carboxylic acid (2-thiazol-2-yl-ethyl)-amide MS (ESI) m/z 435 MH$^+$

Example II-108

3-Benzo[b]thiophen-2-yl-4-methoxy-1H-indazole-5-carboxylic acid [(3R)-2-oxo-tetrahydrofuran-3-yl]-amide MS (ESI) m/z 408 MH$^+$

Example II-109

3-Benzo[b]thiophen-2-yl-4-methoxy-1H-indazole-5-carboxylic acid (tetrahydrofuran-2-ylmethyl)-amide MS (ESI) m/z 408 M$^+$

Example II-110

3-Benzo[b]thiophen-2-yl-4-methoxy-1H-indazole-5-carboxylic acid (2-ethoxy-ethyl)-amide MS (ESI) m/z 396 MH$^+$

Example II-111

3-Benzo[b]thiophen-2-yl-4-methoxy-1H-indazole-5-carboxylic acid cyclopropylmethyl-amide MS (ESI) m/z 378 MH$^+$

Example II-112

3-Benzo[b]thiophen-2-yl-4-methoxy-1H-indazole-5-carboxylic acid (furan-2-ylmethyl)-amide MS (ESI) m/z 404 MH$^+$

Example II-113

3-Benzo[b]thiophen-2-yl-4-methoxy-1H-indazole-5-carboxylic acid (5-methyl-furan-2-ylmethyl)-amide MS (ESI) m/z 418 MH$^+$

Example II-114

3-Benzo[b]thiophen-2-yl-4-methoxy-1H-indazole-5-carboxylic acid cyclopropylamide MS (ESI) m/z 364 MH$^+$

Example II-115

3-Benzo[b]thiophen-2-yl-4-methoxy-1H-indazole-5-carboxylic acid 3-methoxy-benzylamide MS (ESI) m/z 444 MH$^+$

Example II-116

3-Benzo[b]thiophen-2-yl-4-methoxy-1H-indazole-5-carboxylic acid [3-(2-oxo-pyrrolidin-1-yl)-propyl]-amide MS (ESI) m/z 449 MH$^+$

Example II-117

3-Benzo[b]thiophen-2-yl-4-methoxy-1H-indazole-5-carboxylic acid [(1S)-1-hydroxymethyl-2-methyl-propyl]-amide MS (ESI) m/z 410 MH$^+$

Example II-118

3-Benzo[b]thiophen-2-yl-4-methoxy-1H-indazole-5-carboxylic acid (furan-3-ylmethyl)-amide MS (ESI) m/z 404 MH$^+$

Example II-119

3-Benzo[b]thiophen-2-yl-4-methoxy-1H-indazole-5-carboxylic acid (pyridin-2-ylmethyl)-amide MS (ESI) m/z 415 MH$^+$

Example II-120

3-Benzo[b]thiophen-2-yl-4-methoxy-1H-indazole-5-carboxylic acid (thiophen-2-ylmethyl)-amide MS (ESI) m/z 420 MH$^+$

Example II-121

3-Benzo[b]thiophen-2-yl-4-fluoro-1H-indazole-5-carboxylic acid cyclopropanamide

MS (ESI) m/z 352 MH$^+$

Example II-122

3-Benzo[b]thiophen-2-yl-4-fluoro-1H-indazole-5-carboxylic acid (furan-2-ylmethyl)-amide MS (ESI) m/z 392 MH$^+$

Example II-123

3-Benzo[b]thiophen-2-yl-4-fluoro-1H-indazole-5-carboxylic acid [(1S)-1-hydroxymethyl-2-methyl-propyl]-amide MS (ESI) m/z 398 MH$^+$

Example II-124

3-Benzo[b]thiophen-2-yl-4-fluoro-1H-indazole-5-carboxylic acid (2-acetylamino-ethyl)-amide MS (ESI) m/z 397 MH$^+$

Example II-125

3-Benzo[b]thiophen-2-yl-4-fluoro-1H-indazole-5-carboxylic acid (2-thiophen-2-yl-ethyl)-amide MS (ESI) m/z 422 MH$^+$

Example II-126

3-Benzo[b]thiophen-2-yl-4-fluoro-1H-indazole-5-carboxylic acid [(1S)-1-carbamoyl-ethyl]]-amide MS (ESI) m/z 765 2 MH$^+$

Example II-127

4-Fluoro-3-naphthalen-2-yl-1H-indazole-5-carboxylic acid cyclopropanamide

MS (ESI) m/z 346 MH$^+$

Example II-128

4-Fluoro-3-naphthalen-2-yl-1H-indazole-5-carboxylic acid (furan-2-ylmethyl)-amide MS (ESI) m/z 386 MH$^+$

Example II-129

4-Fluoro-3-naphthalen-2-yl-1H-indazole-5-carboxylic acid [(1S)-1-hydroxymethyl-2-methyl-propyl]-amide MS (ESI) m/z 392 MH$^+$

Example II-130

4-Fluoro-3-naphthalen-2-yl-1H-indazole-5-carboxylic acid (2-acetylamino-ethyl)-amide MS (ESI) m/z 391 MH$^+$

Example II-131

4-Fluoro-3-naphthalen-2-yl-1H-indazole-5-carboxylic acid (2-thiophen-2-yl-ethyl)-amide MS (ESI) m/z 416 MH$^+$

Example II-132

4-Fluoro-3-naphthalen-2-yl-1H-indazole-5-carboxylic acid [(1S)-1-carbamoyl-ethyl]-amide MS (ESI) m/z 753 2 MH$^+$

Example II-133

3-Benzo[b]furan-2-yl-4-fluoro-1H-indazole-5-carboxylic acid cyclopropanamide

MS (ESI) m/z 336 MH$^+$

Example II-134

3-Benzo[b]furan-2-yl-4-fluoro-1H-indazole-5-carboxylic acid (furan-2-ylmethyl)-amide MS (ESI) m/z 376 MH$^+$

Example II-135

3-Benzo[b]furan-2-yl-4-fluoro-1H-indazole-5-carboxylic acid [(1S)-1-hydroxymethyl-2-methyl-propyl]-amide MS (ESI) m/z 382 MH$^+$

Example II-136

3-Benzo[b]furan-2-yl-4-fluoro-1H-indazole-5-carboxylic acid (2-acetylamino-ethyl)-amide MS (ESI) m/z 381 MH$^+$

Example II-137

3-Benzo[b]furan-2-yl-4-fluoro-1H-indazole-5-carboxylic acid (2-thiophen-2-yl-ethyl)-amide MS (ESI) m/z 406 MH$^+$

Example II-138

3-Benzo[b]furan-2-yl-4-fluoro-1H-indazole-5-carboxylic acid [(1S)-1-carbamoyl-ethyl]-amide MS (ESI) m/z 733 2 MH$^+$

Example II-139

3-Benzo[b]thiophen-2-yl-6-fluoro-1H-indazole-5-carboxylic acid cyclopropylamide

MS (ESI) m/z 352 MH$^+$

Example II-140

3-Benzo[b]thiophen-2-yl-6-fluoro-1H-indazole-5-carboxylic acid (furan-2-ylmethyl)-amide MS (ESI) m/z 392 MH$^+$

Example II-141

3-Benzo[b]thiophen-2-yl-6-fluoro-1H-indazole-5-carboxylic acid [(2S)-tetrahydrofuran-2-ylmethyl]-amide MS (ESI) m/z 396 MH$^+$

Example II-142

3-Benzo[b]thiophen-2-yl-6-fluoro-1H-indazole-5-carboxylic acid [(2R)-tetrahydrofuran-2-ylmethyl]-amide MS (ESI) m/z 396 MH$^+$

Example II-143

3-Benzo[b]thiophen-2-yl-6-fluoro-1H-indazole-5-carboxylic acid (pyridin-3-ylmethyl)-amide MS (ESI) m/z 403 MH$^+$

Example II-144

3-Benzo[b]thiophen-2-yl-6-fluoro-1H-indazole-5-carboxylic acid [(1S)-1-hydroxymethyl-2-methyl-propyl]-amide MS (ESI) m/z 398 MH$^+$

Example II-145

3-Benzo[b]thiophen-2-yl-6-fluoro-1H-indazole-5-carboxylic acid [3-(2-oxopyrrolidin-1-yl)propyl]-amide MS (ESI) m/z 437 MH$^+$

Example II-146

6-Fluoro-3-naphthalen-2-yl-1H-indazole-5-carboxylic acid cyclopropylamide

MS (ESI) m/z 346 MH$^+$

Example II-147

6-Fluoro-3-naphthalen-2-yl-1H-indazole-5-carboxylic acid (furan-2-ylmethyl)-amide MS (ESI) m/z 386 MH$^+$

Example II-148

6-Fluoro-3-naphthalen-2-yl-1H-indazole-5-carboxylic acid [(2S)-tetrahydrofuran-2-ylmethyl]-amide MS (ESI) m/z 390 MH$^+$

Example II-149

6-Fluoro-3-naphthalen-2-yl-1H-indazole-5-carboxylic acid [(2R)-tetrahydrofuran-2-ylmethyl]-amide MS (ESI) m/z 390 MH$^+$

Example II-150

6-Fluoro-3-naphthalen-2-yl-1H-indazole-5-carboxylic acid (pyridin-3-ylmethyl)-amide MS (ESI) m/z 397 MH$^+$

Example II-151

6-Fluoro-3-naphthalen-2-yl-1H-indazole-5-carboxylic acid [(1S)-1-hydroxymethyl-2-methyl-propyl]-amide MS (ESI) m/z 392 MH$^+$

Example II-152

6-Fluoro-3-naphthalen-2-yl-1H-indazole-5-carboxylic acid [3-(2-oxopyrrolidin-1-yl)propyl]amide MS (ESI) m/z 431 MH$^+$ The compounds according to Examples II-153 to II-197 were synthesized by Synthesis Process II-B using the amines produced in Production Examples II-18 through II-25.

Example II-153

Cyclopropanecarboxylic acid {3-(3-fluoro-phenyl)-4-methoxy-1H-indazol-5-yl}-amide MS (ESI) m/z 326 MH$^+$

Example II-154

(2S)-5-Oxo-pyrrolidine-2-carboxylic acid {3-(3-fluoro-phenyl)-4-methoxy-1H-indazol-5-yl}-amide MS (ESI) m/z 369 MH$^+$

Example II-155

(2R)-5-Oxo-pyrrolidine-2-carboxylic acid {3-(3-fluoro-phenyl)-4-methoxy-1H-indazol-5-yl}-amide MS (ESI) m/z 369 MH$^+$

Example II-156

Pyridin-3-yl-acetic acid {3-(3-fluoro-phenyl)-4-methoxy-1H-indazol-5-yl}-amide

MS (ESI) m/z 377 MH$^+$

Example II-157

Cyclopropanecarboxylic acid {4-bromo-3-(3-fluoro-phenyl)-1H-indazol-5-yl}-amide

MS (ESI) m/z 376, 378 MH$^+$

Example II-158

Pyridin-3-yl-acetic acid {4-bromo-3-(3-fluoro-phenyl)-1H-indazol-5-yl}-amide

MS (ESI) m/z 425, 427 MH$^+$

Example II-159

Cyclopropanecarboxylic acid {4-fluoro-3-(3-fluoro-phenyl)-1H-indazol-5-yl}-amide MS (ESI) m/z 314 MH$^+$

Example II-160

(2S)-5-Oxo-pyrrolidine-2-carboxylic acid {4-fluoro-3-(3-fluoro-phenyl)-1H-indazol-5-yl}-amide MS (ESI) m/z 357 MH$^+$

Example II-161

(2R)-5-Oxo-pyrrolidine-2-carboxylic acid {4-fluoro-3-(3-fluoro-phenyl)-1H-indazol-5-yl}-amide MS (ESI) m/z 357 MH$^+$

Example II-162

3-Dimethylamino-N-{4-fluoro-3-(3-fluoro-phenyl)-1H-indazol-5-yl}-propionamide

MS (ESI) m/z 344 MH$^+$

Example II-163

Cyclopropanecarboxylic acid {6-fluoro-3-(3-fluoro-phenyl)-1H-indazol-5-yl}-amide MS (ESI) m/z 314 MH$^+$

Example II-164

(2S)-5-Oxo-pyrrolidine-2-carboxylic acid {6-fluoro-3-(3-fluoro-phenyl)-1H-indazol-5-yl}-amide MS (ESI) m/z 357 MH$^+$

Example II-165

(2R)-5-Oxo-pyrrolidine-2-carboxylic acid {6-fluoro-3-(3-fluoro-phenyl)-1H-indazol-5-yl}-amide MS (ESI) m/z 357 MH$^+$

Example II-166

Pyridin-3-yl-acetic acid {6-fluoro-3-(3-fluoro-phenyl)-1H-indazol-5-yl}-amide

MS (ESI) m/z 365 MH$^+$

Example II-167

3-Dimethylamino-N-{6-fluoro-3-(3-fluoro-phenyl)-1H-indazol-5-yl}-propionamide

MS (ESI) m/z 345 MH$^+$

Example II-168

Cyclopropanecarboxylic acid {3-(3-fluoro-phenyl)-6-methoxy-1H-indazol-5-yl}-amide MS (ESI) m/z 326 MH$^+$

Example II-169

(2S)-5-Oxo-pyrrolidine-2-carboxylic acid {3-(3-fluoro-phenyl)-6-methoxy-1H-indazol-5-yl}-amide MS (ESI) m/z 369 MH$^+$

Example II-170

(2R)-5-Oxo-pyrrolidine-2-carboxylic acid {3-(3-fluoro-phenyl)-6-methoxy-1H-indazol-5-yl}-amide MS (ESI) m/z 369 MH$^+$

Example II-171

Pyridin-3-yl-acetic acid {3-(3-fluoro-phenyl)-6-methoxy-1H-indazol-5-yl}-amide

MS (ESI) m/z 377 MH$^+$

Example II-172

3-Dimethylamino-N-{3-(3-fluoro-phenyl)-6-methoxy-1H-indazol-5-yl}-propionamide

MS (ESI) m/z 357 MH$^+$

Example II-173

N-{3-(3-Fluoro-phenyl)-6-methoxy-1H-indazol-5-yl}-2-thiophen-2-yl-acetamide

MS (ESI) m/z 382 MH$^+$

Example II-174

Furan-2-carboxylic acid {3-(3-fluoro-phenyl)-6-methoxy-1H-indazol-5-yl}-amide

MS (ESI) m/z 352 MH$^+$

Example II-175

N-{3-(3-Fluoro-phenyl)-6-methoxy-1H-indazol-5-yl}-3-methoxy-propionamide

MS (ESI) m/z 344 MH$^+$

Example II-176

N-[3-(3-Fluorophenyl)-7-methyl-1H-indazol-5-yl]acetamide

MS (ESI) m/z 284 MH$^+$

Example II-177

Cyclopropanecarboxylic acid [3-(3-fluorophenyl)-7-methyl-1H-indazol-5-yl]amide

MS (ESI) m/z 310 MH$^+$

Example II-178

(2R)-5-Oxo-pyrrolidine-2-carboxylic acid [3-(3-fluorophenyl)-7-methyl-1H-indazol-5-yl]amide MS (ESI) m/z 353 MH$^+$

Example II-179

(2S)-5-Oxo-pyrrolidine-2-carboxylic acid [3-(3-fluorophenyl)-7-methyl-1H-indazol-5-yl]amide MS (ESI) m/z 353 MH$^+$

Example II-180

Tetrahydrofuran-3-carboxylic acid [3-(3-fluorophenyl)-7-methyl-1H-indazol-5-yl]amide MS (ESI) m/z 340 MH$^+$

Example II-181

Tetrahydrofuran-2-carboxylic acid [3-(3-fluorophenyl)-7-methyl-1H-indazol-5-yl]amide MS (ESI) m/z 340 MH$^+$

Example II-182

N-[3-(3-Fluorophenyl)-7-methyl-1H-indazol-5-yl]-2-thiophen-2-yl-acetamide

MS (ESI) m/z 366 MH$^+$

Example II-183

N-[3-(3-Fluorophenyl)-7-methyl-1H-indazol-5-yl]-2-thiophen-3-yl-acetamide

MS (ESI) m/z 366 MH$^+$

Example II-184

Cyclopropanecarboxylic acid {6-fluoro-3-naphthalen-2-yl-1H-indazol-5-yl}-amide

MS (ESI) m/z 346 MH$^+$

Example II-185

N-(6-Fluoro-3-naphthalen-2-yl-1H-indazol-5-yl)-acetamide

MS (ESI) m/z 320 MH$^+$

Example II-186

(2S)-5-Oxo-pyrrolidine-2-carboxylic acid {6-fluoro-3-naphthalen-2-yl-1H-indazol-5-yl}-amide MS (ESI) m/z 389 MH$^+$

Example II-187

(2R)-5-Oxo-pyrrolidine-2-carboxylic acid {6-fluoro-3-naphthalen-2-yl-1H-indazol-5-yl}-amide MS (ESI) m/z 389 MH$^+$

Example II-188

Pyridin-3-yl-acetic acid (6-fluoro-3-naphthalen-2-yl-1H-indazol-5-yl)-amide

MS (ESI) m/z 397 MH$^+$

Example II-189

N-(6-Fluoro-3-naphthalen-2-yl-1H-indazol-5-yl)-2-thiophen-2-yl-acetamide

MS (ESI) m/z 402 MH$^+$

Example II-190

Furan-2-carboxylic acid (6-Fluoro-3-naphthalen-2-yl-1H-indazol-5-yl)-amide

MS (ESI) m/z 372 MH$^+$

Example II-191

N-(6-Fluoro-3-naphthalen-2-yl-1H-indazol-5-yl)-3-methoxy-propionamide

MS (ESI) m/z 364 MH$^+$

Example II-192

Cyclopropanecarboxylic acid (3-benzo[b]thiophen-2-yl-6-fluoro-1H-indazol-5-yl)-amide MS (ESI) m/z 352 MH$^+$

Example II-193

N-(3-Benzo[b]thiophen-2-yl-6-fluoro-1H-indazol-5-yl)-acetamide

MS (ESI) m/z 326 MH$^+$

Example II-194

(2R)-5-Oxo-pyrrolidine-2-carboxylic acid (3-benzo[b]thiophen-2-yl-6-fluoro-1H-indazol-5-yl)-amide MS (ESI) m/z 395 MH$^+$

Example II-195

N-(3-Benzo[b]thiophen-2-yl-6-fluoro-1H-indazol-5-yl)-2-thiophen-2-yl-acetamide

MS (ESI) m/z 408 MH$^+$

Example II-196

Furan-2-carboxylic acid (3-benzo[b]thiophen-2-yl-6-fluoro-1H-indazol-5-yl)-amide MS (ESI) m/z 378 MH$^+$

Example II-197

N-(3-Benzo[b]thiophen-2-yl-6-fluoro-1H-indazol-5-yl)-3-methoxy-propionamide

MS (ESI) m/z 370 MH$^+$

The compounds according to Examples II-198 to II-211 were synthesized by Synthesis Process II-C using the amines produced in Production Examples II-26 through II-30.

Example II-198

N-{3-(3-Fluoro-phenyl)-4-methoxy-1H-indazol-5-ylmethyl}-3-methoxy-benzamide

MS (ESI) m/z 406 MH$^+$

Example II-199

N-{6-Fluoro-3-(3-fluoro-phenyl)-1H-indazol-5-ylmethyl}-3-methoxy-benzamide $^1$H-NMR (400 MHz, CD$_3$OD) δ 3.83 (3H, s), 4.73 (2H, d, J=6.0 Hz), 7.06-7.18 (2H, m), 7.29 (1H, d, J=10.6 Hz), 7.33-7.76 (6H, m), 8.05 (1H, d, J=7.2 Hz), 8.99 (1H, brs)

Example II-200

N-{3-(3-Fluoro-phenyl)-6-methoxy-1H-indazol-5-ylmethyl}-3-methoxy-nicotinamide

MS (ESI) m/z 407 MH$^+$

Example II-201

N-{3-(3-Fluoro-phenyl)-6-methoxy-1H-indazol-5-ylmethyl}-nicotinamide

MS (ESI) m/z 377 MH$^+$

Example II-202

3-Cyano-N-{3-(3-fluoro-phenyl)-6-methoxy-1H-indazol-5-ylmethyl}-benzamide

MS (ESI) m/z 401 MH$^+$

Example II-203

3-Fluoro-N-{3-(3-fluoro-phenyl)-6-methoxy-1H-indazol-5-ylmethyl}-benzamide

MS (ESI) m/z 394 MH$^+$

Example II-204

N-{6-Fluoro-3-(3-fluoro-phenyl)-1H-indazol-5-ylmethyl}-3-methoxy-nicotinamide

MS (ESI) m/z 395 MH$^+$

Example II-205

N-{6-Fluoro-3-(3-fluoro-phenyl)-1H-indazol-5-ylmethyl}-nicotinamide

MS (ESI) m/z 365 MH$^+$

Example II-206

3-Cyano-N-{6-fluoro-3-(3-fluoro-phenyl)-1H-indazol-5-ylmethyl}-benzamide

MS (ESI) m/z 389 MH$^+$

Example II-207

3-Fluoro-N-{6-fluoro-3-(3-fluoro-phenyl)-1H-indazol-5-ylmethyl}-benzamide

MS (ESI) m/z 382 MH$^+$

Example II-208

N-{6-Fluoro-3-naphthalen-2-yl-1H-indazol-5-ylmethyl}-3-methoxy-benzamide

MS (ESI) m/z 426 MH$^+$

Example II-209

N-{6-Fluoro-3-naphthalen-2-yl-1H-indazol-5-ylmethyl}-2-methoxy-benzamide

MS (ESI) m/z 426 MH$^+$

Example II-210

N-(3-Benzo[b]thiophen-2-yl-6-fluoro-1H-indazol-5-ylmethyl)-3-methoxy-benzamide

MS (ESI) m/z 432 MH$^+$

Example II-211

N-(3-Benzo[b]thiophen-2-yl-6-fluoro-1H-indazol-5-ylmethyl)-2-methoxy-benzamide

MS (ESI) m/z 432 MH$^+$

The compounds according to Examples II-212 to II-218 were synthesized by Synthesis Process II-D using the amines produced in Production Examples II-18, II-19, II-22, II-23, II-24, II-26, and II-28, respectively.

Example II-212

N-{3-(3-Fluoro-phenyl)-4-methoxy-1H-indazol-5-yl}-methanesulfonamide

MS (ESI) m/z 336 MH$^+$

Example II-213

N-{4-Fluoro-3-(3-Fluoro-phenyl)-1H-indazol-5-yl}-methanesulfonamide

MS (ESI) m/z 324 MH$^+$

Example II-214

N-{3-(3-Fluoro-phenyl)-6-methoxy-1H-indazol-5-yl}-methanesulfonamide

MS (ESI) m/z 336 MH$^+$

Example II-215

N-[3-(3-Fluorophenyl)-7-methyl-1H-indazol-5-yl]methanesulfonamide

MS (ESI) m/z 320 MH$^+$

Example II-216

N-{3-(3-Fluoro-phenyl)-6-methoxy-1H-indazol-5-ylmethyl}-3-methoxy-benzenesulfonamide MS (ESI) m/z 442 MH$^+$

Example II-217

N-{6-Fluoro-3-(3-fluoro-phenyl)-1H-indazol-5-ylmethyl}-3-methoxy-benzenesulfonamide MS (ESI) m/z 430 MH$^+$

Example II-218

N-(3-Benzo[b]thiophen-2-yl-6-fluoro-1H-indazol-5-yl)-methanesulfonamide

MS (ESI) m/z 362 MH$^+$

The compounds according to Examples II-219 to II-225 were synthesized by Synthesis Process II-E using the amines produced in Production Examples II-18 through II-25, respectively.

Example II-219

3-(3-Fluoro-phenyl)-4-methoxy-1H-indazol-5-yl-amine

MS (ESI) m/z 258 MH$^+$

Example II-220

4-Bromo-3-(3-fluoro-phenyl)-1H-indazol-5-yl-amine

MS (ESI) m/z 306, 308 MH$^+$

Example II-221

4-Fluoro-3-(3-fluoro-phenyl)-1H-indazol-5-yl-amine

MS (ESI) m/z 246 MH$^+$

Example II-222

6-Fluoro-3-(3-fluoro-phenyl)-1H-indazol-5-yl-amine

MS (ESI) m/z 246 MH$^+$

Example II-223

3-(3-Fluoro-phenyl)-6-methoxy-1H-indazol-5-yl-amine

MS (ESI) m/z 258 MH$^+$

Example II-224

6-Fluoro-3-naphthalen-2-yl-1H-indazol-5-ylamine

MS (ESI) m/z 278 MH$^+$

Example II-225

3-Benzo[b]thiophen-2-yl-6-fluoro-1H-indazol-5-ylamine

MS (ESI) m/z 284 MH$^+$

Example II-226-a

Cyclopropanecarboxylic acid {4-bromo-3-(3-fluoro-phenyl)-1-trityl-1H-indazol-5-yl}-amide A total of 513 mg of 4-bromo-3-(3-fluoro-phenyl)-1-trityl-1H-indazol-5-yl-amine obtained in Production Example II-21 was dissolved in 19 ml of tetrahydrofuran. Under ice-cooling and stirring, 0.261 ml of triethylamine and 0.089 ml of cyclopropanecarbonyl chloride were added, and the mixture was stirred at room temperature for 90 minutes. Water was added to the reaction mixture, followed by extracting with ethyl acetate. The resulting organic layer was washed with brine, dried over magnesium sulfate and the solvent was evaporated. The residue was purified and separated by silica gel column chromatography (ethyl acetate:hexane=1:2), to give 471 mg of the title compound as pale yellow crystals.

$^1$H-NMR (400 MHz, CDCl$_3$) δ 0.82-0.90 (2H, m), 1.02-1.09 (2H, m), 1.53-1.60 (1H, m), 6.45 (1H, d, J=9.2 Hz), 7.05-7.13 (1H, m), 7.19-7.93 (20H, m)

Example II-226-b 5-(Cyclopropanecarbonyl-amide)-3-(3-fluoro-phenyl)-1-trityl-1H-indazole-4-carboxylic acid A total of 17.8 mg of the title compound was obtained by the procedure of Production Example II-2-d, except from 144 mg of cyclopropanecarboxylic acid {4-bromo-3-(3-fluoro-phenyl)-1-trityl-1H-indazol-5-yl}amide obtained in Example II-226-a.

$^1$H-NMR (400 MHz, CD$_3$OD) δ 0.72-1.71 (5H, m), 6.48 (1H, d, J=9.2 Hz), 6.98-7.05 (1H, m), 7.20-7.50 (19H, m)

Example II-226-c 5-(Cyclopropanecarbonyl-amide)-3-(3-fluoro-phenyl)-1H-indazole-4-carboxylic acid 178 mg of 5-(cyclopropanecarbonyl-amide)-3-(3-fluoro-phenyl)-1-trityl-1H-indazole-4-carboxylic acid obtained in Example II-226-b was dissolved in 2 ml of tetrahydrofuran and 2 ml of dichloromethane. 0.5 ml of trifluoroacetic acid was added, followed by stirring at room temperature for 16 hours. Water was added to the reaction mixture, followed by extracting with ethyl acetate. The resulting organic layer was washed with brine, dried over magnesium sulfate and the solvent was evaporated. The residue was purified and separated by silica gel column chromatography (ethyl acetate), to give 96.9 mg of the title compound as pale pink crystals.

$^1$H-NMR (400 MHz, CD$_3$OD) δ 0.83-1.00 (4H, m), 1.73-1.83 (1H, m), 7.10-7.17 (1H, m), 7.23-7.28 (1H, m), 7.31-7.36 (1H, m), 7.44 (1H, dt, J=6.0, 8.0 Hz), 7.68 (1H, d, J=9.2 Hz), 7.87 (1H, d, J=9.2 Hz)

Example II-227

N-{3-(3-Fluoro-phenyl)-6-methoxy-1H-indazol-5-ylmethyl}-3-methoxy-benzamide

A total of 25.6 mg of C-{3-(3-fluoro-phenyl)-6-methoxy-1H-indazol-5-yl}-methylamine obtained in Production Example 26 was dissolved in 1.9 ml of dimethylformamide, 15.3 mg of 1-hydroxybenzotriazole, 0.066 ml of diisopropylethylamine and 14.4 mg of 3-methoxybenzoic acid were added thereto, and 27.2 mg of 1-ethyl-3-(3'-dimethylamino-propyl)carbodiimide hydrochloride (i.e., WSC.HCl) was added thereto under ice-cooling and stirring. After stirring at room temperature for 5 hours, water was added and the mixture was extracted with ethyl acetate. The resulting organic layer was washed with 0.5 N aqueous sodium hydroxide solution, 1 N hydrochloric acid and saturated brine, dried over magnesium sulfate, and the solvent was evaporated. The residue was purified and separated by silica gel column chromatography (dichloromethane:methanol=10:1), to give 9.24 mg of the title compound as pale yellow crystals.

$^1$H-NMR (400 MHz, CD$_3$OD) δ 3.83 (3H, s), 3.98 (3H, s), 4.66 (2H, s), 7.03 (1H, s), 7.07-7.14 (2H, m), 7.34-7.43 (3H, m), 7.47 (1H, dt, J=6.0, 8.0 Hz), 7.59-7.64 (1H, m), 7.72 (1H, d, J=8.0 Hz), 7.89 (1H, s).

The compounds according to Examples II-228 to II-265 were synthesized by Synthesis Process II-A using the carboxylic acids produced in Production Examples II-31 and II-32, respectively.

Example II-228

7-Fluoro-3-(3-fluorophenyl)-1H-indazole-5-carboxylic acid cyclopropylamide

MS (ESI) m/z 314 MH$^+$

Example II-229

7-Fluoro-3-(3-fluorophenyl)-1H-indazole-5-carboxylic acid cyclopropylmethylamide MS (ESI) m/z 328 MH$^+$

Example II-230

7-Fluoro-3-(3-fluorophenyl)-1H-indazole-5-carboxylic acid (2-methylsulfanylethyl)amide MS (ESI) m/z 348 MH$^+$

Example II-231

7-Fluoro-3-(3-fluorophenyl)-1H-indazole-5-carboxylic acid [(1S)-1-hydroxymethyl-2-methylpropyl]amide MS (ESI) m/z 360 MH$^+$

Example II-232

7-Fluoro-3-(3-fluorophenyl)-1H-indazole-5-carboxylic acid [(1S)-2-hydroxy-1-phenylethyl]amide MS (ESI) m/z 394 MH$^+$

Example II-233

7-Fluoro-3-(3-fluorophenyl)-1H-indazole-5-carboxylic acid [(2R)-tetrahydrofuran-2-ylmethyl]amide MS (ESI) m/z 358 MH$^+$

Example II-234

7-Fluoro-3-(3-fluorophenyl)-1H-indazole-5-carboxylic acid [(2S)-tetrahydrofuran-2-ylmethyl]amide MS (ESI) m/z 358 MH$^+$

Example II-235

7-Fluoro-3-(3-fluorophenyl)-1H-indazole-5-carboxylic acid [(1S)-1-hydroxymethyl-3-methylsulfanylpropyl]amide MS (ESI) m/z 392 MH$^+$

Example II-236

7-Fluoro-3-(3-fluorophenyl)-1H-indazole-5-carboxylic acid (2-hydroxy-1-hydroxymethylethyl)amide MS (ESI) m/z 348 MH$^+$

Example II-237

7-Fluoro-3-(3-fluorophenyl)-1H-indazole-5-carboxylic acid [(1S)-1-hydroxymethyl-3-methylbutyl]amide MS (ESI) m/z 374 MH$^+$

Example II-238

7-Fluoro-3-(3-fluorophenyl)-1H-indazole-5-carboxylic acid [(1S)-2-hydroxy-1-(1H-imidazol-4-ylmethyl)ethyl]amide MS (ESI) m/z 398 MH$^+$

Example II-239

7-Fluoro-3-(3-fluorophenyl)-1H-indazole-5-carboxylic acid [(1S)-1-carbamoylethyl]amide MS (ESI) m/z 345 MH$^+$

Example II-240

7-Fluoro-3-(3-fluorophenyl)-1H-indazole-5-carboxylic acid [(3R)-2-oxo-tetrahydrofuran-3-yl]amide MS (ESI) m/z 358 MH$^+$

Example II-241

7-Fluoro-3-(3-fluorophenyl)-1H-indazole-5-carboxylic acid (furan-2-ylmethyl)amide MS (ESI) m/z 354 MH$^+$

Example II-242

7-Fluoro-3-(3-fluorophenyl)-1H-indazole-5-carboxylic acid (5-methylfuran-2-ylmethyl)amide MS (ESI) m/z 368 MH$^+$

Example II-243

7-Fluoro-3-(3-fluorophenyl)-1H-indazole-5-carboxylic acid (furan-3-ylmethyl)amide MS (ESI) m/z 354 MH$^+$

Example II-244

7-Fluoro-3-(3-fluorophenyl)-1H-indazole-5-carboxylic acid (benzo[b]furan-2-ylmethyl)amide MS (ESI) m/z 404 MH$^+$

Example II-245

7-Fluoro-3-(3-fluorophenyl)-1H-indazole-5-carboxylic acid thiophen-2-ylmethyl)amide MS (ESI) m/z 370 Mm

Example II-246

7-Fluoro-3-(3-fluorophenyl)-1H-indazole-5-carboxylic acid (pyridin-3-ylmethyl)amide MS (ESI) m/z 365 MH$^+$

Example II-247

7-Fluoro-3-naphthalen-2-yl-1H-indazole-5-carboxylic acid cyclopropylamide

MS (ESI) m/z 346 MH$^+$

Example II-248

7-Fluoro-3-naphthalen-2-yl-1H-indazole-5-carboxylic acid cyclopropylmethylamide

MS (ESI) m/z 360 MH$^+$

Example II-249

7-Fluoro-3-naphthalen-2-yl-1H-indazole-5-carboxylic acid (2-methylsulfanylethyl)amide MS (ESI) m/z 380 MH$^+$

Example II-250

7-Fluoro-3-naphthalen-2-yl-1H-indazole-5-carboxylic acid [(1S)-1-hydroxymethyl-2-methylpropyl]amide MS (ESI) m/z 392 MH$^+$

Example II-251

7-Fluoro-3-naphthalen-2-yl-1H-indazole-5-carboxylic acid [(1S)-2-hydroxy-1-phenylethyl]amide MS (ESI) m/z 426 MH$^+$

Example II-252

7-Fluoro-3-naphthalen-2-yl-1H-indazole-5-carboxylic acid [(2R)-tetrahydrofuran-2-ylmethyl]amide MS (ESI) m/z 390 MH$^+$

Example II-253

7-Fluoro-3-naphthalen-2-yl-1H-indazole-5-carboxylic acid [(2S)-tetrahydrofuran-2-ylmethyl]amide MS (ESI) m/z 390 MH$^+$

Example II-254

7-Fluoro-3-naphthalen-2-yl-1H-indazole-5-carboxylic acid [(1S)-1-hydroxymethyl-3-methylsulfanylpropyl]amide MS (ESI) m/z 424 MH$^+$

Example II-255

7-Fluoro-3-naphthalen-2-yl-1H-indazole-5-carboxylic acid (2-hydroxy-1-hydroxymethylethyl)amide MS (ESI) m/z 380 MH$^+$

Example II-256

7-Fluoro-3-naphthalen-2-yl-1H-indazole-5-carboxylic acid [(1S)-1-hydroxymethyl-3-methylbutyl]amide MS (ESI) m/z 406 MH$^+$

Example II-257

7-Fluoro-3-naphthalen-2-yl-1H-indazole-5-carboxylic acid [(1S)-2-hydroxy-1-(1H-imidazol-4-ylmethyl)ethyl]amide MS (ESI) m/z 430 MH$^+$

Example II-258

7-Fluoro-3-naphthalen-2-yl-1H-indazole-5-carboxylic acid [(1S)-1-carbamoylethyl]amide MS (ESI) m/z 377 MH$^+$

Example II-259

7-Fluoro-3-naphthalen-2-yl-1H-indazole-5-carboxylic acid [(3R)-2-oxo-tetrahydrofuran-3-yl]amide MS (ESI) m/z 390 MH$^+$

Example II-260

7-Fluoro-3-naphthalen-2-yl-1H-indazole-5-carboxylic acid (furan-2-ylmethyl)amide MS (ESI) m/z 386 MH$^+$

Example II-261

7-Fluoro-3-naphthalen-2-yl-1H-indazole-5-carboxylic acid (5-methylfuran-2-ylmethyl)amide MS (ESI) m/z 400 MH$^+$

Example II-262

7-Fluoro-3-naphthalen-2-yl-1H-indazole-5-carboxylic acid (furan-3-ylmethyl)amide MS (ESI) m/z 386 MH$^+$

Example II-263

7-Fluoro-3-naphthalen-2-yl-1H-indazole-5-carboxylic acid (benzo[b]furan-2-ylmethyl)amide MS (ESI) m/z 436 MH$^+$

Example II-264

7-Fluoro-3-naphthalen-2-yl-1H-indazole-5-carboxylic acid (thiophen-2-ylmethyl)-amide MS (ESI) m/z 402 MH$^+$

Example II-265

7-Fluoro-3-naphthalen-2-yl-1H-indazole-5-carboxylic acid (pyridin-3-ylmethyl)amide MS (ESI) m/z 397 MH$^+$ The compounds according to Examples II-266 and II-267 were synthesized by Synthesis Process II-D using the amines produced in Production Examples II-33 and II-34, respectively.

Example II-266

N-(3-Benzo[b]thiophen-2-yl-4-fluoro-1H-indazol-5-yl)-methanesulfonamide

MS (ESI) m/z 362 MH$^+$

Example II-267

N-(4-Fluoro-3-naphthalen-2-yl-1H-indazol-5-yl)-methanesulfonamide

MS (ESI) m/z 356 MH$^+$

The compounds according to Examples II-268 to II-278 were synthesized by Synthesis Process II-B using the amines produced in Production Examples II-33 and II-34, respectively.

Example II-268

Cyclopropanecarboxylic acid (3-benzo[b]thiophen-2-yl-4-fluoro-1H-indazol-5-yl)-amide
MS (ESI) m/z 352 MH$^+$

Example II-269

(2S)-5-Oxo-pyrrolidine-2-carboxylic acid (3-benzo[b]thiophen-2-yl-4-fluoro-1H-indazol-5-yl)-amide MS (ESI) m/z 395 MH$^+$

Example II-270

Tetrahydrofuran-2-carboxylic acid (3-benzo[b]thiophen-2-yl-4-fluoro-1H-indazol-5-yl)-amide MS (ESI) m/z 382 MH$^+$

Example II-271

Furan-2-carboxylic acid (3-benzo[b]thiophen-2-yl-4-fluoro-1H-indazol-5-yl)-amide MS (ESI) m/z 378 MH$^+$

Example II-272

N-(3-Benzo[b]thiophen-2-yl-4-fluoro-1H-indazol-5-yl)-2-thiophen-2-yl-acetamide

MS (ESI) m/z 408 MH$^+$

Example II-273

Thiophene-2-carboxylic acid (3-benzo[b]thiophen-2-yl-4-fluoro-1H-indazol-5-yl)-amide MS (ESI) m/z 394 MH$^+$

Example II-274

Cyclopropanecarboxylic acid (4-fluoro-3-naphthalen-2-yl-1H-indazol-5-yl)-amide

MS (ESI) m/z 346 MH$^+$

Example II-275

(2S)-5-Oxo-pyrrolidine-2-carboxylic acid (4-fluoro-3-naphthalen-2-yl-1H-indazol-5-yl)-amide MS (ESI) m/z 389 MH$^+$

Example II-276

Tetrahydrofuran-2-carboxylic acid (4-fluoro-3-naphthalen-2-yl-1H-indazol-5-yl)-amide MS (ESI) m/z 376 MH$^+$

Example II-277

Furan-2-carboxylic acid (4-fluoro-3-naphthalen-2-yl-1H-indazol-5-yl)-amide

MS (ESI) m/z 372 MH$^+$

Example II-278

N-(4-Fluoro-3-naphthalen-2-yl-1H-indazol-5-yl)-2-thiophen-2-yl-acetamide

MS (ESI) m/z 402 MH$^+$

The compounds according to Examples II-279 to II-282 were synthesized by Synthesis Process II-A using the carboxylic acid produced in Production Example II-35.

Example II-279

3-Benzo[b]furan-2-yl-4-propoxy-1H-indazole-5-carboxylic acid cyclopropylamide

MS (ESI) m/z 376 MH$^+$

Example II-280

3-Benzo[b]furan-2-yl-4-propoxy-1H-indazole-5-carboxylic acid (furan-2-ylmethyl)amide MS (ESI) m/z 416 MH$^+$

Example II-281

3-Benzo[b]furan-2-yl-4-propoxy-1H-indazole-5-carboxylic acid ((1S)-1-hydroxymethyl-2-methyl-propyl)-amide MS (ESI) m/z 422 MH$^+$

Example II-282

3-Benzo[b]furan-2-yl-4-propoxy-1H-indazole-5-carboxylic acid ((1S)-2-hydroxy-1-phenyl-ethyl)-amide MS (ESI) m/z 456 MH$^+$ The compounds according to Examples II-283 to II-315 were synthesized by Synthesis Process II-B using the amines produced in Production Examples II-36 through II-39, respectively.

Example II-283

N-[7-Fluoro-3-(3-fluorophenyl)-1H-indazol-5-yl]acetamide

MS (ESI) m/z 288 MH$^+$

Example II-284

(2R)-5-Oxo-pyrrolidine-2-carboxylic acid [7-fluoro-3-(3-fluorophenyl)-1H-indazol-5-yl]amide MS (ESI) m/z 357 MH$^+$

Example II-285

(2S)-5-Oxo-pyrrolidine-2-carboxylic acid [7-fluoro-3-(3-fluorophenyl)-1H-indazol-5-yl]amide MS (ESI) m/z 357 MH$^+$

Example II-286

Tetrahydrofuran-3-carboxylic acid [7-fluoro-3-(3-fluorophenyl)-1H-indazol-5-yl]amide MS (ESI) m/z 344 MH$^+$

Example II-287

Tetrahydrofuran-2-carboxylic acid [7-fluoro-3-(3-fluorophenyl)-1H-indazol-5-yl]amide MS (ESI) m/z 344 MH$^+$

Example II-288

N-[7-Fluoro-3-(3-fluorophenyl)-1H-indazol-5-yl]-2-thiophen-3-ylacetamide

MS (ESI) m/z 370 MH$^+$

Example II-289

N-[7-Fluoro-3-(3-fluorophenyl)-1H-indazol-5-yl]-2-thiophen-2-ylacetamide

MS (ESI) m/z 370 MH$^+$

Example II-290

N-(7-Fluoro-3-naphthalen-2-yl-1H-indazol-5-yl)acetamide

MS (ESI) m/z 320 MH$^+$

Example II-291

Cyclopropylcarboxylic acid (7-fluoro-3-naphthalen-2-yl-1H-indazol-5-yl)amide

MS (ESI) m/z 346 MH$^+$

Example II-292

(2R)-5-Oxo-pyrrolidine-2-carboxylic acid (7-fluoro-3-naphthalen-2-yl-1H-indazol-5-yl)amide MS (ESI) m/z 389 MH$^+$

Example II-293

(2S)-5-Oxo-pyrrolidine-2-carboxylic acid (7-fluoro-3-naphthalen-2-yl-1H-indazol-5-yl)amide MS (ESI) m/z 389 MH$^+$

Example II-294

Tetrahydrofuran-3-carboxylic acid (7-fluoro-3-naphthalen-2-yl-1H-indazol-5-yl)amide MS (ESI) m/z 376 MH$^+$

Example II-295

Tetrahydrofuran-2-carboxylic acid (7-fluoro-3-naphthalen-2-yl-1H-indazol-5-yl)amide MS (ESI) m/z 376 MH$^+$

Example II-296

N-(7-Fluoro-3-naphthalen-2-yl-1H-indazol-5-yl)-2-thiophen-3-ylacetamide

MS (ESI) m/z 402 MH$^+$

Example II-297

N-(7-Fluoro-3-naphthalen-2-yl-1H-indazol-5-yl)-2-thiophen-2-ylacetamide

MS (ESI) m/z 402 MH$^+$

Example II-298

N-(4-Methoxy-3-naphthalen-2-yl-1H-indazol-5-yl)-acetamide

MS (ESI) m/z 332 MH$^+$

Example II-299

Cyclopropanecarboxylic acid (4-methoxy-3-naphthalen-2-yl-1H-indazol-5-yl)-amide

MS (ESI) m/z 358 MH$^+$

Example II-300

(2R)-5-Oxo-pyrrolidine-2-carboxylic acid (4-methoxy-3-naphthalen-2-yl-1H-indazol-5-yl)-amide MS (ESI) m/z 401 MH$^+$

Example II-301

(2S)-5-Oxo-pyrrolidine-2-carboxylic acid (4-methoxy-3-naphthalen-2-yl-1H-indazol-5-yl)-amide MS (ESI) m/z 401 MH$^+$

Example II-302

Furan-2-carboxylic acid (4-methoxy-3-naphthalen-2-yl-1H-indazol-5-yl)-amide

MS (ESI) m/z 384 MH$^+$

Example II-303

Thiophene-2-carboxylic acid (4-methoxy-3-naphthalen-2-yl-1H-indazol-5-yl)-amide

MS (ESI) m/z 400 M$^+$

Example II-304

N-(4-Methoxy-3-naphthalen-2-yl-1H-indazol-5-yl)-2-thiophen-2-yl-acetamide

MS (ESI) m/z 414 MH+

Example II-305

3-Methoxy-N-(4-methoxy-3-naphthalen-2-yl-1H-indazol-5-yl)propionamide

MS (ESI) m/z 376 MH+

Example II-306

3-Dimethylamino-N-(4-methoxy-3-naphthalen-2-yl-1H-indazol-5-yl)propionamide

MS (ESI) m/z 389 MH+

Example II-307

N-(3-Benzo[b]thiophen-2-yl-4-methoxy-1H-indazol-5-yl)-acetamide

MS (ESI) m/z 338 MH+

Example II-308

Cyclopropanecarboxylic acid (3-benzo[b]thiophen-2-yl-4-methoxy-1H-indazol-5-yl)-amide MS (ESI) m/z 364 MH+

Example II-309

(2R)-5-Oxo-pyrrolidine-2-carboxylic acid (3-benzo[b]thiophen-2-yl-4-methoxy-1H-indazol-5-yl)-amide MS (ESI) m/z 407 MH+

Example II-310

(2S)-5-Oxo-pyrrolidine-2-carboxylic acid (3-benzo[b]thiophen-2-yl-4-methoxy-1H-indazol-5-yl)-amide MS (ESI) m/z 407 MH+

Example II-311

Furan-2-carboxylic acid (3-benzo[b]thiophen-2-yl-4-methoxy-1H-indazol-5-yl)-amide MS (ESI) m/z 390 MH+

Example II-312

Thiophene-2-carboxylic acid (3-benzo[b]thiophen-2-yl-4-methoxy-1H-indazol-5-yl)-amide MS (ESI) m/z 406 M+

Example II-313

N-(3-Benzo[b]thiophen-2-yl-4-methoxy-1H-indazol-5-yl)-2-thiophen-2-yl-acetamide

MS (ESI) m/z 420 MH+

Example II-314

N-(3-Benzo[b]thiophen-2-yl-4-methoxy-1H-indazol-5-yl)-3-methoxy-propionamide

MS (ESI) m/z 382 MH+

Example II-315

N-(3-Benzo[b]thiophen-2-yl-4-methoxy-1H-indazol-5-yl)-3-dimethylamino-propionamide MS (ESI) m/z 395 MH+

The compounds according to Examples II-316 to II-319 were synthesized by Synthesis Process II-C using the amine produced in Production Example II-40.

Example II-316

N-(7-Fluoro-3-naphthalen-2-yl-1H-indazol-5-ylmethyl)-3-methoxybenzamide

MS (ESI) m/z 426 MH+

Example II-317

N-(7-Fluoro-3-naphthalen-2-yl-1H-indazol-5-ylmethyl)-2-methoxybenzamide

MS (ESI) m/z 426 MH+

Example II-318

3-Cyano-N-(7-fluoro-3-naphthalen-2-yl-1H-indazol-5-ylmethyl)benzamide

MS (ESI) m/z 421 MH+

Example II-319

3-Fluoro-N-(7-fluoro-3-naphthalen-2-yl-1H-indazol-5-ylmethyl)benzamide

MS (ESI) m/z 414 MH+

The compounds according to Examples II-320 to II-323 were synthesized by Synthesis Process II-D using the amines produced in Production Examples II-36 through II-39, respectively.

Example II-320

N-[7-Fluoro-3-(3-fluorophenyl)-1H-indazol-5-yl]methanesulfonamide

MS (ESI) m/z 324 MH+

Example II-321

N-(7-Fluoro-3-naphthalen-2-yl-1H-indazol-5-yl)methanesulfonamide

MS (ESI) m/z 356 MH+

Example II-322

N-(4-Methoxy-3-naphthalen-2-yl-1H-indazol-5-yl)-methanesulfonamide

MS (ESI) m/z 368 MH+

Example II-323

N-(3-Benzo[b]thiophen-2-yl-4-methoxy-1H-indazol-5-yl)-methanesulfonamide

MS (ESI) m/z 374 MH+

The compounds according to Examples II-324 to II-340 were synthesized by Synthesis Process II-A using the carboxylic acids produced in Production Examples II-41 and II-42, respectively.

Example II-324

6-Methoxy-3-naphthalen-2-yl-1H-indazole-5-carboxylic acid cyclopropylamide

MS (ESI) m/z 358 MH+

Example II-325

6-Methoxy-3-naphthalen-2-yl-1H-indazole-5-carboxylic acid [(3R)-2-oxo-tetrahydro-furan-3-yl]-amide MS (ESI) m/z 402 MH+

Example II-326

6-Methoxy-3-naphthalen-2-yl-1H-indazole-5-carboxylic acid (furan-2-ylmethyl)-amide MS (ESI) m/z 398 MH+

Example II-327

6-Methoxy-3-naphthalen-2-yl-1H-indazole-5-carboxylic acid [(1S)-2-hydroxy-1-phenyl-ethyl]-amide MS (ESI) m/z 438 MH+

Example II-328

6-Methoxy-3-naphthalen-2-yl-1H-indazole-5-carboxylic acid [(1S)-1-hydroxymethyl-2-methyl-propyl]-amide MS (ESI) m/z 404 MH+

Example II-329

6-Methoxy-3-naphthalen-2-yl-1H-indazole-5-carboxylic acid cyclopropylmethylamide MS (ESI) m/z 372 MH+

Example II-330

6-Methoxy-3-naphthalen-2-yl-1H-indazole-5-carboxylic acid (thiophen-2-ylmethyl)-amide MS (ESI) m/z 414 M+

Example II-331

6-Methoxy-3-naphthalen-2-yl-1H-indazole-5-carboxylic acid [(1S)-1-carbamoyl-ethyl]-amide MS (ESI) m/z 389 MH+

Example II-332

6-Methoxy-3-naphthalen-2-yl-1H-indazole-5-carboxylic acid (tetrahydrofuran-2-ylmethyl)-amide MS (ESI) m/z 402 MH+

Example II-333

3-Benzo[b]thiophen-2-yl-6-methoxy-1H-indazole-5-carboxylic acid cyclopropylamide MS (ESI) m/z 364 MH+

Example II-334

3-Benzo[b]thiophen-2-yl-6-methoxy-1H-indazole-5-carboxylic acid [(3R)-2-oxo-tetrahydro-furan-3-yl]-amide MS (ESI) m/z 408 MH+

Example II-335

3-Benzo[b]thiophen-2-yl-6-methoxy-1H-indazole-5-carboxylic acid (furan-2-ylmethyl)-amide MS (ESI) m/z 404 MH+

Example II-336

3-Benzo[b]thiophen-2-yl-6-methoxy-1H-indazole-5-carboxylic acid [(1S)-2-hydroxy-1-phenyl-ethyl]-amide MS (ESI) m/z 444 MH+

Example II-337

3-Benzo[b]thiophen-2-yl-6-methoxy-1H-indazole-5-carboxylic acid [(1S)-1-hydroxymethyl-2-methyl-propyl]-amide MS (ESI) m/z 410 MH+

Example II-338

3-Benzo[b]thiophen-2-yl-6-methoxy-1H-indazole-5-carboxylic acid cyclopropylmethyl-amide MS (ESI) m/z 378 MH+

Example II-339

3-Benzo[b]thiophen-2-yl-6-methoxy-1H-indazole-5-carboxylic acid (thiophen-2-ylmethyl)-amide MS (ESI) m/z 420 MH+

Example II-340

3-Benzo[b]thiophen-2-yl-6-methoxy-1H-indazole-5-carboxylic acid (tetrahydrofuran-2-ylmethyl)-amide MS (ESI) m/z 408 MH+

The compounds according to Examples II-341 to II-344 were synthesized by Synthesis Process II-B using the amine produced in Production Example II-43.

Example II-341

Cyclopropanecarboxylic acid (3-benzo[b]furan-2-yl-4-fluoro-1H-indazole-5-yl)-amide MS (ESI) m/z 336 MH+

Example II-342

(2S)-5-Oxo-pyrrolidine-2-carboxylic acid (3-benzo[b]furan-2-yl-4-fluoro-1H-indazole-5-yl)-amide MS (ESI) m/z 379 MH+

Example II-343

Furan-2-carboxylic acid (3-benzo[b]furan-2-yl-4-fluoro-1H-indazole-5-yl)-amide

MS (ESI) m/z 362 MH+

Example II-344

N-(3-Benzo[b]furan-2-yl-4-fluoro-1H-indazole-5-yl)-2-thiophen-2-yl-acetamide

MS (ESI) m/z 392 MH+

The compounds (I) according to the present invention or a salt thereof exhibited an excellent action in tests for determining JNK inhibitory action. For example, the inhibitory actions on JNK 3 were as follows.

Test Example 1 Determination of JNK 3 Inhibition

Human JNK 3 was expressed as a fusion protein (GST-JNK 3) with glutathione S-transferase (GST) in *Escherichia coli* and was purified using glutathione Sepharose 4B beads. The amino acid sequence 1-169 of c-Jun was peppered as a fusion protein (GST-c-Jun) with GST in *Escherichia coli*, was purified using glutathione Sepharose 4B beads and was used as a substrate. A test compound was diluted with 100% dimethyl sulfoxide into 10 mM and was then further diluted with 10% aqueous dimethyl sulfoxide solution to yield a dilution series. To each well of 96-well OPTI plate (available from Packard) were placed 20 μl of the diluted compound, 30 μl of a substrate solution (1.2 μg of GST-c-Jun, 0.04 μg of GST-JNK 3, 0.2 μCi of [γ-$^{33}$P]ATP, 25 mM of HEPES pH=7.5, 10 mM of magnesium acetate, and 3.33 μM of ATP), and 50 μl of an enzyme solution (0.04 μg of GST-JNK 3, 25 mM of HEPES pH=7.5, and 10 mM magnesium acetate) up to 100 μl, and the mixture was allowed to react for 30 minutes. After terminating the reaction by adding 100 μl of a reaction terminator (80 mM ATP, 50 mg/ml glutathione SPA beads (available from Amersham Pharmacia Biotech)), the reaction mixture was shaken for 30 minutes. The mixture was centrifuged at room temperature at 1000×g for 5 minutes, and the emission intensity thereof was determined on a TopCount™ illuminator (available from Packard). The activity is expressed by the 50% inhibitory concentration on the enzymatic activity of JNK, i.e., $IC_{50}$ (nM). Results: The compounds (I) according to the present invention or a salt thereof showed an excellent JNK 3-inhibitory activity. Examples of $IC_{50}$ thereof will be shown below.

| Ex. No. | $IC_{50}$ |
|---|---|
| I-16 | 51 nM |
| I-26 | 113 nM |
| I-48 | 109 nM |
| I-55 | 52 nM |
| I-94 | 163 nM |
| II-5 | 100 nM |
| II-93 | 137 nM |
| II-126 | 143 nM |
| II-184 | 86 nM |
| II-189 | 194 nM |
| I-104 | 55 nM |
| I-132 | 197 nM |
| I-137 | 54 nM |
| I-143 | 221 nM |
| I-163 | 80 nM |
| II-208 | 143 nM |
| II-218 | 215 nM |
| II-259 | 148 nM |
| II-281 | 84 nM |
| II-288 | 71 nM |

The structural formulae of the compounds according to Production examples and Examples will be listed below.

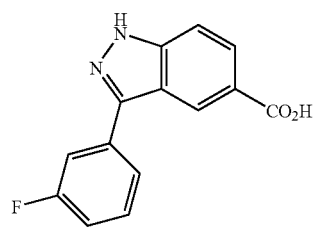

Production Example I-1-c

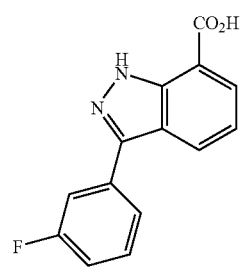

Production Example I-2-b

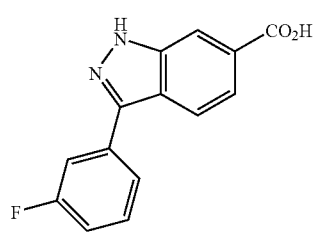

Production Example I-3-d

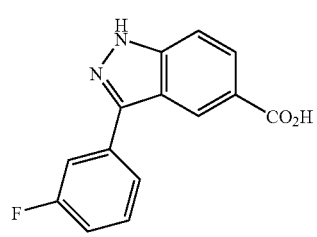

Production Example I-4-f

-continued
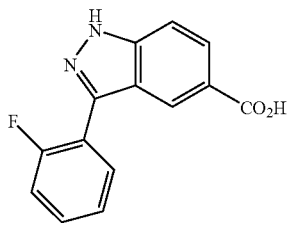
Production Example I-5-b
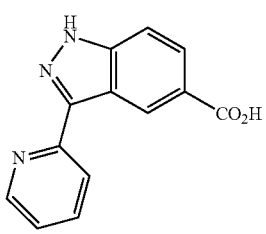
Production Example I-6-b
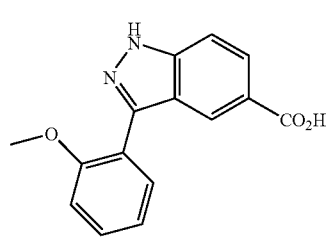
Production Example I-7-b
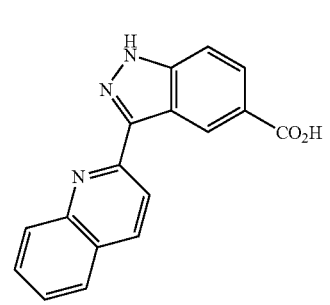
Production Example I-8-b
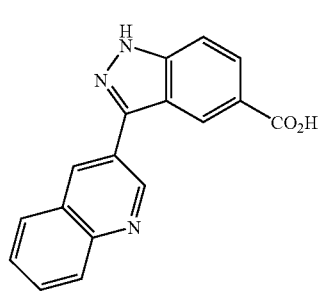
Production Example I-9-b
Production Example I-10-b
-continued
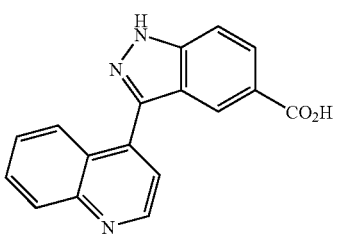
Production Example I-11-b
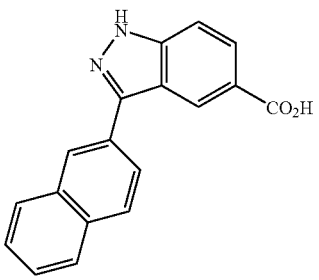
Production Example I-12-b
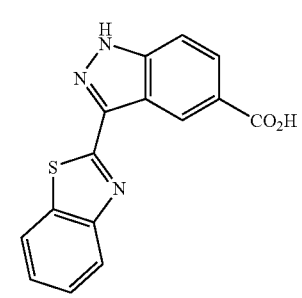
Production Example I-13-d
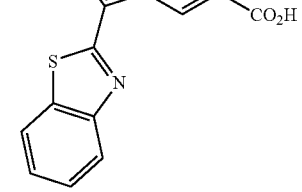
Production Example I-14-d
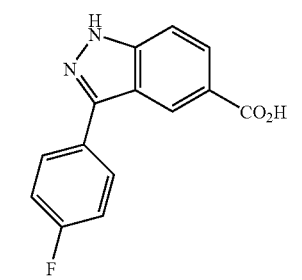
Production Example I-15-b
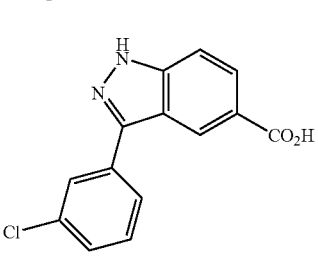
Production Example I-16-b
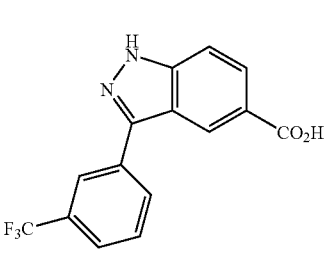

-continued
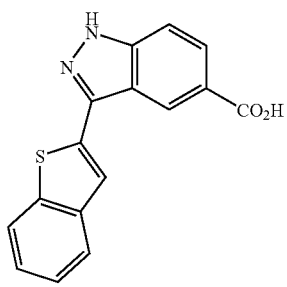
Production Example I-17-b
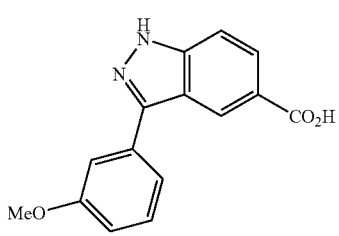
Production Example I-18-b
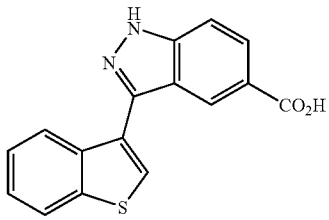
Production Example I-19-b
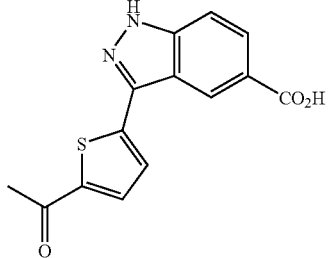
Production Example I-20-b
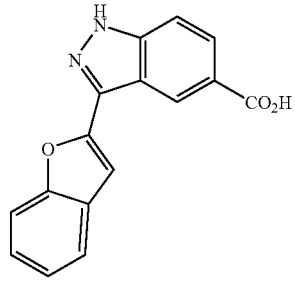
Production Example I-21-e
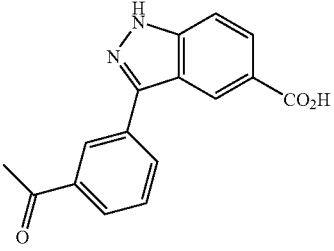
Production Example I-22-b
-continued
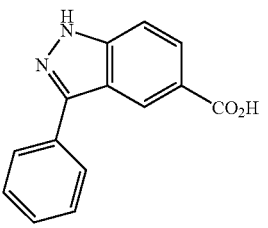
Production Example I-23-b
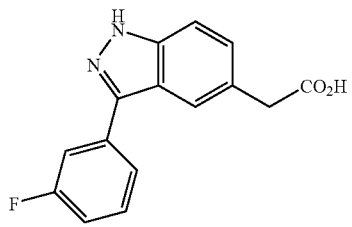
Production Example I-24-d
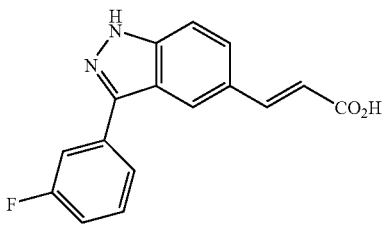
Production Example I-25-c
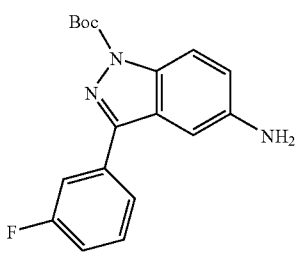
Production Example I-26-d
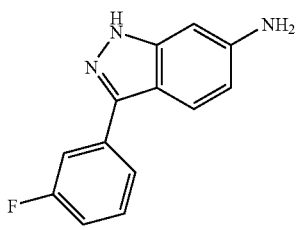
Production Example I-27-c
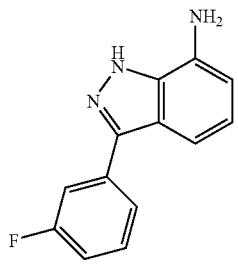
Production Example I-28-b -continued
Production Example I-29-c
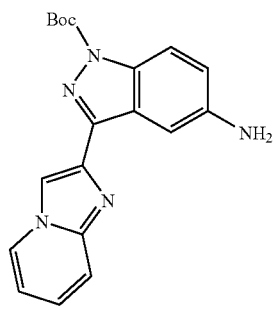
Production Example I-30-c
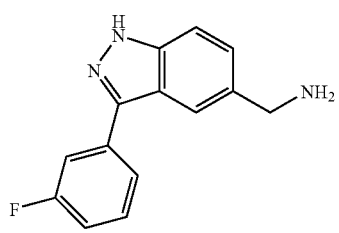
Production Example I-31
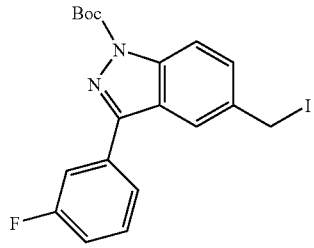
Production Example I-32-c
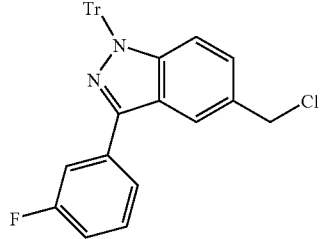
Production Example I-33
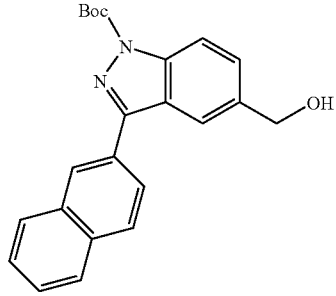
Production Example I-34
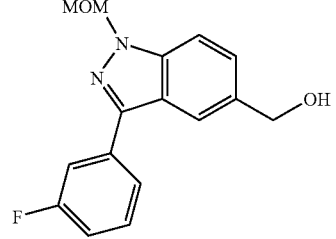
-continued
Production Example I-35-b
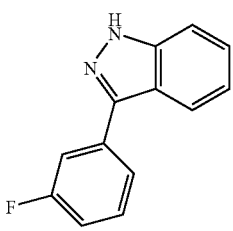
Production Example I-36-g
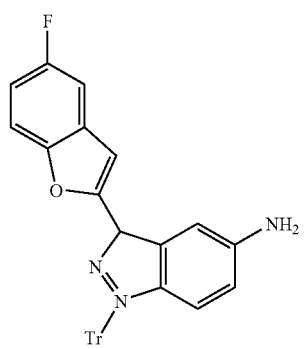
Example I-1
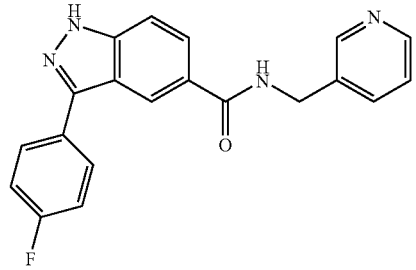
Example I-2
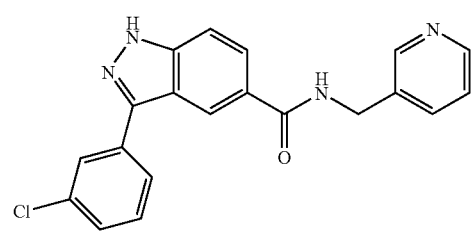
Example I-3
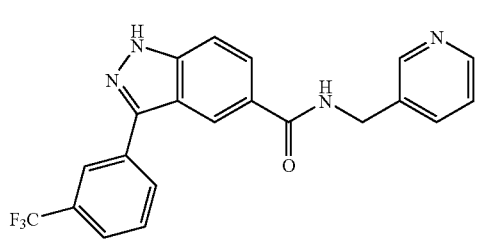
Example I-4
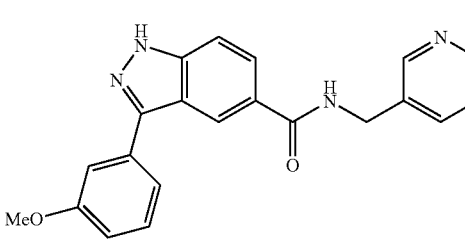

Example I-5
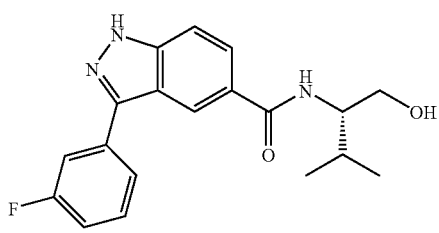
Example I-6
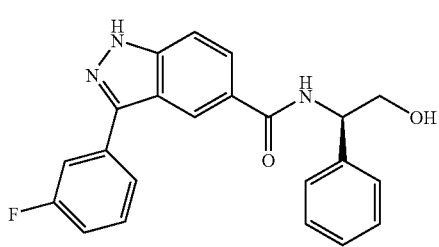
Example I-7
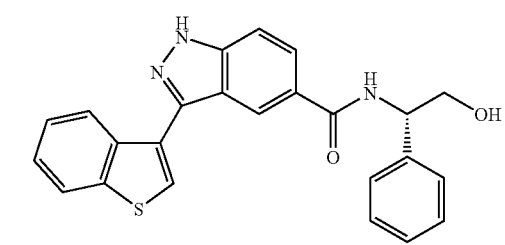
Example I-8
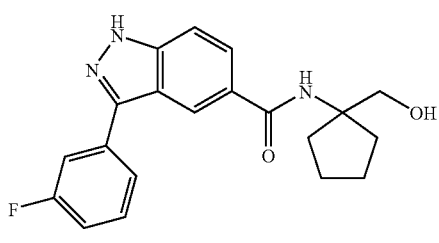
Example I-9
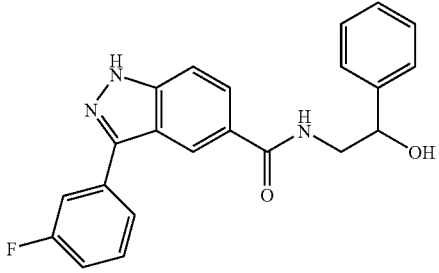
Example I-10
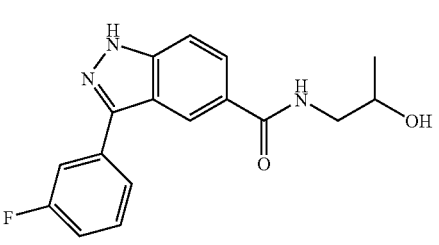
Example I-11
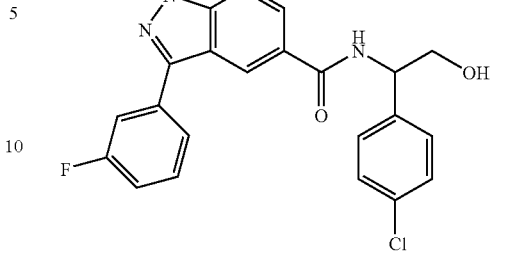
Example I-12
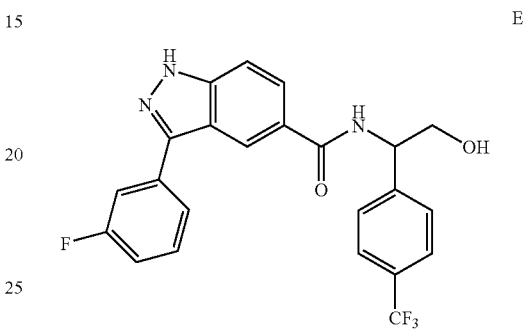
Example I-13
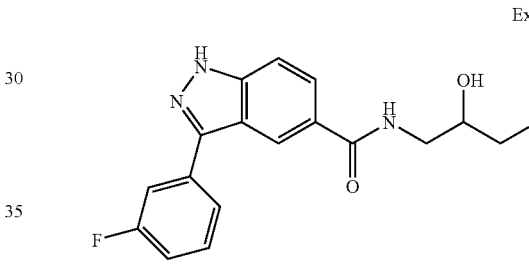
Example I-14
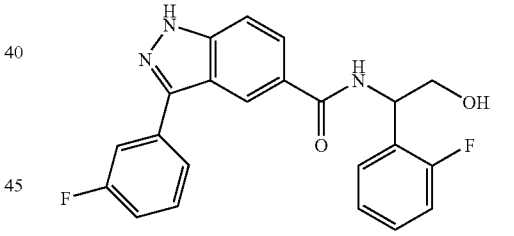
Example I-15
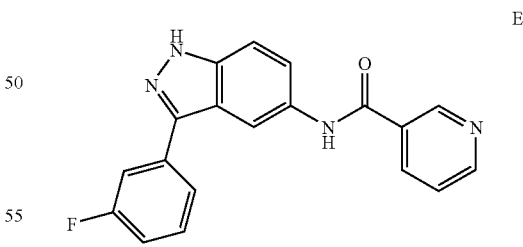
Example I-16
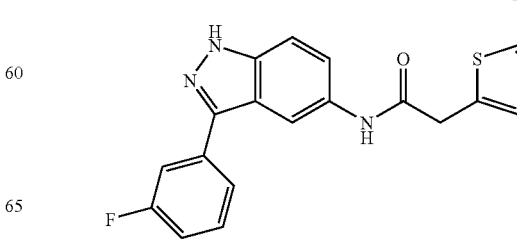

-continued
Example I-17
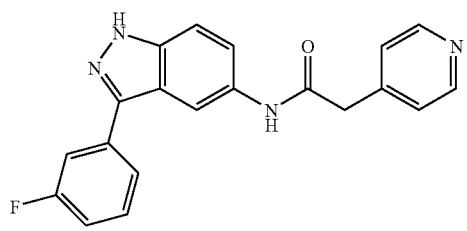
Example I-18
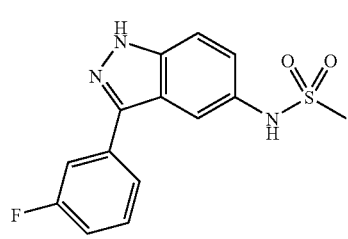
Example I-19
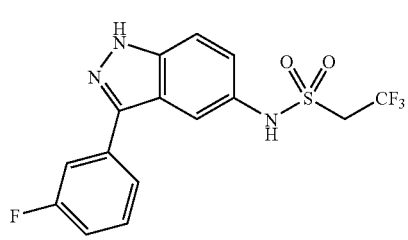
Example I-20
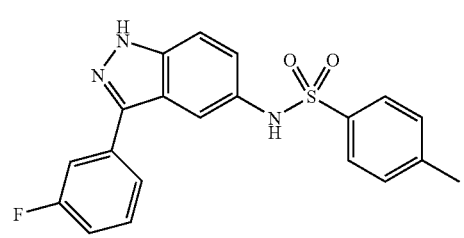
Example I-21
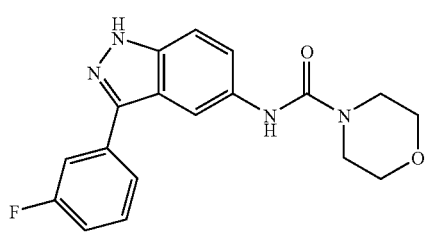
Example I-22
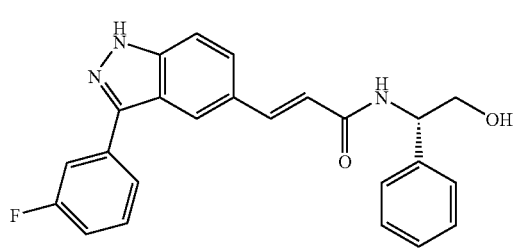
-continued
Example I-23
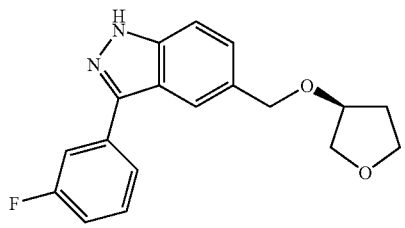
Example I-24
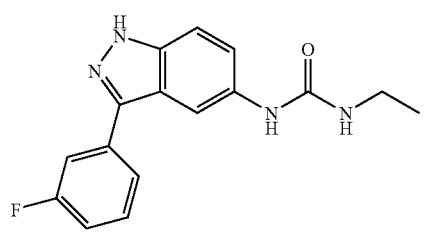
Example I-25
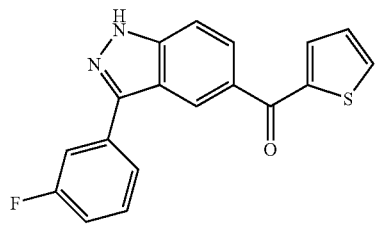
Example I-26
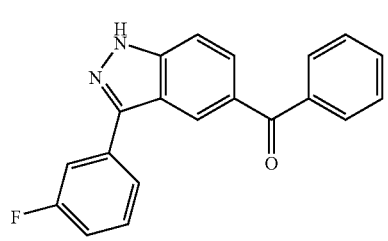
Example I-27
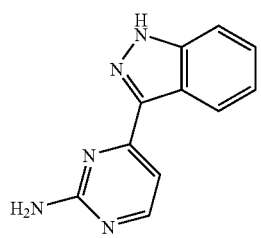
Example I-28
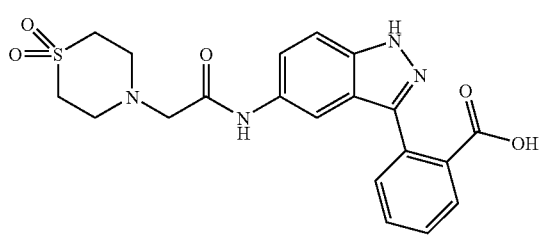

-continued
Example I-29
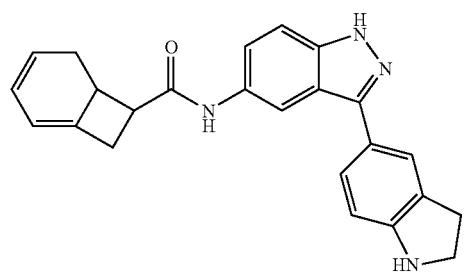
Example I-30
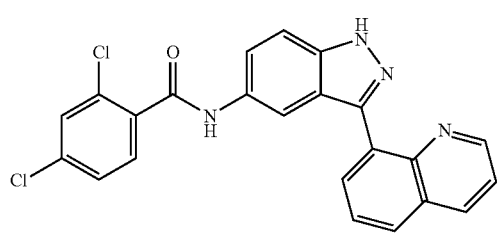
Example I-31
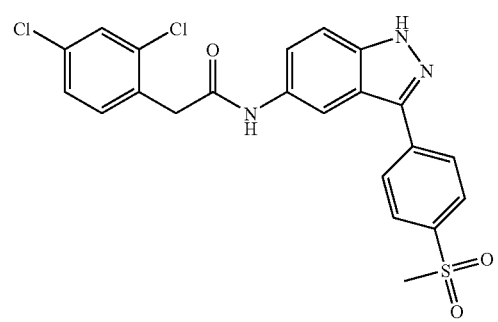
Example I-32
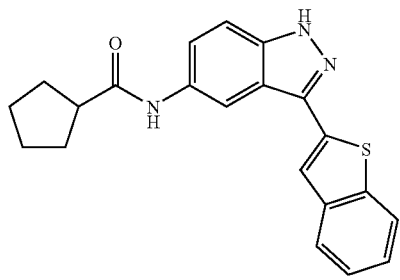
Example I-33
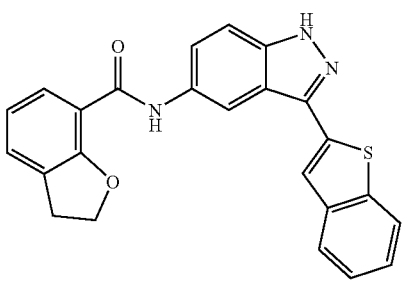
-continued
Example I-34
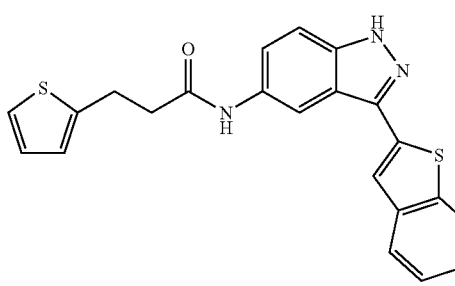
Example I-35
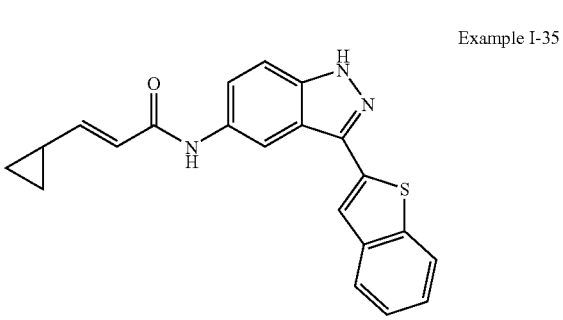
Example I-36
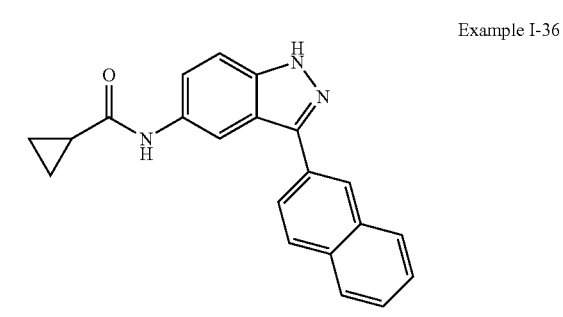
Example I-37
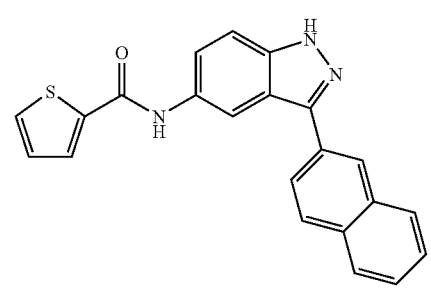
Example I-38
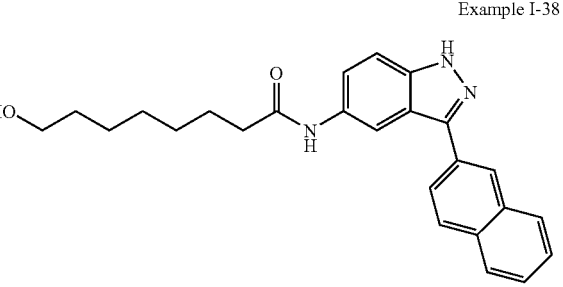

-continued
Example I-39
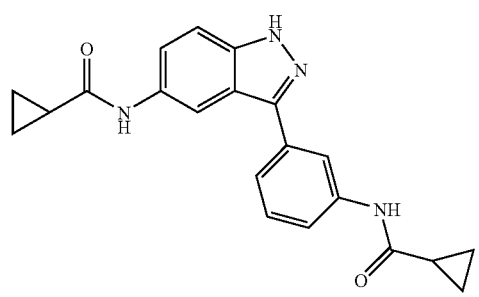
Example I-40
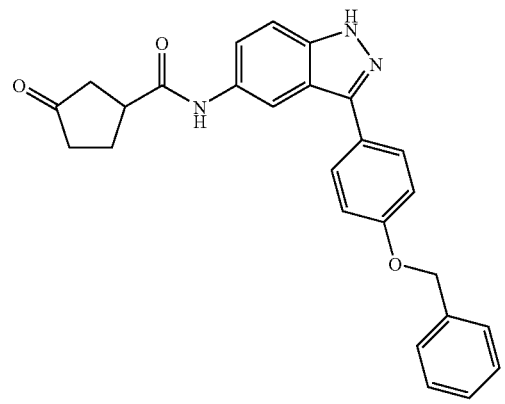
Example I-41
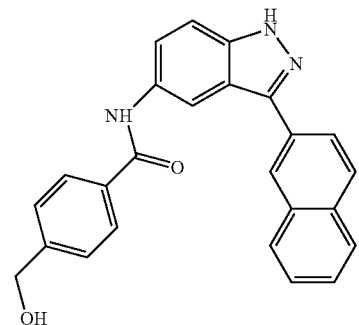
Example I-42
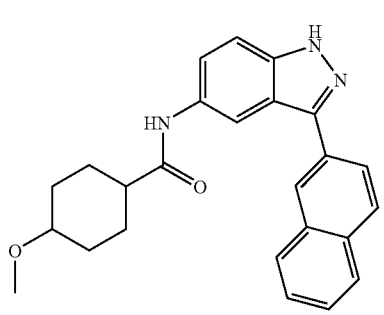
-continued
Example I-43
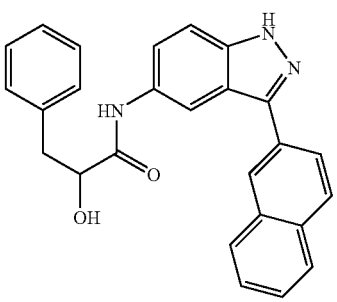
Example I-44
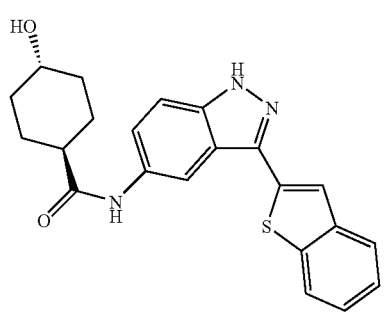
Example I-45
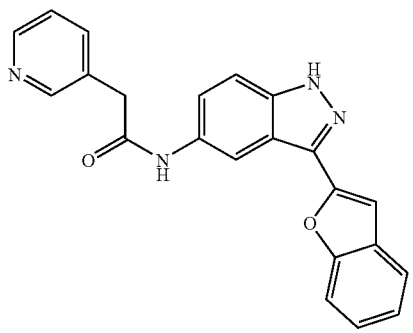
Example I-46
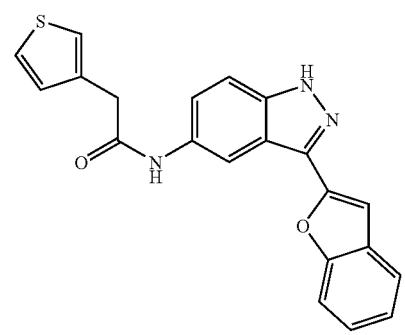
Example I-47
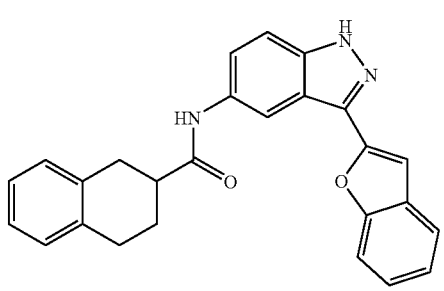

-continued
Example I-49
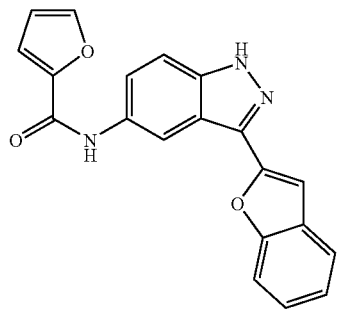
Example I-50
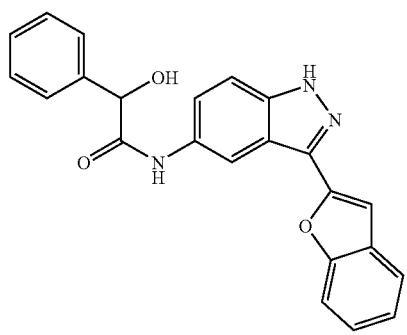
Example I-51
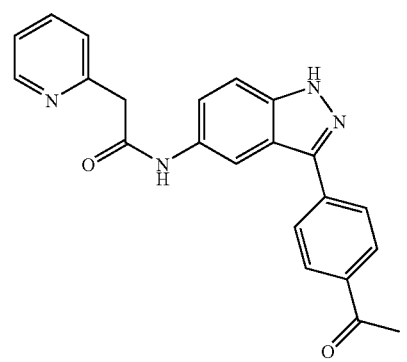
Example I-52
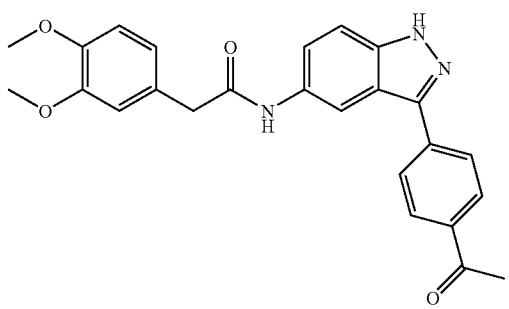
-continued
Example I-53
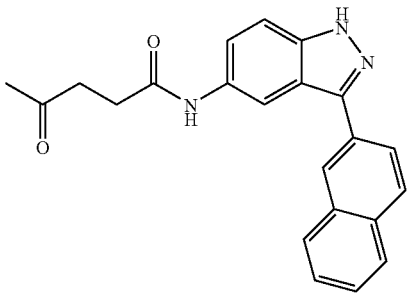
Example I-54
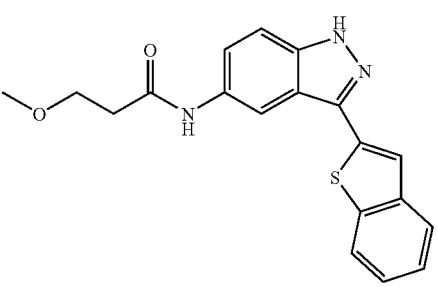
Example I-55
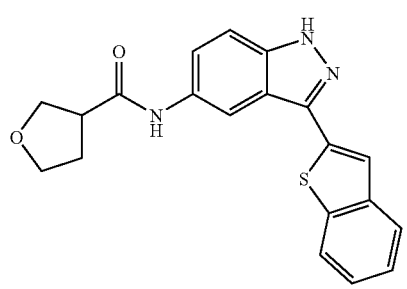
Example I-56
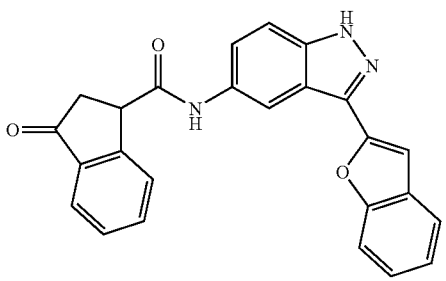
Example I-57
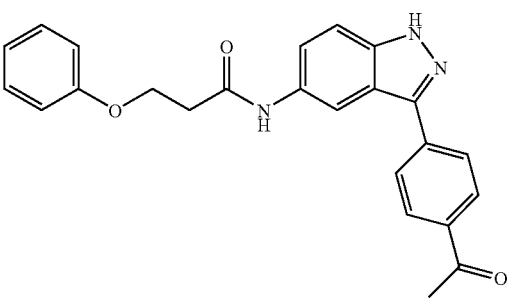

-continued
Example I-58
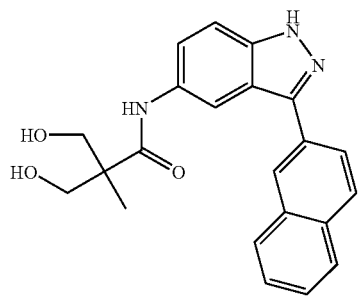
Example I-59
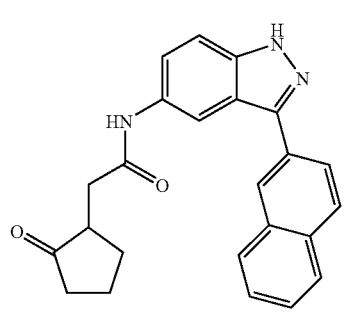
Example I-60
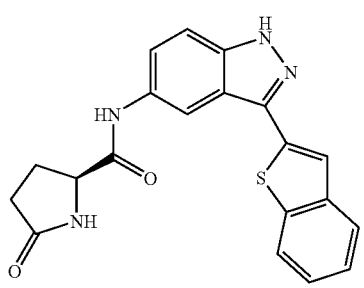
Example I-61
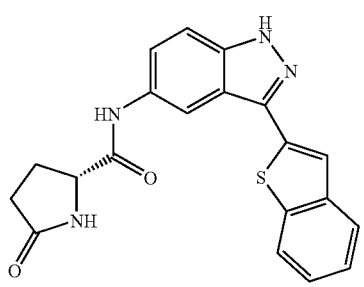
Example I-62
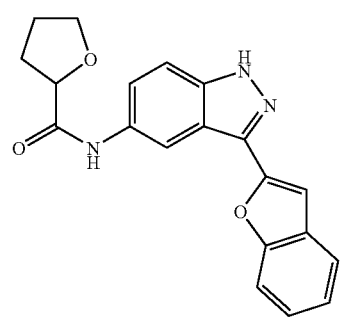
-continued
Example I-63
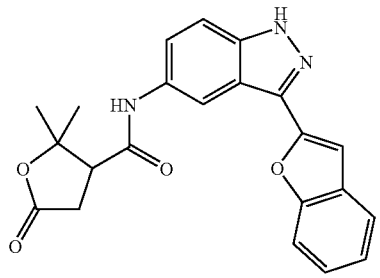
Example I-64
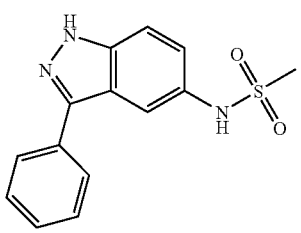
Example I-65
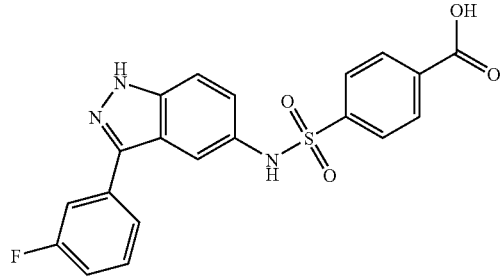
Example I-66
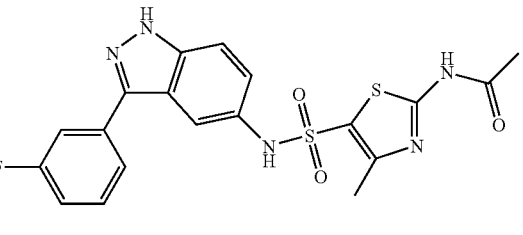
Example I-67
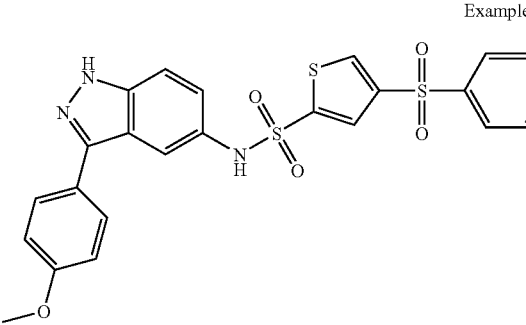

-continued

Example I-68

Example I-69

Example I-70

Example I-71

Example I-72

-continued

Example I-73

Example I-74

Example I-75

Example I-76

Example I-77

-continued

Example I-78

Example I-79

Example I-80

Example I-81

Example I-82

-continued

Example I-83

Example I-84

Example I-85

Example I-86

Example I-87

Example I-88
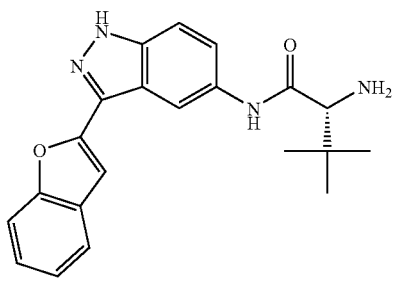
Example I-89
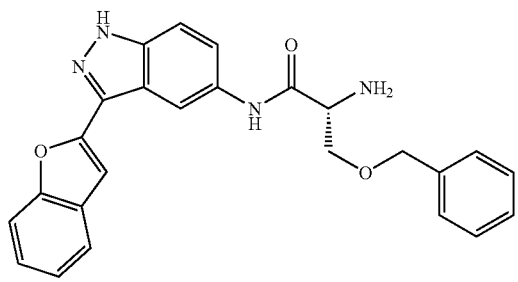
Example I-90
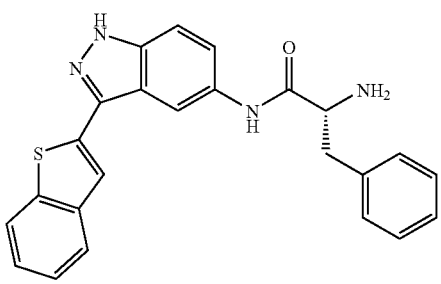
Example I-91
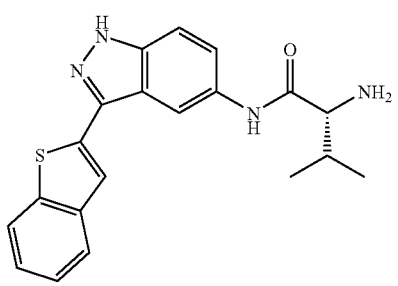
Example I-92
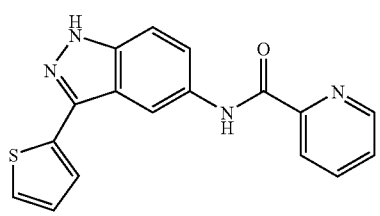
Example I-93
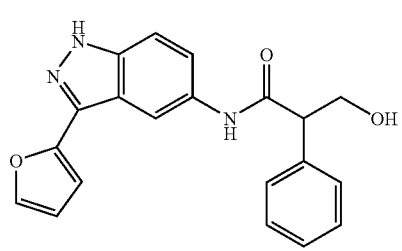
Example I-94
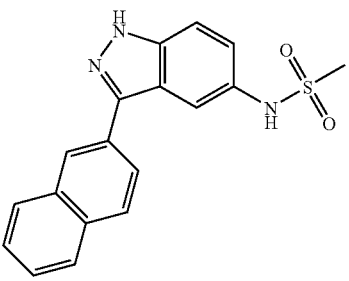
Example I-95
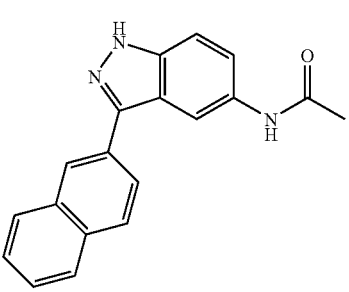
Example I-96
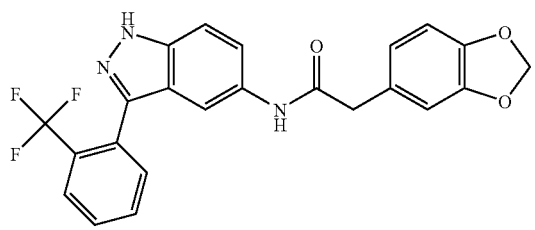
Example I-97
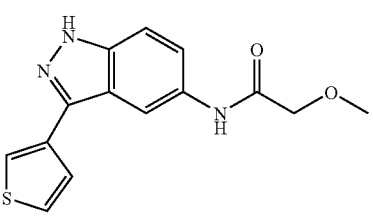
Example I-98
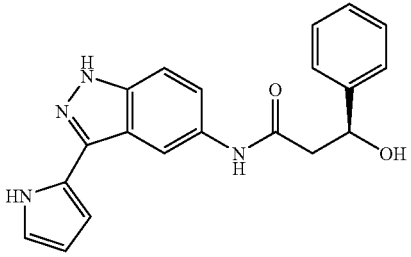
Example I-99
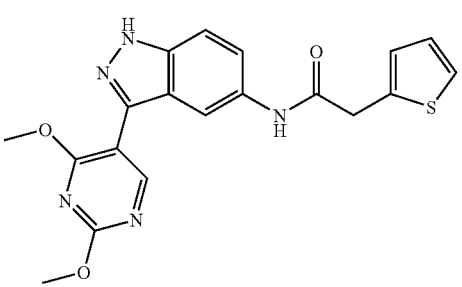

-continued
Example I-100
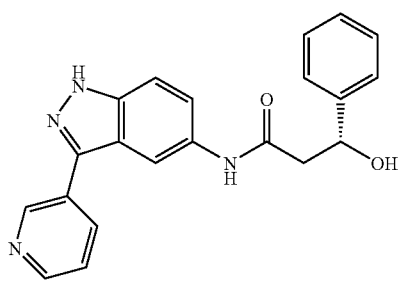
Example I-101
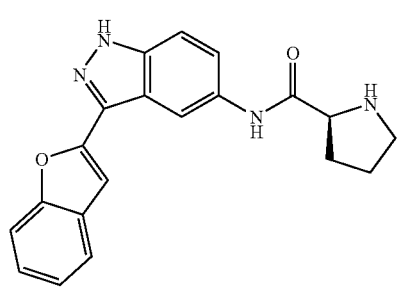
Example I-102
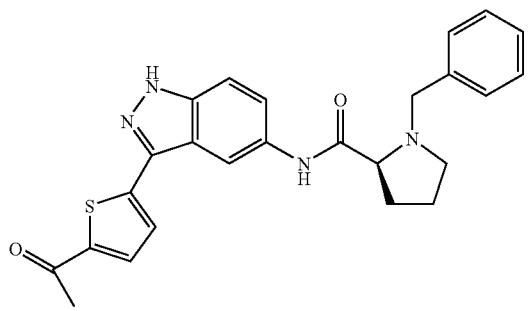
Example I-103
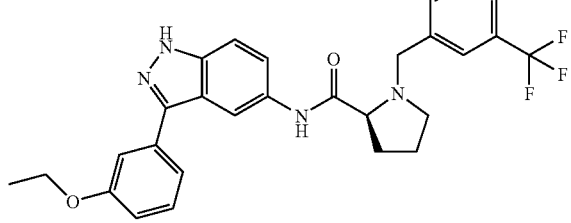
Example I-104
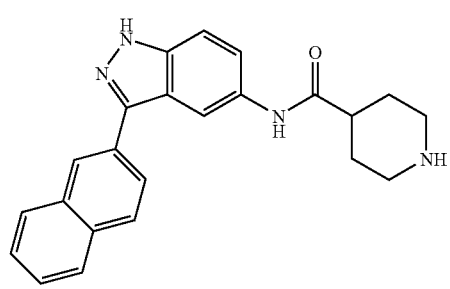
-continued
Example I-105
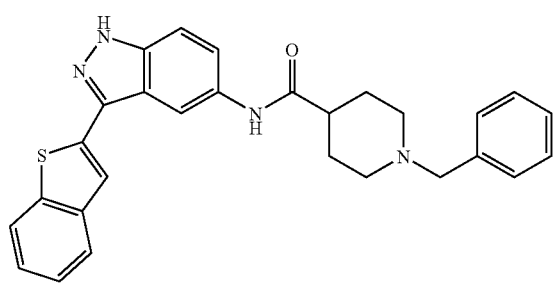
Example I-106
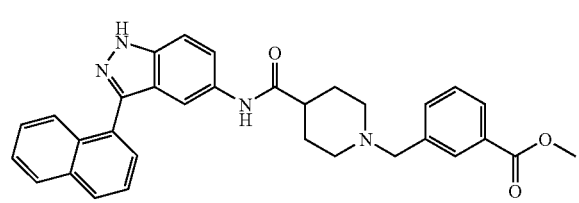
Example I-107
Example I-108
Example I-109
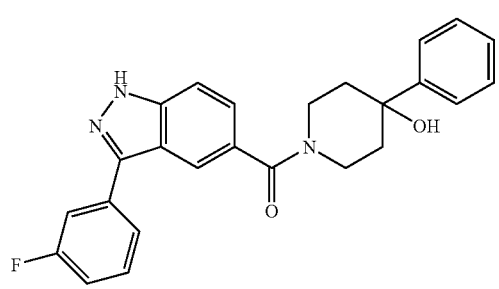
Example I-110

-continued
Example I-111
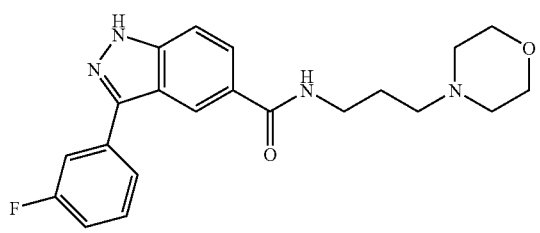
Example I-112
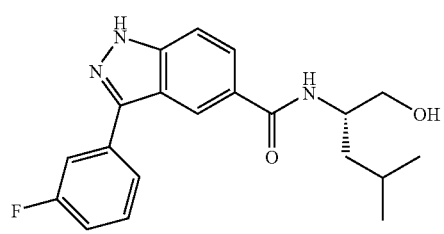
Example I-113
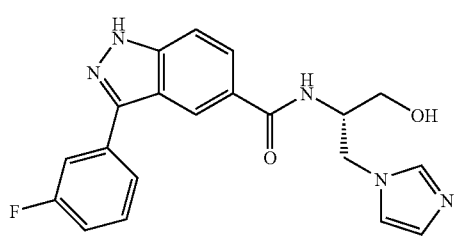
Example I-114
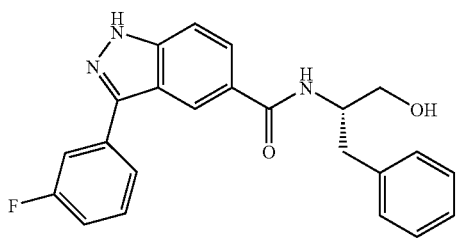
Example I-115
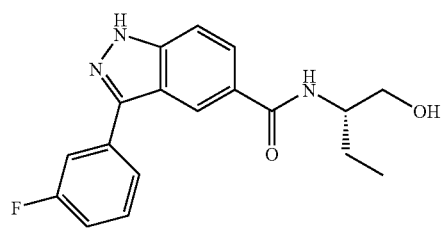
Example I-116
-continued
Example I-117
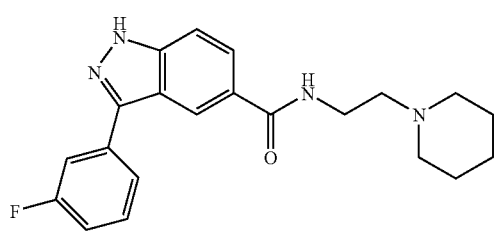
Example I-118
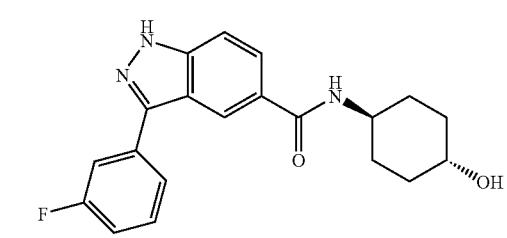
Example I-119
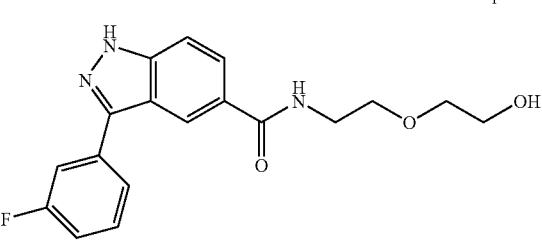
Example I-120
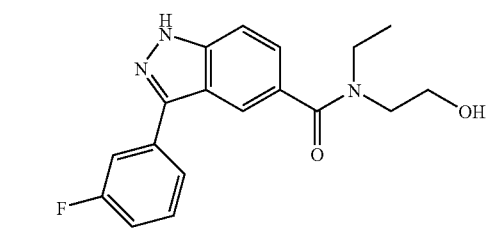
Example I-121
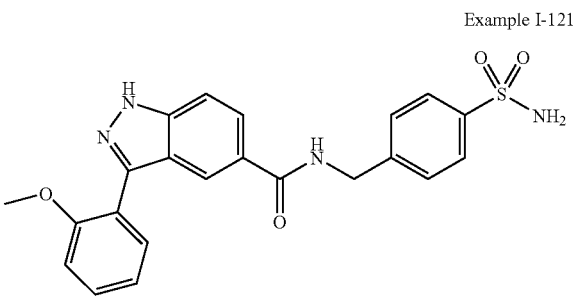
Example I-122
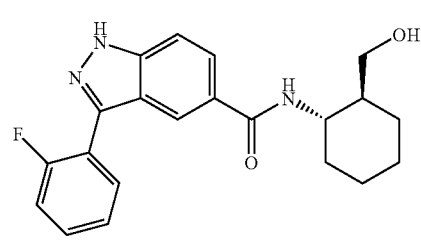

-continued
Example I-123
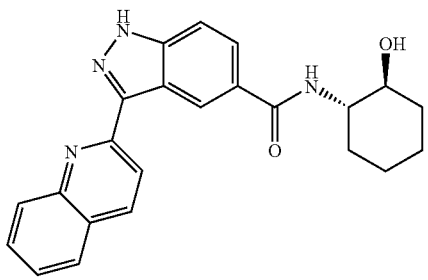
Example I-128
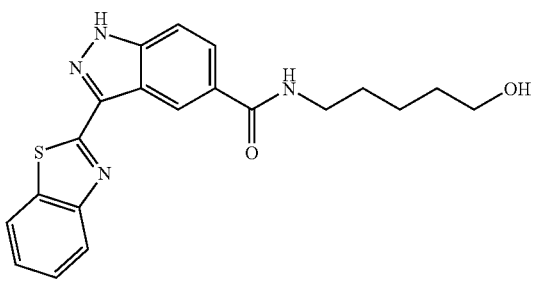
Example I-124
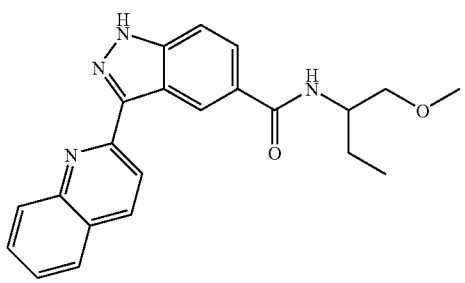
Example I-129
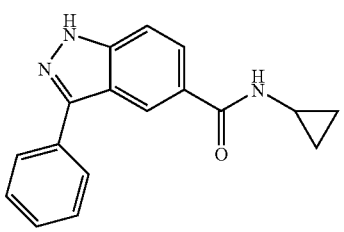
Example I-125
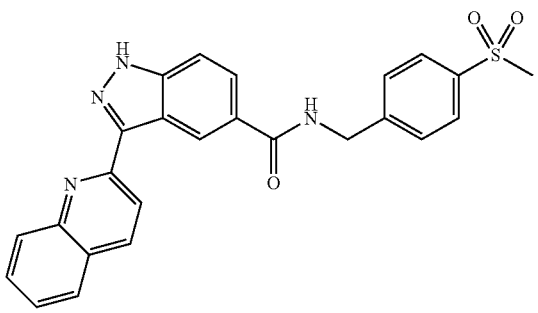
Example I-130
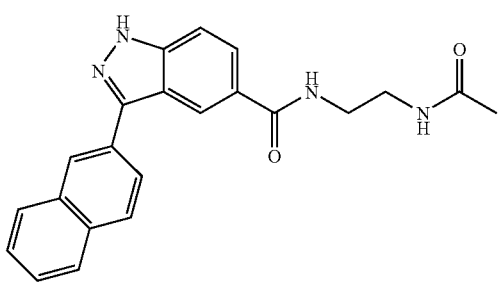
Example I-126
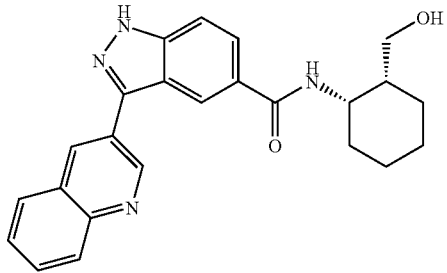
Example I-131
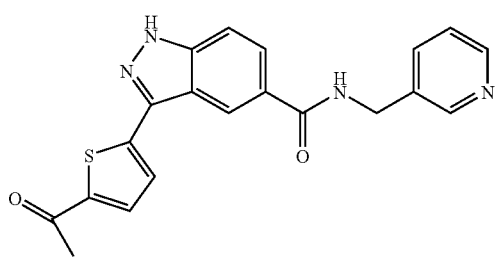
Example I-127
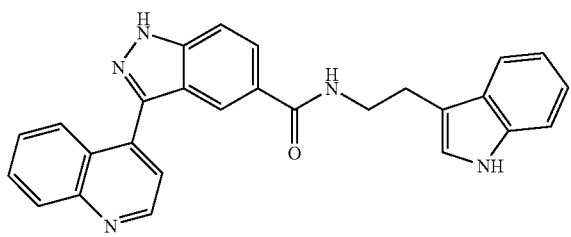
Example I-132
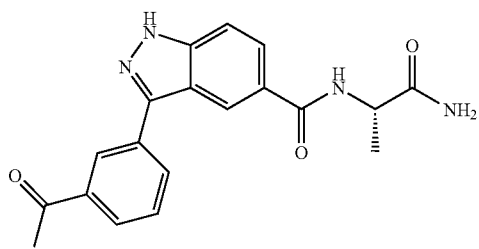

-continued
Example I-133
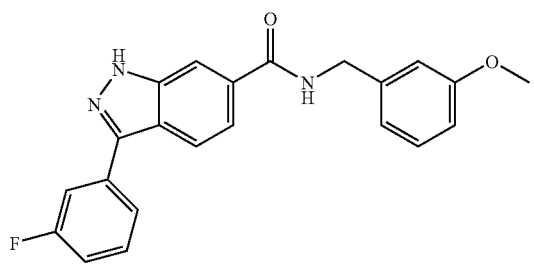
Example I-134
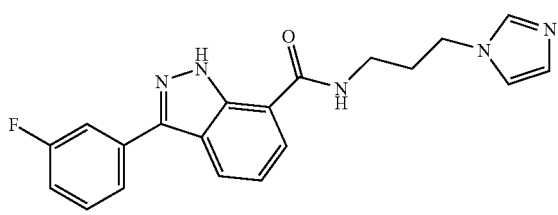
Example I-135
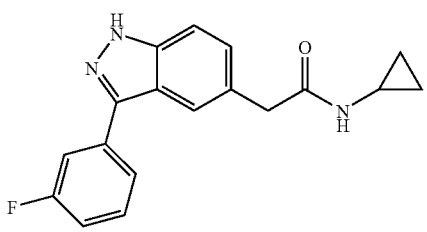
Example I-136
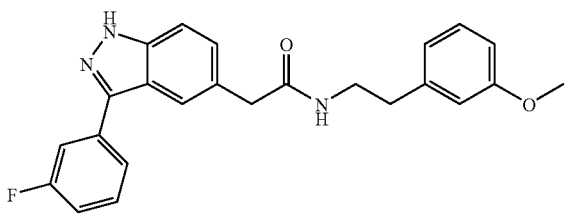
Example I-137
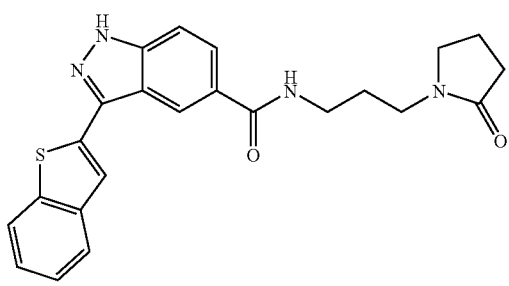
Example I-138
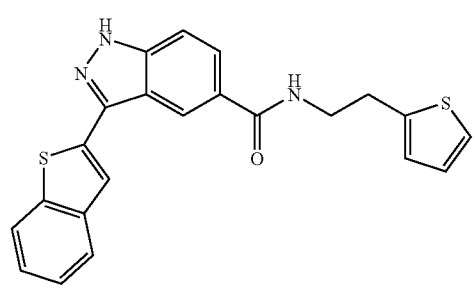
-continued
Example I-139
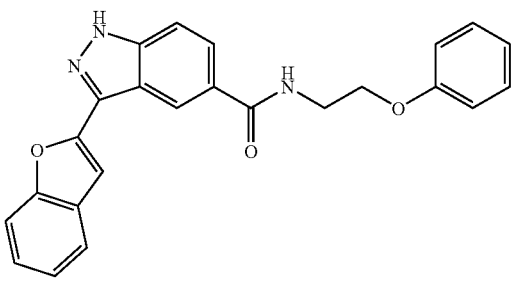
Example I-140
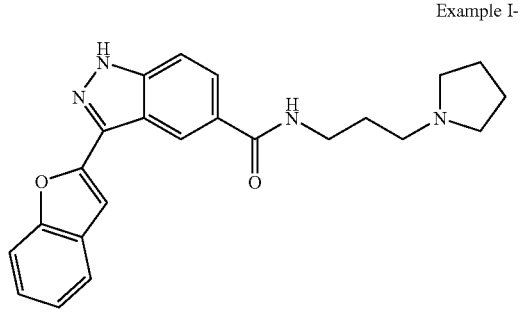
Example I-141
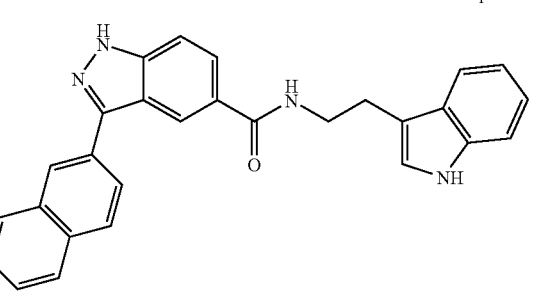
Example I-142
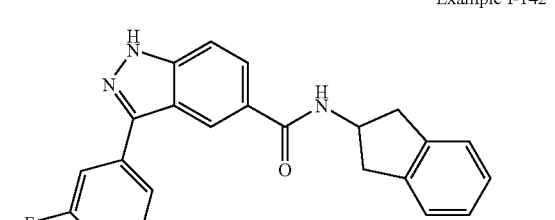
Example I-143
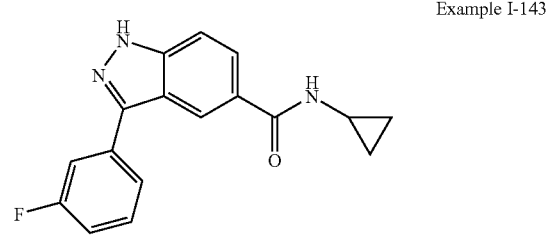
Example I-144
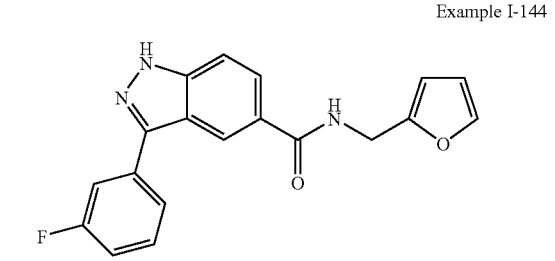

-continued
Example I-145
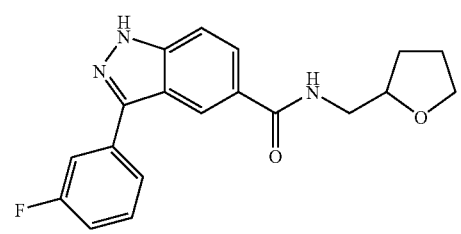
Example I-146
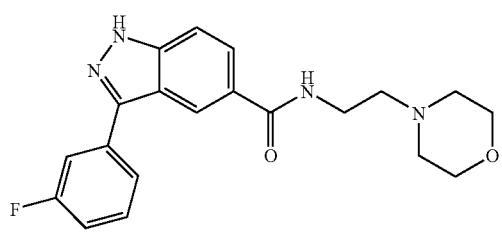
Example I-147
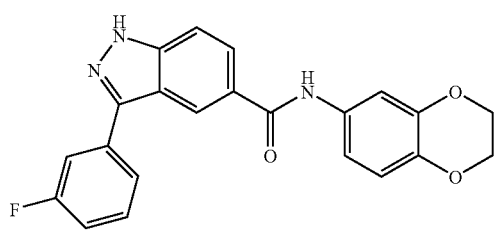
Example I-148
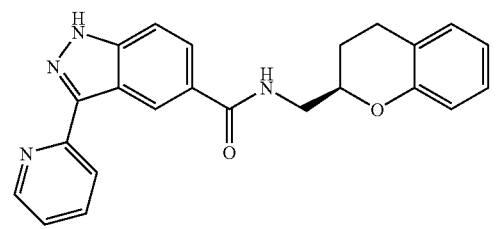
Example I-149
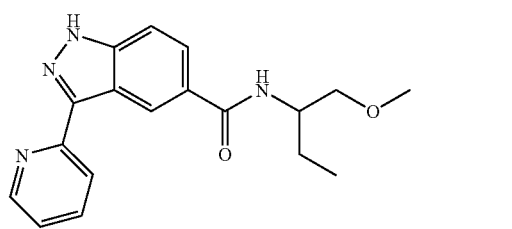
Example I-150
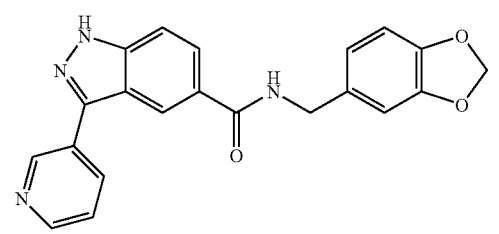
-continued
Example I-151
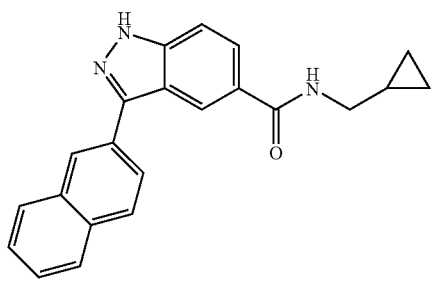
Example I-152
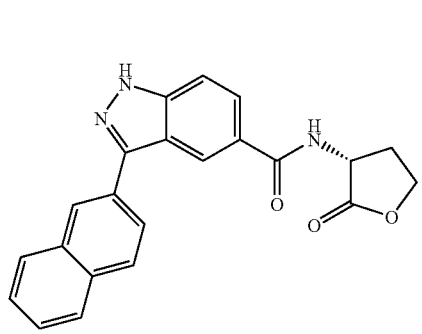
Example I-153
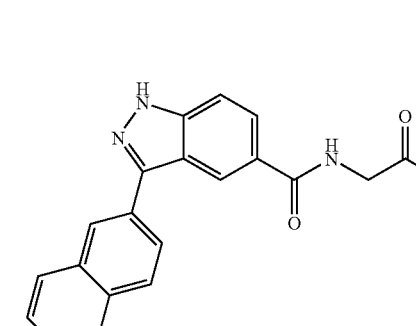
Example I-154
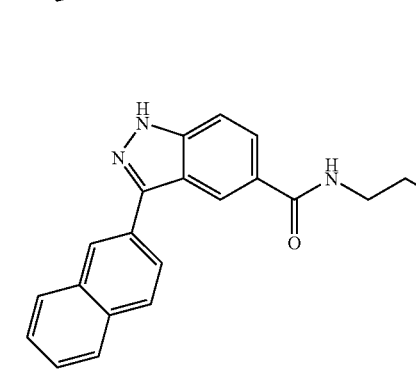
Example I-155
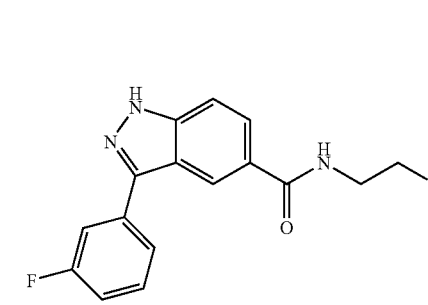

-continued
Example I-156
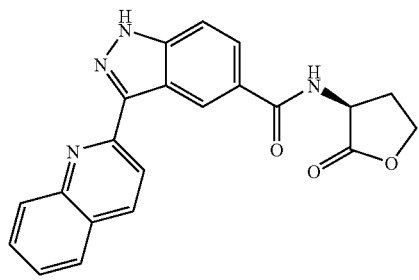
Example I-157
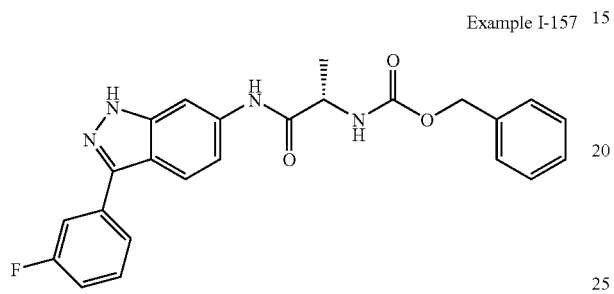
Example I-158
Example I-159
Example I-160
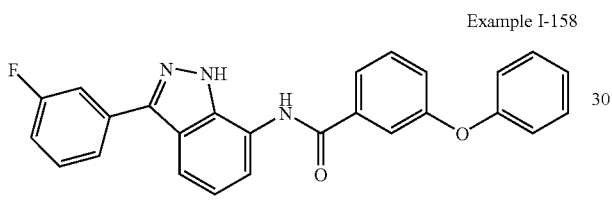
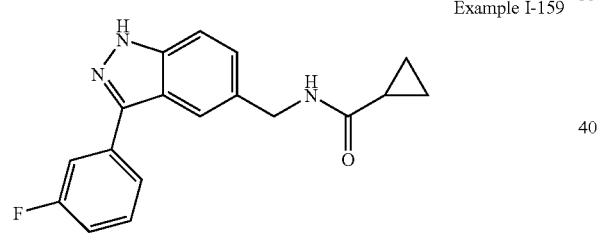
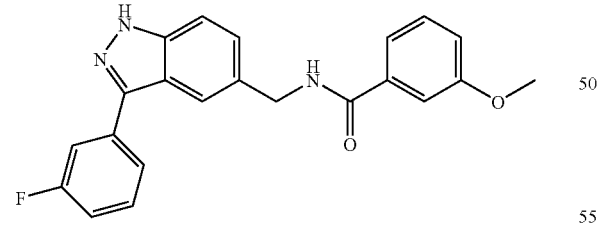
Example I-161
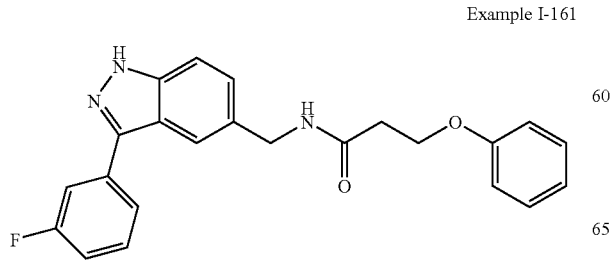
-continued
Example I-162
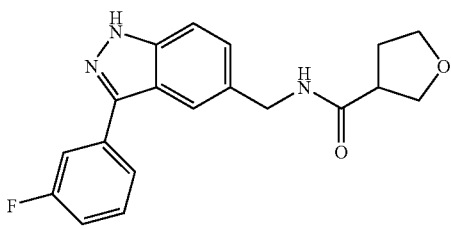
Example I-163
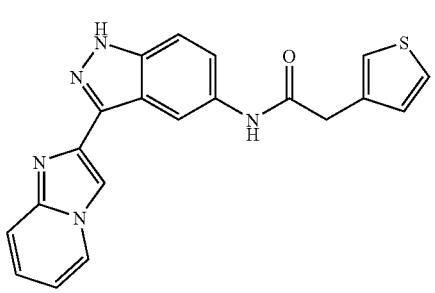
Example I-164
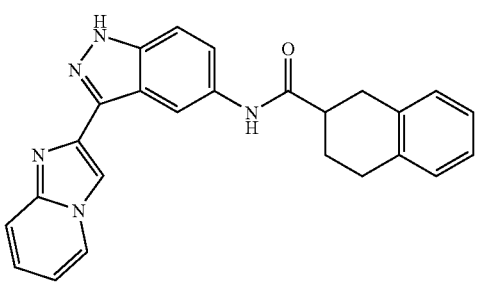
Example I-165
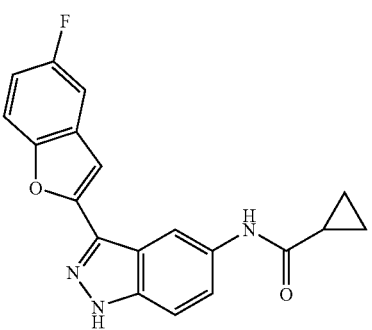
Example I-166
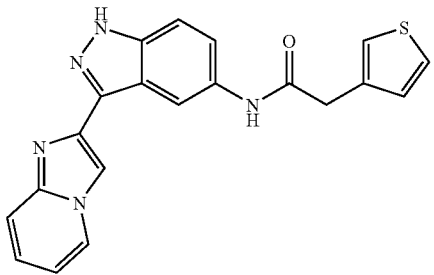

Example I-167
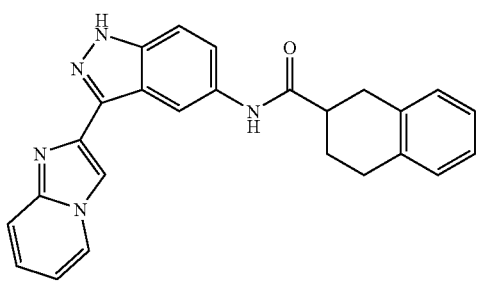
Example I-168
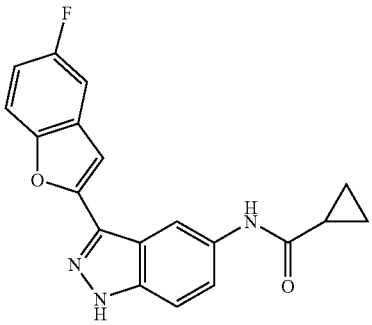
Example I-169
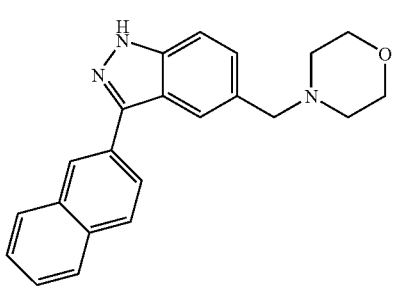
Example I-170
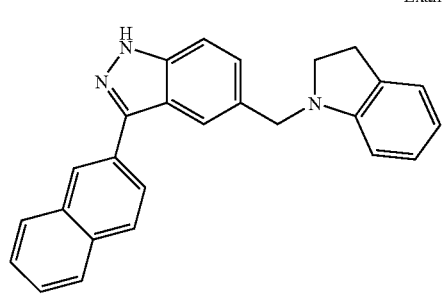
Example I-171
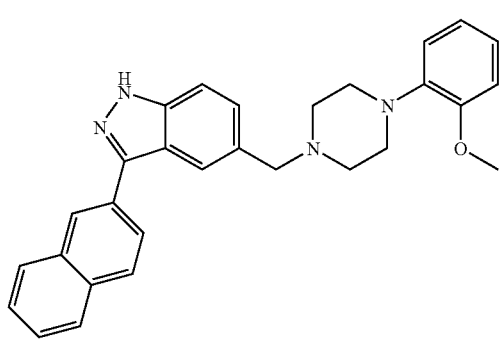
Example I-172
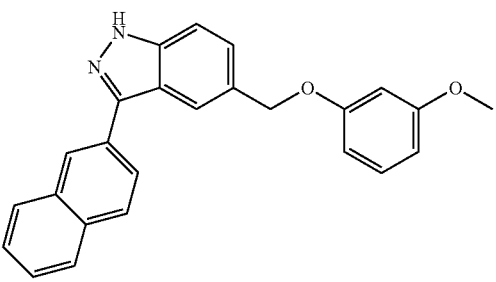
Example I-173
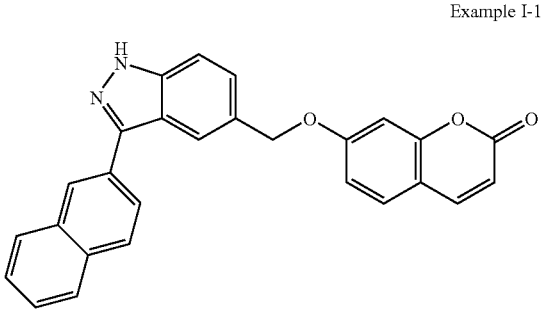
Production Example II-1-e
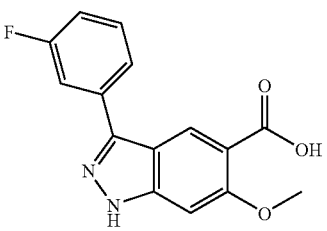
Production Example II-2-d
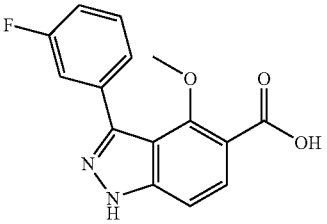
Production Example II-3-d
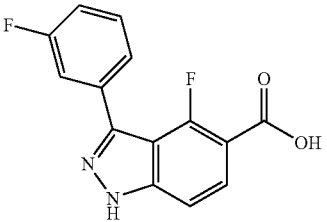
Production Example II-4-d
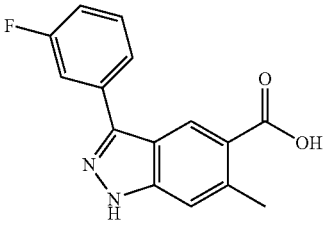

Production Example II-5-f
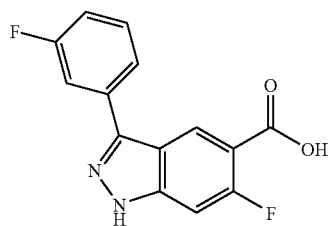
Production Example II-6
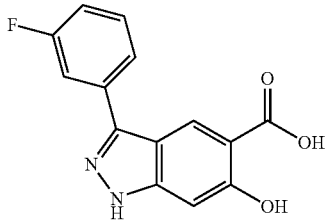
Production Example II-7-f
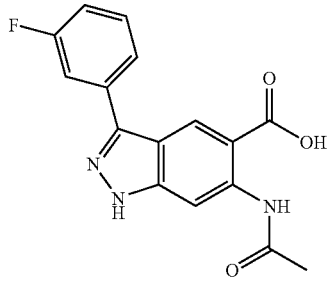
Production Example II-8-d
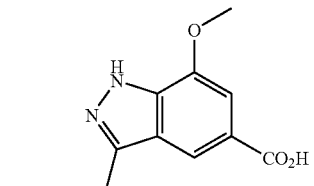
Production Example II-9-e
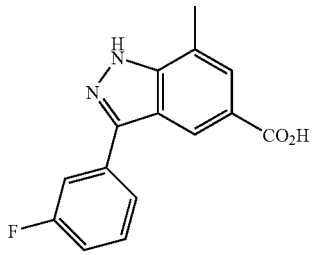
Production Example II-10-d
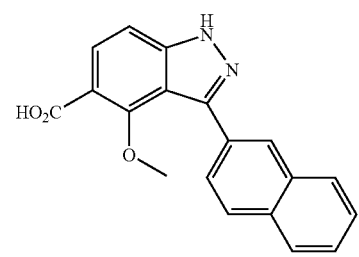
Production Example II-11-e
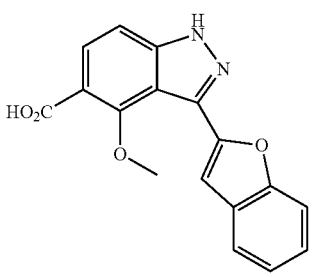
Production Example II-12-d
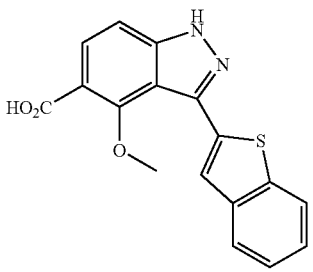
Production Example II-13-g
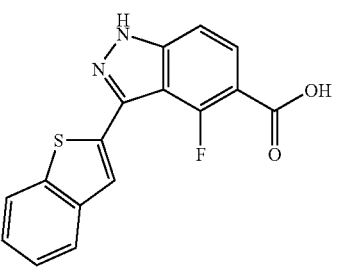
Production Example II-14-b
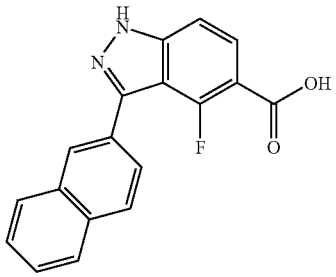
Production Example II-15-b
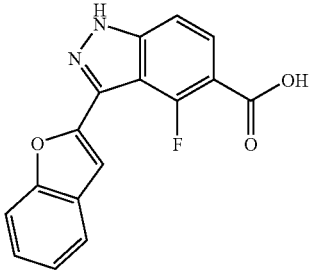

-continued
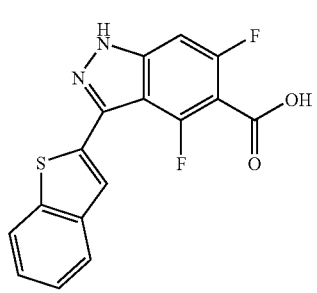
Production Example II-16-d
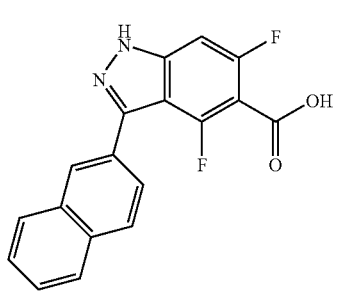
Production Example II-17-d
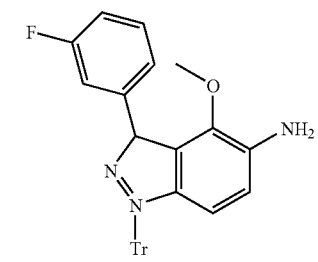
Production Example II-18-b
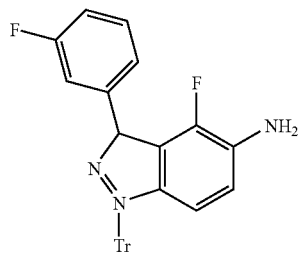
Production Example II-19-c
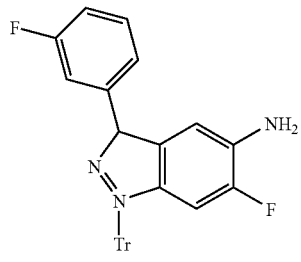
Production Example II-20-c
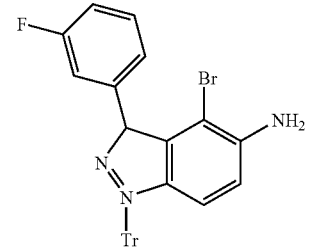
Production Example II-21
-continued
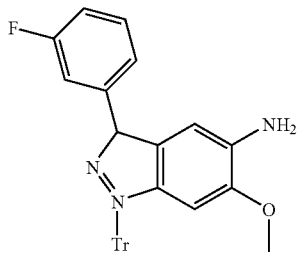
Production Example II-22-c
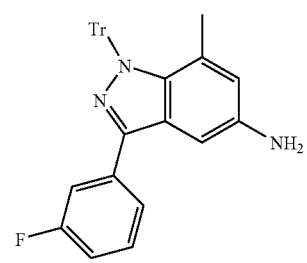
Production Example II-23
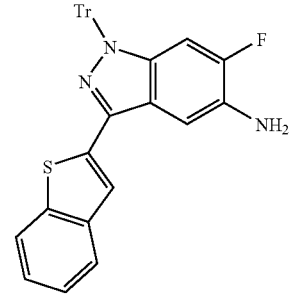
Production Example II-24-c
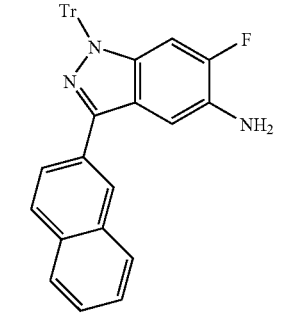
Production Example II-25-c
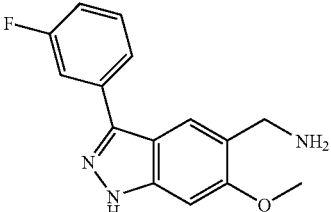
Production Example II-26
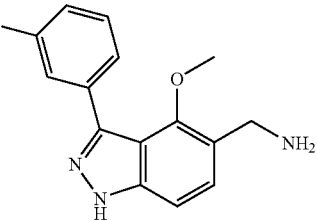
Production Example II-27-c -continued
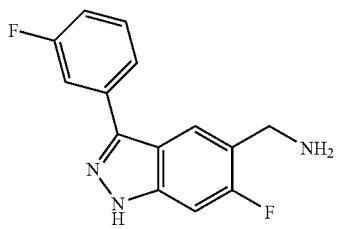
Production Example II-28
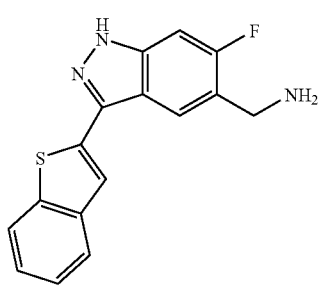
Production Example II-29
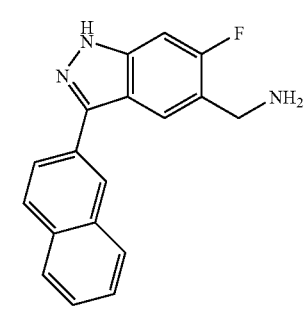
Production Example II-30
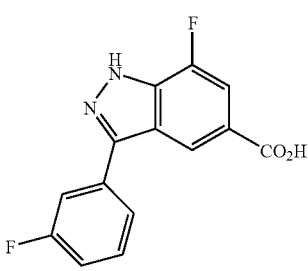
Production Example II-31-e
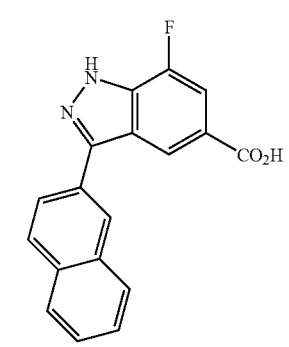
Production Example II-32-d
-continued
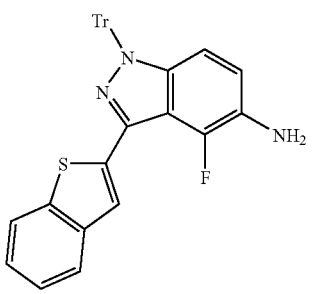
Production Example II-33-c
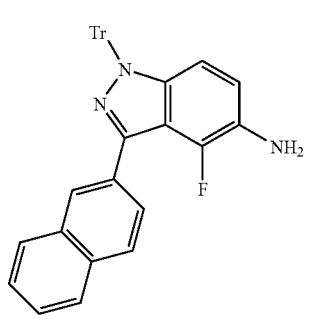
Production Example II-34-c
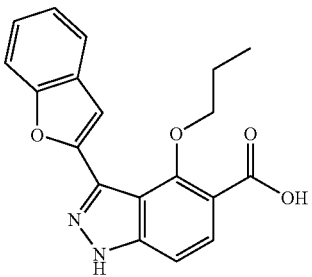
Production Example II-35-e
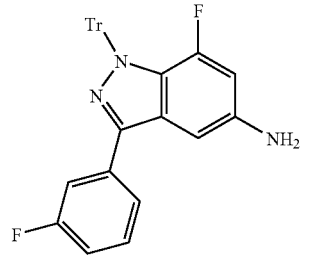
Production Example II-36-b
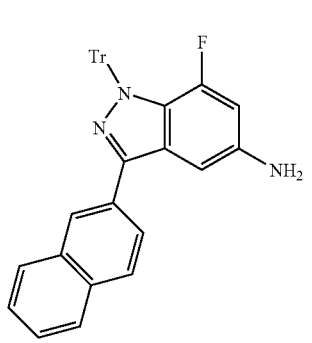
Production Example II-37-b Production Example II-38-b
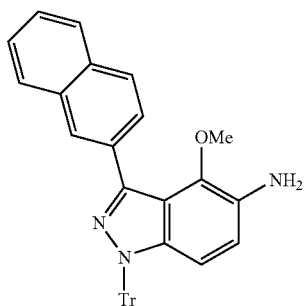
Production Example II-39-b
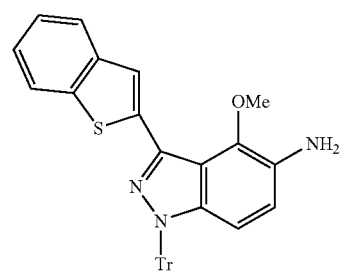
Production Example II-40
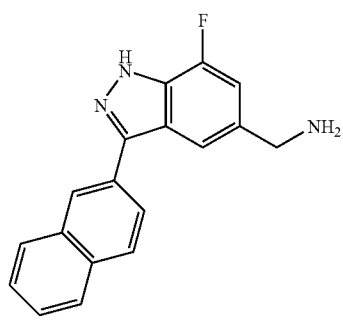
Production Example II-41-g
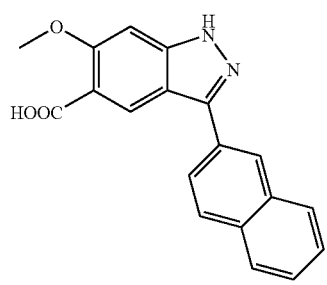
Production Example II-42-b
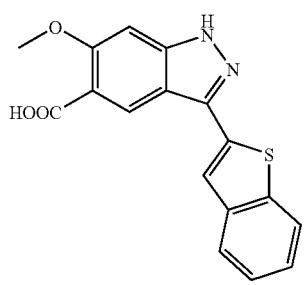
Production Example II-43-c
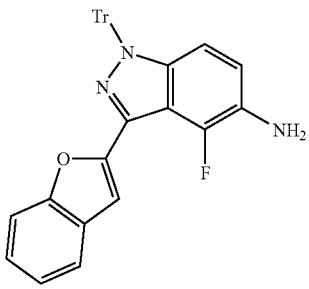
Example II-1
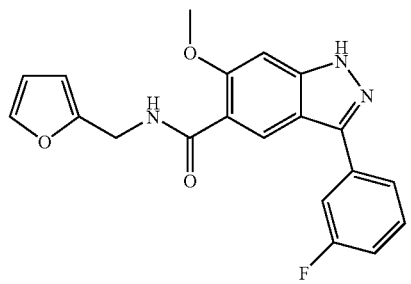
Example II-2
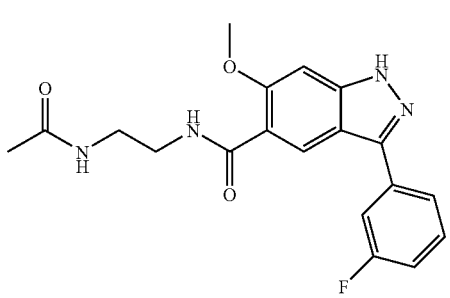
Example II-3
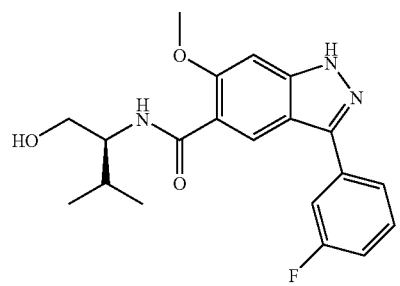
Example II-4
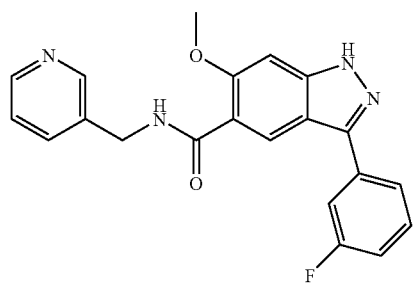

Example II-5
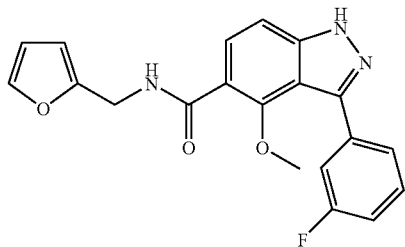
Example II-6
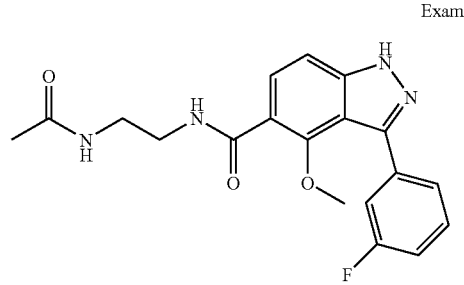
Example II-7
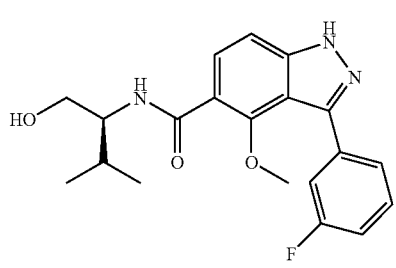
Example II-8
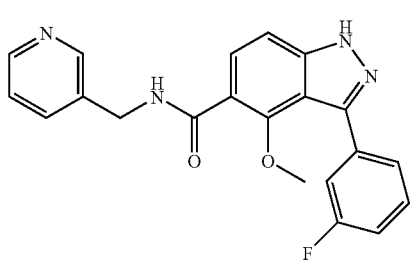
Example II-9
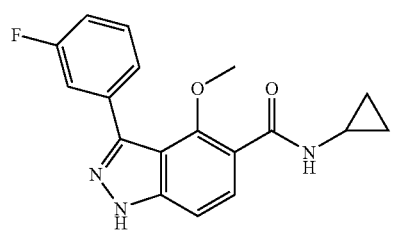
Example II-10
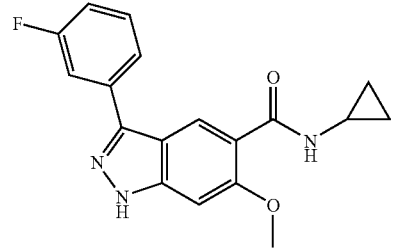
Example II-11
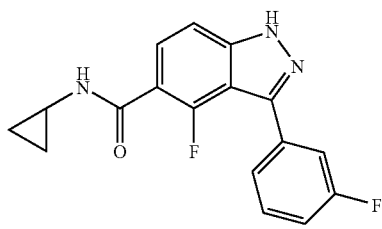
Example II-12
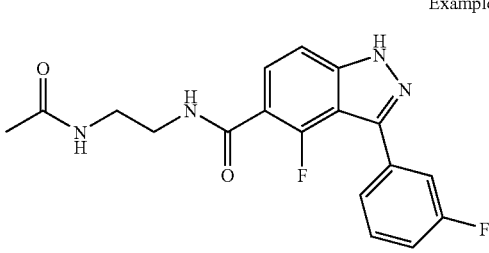
Example II-13
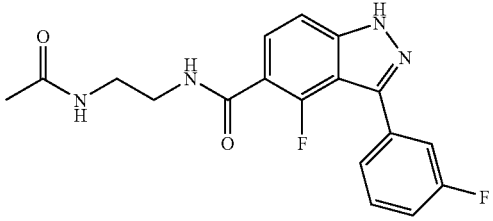
Example II-14
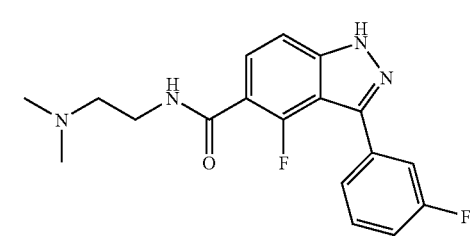
Example II-15
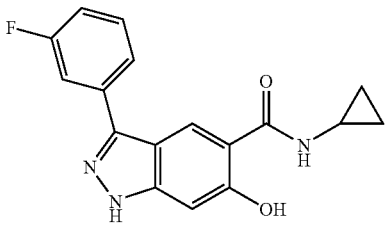
Example II-16
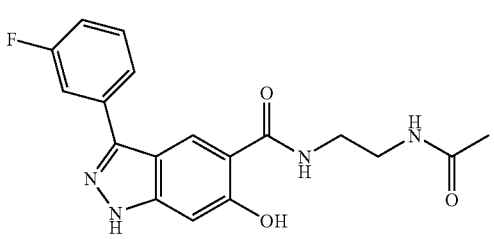

Example II-17
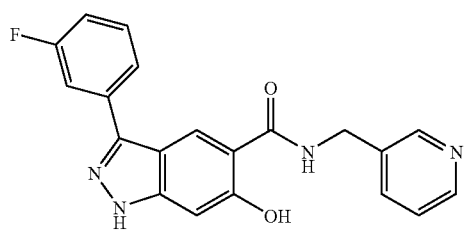
Example II-18
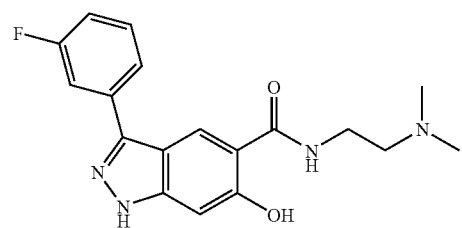
Example II-19
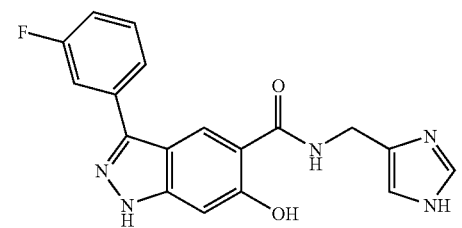
Example II-20
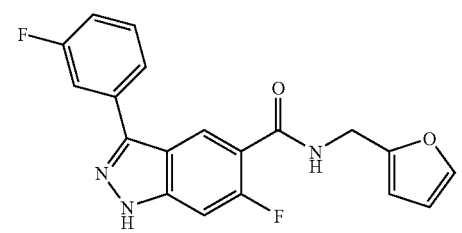
Example II-21
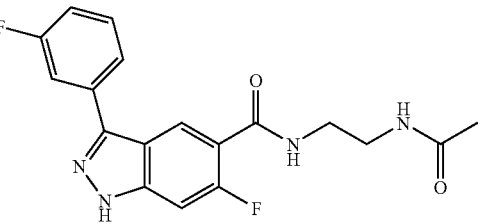
Example II-22
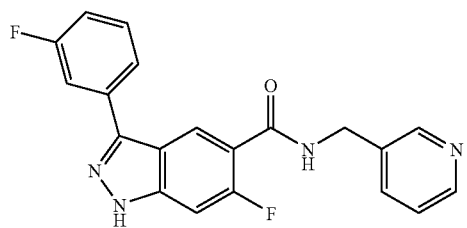
Example II-23
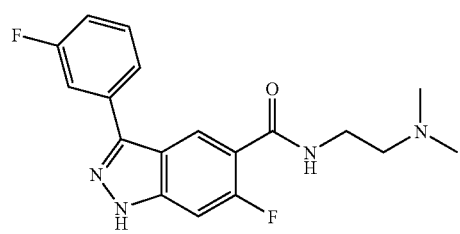
Example II-24
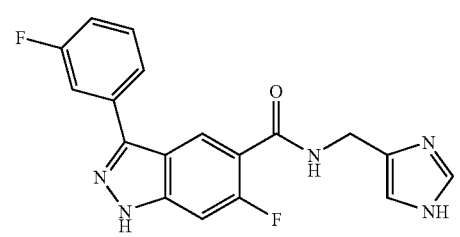
Example II-25
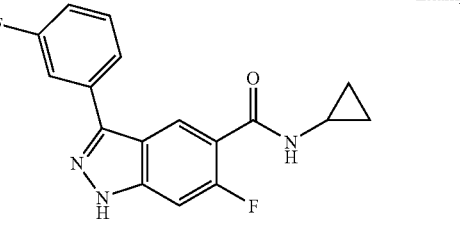
Example II-26
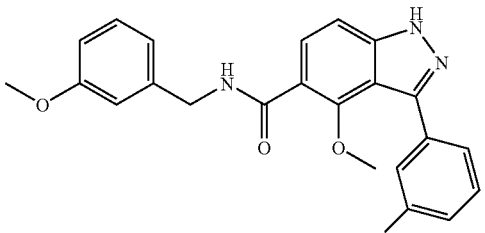
Example II-27
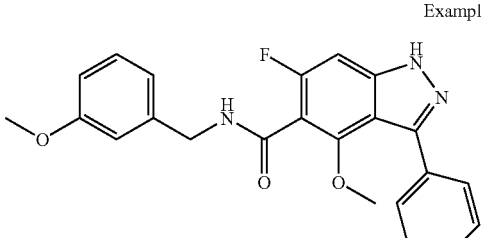
Example II-28
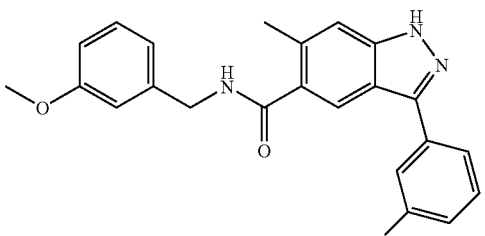

Example II-29
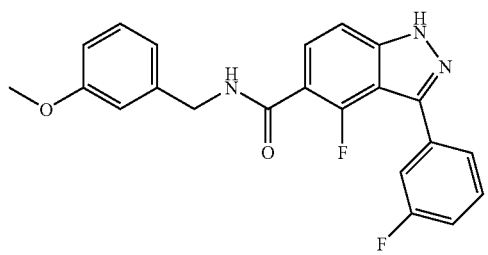
Example II-30
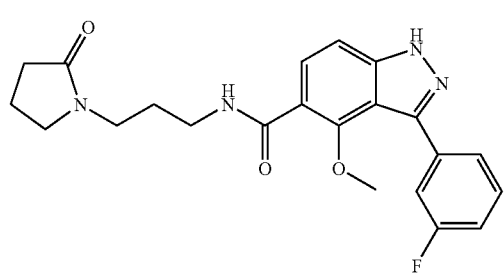
Example II-31
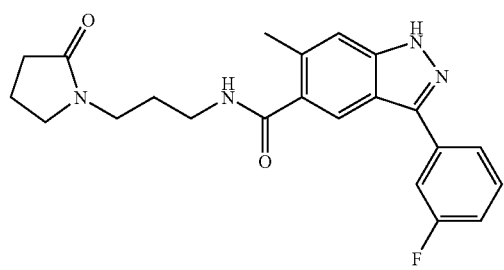
Example II-32
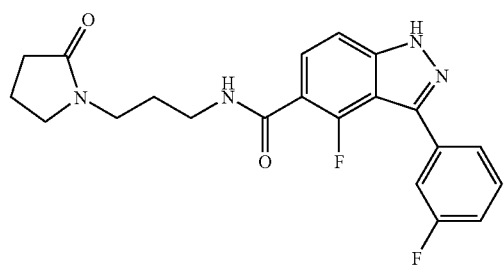
Example II-33
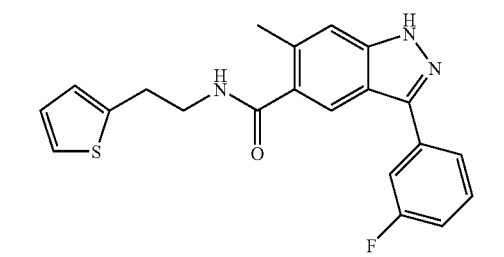
Example II-34
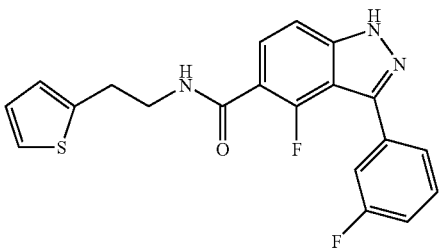
Example II-35
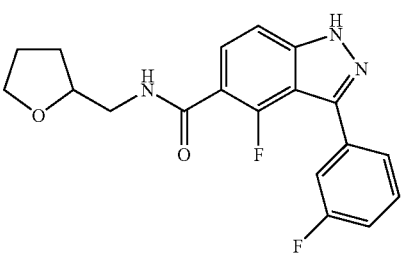
Example II-36
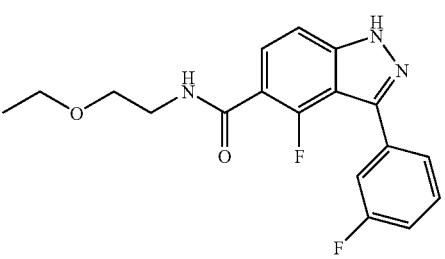
Example II-37
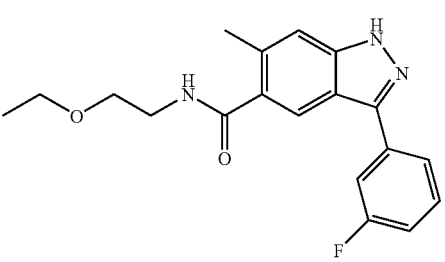
Example II-38
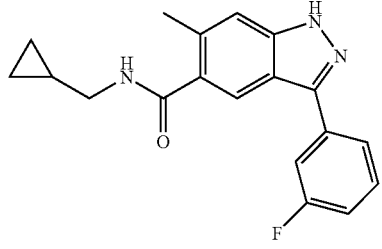
Example II-39
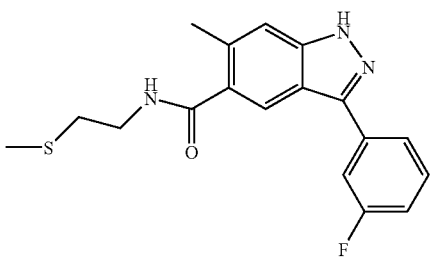

Example II-40
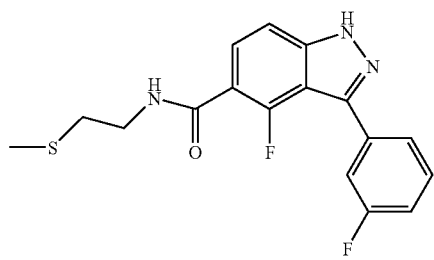
Example II-41
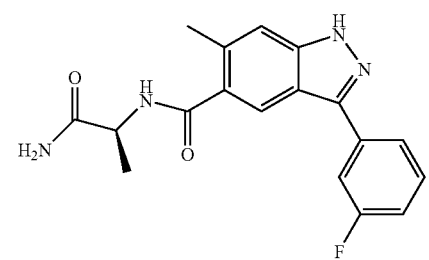
Example II-42
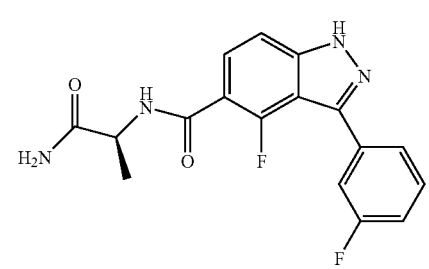
Example II-43
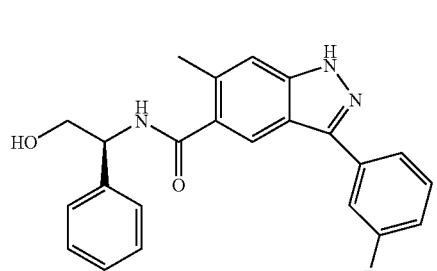
Example II-44
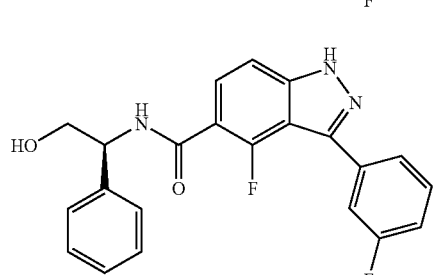
Example II-45
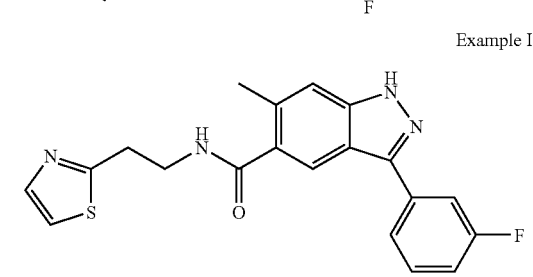
Example II-46
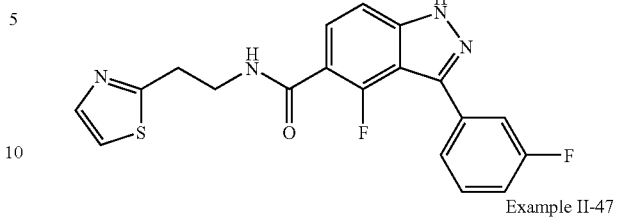
Example II-47
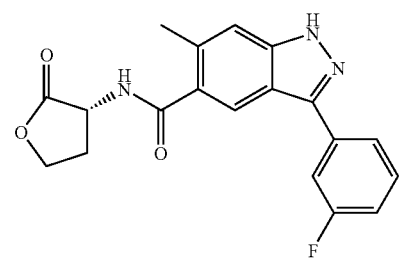
Example II-48
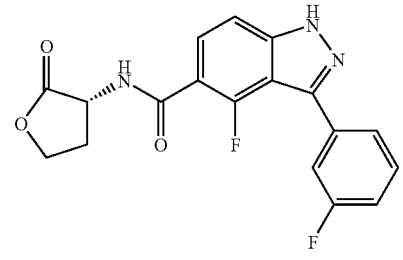
Example II-49
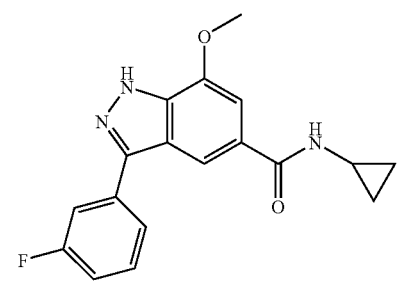
Example II-50
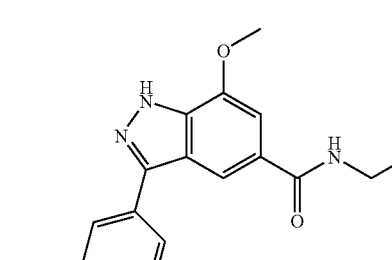
Example II-51
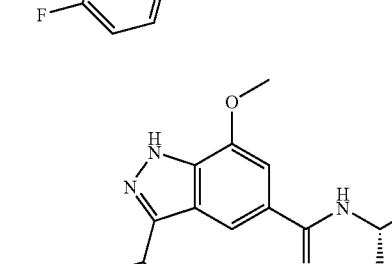

-continued
Example II-52
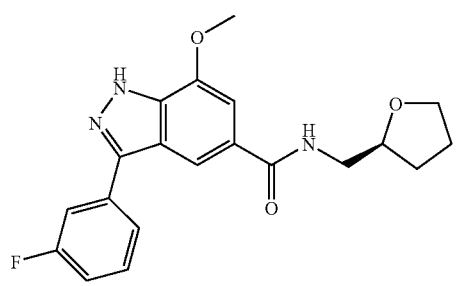
Example II-53
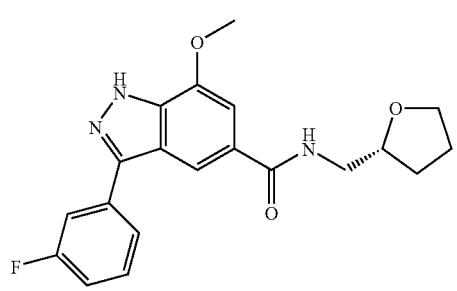
Example II-54
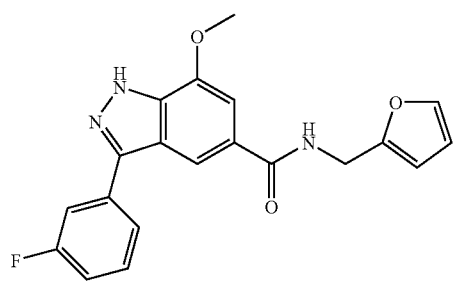
Example II-55
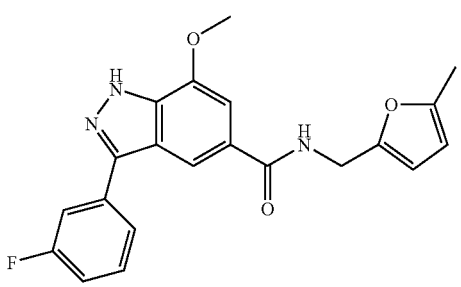
Example II-56
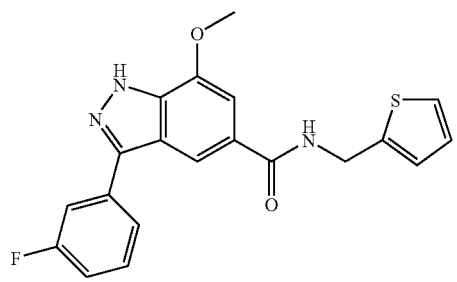
-continued
Example II-57
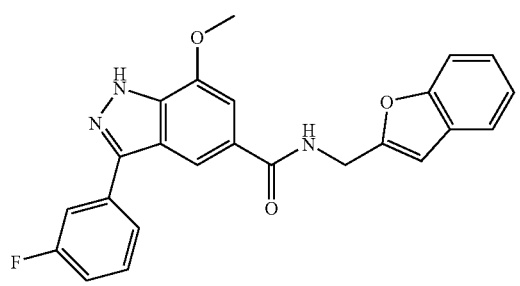
Example II-58
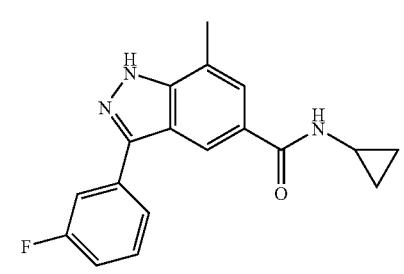
Example II-59
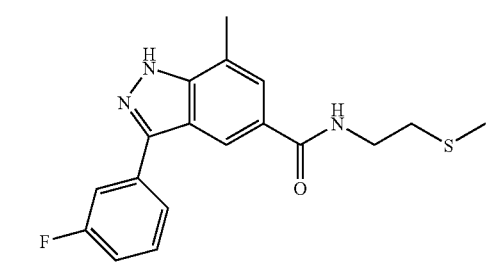
Example II-60
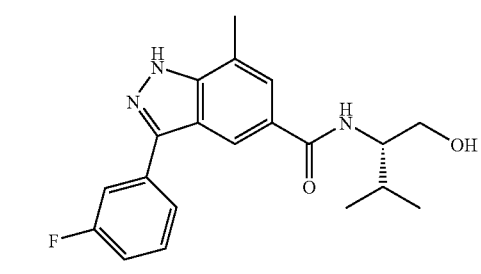
Example II-61
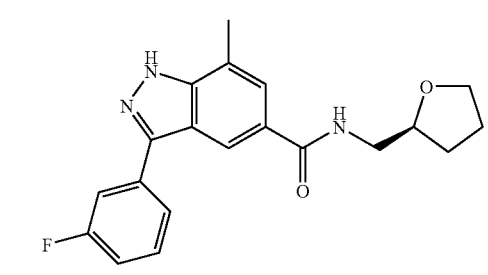

Example II-62
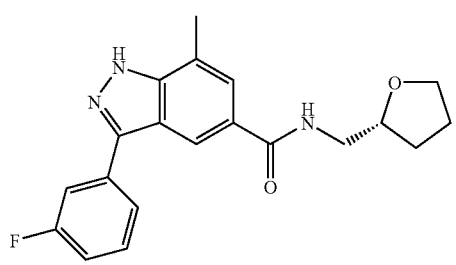
Example II-63
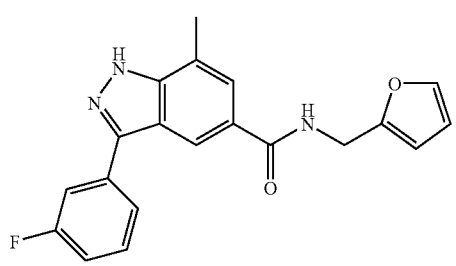
Example II-64
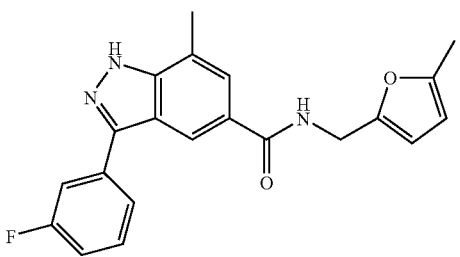
Example II-65
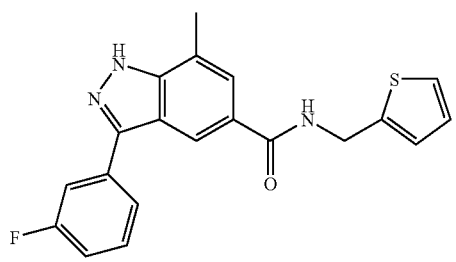
Example II-66
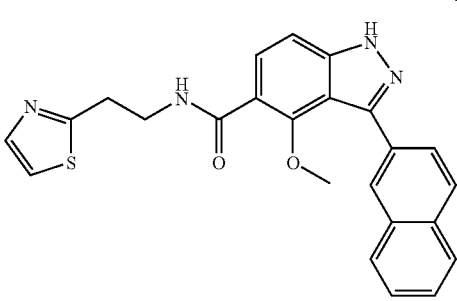
Example II-67
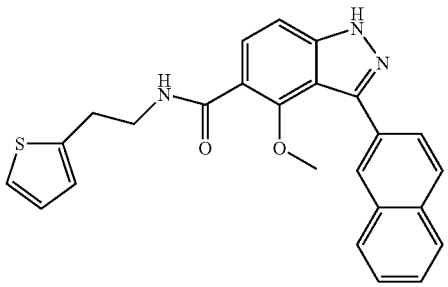
Example II-68
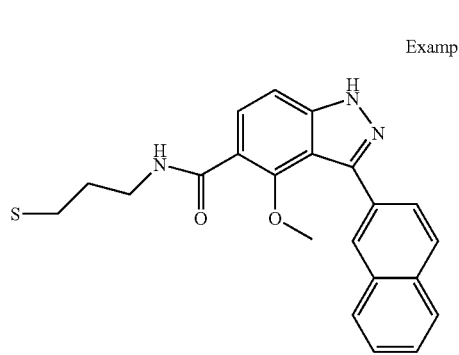
Example II-69
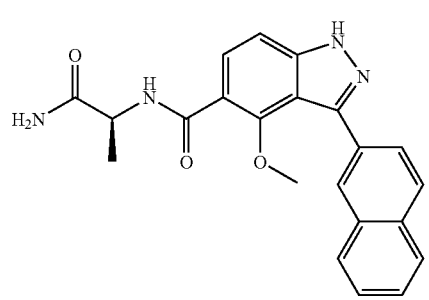
Example II-70
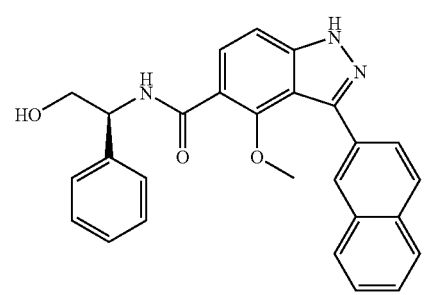
Example II-71

Example II-72
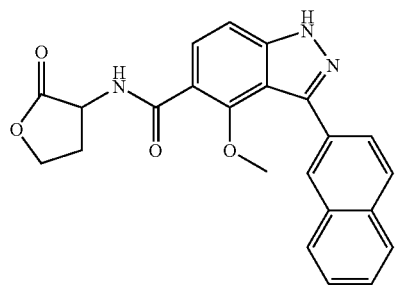
Example II-77
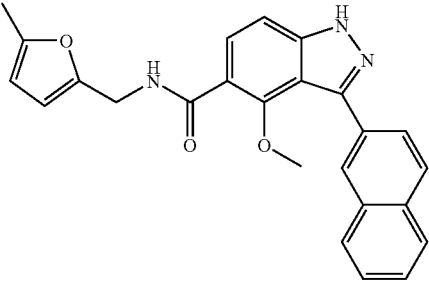
Example II-73
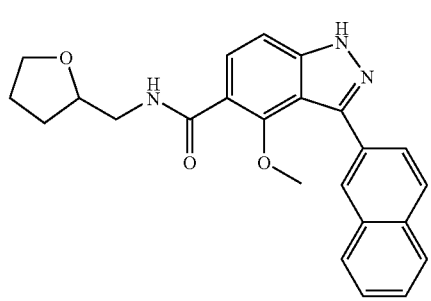
Example II-78
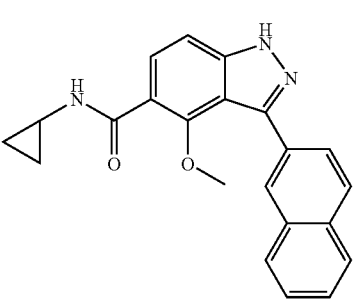
Example II-74
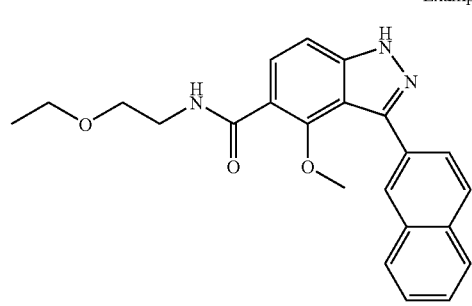
Example II-79
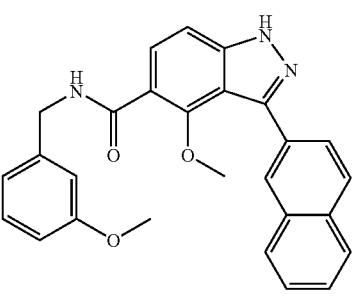
Example II-75
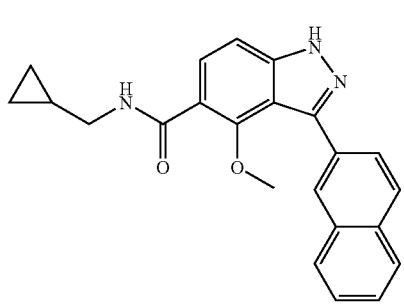
Example II-80
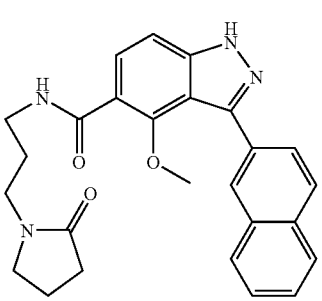
Example II-76
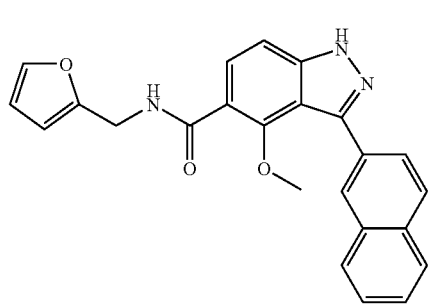
Example II-81
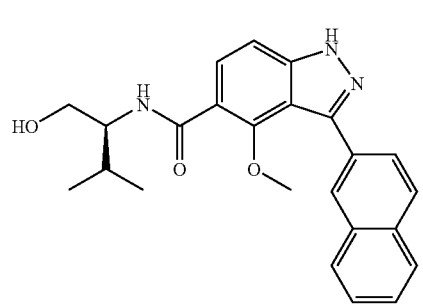

Example II-82
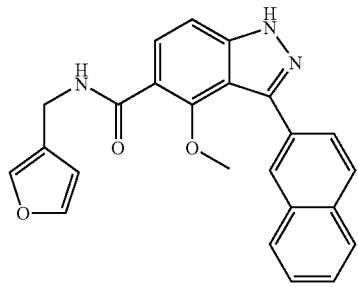
Example II-83
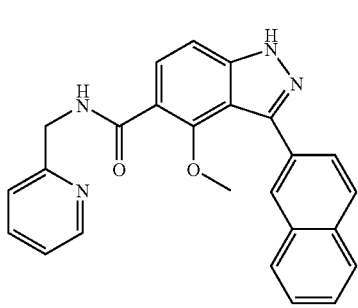
Example II-84
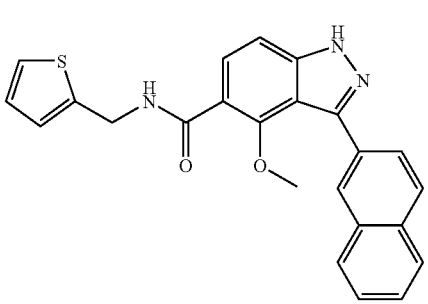
Example II-85
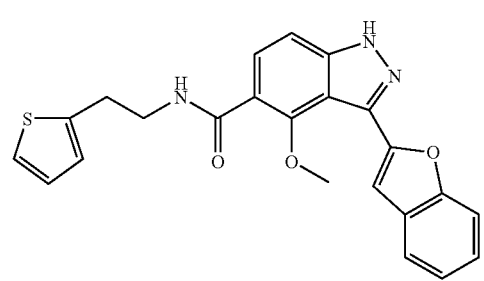
Example II-86
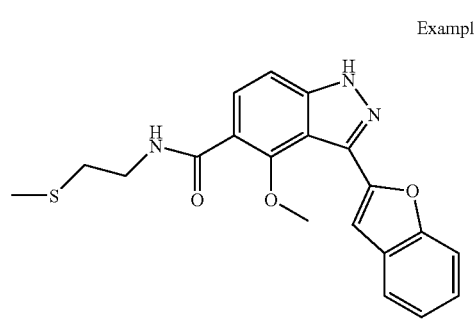
Example II-87
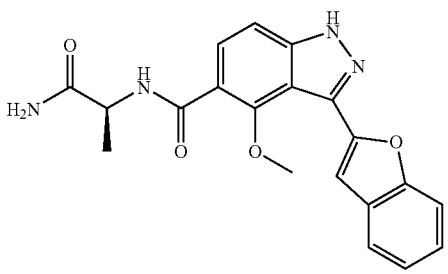
Example II-88
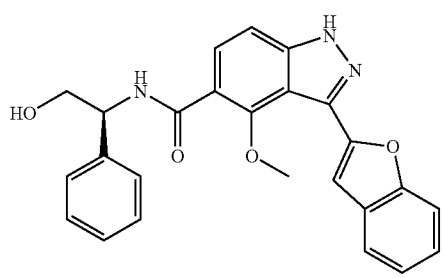
Example II-89
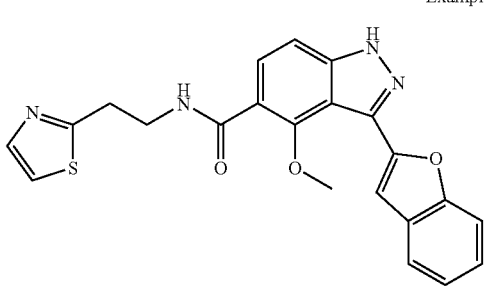
Example II-90
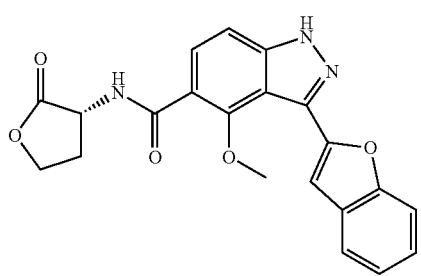
Example II-91
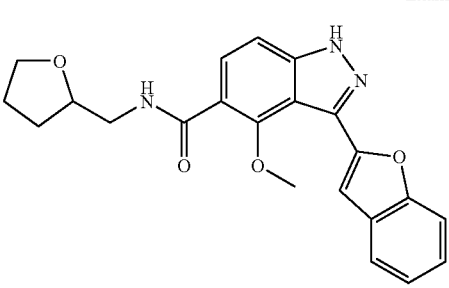

Example II-92
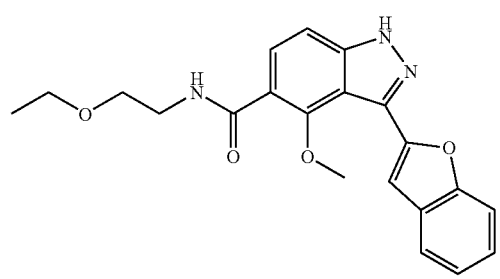
Example II-93
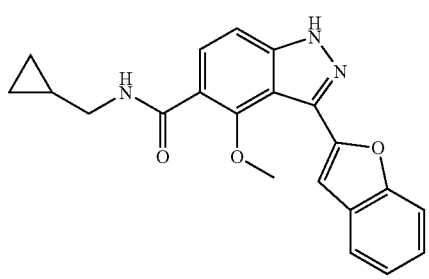
Example II-94
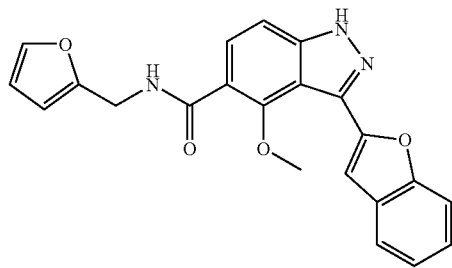
Example II-95
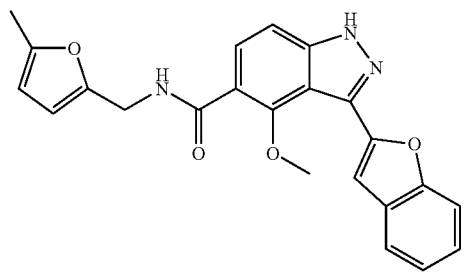
Example II-96
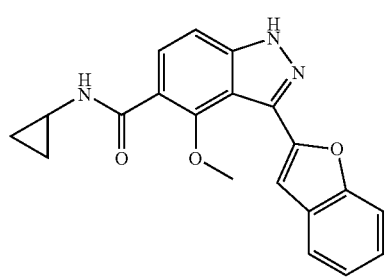
Example II-97
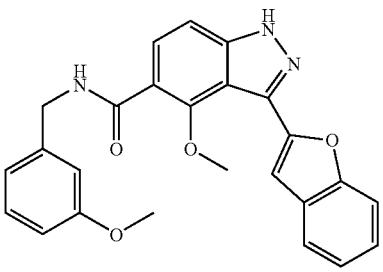
Example II-98
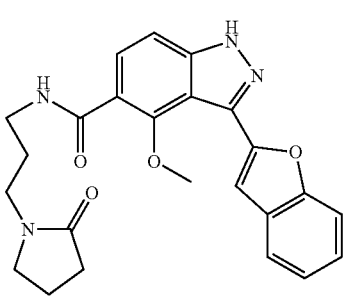
Example II-99
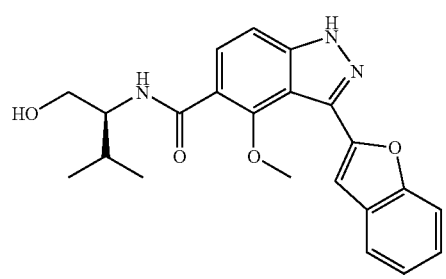
Examlpe II-100
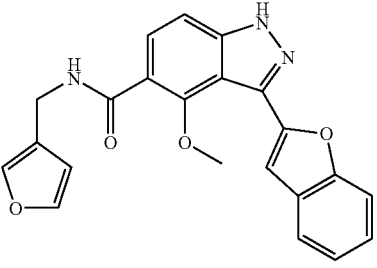
Example II-101
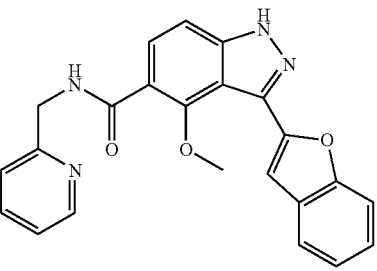

-continued
Example II-102
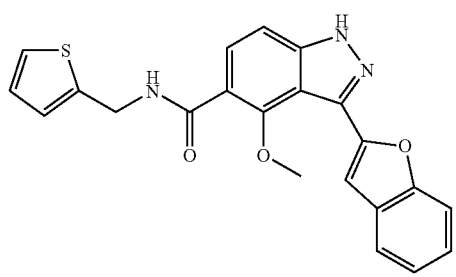
Example II-103
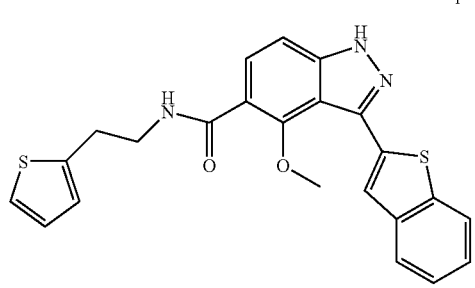
Example II-104
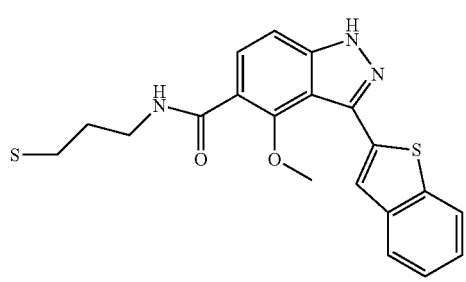
Example II-105
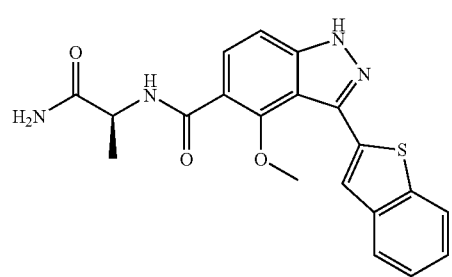
Example II-106
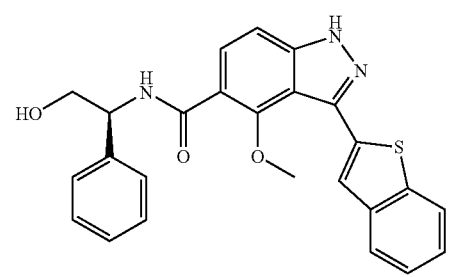
-continued
Example II-107
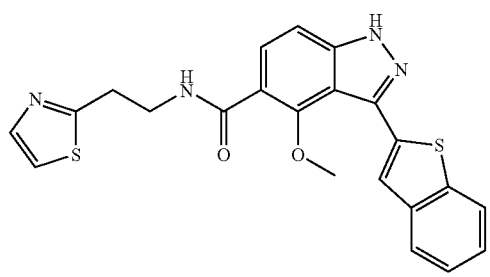
Example II-108
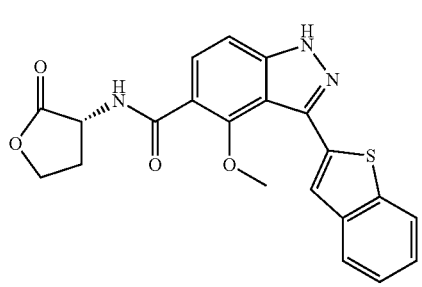
Example II-109
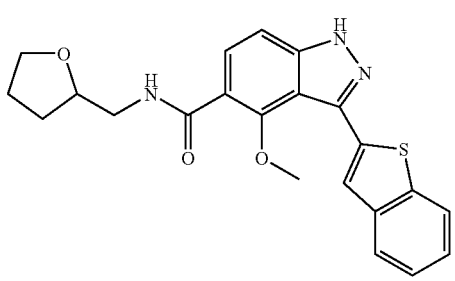
Example II-110
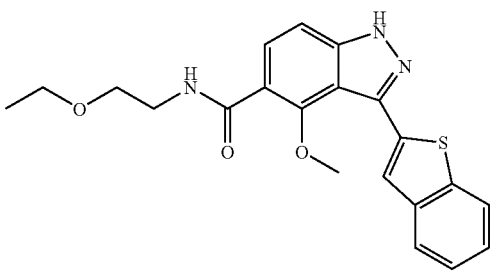
Example II-111
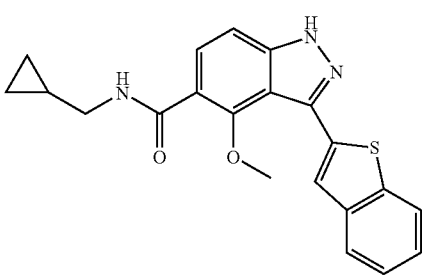

-continued
Example II-112
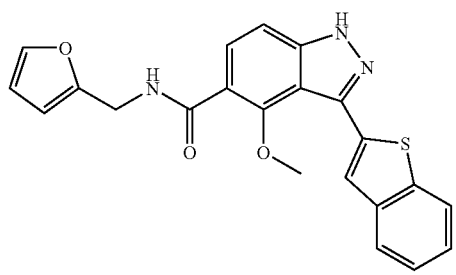
Example II-113
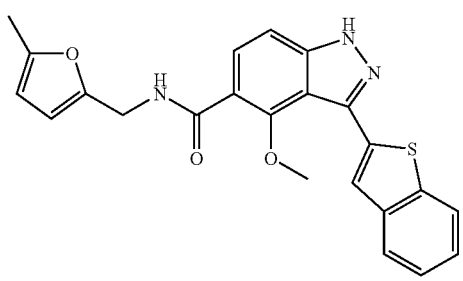
Example II-114
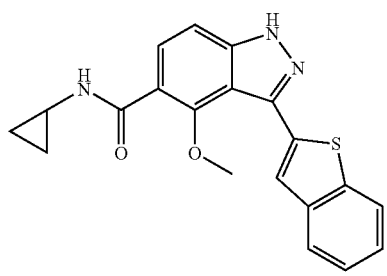
Example II-115
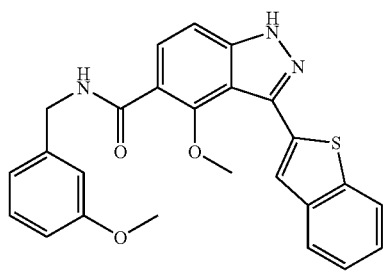
Example II-116
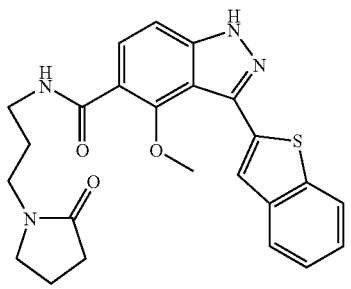
-continued
Example II-117
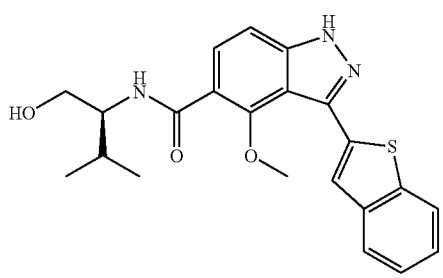
Example II-118
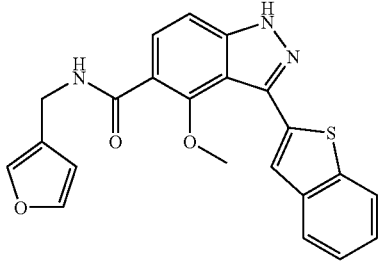
Example II-119
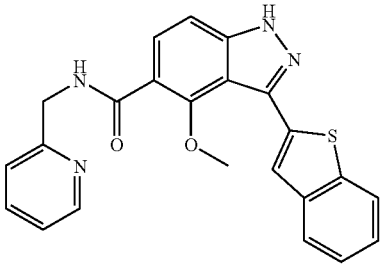
Example II-120
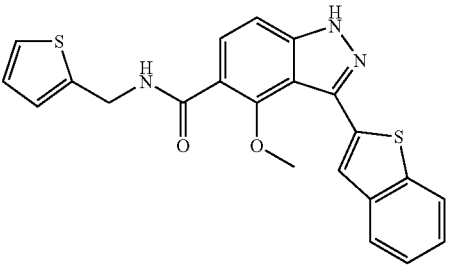
Example II-121
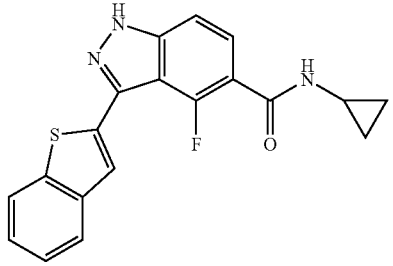

-continued

Example II-122

Example II-123

Example II-124

Example II-125

Example II-126

-continued

Example II-127

Example II-128

Example II-129

Example II-130

Example II-131

-continued
Example II-132
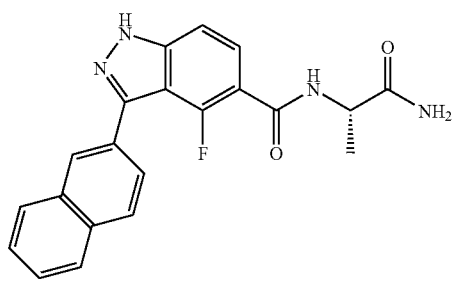
Example II-133
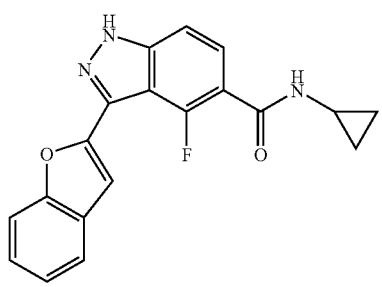
Example II-134
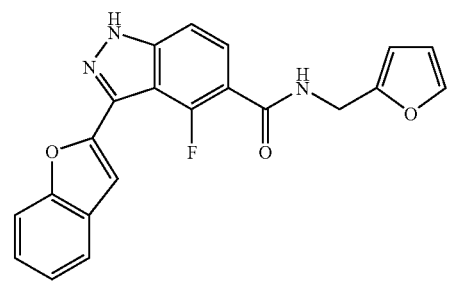
Example II-135
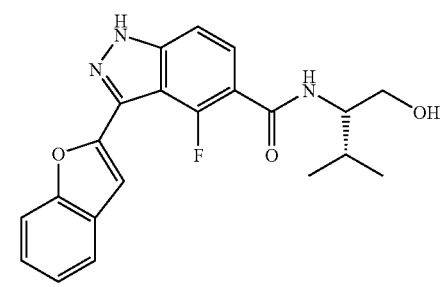
Example II-136
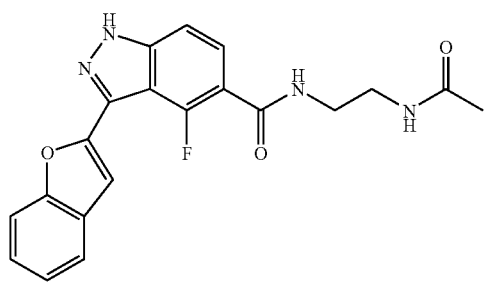
-continued
Example II-137
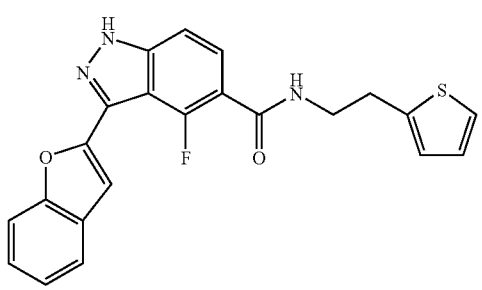
Example II-138
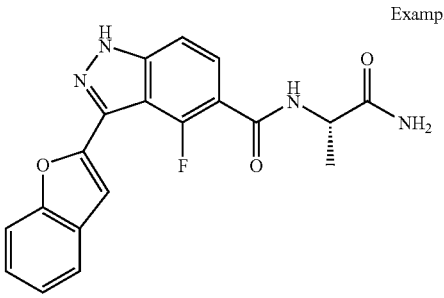
Example II-139
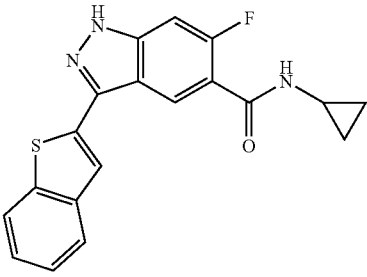
Example II-140
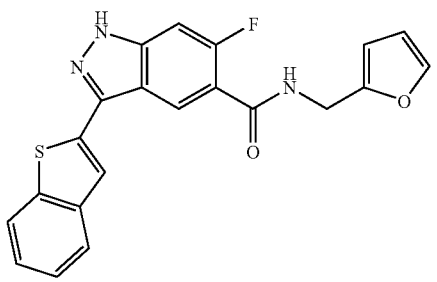
Example II-141
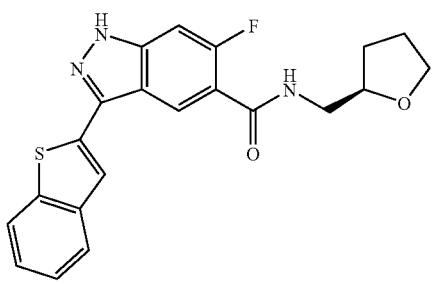

-continued
Example II-142
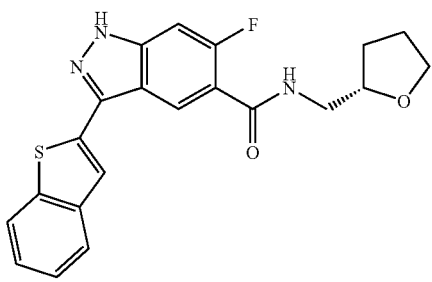
Example II-143
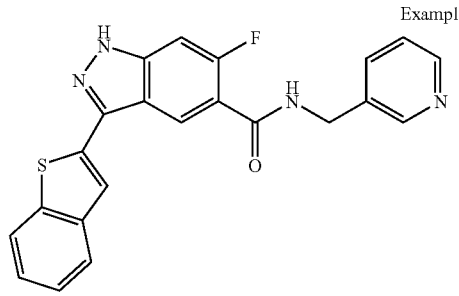
Example II-144
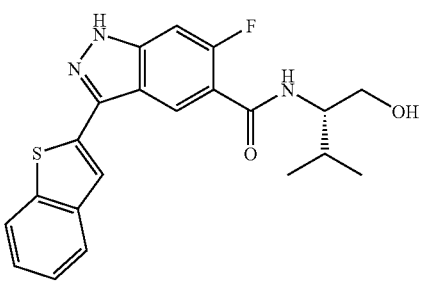
Example II-145
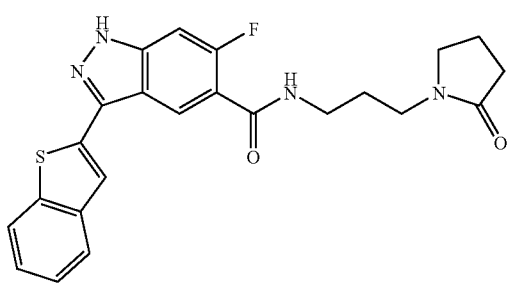
Example II-146
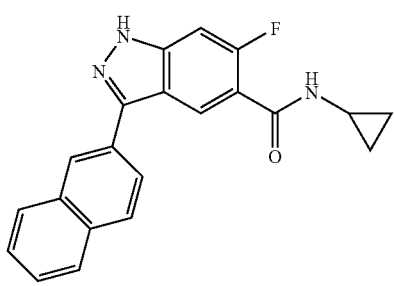
-continued
Example II-147
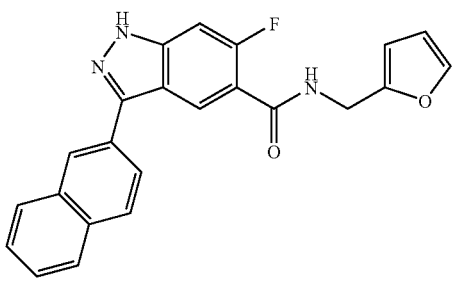
Example II-148
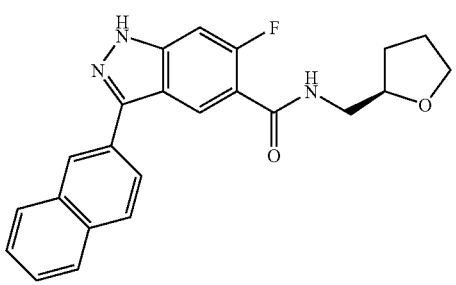
Example II-149
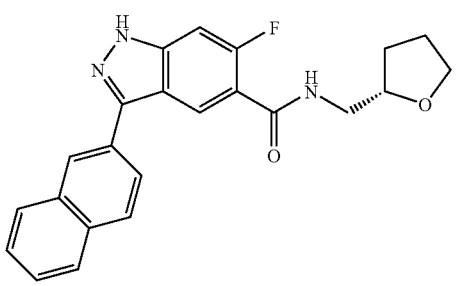
Example II-150
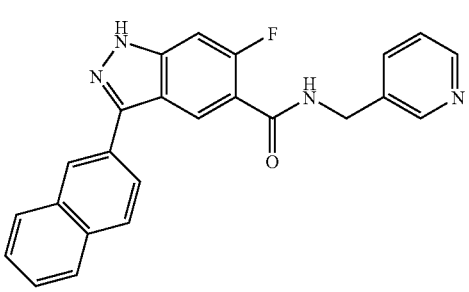
Example II-151
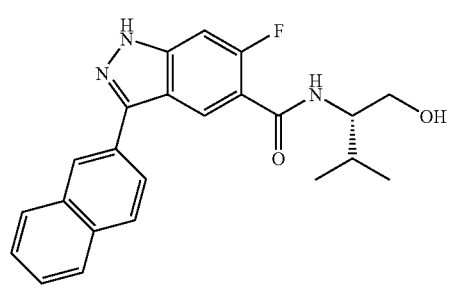

Example II-152
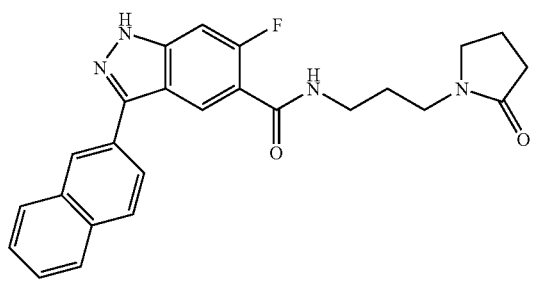
Example II-153
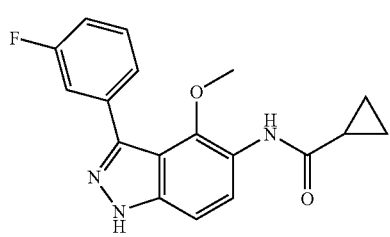
Example II-154
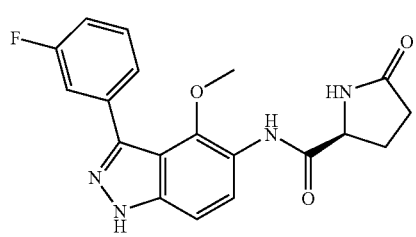
Example II-155
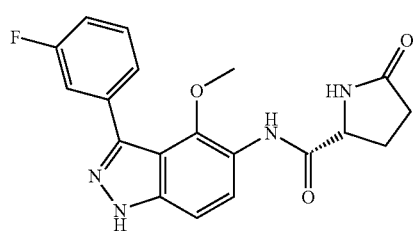
Example II-156
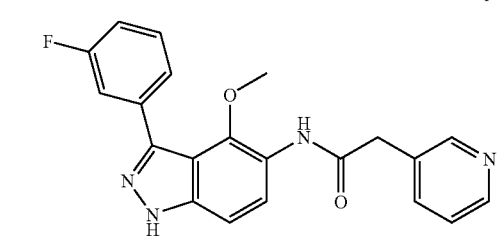
Example II-157
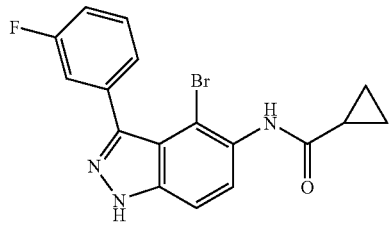
Example II-158
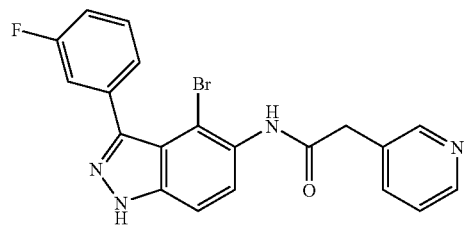
Example II-159
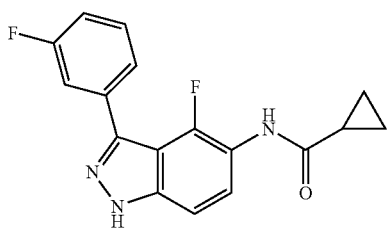
Example II-160
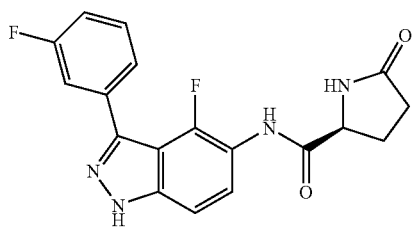
Example II-161
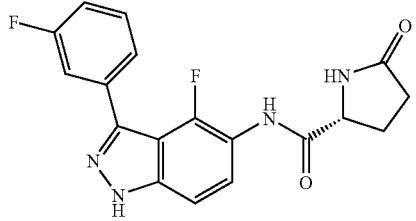
Example II-162
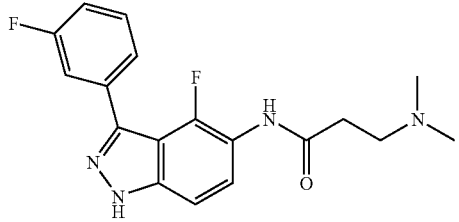
Example II-163
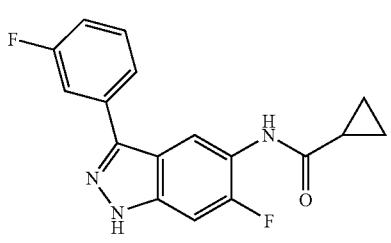

Example II-164
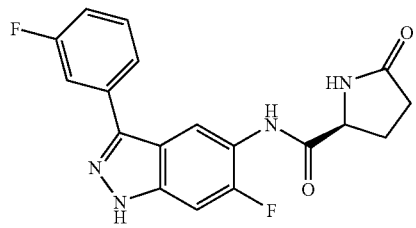
Example II-165
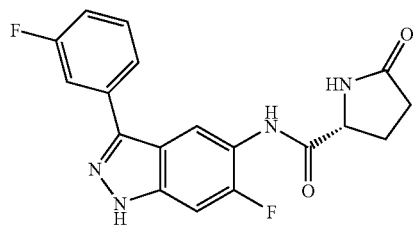
Example II-166
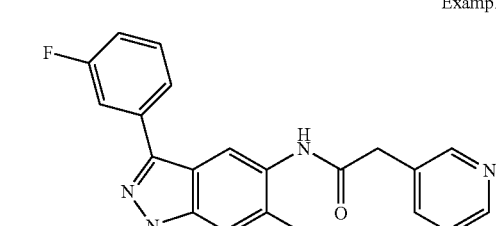
Example II-167
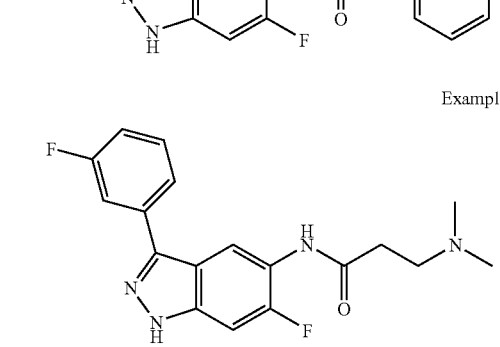
Example II-168
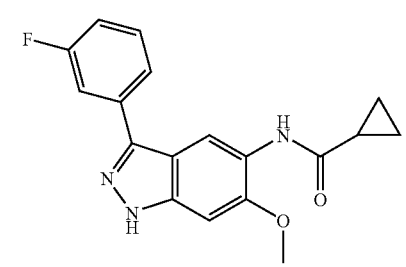
Example II-169
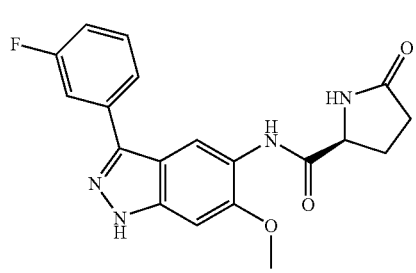
Example II-170
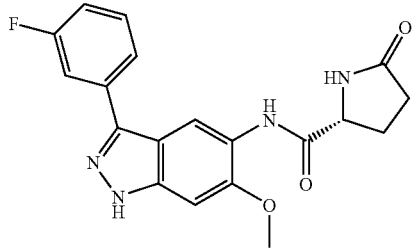
Example II-171
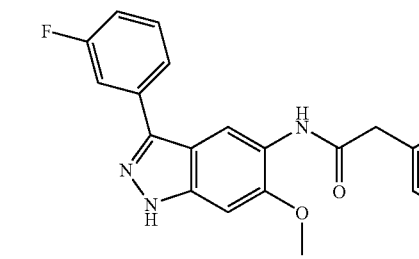
Example II-172
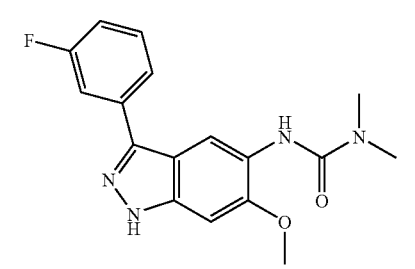
Example II-173
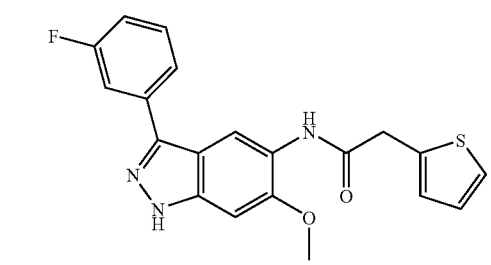
Example II-174
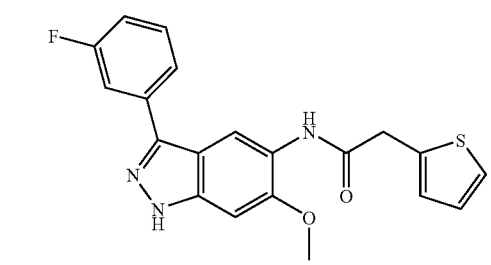
Example II-175
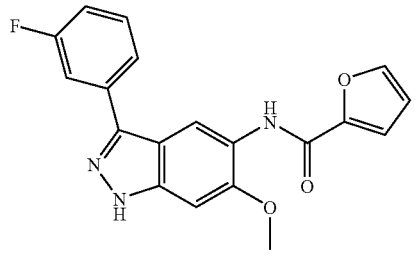

Example II-176
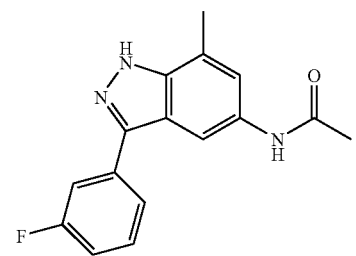
Example II-177
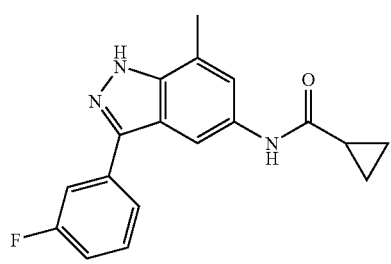
Example II-178
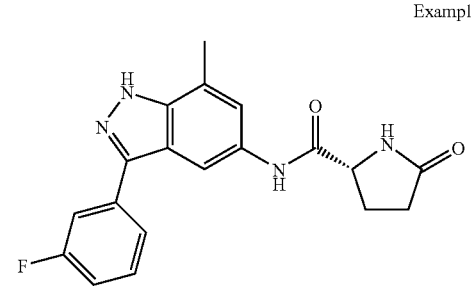
Example II-179
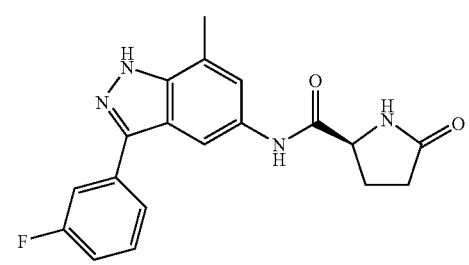
Example II-180
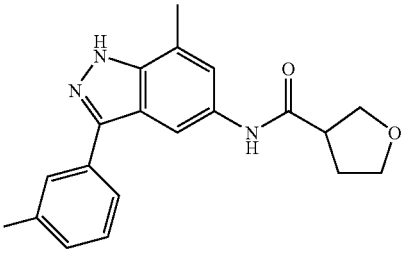
Example II-181
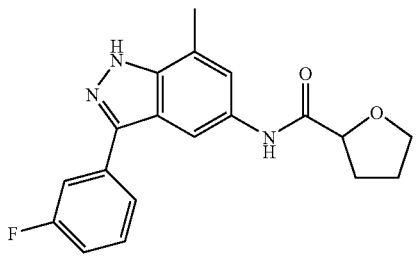
Example II-182
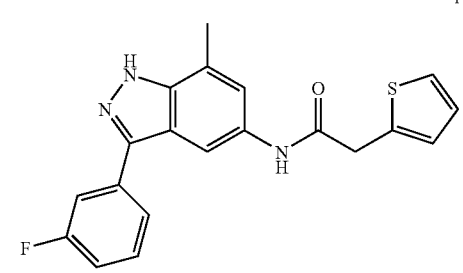
Example II-183
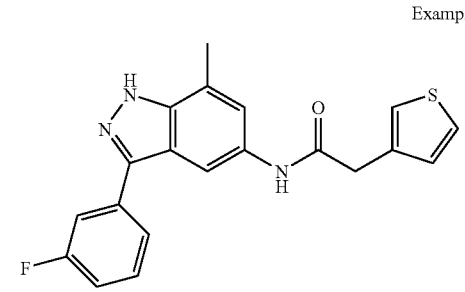
Example II-184
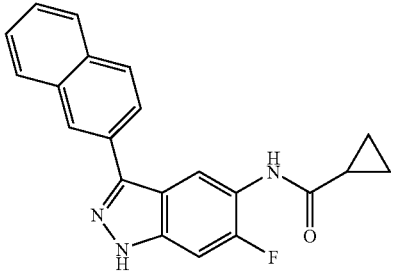
Example II-185
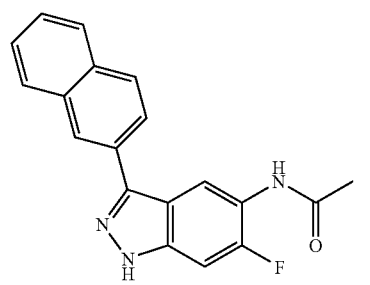
Example II-186
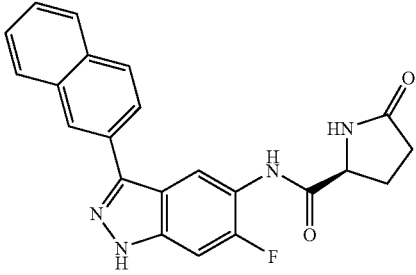

-continued
Example II-187
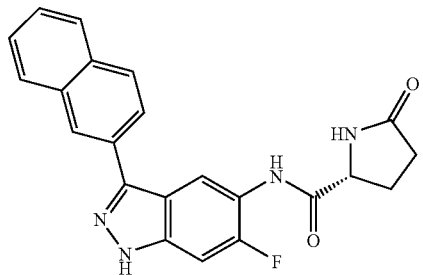
Example II-188
Example II-189
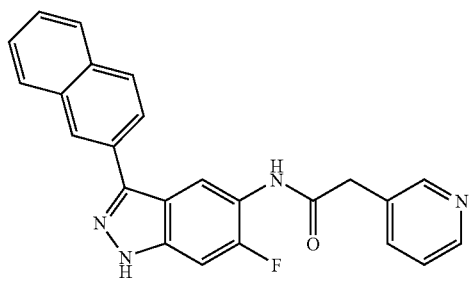
Example II-190
Example II-191
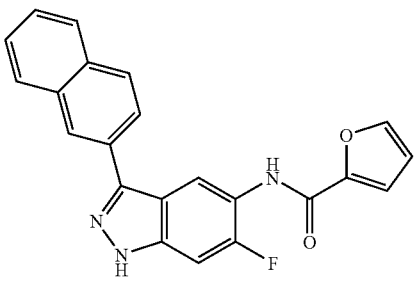
-continued
Example II-192
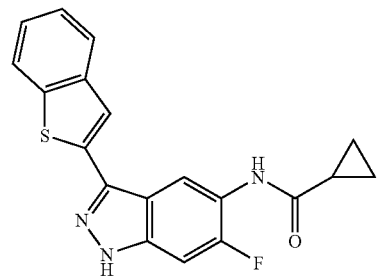
Example II-193
Example II-194
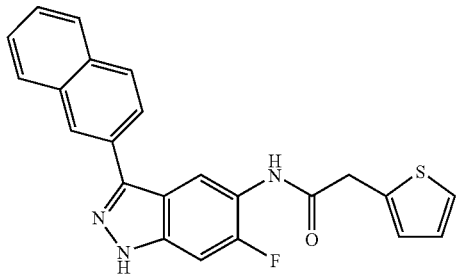
Example II-195
Example II-196
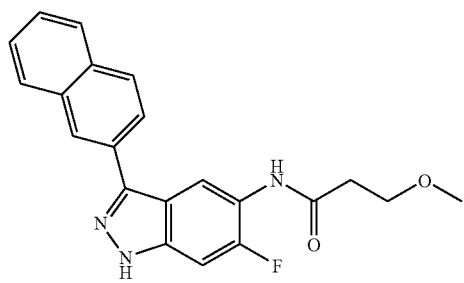

Example II-197
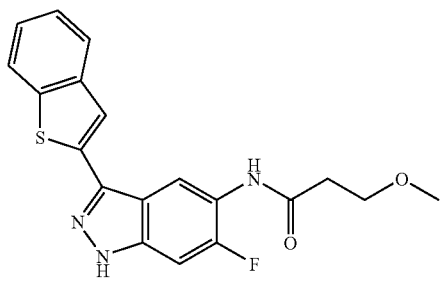
Example II-198
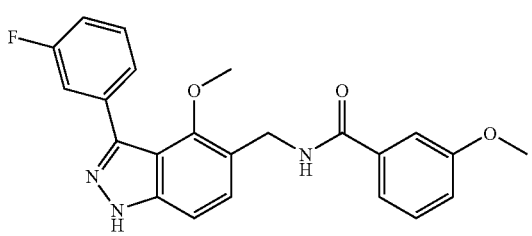
Example II-199
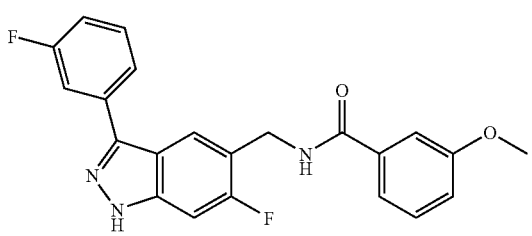
Example II-200
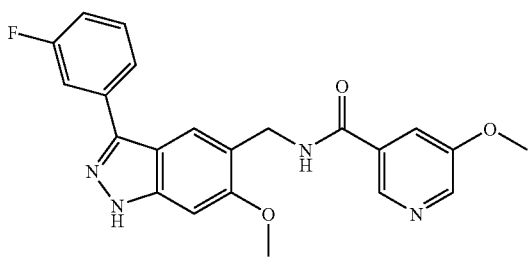
Example II-201
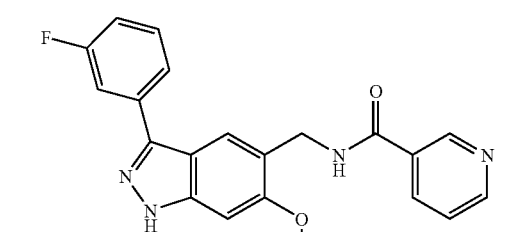
Example II-202
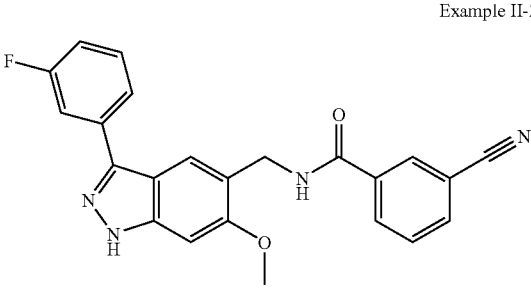
Example II-203
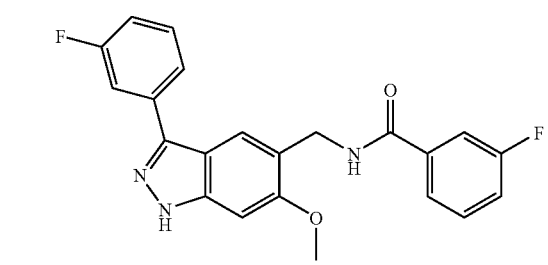
Example II-204
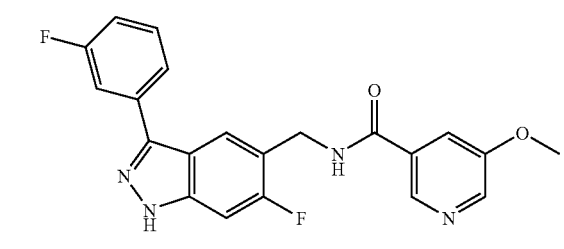
Example II-205
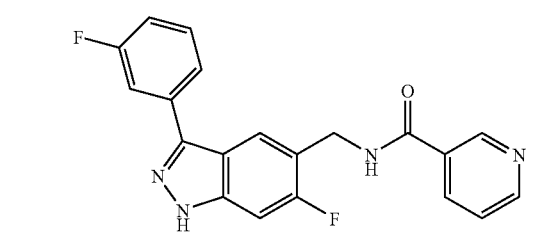
Example II-206
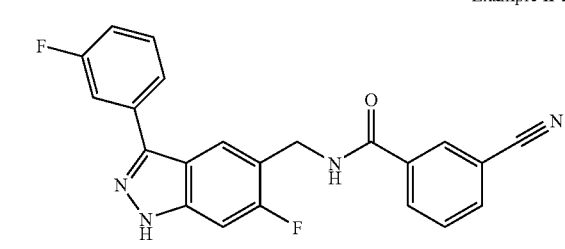
Example II-207
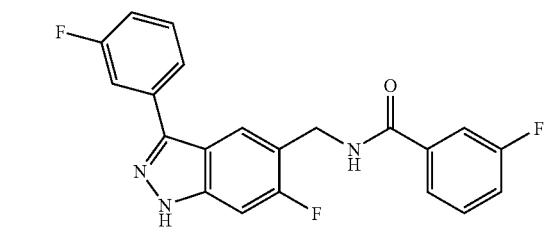
Example II-208
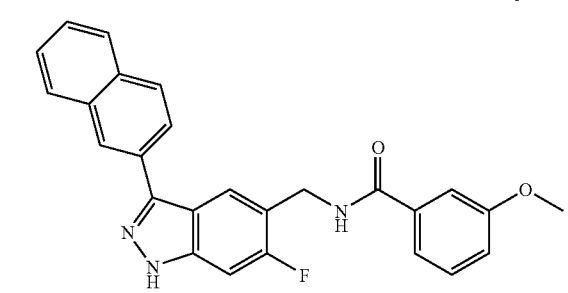

Example II-209

Example II-210

Example II-211

Example II-212

Example II-213

Example II-214

Example II-215

Example II-216

Example II-217

Example II-218

Example II-219

Example II-220

Example II-221
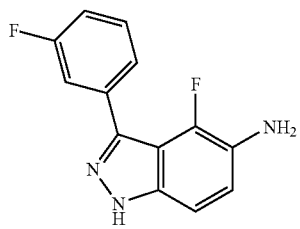
Example II-222
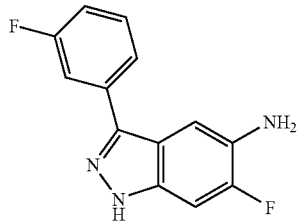
Example II-223
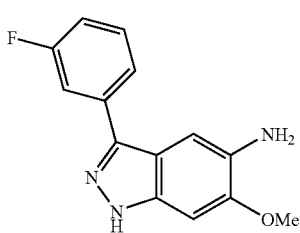
Example II-224
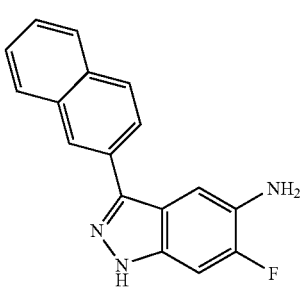
Example II-225
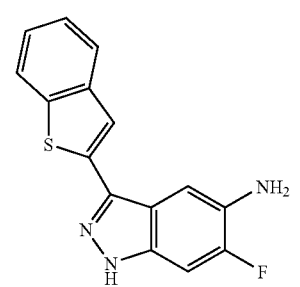
Example II-226-c
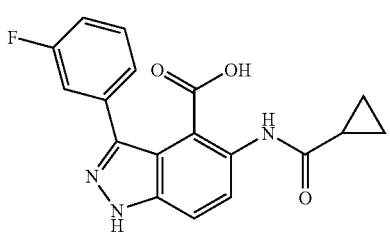
Example II-227
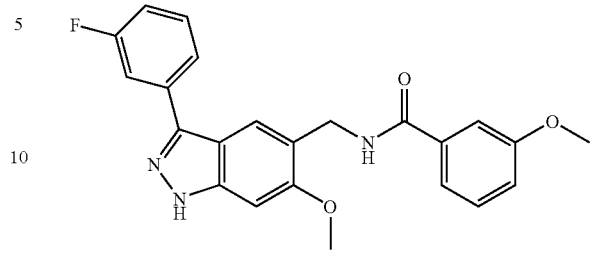
Example II-229
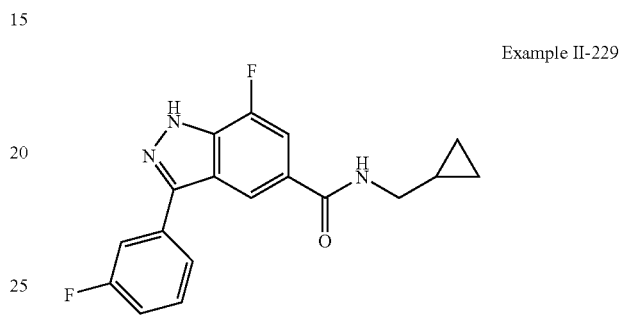
Example II-230
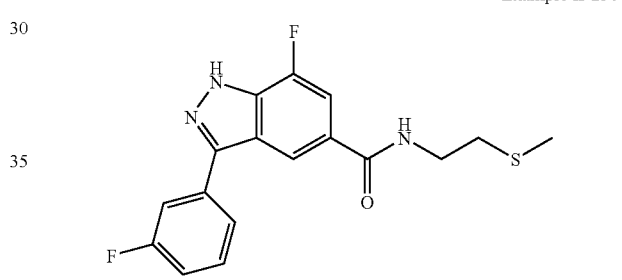
Example II-231
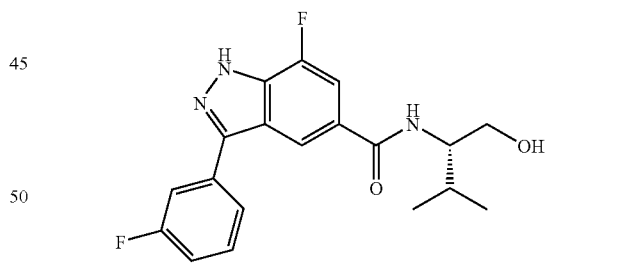
Example II-232
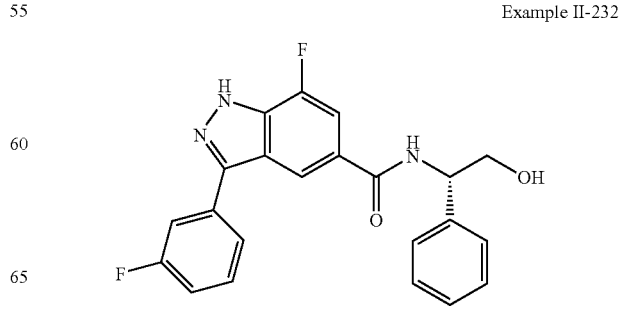

Example II-233
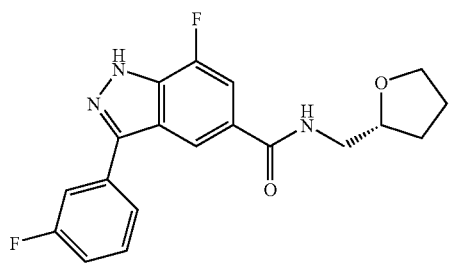
Example II-234
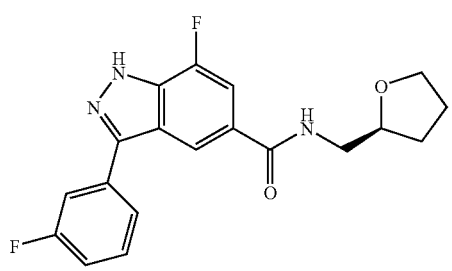
Example II-235
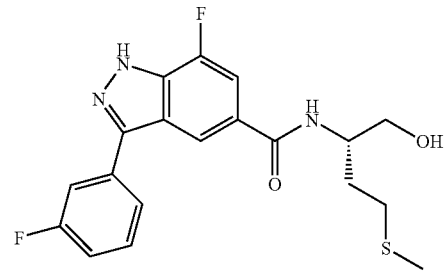
Example II-236
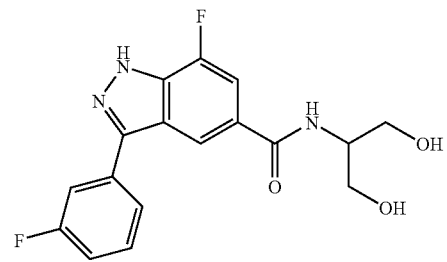
Example II-237
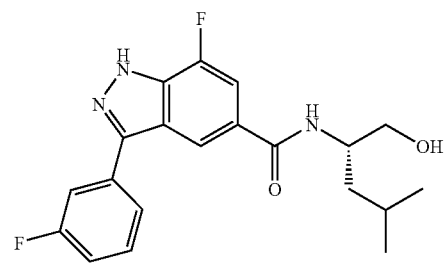
Example II-238
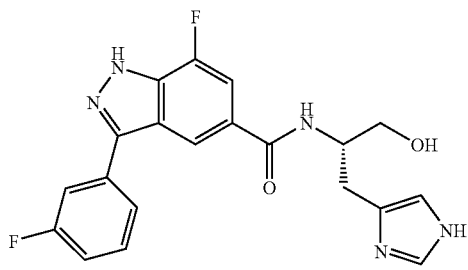
Example II-239
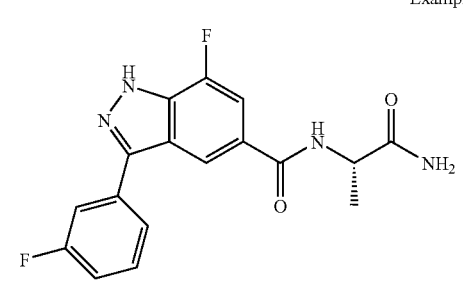
Example II-240
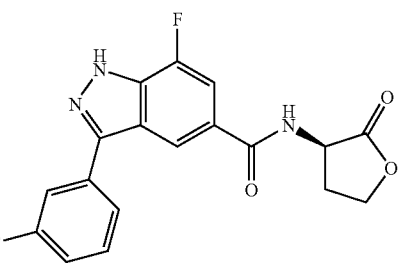
Example II-241
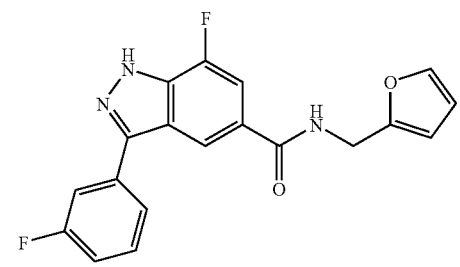
Example II-242
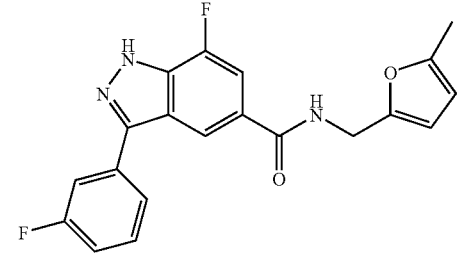

-continued
Example II-243
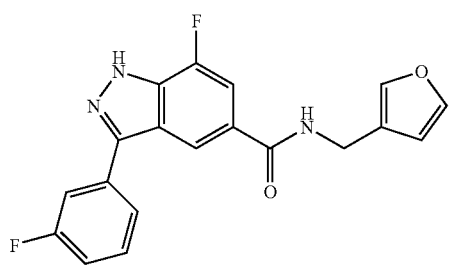
Example II-244
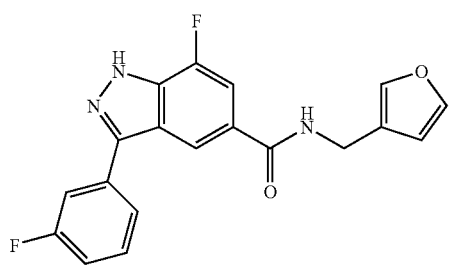
Example II-245
Example II-246
Example II-247
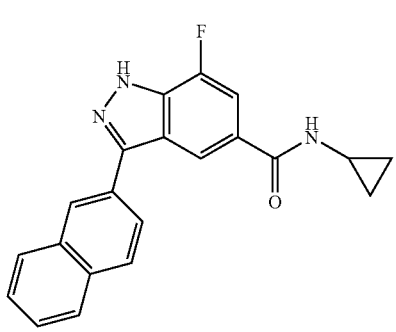
-continued
Example II-248
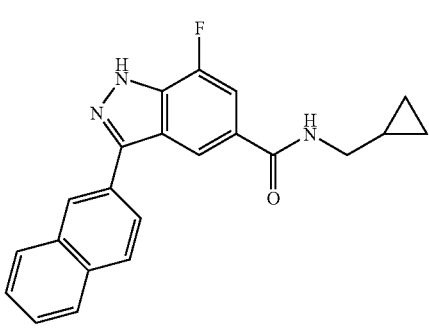
Example II-249
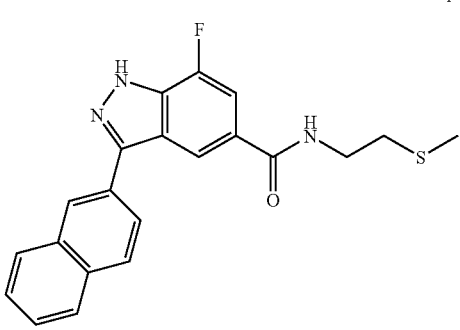
Example II-250
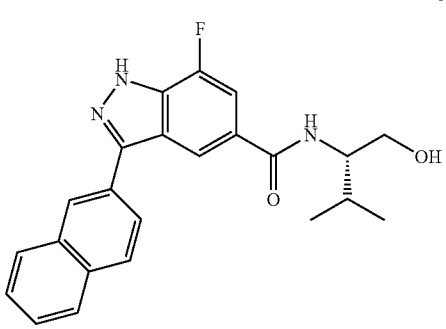
Example II-251
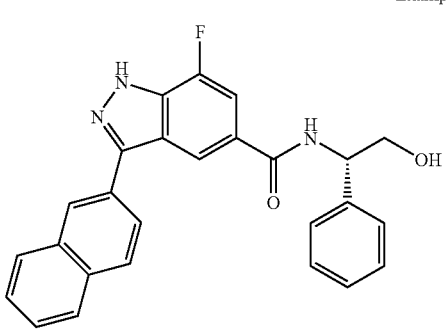

-continued
Example II-252
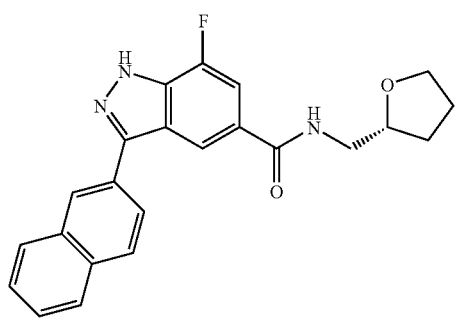
Example II-253
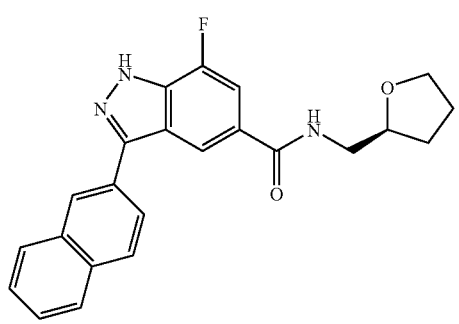
Example II-254
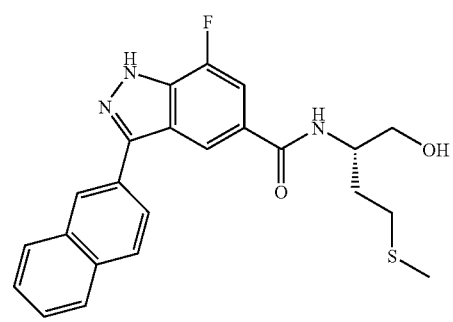
Example II-255
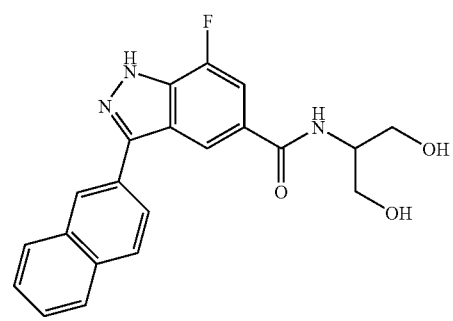
-continued
Example II-256
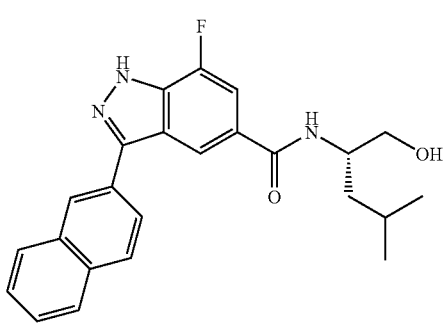
Example II-257
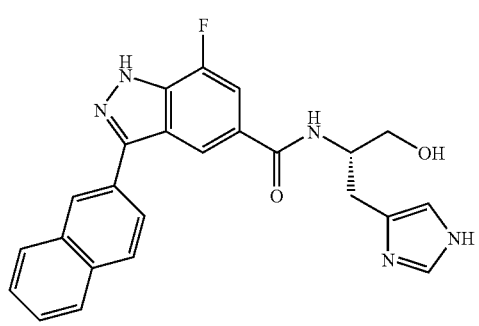
Example II-258
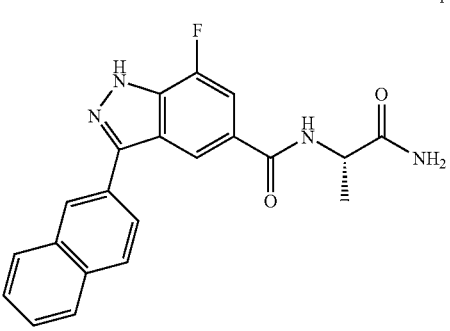
Example II-259
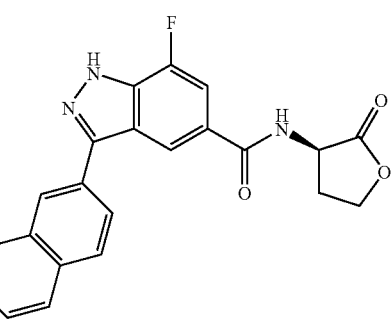

Example II-260
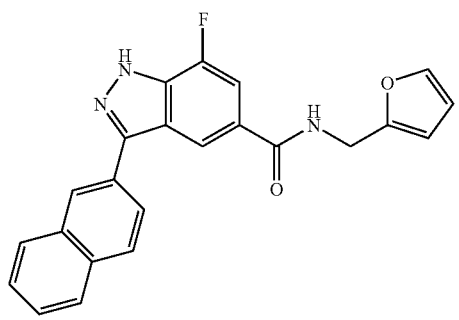
Example II-261
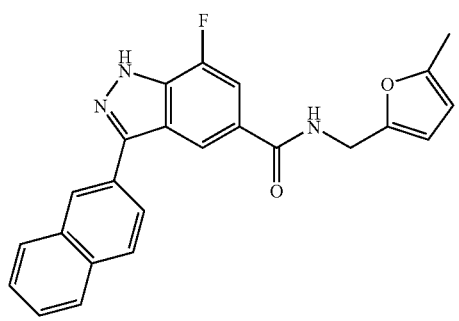
Example II-262
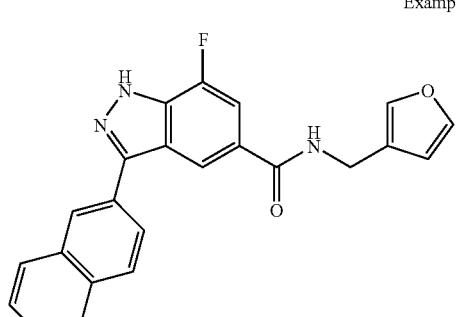
Example II-263
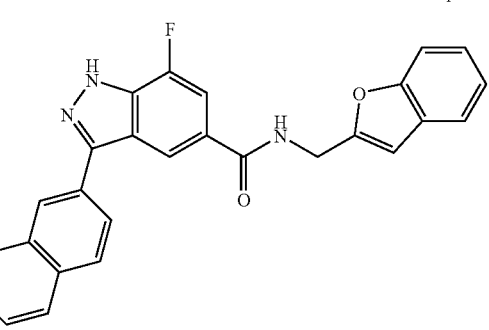
Example II-264
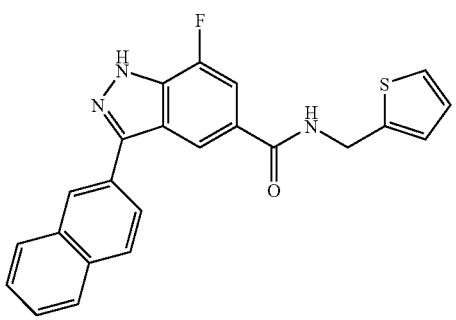
Example II-265
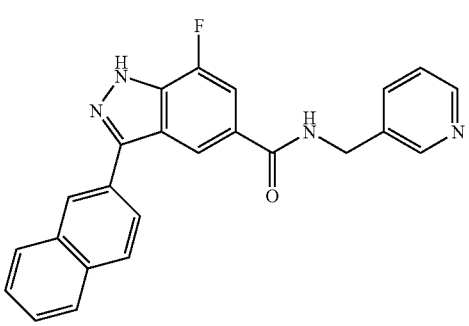
Example II-266
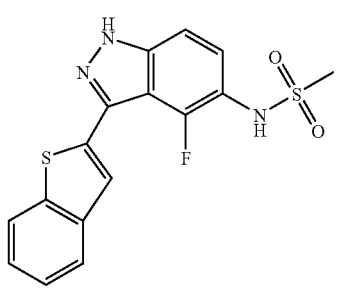
Example II-267
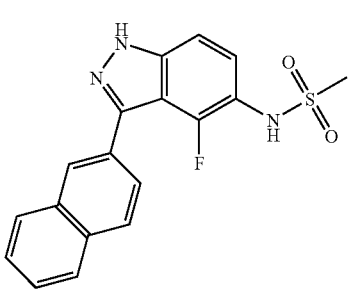
Example II-268
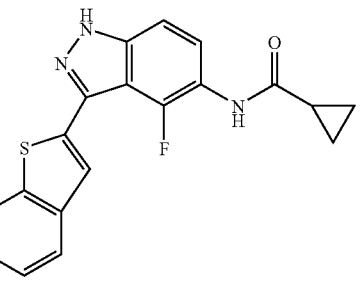

-continued

Example II-269

Example II-270

Example II-271

Example II-272

Example II-273

-continued

Example II-274

Example II-275

Example II-276

Example II-277

Example II-278

Example II-279
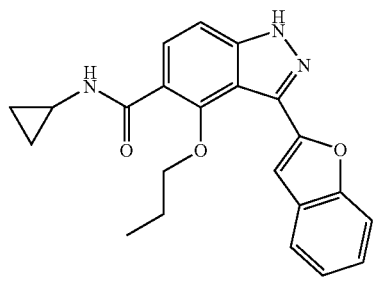
Example II-284
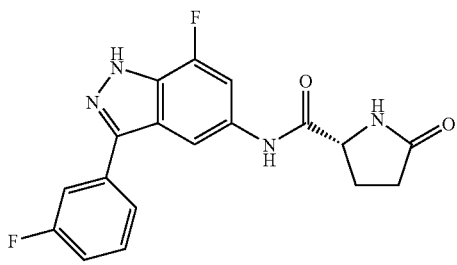
Example II-280
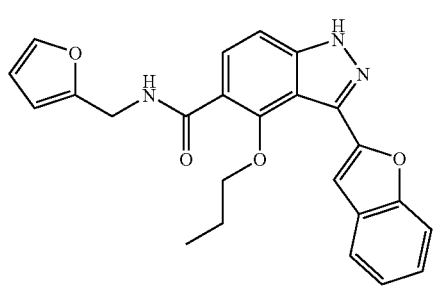
Example II-285
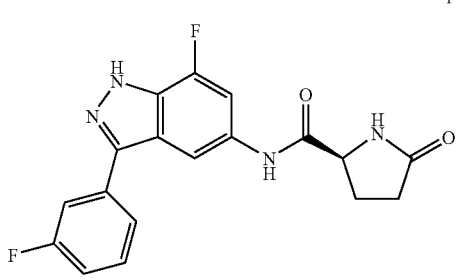
Example II-281
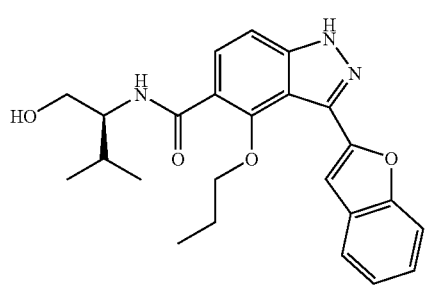
Example II-286
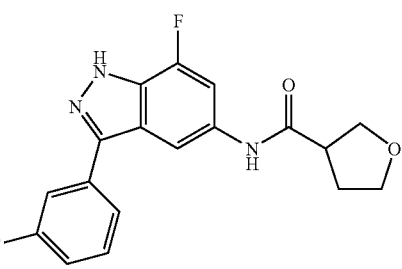
Example II-282
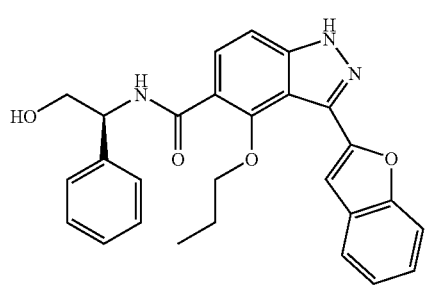
Example II-287
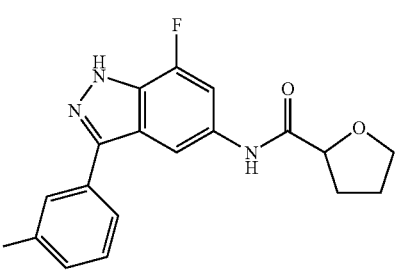
Example II-283
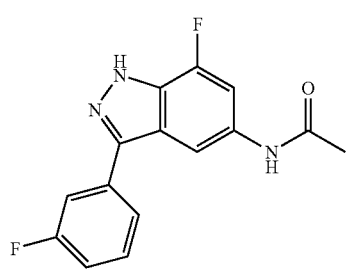
Example II-288
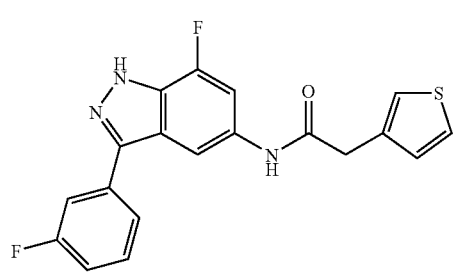

-continued
Example II-289
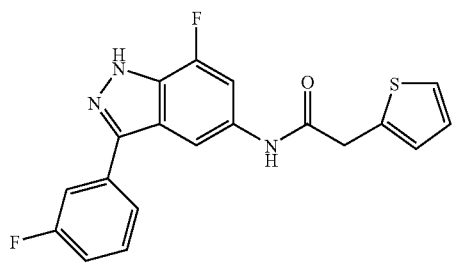
Example II-290
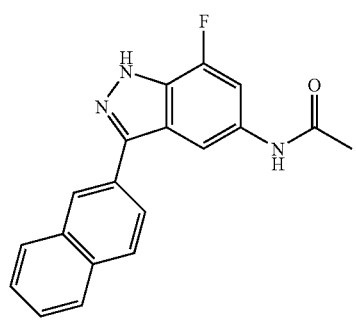
Example II-291
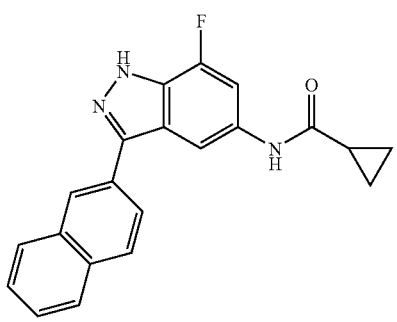
Example II-292
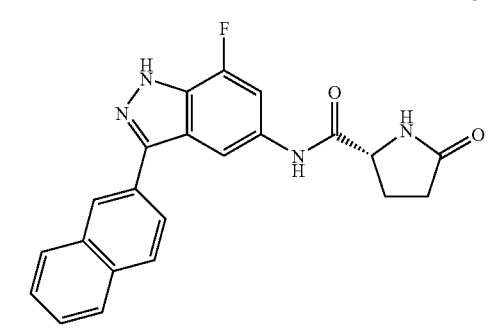
Example II-293
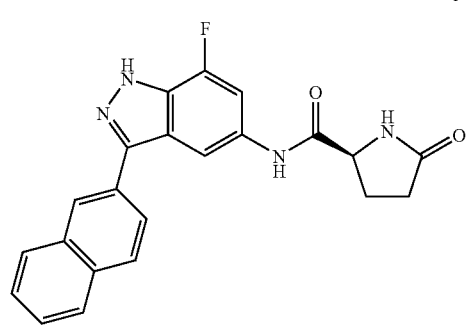
-continued
Example II-294
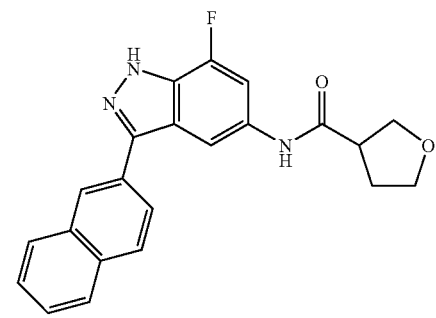
Example II-295
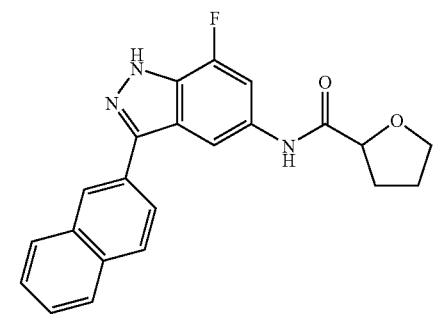
Example II-296
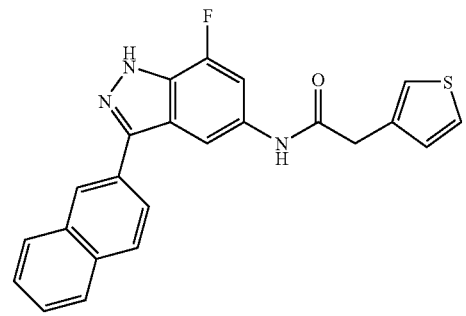
Example II-297
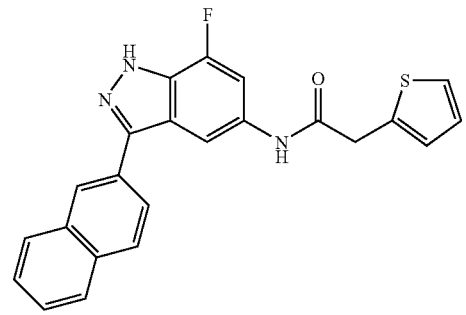
Example II-298
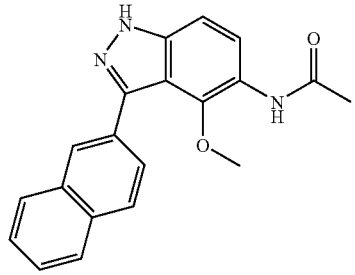

Example II-299
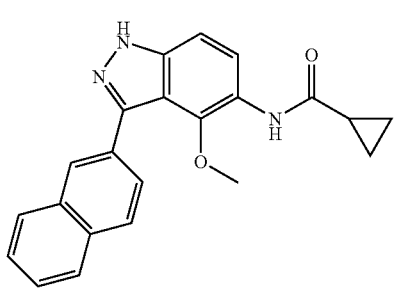
Example II-304
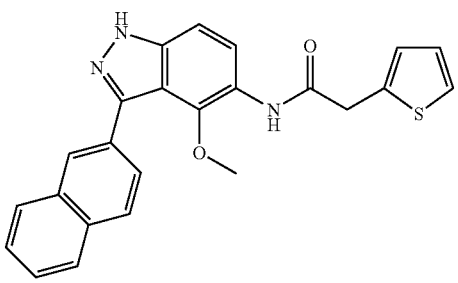
Example II-300
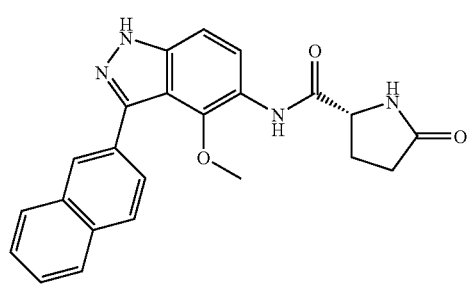
Example II-305
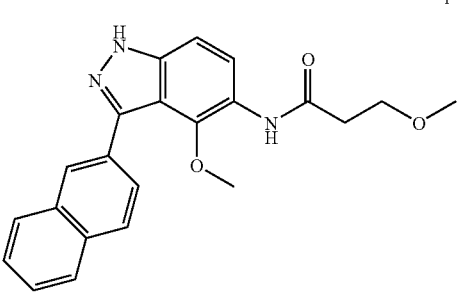
Example II-301
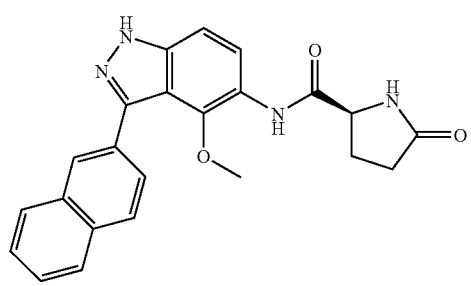
Example II-306
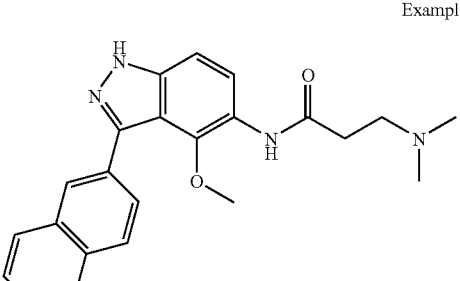
Example II-302
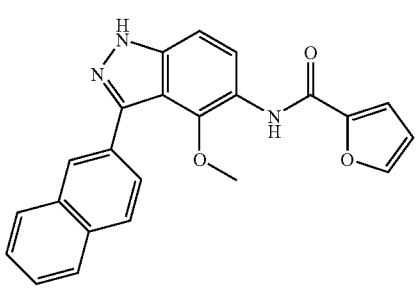
Example II-307
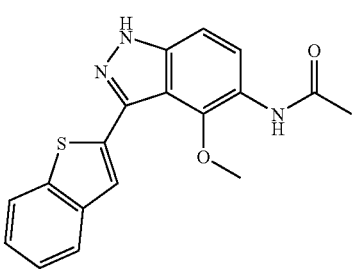
Example II-303
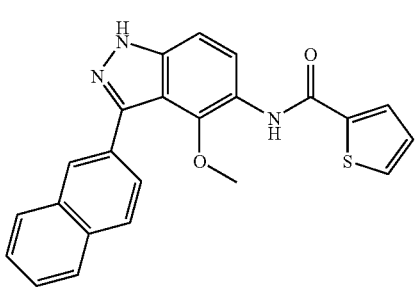
Example II-308
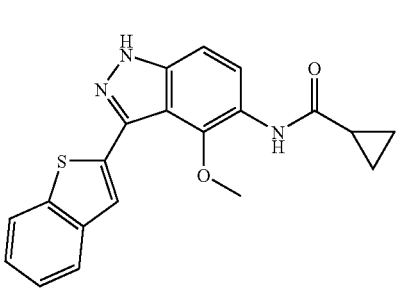

Example II-309
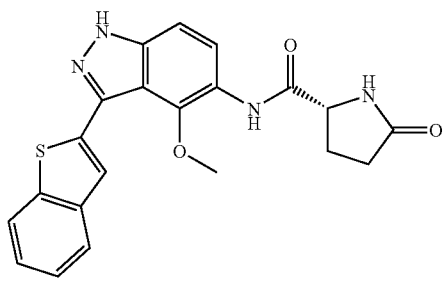
Example II-310
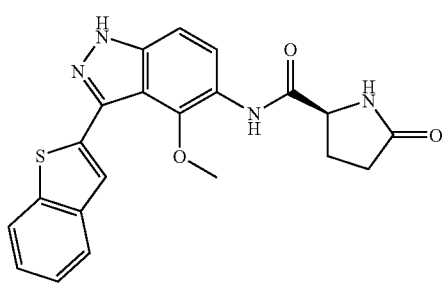
Example II-311
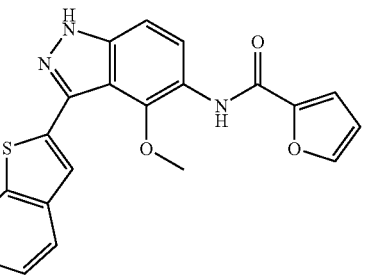
Example II-312
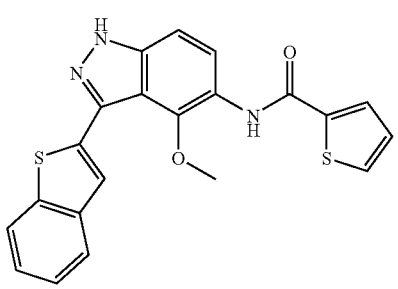
Example II-313
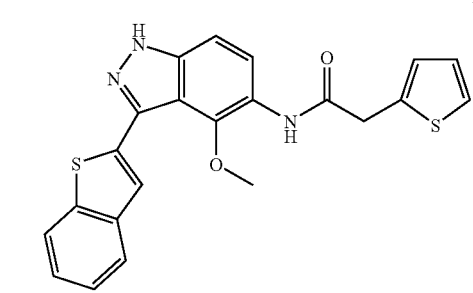
Example II-314
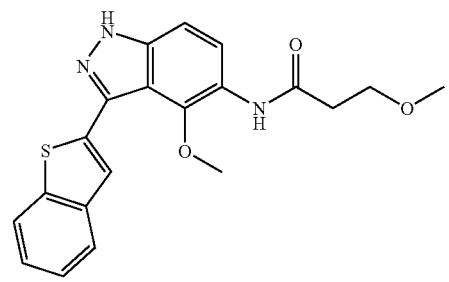
Example II-315
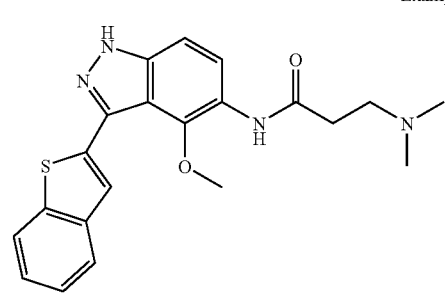
Example II-316
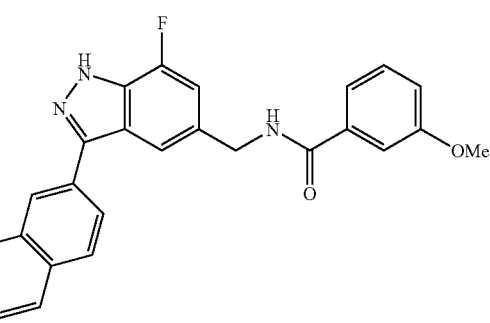
Example II-317
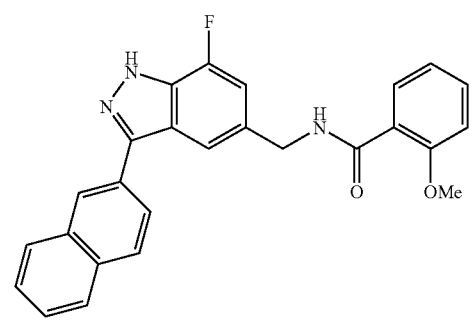
Example II-318
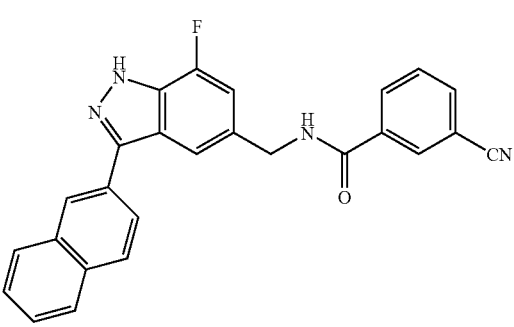

Example II-319

Example II-320

Example II-321

Example II-322

Example II-323

Example II-324

Example II-325

Example II-326

Example II-327

Example II-328

Example II-329
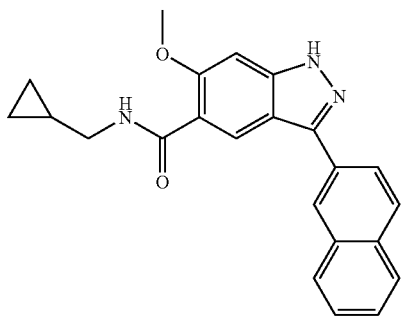
Example II-330
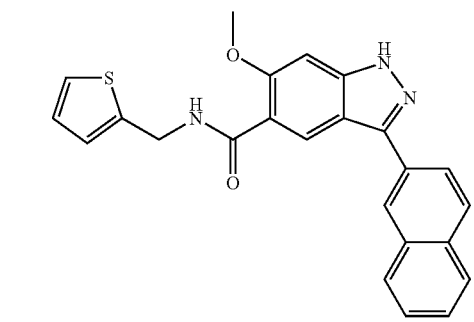
Example II-331
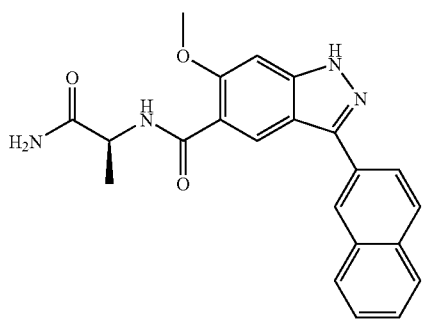
Example II-332
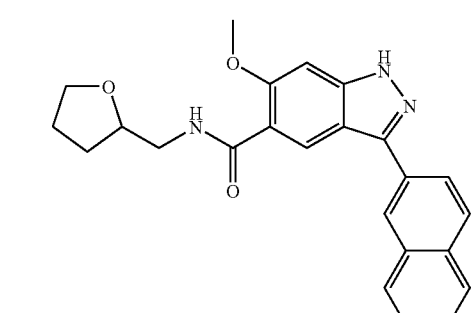
Example II-333
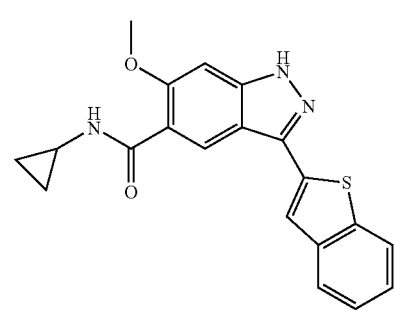
Example II-334
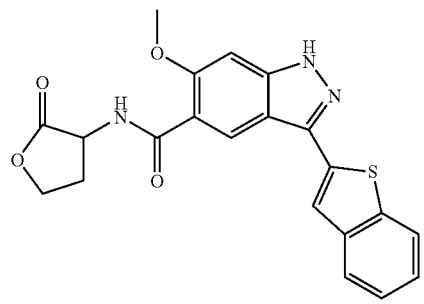
Example II-335
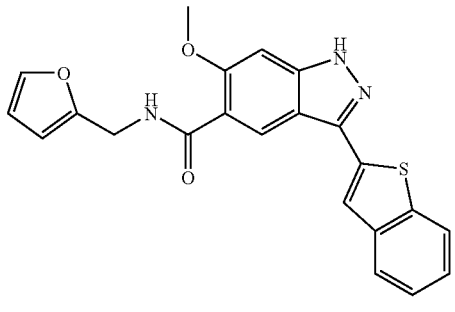
Example II-336
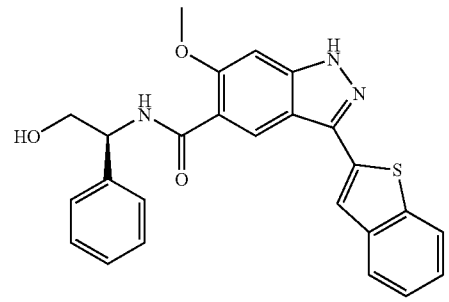
Example II-337
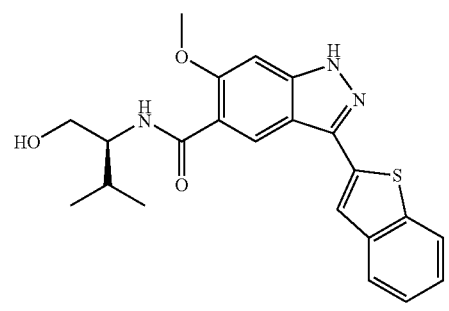
Example II-338
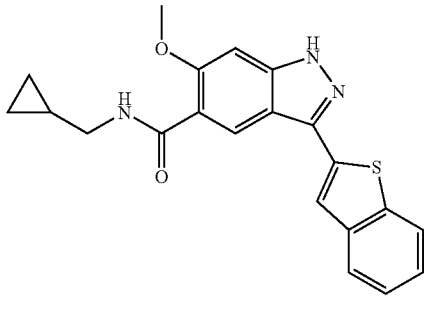

Example II-339

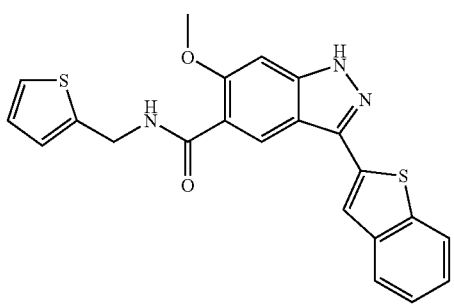

Example II-340

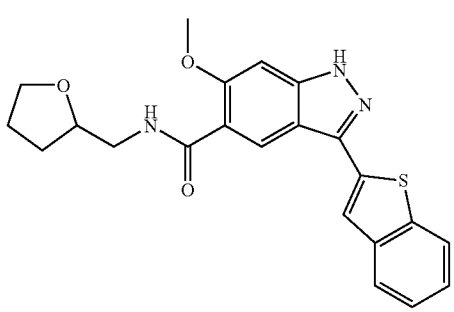

Example II-341

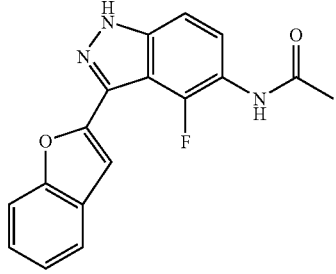

Example II-342

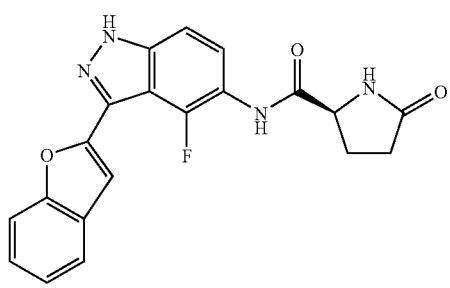

Example II-343

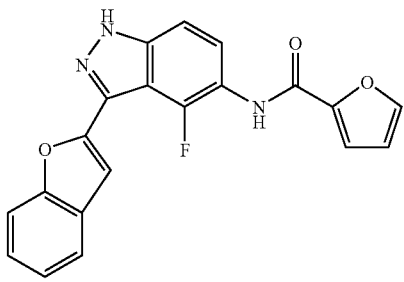

Example II-344

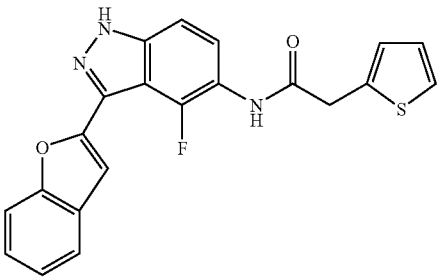

The invention claimed is:

1. A compound having the following formula or a salt thereof

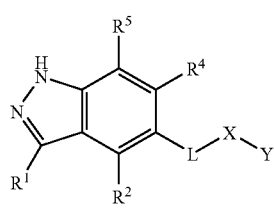

(I)

wherein

R$^1$ is a 2-thienyl, 2-furyl, 2-benzofuryl, or 2-benzothienyl group, each of which may be substituted;

R$^2$, R$^4$, and R$^5$ each independently is a hydrogen atom, a halogen atom, a hydroxyl group, a cyano group, a nitro group, a carboxyl group, a C$_1$-C$_6$ alkyl group which may be substituted, a C$_1$-C$_6$ alkoxy group which may be substituted, a C$_2$-C$_7$ acyl group which may be substituted, —CO—NR$^{2a}$R$^{2b}$, —NR$^{2b}$CO—R$^{2a}$, or —NR$^{2a}$R$^{2b}$, wherein R$^{2a}$ and R$^{2b}$ each independently is a hydrogen atom or a C$_1$-C$_6$ alkyl group which may be substituted, provided that one of R$^2$, R$^4$, and R$^5$ is not a hydrogen atom and that both of the remaining two of R$^2$, R$^4$, and R$^5$ are hydrogen atoms;

L is a single bond, a C$_1$-C$_6$ alkylene group which may be substituted, a C$_2$-C$_6$ alkenylene group which may be substituted, or a C$_2$-C$_6$ alkynylene group which may be substituted;

X is a single bond, or a group having the formula —NR$^6$—, —O—, —CO—, —S—, —SO—, —SO$_2$—, —CO—NR$^8$—V$^2$—, —C(O)O—, —NR$^8$—C(O)O—, —NR$^8$—S—, —NR$^8$—SO—, —NR$^8$—SO$_2$—V$^2$—, —NR$^9$—CO—NR$^{10}$, —NR$^9$—CS—NR$^{10}$, —S(O)$_m$—NR$^{11}$—V$^2$—, —C(=NR$^{12}$)—NR$^{13}$—, —OC(O)—, —OC(O)—N—R$^{14}$— or —CH$_2$—NR$^8$—COR$^6$, wherein R$^6$, R$^8$, R$^9$, R$^{10}$, R$^{11}$, R$^{12}$, R$^{13}$ and R$^{14}$ each independently is a hydrogen atom, a halogen atom, a hydroxyl group, a C$_1$-C$_6$ alkyl group which may be substituted, a C$_2$-C$_6$ alkenyl group which may be substituted, a C$_2$-C$_6$ alkynyl group which may be substituted, a C$_1$-C$_6$ alkoxy group which may be substituted, a C$_2$-C$_6$ alkenyloxy group which may be substituted, a C$_1$-C$_6$ alkylthio group which may be substituted, a C$_2$-C$_6$ alkenylthio group which may be substituted, a C$_3$-C$_8$ cycloalkyl group which may be substituted, a C$_3$-C$_8$ cycloalkenyl group which may be substituted, a 5- to 14-membered non-aromatic heterocyclic group which may be substituted, a $C_6$-$C_{14}$ aromatic cyclic hydrocarbon group which may be substituted or a 5- to 14-membered aromatic heterocyclic group which may be substituted; $V^2$ is a single bond or a $C_1$-$C_6$ alkylene group which may be substituted; and m is 0, 1 or 2; and Y is a hydrogen atom, a halogen atom, a nitro group, a hydroxyl group, a cyano group, a carboxyl group, a $C_1$-$C_6$ alkyl group which may be substituted, a $C_2$-$C_6$ alkenyl group which may be substituted, a $C_2$-$C_6$ alkynyl group which may be substituted, a $C_1$-$C_6$ alkoxy group which may be substituted, a $C_3$-$C_8$ cycloalkyl group which may be substituted, a $C_3$-$C_8$ cycloalkenyl group which may be substituted, a 5- to 14-membered non-aromatic heterocyclic group which may be substituted, a $C_6$-$C_{14}$ aromatic cyclic hydrocarbon group which may be substituted, a 5- to 14-membered aromatic heterocyclic group which may be substituted, an amino group or —W—$R^{15}$, wherein W is —CO— or —$SO_2$—; and $R^{15}$ is a $C_1$-$C_6$ alkyl group which may be substituted, a $C_6$-$C_{14}$ aromatic cyclic hydrocarbon group which may be substituted, a 5- to 14-membered aromatic heterocyclic group which may be substituted or an amino group.

2. The compound according to claim 1 or a salt thereof, wherein one of $R^2$, $R^4$, and $R^5$, is a halogen atom or a $C_1$-$C_6$ alkoxy group which may be substituted.

3. The compound according to claim 1 or a salt thereof, wherein $R^5$ is a hydrogen atom.

4. The compound according to claim 1 or a salt thereof, wherein $R^4$ is a hydrogen atom.

5. The compound according to claim 1 or a salt thereof, wherein $R^2$ is a hydrogen atom.

6. The compound according to claim 1 or a salt thereof, wherein L is a single bond or a methylene group.

7. The compound according to claim 1 or a salt thereof, wherein L is a single bond.

8. The compound according to claim 1 or a salt thereof, wherein X is a group having the formula —CO—$NR^8$—$V^2$— or —$NR^8$—$SO_2$—$V^2$—.

9. The compound according to claim 8 or a salt thereof, wherein $R^8$ is a hydrogen atom.

10. The compound according to claim 1 or a salt thereof, wherein Y is a $C_1$-$C_6$ alkyl group, a $C_6$-$C_{14}$ aromatic cyclic hydrocarbon group, a $C_1$-$C_6$ alkoxy group, a $C_3$-$C_8$ cycloalkyl group, a 5- to 14-membered non-aromatic heterocyclic group and a 5- to 14-membered aromatic heterocyclic group, and Y is a group which may be substituted by one to three members selected from Substituent Group "a2":

<Substituent Group "a2"> (1) (a) $C_1$-$C_6$ alkyl groups, (b) $C_2$-$C_6$ alkenyl groups, (c) $C_2$-$C_6$ alkynyl groups, (d) $C_1$-$C_6$ alkoxy groups, (e) $C_2$-$C_7$ acyl groups, (f) an amide group, (g) an amino group, (h) a $C_3$-$C_8$ cycloalkyl group, (i) $C_3$-$C_8$ cycloalkenyl groups, (j) $C_6$-$C_{14}$ aromatic cyclic hydrocarbon groups, (k) 5- to 14-membered aromatic heterocyclic groups, (l) $C_6$-$C_{14}$ aryloxy groups, and (m) 5- to 14-membered non-aromatic heterocyclic groups, each of which may be substituted by one to three members selected from Substituent Group "b2", (2) halogen atoms, (3) a hydroxyl group, (4) a nitro group, (5) a cyano group, and (6) a carboxyl group:

<Substituent Group "b2"> $C_1$-$C_6$ alkyl groups, halogen atoms, a hydroxyl group, a nitro group, a cyano group, and a carboxyl group.

11. The compound according to claim 10 or a salt thereof, wherein Substituent Group "a2" is (1) (a) $C_1$-$C_6$ alkyl groups, (b) $C_1$-$C_6$ alkoxy groups, (c) $C_2$-$C_7$ acyl groups, (d) an amide group, (e) an amino group, and (f) $C_3$-$C_8$ cycloalkyl groups, each of which may be substituted by one to three groups selected from the following Substituent Group "b2", (2) halogen atoms, (3) a hydroxyl group, (4) a nitro group, (5) a cyano group, and (6) a carboxyl group, and Substituent Group "b2" is $C_1$-$C_6$ alkyl groups, halogen atoms, a hydroxyl group, a nitro group, a cyano group, and a carboxyl group.

12. The compound according to claim 10 or a salt thereof, wherein Substituent Group "a2" is (1) $C_1$-$C_6$ alkoxy groups, (2) halogen atoms, and (3) a cyano group.

13. The compound according to claim 1 or a salt thereof, wherein Y is a $C_3$-$C_8$ cycloalkyl group, a phenyl group, a 5- or 6-membered non-aromatic heterocyclic group or a 5- or 6-membered aromatic heterocyclic group, and Y is a group which may be substituted by one to three members selected from Substituent Group "a2":

<Substituent Group "a2"> (1) (a) $C_1$-$C_6$ alkyl groups, (b) $C_2$-$C_6$ alkenyl groups, (c) $C_2$-$C_6$ alkynyl groups, (d) $C_1$-$C_6$ alkoxy groups, (e) $C_2$-$C_7$ acyl groups, (f) an amide group, (g) an amino group, (h) a $C_3$-$C_8$ cycloalkyl group, (i) $C_3$-$C_8$ cycloalkenyl groups, (j) $C_6$-$C_{14}$ aromatic cyclic hydrocarbon groups, (k) 5- to 14-membered aromatic heterocyclic groups, (l) $C_6$-$C_{14}$ aryloxy groups, and (m) 5- to 14-membered non-aromatic heterocyclic groups, each of which may be substituted by one to three members selected from Substituent Group "b2", (2) halogen atoms, (3) a hydroxyl group, (4) a nitro group, (5) a cyano group, and (6) a carboxyl group:

<Substituent Group "b2"> $C_1$-$C_6$ alkyl groups, halogen atoms, a hydroxyl group, a nitro group, a cyano group, and a carboxyl group.

14. The compound according to claim 1 or a salt thereof, wherein Y is a furyl group, a thienyl group, a pyrrolyl group, a phenyl group, a pyridyl group, a $C_3$-$C_8$ cycloalkyl group, a tetrahydrofuranyl group, a tetrahydrothiophenyl group, a pyrrolidinyl group, a tetrahydrofuran-2-one-yl group, a pyrrolidin-2-one-yl group or a group represented by having the formula

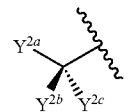

wherein $Y^{2a}$ is a group having the formula —$CONH_2$ or —$CH_2OH$; and $Y^{2b}$ and $Y^{2c}$ each independently is a hydrogen atom, a phenyl group which may be substituted or a $C_1$-$C_6$ alkyl group which may be substituted), and wherein Y is a group which may be substituted by one to three members selected from the Substituent Group "a2":

<Substituent Group "a2"> (1) (a) $C_1$-$C_6$ alkyl groups, (b) $C_2$-$C_6$ alkenyl groups, (c) $C_2$-$C_6$ alkynyl groups, (d) $C_1$-$C_6$ alkoxy groups, (e) $C_2$-$C_7$ acyl groups, (f) an amide group, (g) an amino group, (h) a $C_3$-$C_8$ cycloalkyl group, (i) $C_3$-$C_8$ cycloalkenyl groups, (j) $C_6$-$C_{14}$ aromatic cyclic hydrocarbon groups, (k) 5- to 14-membered aromatic heterocyclic groups, (l) $C_6$-$C_{14}$ aryloxy groups, and (m) 5- to 14-membered non-aromatic heterocyclic groups, each of which may be substituted by one to three members selected from Substituent Group "b2", (2) halogen atoms, (3) a hydroxyl group, (4) a nitro group, (5) a cyano group, and (6) a carboxyl group:

<Substituent Group "b2"> $C_1$-$C_6$ alkyl groups, halogen atoms, a hydroxyl group, a nitro group, a cyano group, and a carboxyl group.

15. The compound according to claim 1 or a salt thereof, wherein Y is a furyl group or a thienyl group; and Y is a group which may be substituted by one to three members selected from the Substituent Group "a2":

<Substituent Group "a2"> (1) (a) $C_1$-$C_6$ alkyl groups, (b) $C_2$-$C_6$ alkenyl groups, (c) $C_2$-$C_6$ alkynyl groups, (d) $C_1$-$C_6$ alkoxy groups, (e) $C_2$-$C_7$ acyl groups, (f) an amide group, (g) an amino group, (h) a $C_3$-$C_8$ cycloalkyl group, (i) $C_3$-$C_8$ cycloalkenyl groups, (j) $C_6$-$C_{14}$ aromatic cyclic hydrocarbon groups, (k) 5- to 14-membered aromatic heterocyclic groups, (l) $C_6$-$C_{14}$ aryloxy groups, and (m) 5- to 14-membered non-aromatic heterocyclic groups, each of which may be substituted by one to three members selected from Substituent Group "b2", (2) halogen atoms, (3) a hydroxyl group, (4) a nitro group, (5) a cyano group, and (6) a carboxyl group:

<Substituent Group "b2"> $C_1$-$C_6$ alkyl groups, halogen atoms, a hydroxyl group, a nitro group, a cyano group, and a carboxyl group.

16. A pharmaceutical composition comprising the compound according to claim 1 or a salt thereof, and a pharmacologically acceptable carrier.

* * * * *

UNITED STATES PATENT AND TRADEMARK OFFICE
CERTIFICATE OF CORRECTION

PATENT NO.         : 7,776,890 B2                                Page 1 of 1
APPLICATION NO.    : 12/426818
DATED              : August 17, 2010
INVENTOR(S)        : Hitoshi Oinuma et al.

It is certified that error appears in the above-identified patent and that said Letters Patent is hereby corrected as shown below:

Title Page; should read;
Correct section (62), Related U.S. Application Data, as follows:

-- Division of application No. 11/202,234, filed on Aug. 12, 2005, now Pat. No. 7,541,376, which is a Division of application No. 10/469,399, filed on Aug. 28, 2003, now Pat. No. 6,982,274, which is a 371 of PCT/JP02/03735, filed on Apr. 15, 2002. --.

Insert the following:

-- (30)          Foreign Application Priority Data

April 16, 2001   (JP)   ............... 2001-116521 --.

Signed and Sealed this
Twelfth Day of April, 2011

David J. Kappos
*Director of the United States Patent and Trademark Office*